US008513424B2

(12) United States Patent
Wacker et al.

(10) Patent No.: US 8,513,424 B2
(45) Date of Patent: Aug. 20, 2013

(54) PYRIDONE GPR119 G PROTEIN-COUPLED RECEPTOR AGONISTS

(75) Inventors: Dean A. Wacker, Yardley, PA (US); Karen A. Rossi, Newtown, PA (US); Ying Wang, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/494,489

(22) Filed: Jun. 12, 2012

(65) Prior Publication Data
US 2012/0258959 A1 Oct. 11, 2012

Related U.S. Application Data

(60) Division of application No. 13/159,497, filed on Jun. 14, 2011, which is a continuation of application No. 12/173,856, filed on Jul. 16, 2008, now Pat. No. 8,003,796.

(60) Provisional application No. 60/950,162, filed on Jul. 17, 2007.

(51) Int. Cl.
*C07D 405/00* (2006.01)
*A61K 31/505* (2006.01)

(52) U.S. Cl.
USPC .......................................... 546/210; 514/274

(58) Field of Classification Search
None
See application file for complete search history.

(56) References Cited

U.S. PATENT DOCUMENTS

| | | | |
|---|---|---|---|
| 3,826,643 | A | 7/1974 | Diehl et al. |
| 5,488,064 | A | 1/1996 | Sher |
| 5,491,134 | A | 2/1996 | Sher et al. |
| 5,541,204 | A | 7/1996 | Sher et al. |
| 5,612,359 | A | 3/1997 | Murugesan |
| 5,770,615 | A | 6/1998 | Cheng et al. |
| 5,776,983 | A | 7/1998 | Washburn et al. |
| 6,043,265 | A | 3/2000 | Murugesan et al. |
| 6,566,384 | B1 | 5/2003 | Owen et al. |
| 2003/0181420 | A1 | 9/2003 | Bayne et al. |
| 2005/0080111 | A1 | 4/2005 | Bayne et al. |
| 2005/0245515 | A1 | 11/2005 | Dehmlow et al. |
| 2006/0155128 | A1 | 7/2006 | Jones et al. |
| 2006/0292073 | A1 | 12/2006 | Goodman et al. |

FOREIGN PATENT DOCUMENTS

| | | |
|---|---|---|
| EP | 1 338 651 | 8/2003 |
| WO | WO 96/38144 | 12/1996 |
| WO | WO 97/12613 | 4/1997 |
| WO | WO 97/12615 | 4/1997 |
| WO | WO 99/26659 | 6/1999 |
| WO | WO 00/01389 | 1/2000 |
| WO | WO 00/39102 | 7/2000 |
| WO | WO 02/02519 | 1/2002 |
| WO | WO 2004/065380 | 8/2004 |
| WO | WO 2004/076413 | 9/2004 |
| WO | WO 2004/089885 | 10/2004 |
| WO | WO 2005/007647 | 1/2005 |
| WO | WO 2005/007658 | 1/2005 |
| WO | WO 2005/025504 | 3/2005 |
| WO | WO 2005/089786 | 9/2005 |
| WO | WO 2005/121121 | 12/2005 |
| WO | WO 2006/067532 | 6/2006 |
| WO | WO2006/083491 | 8/2006 |
| WO | WO2007/003961 A2 | 1/2007 |

OTHER PUBLICATIONS

Ahrén, B., "Autonomic regulation of islet hormone secretion—Implications for health and disease", Diabetologia, vol. 43, pp. 393-410 (2000).
Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).
Boger, D.L. et al., "Total Syntheses of Azafluoranthene Alkaloids: Rufescine and Imeluteine", J. Org. Chem., vol. 49, No. 21, pp. 4050-4055 (1984).
Brancati, F.L. et al., "Body Weight Patterns from 20 to 49 Years of Age and Subsequent Risk for Diabetes Mellitus", Arch. Intern. Med., vol. 159, pp. 957-963 (1999).
Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).
Bundgaard, H., ed., Design of Prodrugs, Elsevier Science Publishers B.V., publ. (1985) (table of contents).
Butler, A.E. et al., "β-Cell Deficit and Increased β-Cell Apoptosis in Humans with Type 2 Diabetes", Diabetes, vol. 52, pp. 102-110 (2003).
Chu, Z.-L. et al., "A Role for β-Cell-Expressed G Protein-Coupled Receptor 119 in Glycemic Control by Enhancing Glucose-Dependent Insulin Release", Endocrinology, vol. 148, No. 6, pp. 2601-2609 (2007).
Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).
Deng, H. et al., "Aryllead(IV) Reagents in Synthesis: Formation of the C11 Quaternary Center of N-Methylwelwitindolinone C Isothiocyanate", Organic Letters, vol. 3, No. 19, pp. 3001-3004 (2001).
Donetti, A. et al., "(Imidazolylphenyl)formamidines. A Structurally Novel Class of Potent Histamine $H_2$ Antagonists", J. Med. Chem., vol. 27, No. 3, pp. 380-386 (1984).
Ford, E.S. et al., "Prevalence of the Metabolic Syndrome Among US Adults", Journal of the American Medical Association, vol. 287, No. 3, pp. 356-359 (2002).
Fredriksson, R. et al., "Seven evolutionary conserved human rhodopsin G protein-coupled receptors lacking close relatives", FEBS Letters, vol. 554, pp. 381-388 (2003).

(Continued)

*Primary Examiner* — Janet Andres
*Assistant Examiner* — Heidi Reese
(74) *Attorney, Agent, or Firm* — Terence J. Bogie

(57) ABSTRACT

Novel compounds are provided which are GPR119 G protein-coupled receptor modulators. GPR119 G protein-coupled receptor modulators are useful in treating, preventing, or slowing the progression of diseases requiring GPR119 G protein-coupled receptor modulator therapy. These novel compounds have the structure Formula I or Formula IA.

5 Claims, No Drawings

(56) References Cited

OTHER PUBLICATIONS

Frlan, R. et al., "Recent Progress in Diaryl Ether Synthesis", Synthesis, No. 14, pp. 2271-2285 (2006).
Gennaro, A.R., ed., Remington's Pharmaceutical Sciences, 17th Edition, Mack Publishing Company, publ., p. 1418 (1985).
Gomtsyan, A. et al., "Design, Synthesis, and Structure-Activity Relationship of 6-Alkynylpyrimidines as Potent Adenosine Kinase Inhibitors", J. Med. Chem., vol. 45, No. 17, pp. 3639-3648 (2002).
Greene, T.W. et al., Protective Groups in Organic Synthesis, Second Edition, John Wiley & Sons, Inc., publ., pp. ix-x (table of contents) (1991).
Haning, H. et al., "Novel heterocyclic thyromimetics", Bioorganic & Medicinal Chemistry Letters, vol. 15, pp. 1835-1840 (2005).
Hara, S., "Ileal Na+/bile acid cotransporter inhibitors", Drugs of the Future, vol. 24, No. 4, pp. 425-430 (1999).
Hertzog, D.L., "Recent advances in the cannabinoids", Expert Opin. Ther. Patents, vol. 14, No. 10, pp. 1435-1452 (2004).
Hill, J.O. et al., "Environmental Contributions to the Obesity Epidemic", Science, vol. 280, pp. 1371-1374 (1998).
Hong, C.Y. et al., "Asymmetric Synthesis of Either Enantiomer of Opium Alkaloids and Morphinans. Total Synthesis of (−)- and (+)-Dihydrocodeinone and (−)- and (+)-Morphine", J. Am. Chem. Soc., vol. 115, No. 23, pp. 11028-11029 (1993).
Itoh, T. et al., "A General Palladium-Catalyzed Coupling of Aryl Bromides/Triflates and Thiols", Organic Letters, vol. 6, No. 24, pp. 4587-4590 (2004).
Jiang, G. et al., "Prevention of obesity in mice by antisense oligonucleotide inhibitors of stearoyl-CoA desaturase-1", The Journal of Clinical Investigation, vol. 115, No. 4, pp. 1030-1038 (2005).
Justus, K. et al., "First Synthesis of a Strained 14-Membered Biaryl Ether Lactone by Macrolactonization", Tetrahedron Letters, vol. 32, No. 14, pp. 5781-5784 (1991).
Katritzky, A.R. et al., "Efficient Transformations of Aldehydes and Ketones into One-Carbon Homologated Carboxylic Acids", Synthesis, pp. 1425-1427 (1996).
Ketcha, D.M. et al., "The Reduction of N-(phenylsulfonyl)indoles with Sodium Cyanoborohydride in Trifluoroacetic Acid", Tetrahedron Letters, vol. 30, No. 49, pp. 6833-6836 (1989).
Le Stunff, C. et al., "Early Changes in Postprandial Insulin Secretion, Not in Insulin Sensitivity, Characterize Juvenile Obesity", Diabetes, vol. 43, pp. 696-702 (1994).
Magnus, P. et al., "Studies on the Synthesis of the Antitumor Agent CC-1065. Synthesis of the Unprotected Cyclopropapyrroloindole a Portion Using the 3,3'-Bipyrrole Strategy", J. Am. Chem. Soc., vol. 109, No. 9, pp. 2706-2711 (1987).
NCBI Entrez Accession No. AAP72125 (gi:32165516), Fredriksson, R. et al., Dec. 8, 2003.
NCBI Entrez Accession No. AY288423 (gi:32165529), Fredriksson, R. et al., Dec. 8, 2003.
Nishio, T. et al., "Reduction of Indolin-2-ones and Desulfurization of Indoline-2-thiones to Indoline and Indole Derivatives", Helvetica Chimica Acta, vol. 73, pp. 1719-1723 (1990).
Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., vol. 43, No. 22, pp. 4288-4312 (2000).

Overton, H.A. et al., "Deorphanization of a G protein-coupled receptor for oleoylethanolamide and its use in the discovery of small-molecule hypophagic agents", Cell Metabolism, vol. 3, pp. 167-175 (2006).
Pedersen, O., "The Impact of Obesity on the Pathogenesis of Non-Insulin-Dependent Diabetes Mellitus: A Review of Current Hypotheses", Diabetes/Metabolism Reviews, vol. 5, No. 6, pp. 495-509 (1989).
Perry, I.J. et al., "Prospective study of risk factors for development of non-insulin dependent diabetes in middle aged British men", BMJ, vol. 310, pp. 560-564 (1995).
Prentki, M. et al., "Islet β cell failure in type 2 diabetes", The Journal of Clinical Investigation, vol. 116, No. 7, pp. 1802-1812 (2006).
Radinov, R. et al., "Lithiation of Polychloropyrimidines and Dichloropyridines", J. Org. Chem., vol. 56, No. 15, pp. 4793-4796 (1991).
Schubert, U., "The Homologation of Hagemann's Ester", Synthesis, pp. 364-365 (1978).
Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).
Sirowej, H. et al., "Preparation of substituted indoles by reduction of isatin and oxindole derivatives with diborane/tetrahydrofuran", Synthesis, No. 2, p. 84 (1972).
Soga, T. et al., "Lysophosphatidylcholine enhances glucose-dependent insulin secretion via an orphan G-protein-coupled receptor", Biochemical and Biophysical Research Communications, vol. 326, pp. 744-751 (2005).
Takahashi, K. et al., "Efficient Method for a One-Carbon Homologation of Aldehydes and Benzophenone to Carboxylic Acids", J. Org. Chem., vol. 48, No. 20, pp. 3566-3569 (1983).
Testa, B. et al., Hydrolysis in Drug and Prodrug Metabolism: Chemistry, Biochemistry, and Enzymology, Wiley-VCH GmbH & Co., publ., pp. xi-xx (table of contents) (2003).
Urgaonkar, S. et al., "Application of a New Bicyclic Triaminophosphine Ligand in Pd-Catalyzed Buchwald-Hartwig Amination Reactions of Aryl Chlorides, Bromides, and Iodides", J. Org. Chem. vol. 68, No. 22, pp. 8416-8423 (2003).
Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).
Yang, B.H. et al., "Palladium-catalyzed amination of aryl halides and sulfonates", Journal of Organometallic Chemistry, vol. 576, pp. 125-146 (1999).
Young, S.D. et al., "L-743,726 (DMP-266): a Novel, Highly Potent Nonnucleoside Inhibitor of the Human Immunodeficiency Virus Type 1 Reverse Transcriptase", Antimicrobial Agents and Chemotherapy, vol. 39, No. 12, pp. 2602-2605 (1995).
Zhang, X. et al., "Dimethyldioxirane Oxidation of Indole Derivatives. Formation of Novel Indole-2,3-epoxides and a Versatile Synthetic Route to Indolinones and Indolines", J. Am. Chem. Soc., vol. 115, No. 19, pp. 8867-8868 (1993).
West, Anthony R., Solid Chemistry and its Application, Wiley, New York, 1988, pp. 358 & 365.
Vippagunta, S. Adv Drug Deliv Rev. 2001 vol. 48 pp. 3-26.
Silverman, R. "The Organic Chemistry of Drug Design Action," 2004, Elsevier, pp. 29-32.

PYRIDONE GPR119 G PROTEIN-COUPLED RECEPTOR AGONISTS

RELATED APPLICATION

This application is a divisional application of U.S. patent application Ser. No. 13/159,497, filed Jun. 14, 2011, issued as U.S. Pat. No. 8,232,404 on Jul. 31, 2012, which is continuation application of U.S. patent application Ser. No. 12/173,856, filed Jul. 16, 2008, issued as U.S. Pat. No. 8,003,796 on Aug. 23, 2011, which claims priority benefit of U.S. Provisional Application No. 60/950,162, filed on Jul. 17, 2007. The entirety of each of these applications is incorporated herein by reference.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., Diabetes, 43:696-702 (1989)). However, over time, β-cell function deteriorates and non-insulin-dependent diabetes develops in about 20% of the obese population (Pederson, P., Diab. Metab. Rev., 5:505-509 (1989)) and (Brancati, F. L. et al., Arch. Intern. Med., 159: 957-963 (1999)). Given its high prevalence in modern societies, obesity has thus become the leading risk factor for NIDDM (Hill, J. O. et al., Science, 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., BMJ, 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", J. Clin. Invest., 116: 1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cell apoptosis in humans with type 2 diabetes", Diabetes, 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Ahren, B., "Autonomic regulation of islet hormone secretion—Implications for health and disease", Diabetologia, 43:393-410 (2003)). Those GPCRs specifically coupled to the elevation of cAMP via the $G_s$ alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in $K^+$ efflux depolarizes the β-cell leading to an influx of $Ca^{++}$ which promotes the release of insulin.

GPR119 (e.g., human GPR119, GenBank® Accession No. AAP72125 and alleles thereof; e.g., mouse GPR119, GenBank® Accession No. AY288423 and alleles thereof) is a GPCR located at chromosome position Xp26.1 (Fredricksson, R. et al., "Seven evolutionarily conserved human rhodopsin G protein-coupled receptors lacking close relatives", *FEBS Lett.*, 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.*, 326:744-751 (2005), International Patent Applications WO 04/065380, WO 04/076413, WO 05/007647, WO 05/007658, WO 05/121121, WO 06/083491, and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan G-protein-coupled receptor", *Biochem. Biophys. Res. Comm.*, 326:744-751 (2005); Chu, Z. L. et al., "A role for β-cell-expressed GPR119 in glycemic control by enhancing glucose-dependent insulin release", *Endocrinology*, doi:10.1210/en.2006-1608 (2007)).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for (3-cell-expressed GPR119 in glycemic control by enhancing glucose-dependent insulin release", *Endocrinology*, doi:10.1210/en.2006-1608 (2007)). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism*, 3:167-175 (2006), WO 05/007647, WO 05/007658).

SUMMARY OF THE INVENTION

In accordance with the present invention, compounds are provided that have the general structure of Formula I or Formula IA:

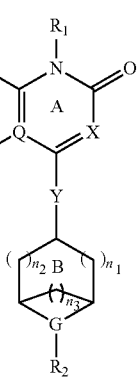

Formula I or

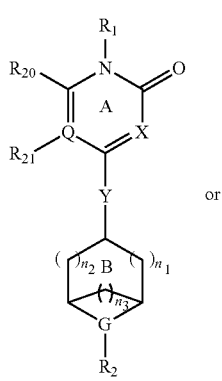

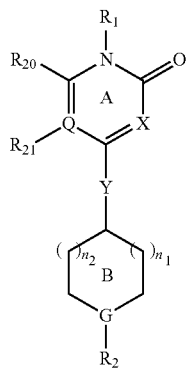

Formula IA wherein $n_1$, $n_2$, $n_3$, G, Q, X, $R_1$, $R_2$, $R_{20}$ and $R_{21}$ are defined below.

Compounds of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In addition, the present invention relates to a formulated product wherein the selected formulation is made by using a compound of Formula I and/or IA as the only active ingredient or by combining (a) a compound of Formula I and/or IA (using any of the compound embodiments listed herein) and (b) an additional active ingredient, for example, dipeptidyl peptidase-IV (DPP4) inhibitor (for example a member selected from saxagliptin, sitagliptin, vildagliptin and alogliptin).

The present invention provides for compounds of Formula I and IA, pharmaceutical compositions employing such compounds, and for methods of using such compounds. In particular, the present invention provides a pharmaceutical composition comprising a therapeutically effective amount of a compound of Formula I and/or IA, alone or in combination with a pharmaceutically acceptable carrier.

Further, in accordance with the present invention, a method is provided for preventing, modulating, or treating the progression or onset of diseases or disorders associated with the activity of the GPR119 G protein-coupled receptor, such as defined above and hereinafter, wherein a therapeutically effective amount of a compound of Formula I and/or IA is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I or IA and another compound of Formula I or IA and/or at least one other type of therapeutic agent, is administered to a mammalian, i.e., human, patient in need of treatment.

DESCRIPTION OF THE INVENTION

In accordance with the present invention, compounds of Formula I and Formula IA are provided:

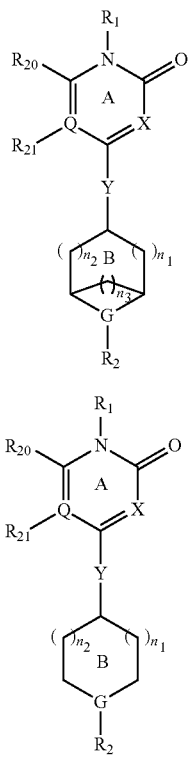

Formula I

Formula IA including enantiomers, diastereomers, solvates and salts thereof (particularly enantiomers, diastereomers and pharmaceutically acceptable salts thereof) having ring A and ring B, wherein:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —$NH_2$, —CN, —$NO_2$, —$C(=O)OH$, —$C(=O)OR_{10}$, —$OCF_3$, —$OR_{11}$, —OH, —SH, —$SR_{11}$, —$S(O)_3H$, —$P(O)_3H_2$, —$C(=O)NR_9R_9$, —$NR_{12}R_{12}$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{11}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{11}$, —$S(O)_2R_{11}$, —$NR_9C(=O)OR_8$ and —$NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'S;

$R_2$ is cycloalkyl, aryl, heteroaryl, heterocyclyl, —$S(O)_2R_5$, —$C(=O)NR_3R_5$, —$C(=O)R_5$ or —$C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{14}$, —$S(O)_2NR_{14}C(=O)OR_{14}$, —$S(O)_2NR_{14}C(=O)NR_{14}R_{14}$, —$C(=O)NR_{14}S(O)_2CF_3$, —$C(=O)R_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O)$_2$R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$ and arylalkyl;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, phenyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

The terms "Formula I" and "Formula IA" and all embodiments thereof shall include enantiomers, diastereomers, solvates and salts thereof (particularly enantiomers, diastereomers and pharmaceutically acceptable salts thereof).

In a second embodiment, compounds of Formula I and Formula IA are provided wherein:

ring A is optionally substituted with one or more R's shown as R$_{20}$ and R$_{2i}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

m is 0-2;

n$_2$ is 0-2;

n$_3$ is 1-2;

R$_1$ is a 6-membered monocyclic aryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$; —S(=O)R$_{14}$, —S(O)$_2$R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$; —OCF$_3$, —OR$_{14}$; —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a third embodiment, compounds of Formula I and Formula IA are provided wherein:

ring A is optionally substituted with one or more R's shown as R$_{20}$ and R$_{21}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

n$_1$ is 0-2;

n$_2$ is 0-2;

n$_3$ is 1-2;

R$_1$ is phenyl, pyridinyl, pyrazinyl or pyrimindinyl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)

$OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{14}$, —$S(O)_2NR_{14}C(=O)OR_{14}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, =O, —$NR_{14}C(=O)OR_{14}$ and —$NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —$C(=O)OH$, —$C(=O)OR_{10}$, —$OCF_3$, —$OR_{10}$, —OH, —$C(=O)NR_9R_9$, —$C(=O)R_{10}$ and —$OC(=O)R_{10}$.

In a fourth embodiment, compounds of Formula I and Formula IA are provided wherein:
ring A is optionally substituted with one or more R's shown as $R_{20}$ and $R_{21}$;
G is CH or N;
Q is C or N;
X is CH or N, provided that Q and X are not both N;
Y is $CH_2$, $N(R_3)$, $C(=O)$, O, $OCR_9R_9$, S, $S(=O)$ or $S(O)_2$;
$n_1$ is 0-2;
$n_2$ is 0-2;
$n_3$ is 1-2;
$R_1$ is phenyl or pyridinyl, each of which may be optionally substituted with one or more members selected from $R_{1a}$, $R_{1b}$, $R_{1c}$, $R_{1d}$ and $R_{1e}$;
$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —$NH_2$, —CN, —$NO_2$, —$C(=O)OH$, —$C(=O)OR_{10}$, —$OCF_3$, —$OR_{11}$, —OH, —SH, —$SR_{11}$, —$S(O)_3H$, —$P(O)_3H_2$, —$C(=O)NR_9R_9$, —$NR_{12}R_{12}$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{11}$, —$NR_9C(=O)H$, —$NR_9C(=O)R_{10}$, —$OC(=O)R_{10}$, —$OC(=O)NR_9R_9$, —$C(=NR_{14})NR_9R_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$; —C(=NR$_{14}$)NR$_{14}$R$_{14}$, —NHC(=NR$_{14}$)NR$_{14}$R$_{14}$; —S(=O)R$_{14}$, —S(O)$_2$R$_{14}$, —NR$_{14}$C(=O)OR$_8$, —NR$_{14}$S(O$_2$)R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a fifth embodiment, compounds of Formula I and Formula IA are provided wherein:

ring A is optionally substituted with one or more R's shown as R$_{20}$ and R$_{21}$;

G is CH or N;

Q is C or N;

X is CH or N, provided that Q and X are not both N;

Y is $CH_2$, $N(R_3)$, $C(=O)$, $O$, $OCR_9R_9$, $S$, $S(=O)$ or $S(O)_2$;

$n_1$ is 0-2;

$n_2$ is 0-2;

$n_3$ is 1-2;

$R_1$ is

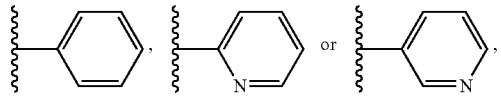

each of which may be optionally substituted with one or more members selected from the group consisting of $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, $-NH_2$, $-CN$, $-NO_2$, $-C(=O)OH$, $-C(=O)OR_{10}$, $-OCF_3$, $-OR_{11}$, $-OH$, $-SH$, $-SR_{11}$, $-S(O)_3H$, $-P(O)_3H_2$, $-C(=O)NR_9R_9$, $-NR_{12}R_{12}$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{11}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{11}$, $-S(O)_2R_{11}$, $-NR_9C(=O)OR_8$ and $-NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is cycloalkyl, aryl, heteroaryl, heterocyclyl, $-S(O)_2R_5$, $-C(=O)NR_3R_5$, $-C(=O)R_5$ or $-C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl, wherein the heteroaryl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $=O$, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$, $=O$ and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a sixth embodiment, compounds of Formula I and Formula IA are provided wherein:
ring A is optionally substituted with one or more R's shown as R$_{20}$ and R$_{2i}$;
G is CH or N;
Q is C or N;
X is CH or N, provided that Q and X are not both N;
Y is CH$_2$, N(R$_3$), C(=O), O, OCR$_9$R$_9$, S, S(=O) or S(O)$_2$;
n$_1$ is 0-2;
n$_2$ is 0-2;
n$_3$ is 1-2;
R$_1$ is

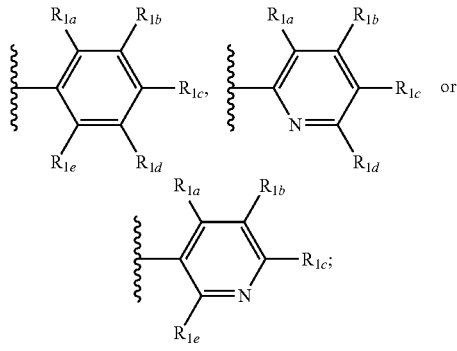

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$; —S(=O)R$_{14}$, —S(O)$_2$R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$; —OCF$_3$, —OR$_{14}$; —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a seventh embodiment, compounds of Formula I and Formula IA are provided wherein:

ring A is optionally substituted with one or more R's shown as R$_{20}$ and R$_{21}$;
G is CH or N;
Q is C or N;
X is CH or N, provided that Q and X are not both N;
Y is CH$_2$, N(R$_3$), C(=O), O, OCR$_9$R$_9$, S, S(=O) or S(O)$_2$;
n$_1$ is 0-2;
n$_2$ is 0-2;
n$_3$ is 1-2;

R$_1$ is

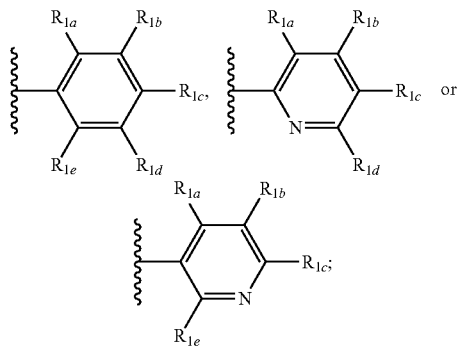

R$_{1a}$, R$_{1b}$, R$_{1d}$ and R$_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

R$_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{14}$, —$S(O)_2NR_{14}C(=O)OR_{14}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, =O, —$NR_{14}C(=O)OR_{14}$ and —$NR_{14}S(O)_2R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O)_2R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O)_2R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —$C(=O)OH$, —$C(=O)OR_{10}$, —$OCF_3$, —$OR_{10}$, —OH, —$C(=O)NR_9R_9$, —$C(=O)R_{10}$ and —$OC(=O)R_{10}$.

In an eighth embodiment, compounds of Formula I and Formula IA are provided wherein:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —$NH_2$, —CN, —$NO_2$, —$C(=O)OH$, —$C(=O)OR_{10}$, —$OCF_3$, —$OR_{11}$, —OH, —SH, —$SR_{11}$, —$S(O)_3H$, —$P(O)_3H_2$, —$C(=O)NR_9R_9$, —$NR_{12}R_{12}$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{11}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{11}$, —$S(O)_2R_{11}$, —$NR_9C(=O)OR_8$ and —$NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is aryl, heteroaryl, heterocyclyl, —$C(=O)NR_3R_5$, —$C(=O)R_5$ or —$C(=O)OR_5$, wherein the aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more R$_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$; —OCF$_3$, —OR$_{14}$; —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$; —S(O)$_2$NR$_{14}$C(=O)NR$_{14}$R$_{14}$; —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$; —C(=NR$_{14}$)NR$_{14}$R$_{14}$, —NHC(=NR$_{14}$)NR$_{14}$R$_{14}$; —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$; —OCF$_3$, —OR$_{14}$; —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$; —NR$_{14}$S(O)$_2$CF$_3$, —C(=O)NR$_{14}$S(O)$_2$R$_{10}$, —S(O)$_2$NR$_{14}$C(=O)OR$_{10}$; —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a ninth embodiment, compounds of Formula I and Formula IA are provided wherein:

ring A is optionally substituted with one or more R's shown as $R_{20}$ and $R_{2i}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'S;

R$_2$ is aryl, heteroaryl or —C(=O)OR$_5$, wherein the aryl and heteroaryl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a tenth embodiment, compounds of Formula I and Formula IA are provided wherein:
ring A is optionally substituted with one or more R's shown as R$_{20}$ and R$_{21}$;
G is CH or N;
Q is C or N;
X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, $-NH_2$, $-CN$, $-NO_2$, $-C(=O)OH$, $-C(=O)OR_{10}$, $-OCF_3$, $-OR_{11}$, $-OH$, $-SH$, $-SR_{11}$, $-S(O)_3H$, $-P(O)_3H_2$, $-C(=O)NR_9R_9$, $-NR_{12}R_{12}$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{11}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{11}$, $-S(O)_2R_{11}$, $-NR_9C(=O)OR_8$ and $-NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is heteroaryl or $-C(=O)OR_5$, wherein the heteroaryl may be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $=O$, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$, $=O$ and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In an eleventh embodiment, compounds of Formula I and Formula IA are provided wherein:

ring A is optionally substituted with one or more R's shown as $R_{20}$ and $R_{21}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O)$_2$R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is heteroaryl which may be optionally substituted with one or more R$_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more R$_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O)$_2$R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twelfth embodiment, compounds of Formula I and Formula IA are provided wherein:

ring A is optionally substituted with one or more R's shown as $R_{20}$ and $R_{2i}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is oxadiazolyl, benzoxazolyl, pyridinyl or pyrimidinyl, each of which may be optionally substituted with one or more R$_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more R$_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)

$OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$; —$OCF_3$, —$OR_{14}$; —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$; —$NR_{14}S(O)_2CF_3$, —$C(=O)NR_{14}S(O)_2R_9$, —$S(O)_2NR_{14}C(=O)OR_9$; —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$; —$S(=O)R_{14}$, —$S(O)_2R_{14}$, —$NR_{14}C(=O)OR_8$, —$NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —$C(=O)OH$, —$C(=O)OR_{10}$, —$OCF_3$, —$OR_{10}$, —OH, —$C(=O)NR_9R_9$, —$C(=O)R_{10}$ and —$OC(=O)R_{10}$.

In a thirteenth embodiment, compounds of Formula I and Formula IA are provided wherein:

ring A is optionally substituted with one or more R's shown as $R_{20}$ and $R_{21}$;
G is CH or N;
Q is C or N;
X is CH or N, provided that Q and X are not both N;
Y is $CH_2$, $N(R_3)$, $C(=O)$, O, $OCR_9R_9$, S, $S(=O)$ or $S(O)_2$;
$n_1$ is 0-2;
$n_2$ is 0-2;
$n_3$ is 1-2;
$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —$NH_2$, —CN, —$NO_2$, —$C(=O)OH$, —$C(=O)OR_{10}$, —$OCF_3$, —$OR_{11}$, —OH, —SH, —$SR_{11}$, —$S(O)_3H$, —$P(O)_3H_2$, —$C(=O)NR_9R_9$, —$NR_{12}R_{12}$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{11}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{11}$, —$S(O)_2R_{11}$, —$NR_9C(=O)OR_8$ and —$NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is pyrimidinyl which may be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{14}$, —$S(O)_2NR_{14}C(=O)OR_{14}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, =O, —$NR_{14}C(=O)OR_{14}$ and —$NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})$ $NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}S$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, $-CN$, $-C(=O)OH$, $-C(=O)OR_{10}$, $-OCF_3$, $-OR_{10}$, $-OH$, $-C(=O)NR_9R_9$, $-C(=O)R_{10}$ and $-OC(=O)R_{10}$.

In a fourteenth embodiment, compounds of Formula I and Formula IA are provided wherein:

ring A is optionally substituted with one or more R's shown as $R_{20}$ and $R_{2i}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

m is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, $-NH_2$, $-CN$, $-NO_2$, $-C(=O)OH$, $-C(=O)OR_{10}$, $-OCF_3$, $-OR_{11}$, $-OH$, $-SH$, $-SR_{11}$, $-S(O)_3H$, $-P(O)_3H_2$, $-C(=O)$ $NR_9R_9$, $-NR_{12}R_{12}$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{11}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{11}$, $-S(O)_2R_{11}$, $-NR_9C(=O)OR_8$ and $-NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of VS;

$R_2$ is $-C(=O)OR_5$;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, =O, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, =O, $-NR_9C(=O)OR_8$ and $-NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, =O, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}C(=O)OR_{10}$, —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C(=O)OR_8$, —$NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_9$, —$S(O)_2NR_{14}C(=O)OR_9$, —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C(=O)OR_8$, —$NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$; —$OCF_3$, —$OR_{14}$; —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$; —$NR_{14}S(O)_2CF_3$, —C(=O)$NR_{14}S(O)_2R_9$, —$S(O)_2NR_{14}C(=O)OR_9$; —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$; —S(=O)$R_{14}$, —$S(O)_2R_{14}$, —$NR_{14}C(=O)OR_8$, —$NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a fifteenth embodiment, compounds of Formula I and Formula IA are provided wherein:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, C(=O), O, $OCR_9R_9$, S, S(=O) or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —$NH_2$, —CN, —$NO_2$, —C(=O)OH, —C(=O)$OR_{10}$, —$OCF_3$, —$OR_{11}$, —OH, —SH, —$SR_{11}$, —$S(O)_3H$, —$P(O)_3H_2$, —C(=O)$NR_9R_9$, —$NR_{12}R_{12}$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(=O)$R_{11}$, —$NR_9C(=O)H$, —$NR_9C(=O)R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{11}$, —$S(O)_2R_{11}$, —$NR_9C(=O)OR_8$ and —$NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is —C(=O)$OR_5$;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —$S(O)_2NR_9R_9$, —$NR_9S(O)_2CF_3$, —C(=O)$R_{10}$, —$NR_9C(=O)H$, —$NR_9C(=O)R_{10}$, —OC(=O)$R_{10}$, —S(=O)$R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(=O)$R_{10}$, —$NR_9C(=O)H$, —$NR_9C(=O)R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$; —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$; —S(O)$_2$NR$_{14}$C(=O)NR$_{14}$R$_{14}$; —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$; —C(=NR$_{14}$)NR$_{14}$R$_{14}$, —NHC(=NR$_{14}$)NR$_{14}$R$_{14}$; —S(=O)R$_{14}$, —S(O)$_2$R$_{14}$, =O, —NR$_{14}$C(=O)OR$_{14}$ and —NR$_{14}$S(O)$_2$R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$; —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$; —NR$_{14}$S(O)$_2$CF$_3$, —C(=O)NR$_{14}$S(O)$_2$R$_{10}$, —S(O)$_2$NR$_{14}$C(=O)OR$_{10}$; —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$; —S(=O)R$_{14}$, —S(O)$_2$R$_{14}$, —NR$_{14}$C(=O)OR$_8$, —NR$_{14}$S(O)$_2$R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a sixteenth embodiment, compounds of Formula I and Formula IA are provided wherein:

ring A is optionally substituted with one or more R's shown as $R_{20}$ and $R_{2i}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O)$_2$R$_8$, wherein: (a) the alkenyl, alkynyl, cycloalkyl, aryl and heterocyclyl may each be optionally substituted with one or more $R_6$'s; and (b) the alkyl may optionally be substituted by one or more of VS;

$R_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, $—NH_2$, $—CN$, $—NO_2$, $—C(=O)OH$, $—C(=O)OR_{10}$, $—OCF_3$, $—OR_{10}$, $—OH$, $—SH$, $—SR_{10}$, $—S(O)_3H$, $—P(O)_3H_2$, $—C(=O)NR_9R_9$, $—NR_9R_9$, $—S(O)_2NR_9R_9$, $—NR_9S(O)_2CF_3$, $—C(=O)NR_9S(O)_2R_9$, $—S(O)_2NR_9C(=O)OR_9$, $—S(O)_2NR_9C(=O)NR_9R_9$, $—C(=O)NR_9S(O)_2CF_3$, $—C(=O)R_{10}$, $—NR_9C(=O)H$, $—NR_9C(=O)R_{10}$, $—OC(=O)R_{10}$, $—C(=NR_{14})NR_9R_9$, $—NHC(=NR_{14})NR_{14}R_{14}$, $—S(=O)R_{10}$, $—S(O)_2R_{10}$, $=O$, $—NR_9C(=O)OR_8$ and $—NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $—NH_2$, $—CN$, $—NO_2$, $—C(=O)OH$, $—C(=O)OR_{14}$, $—OCF_3$, $—OR_{14}$, $—OH$, $—SH$, $—SR_{14}$, $—S(O)_3H$, $—P(O)_3H_2$, $—C(=O)NR_{14}R_{14}$, $—NR_{14}R_{14}$, $—S(O)_2NR_{14}R_{14}$, $—NR_{14}S(O)_2CF_3$, $—C(=O)NR_{14}S(O)_2R_{14}$, $—S(O)_2NR_{14}C(=O)OR_{14}$, $—S(O)_2NR_{14}C(=O)NR_{14}R_{14}$, $—C(=O)NR_{14}S(O)_2CF_3$, $—C(=O)R_{14}$, $—NR_{14}C(=O)H$, $—NR_{14}C(=O)R_{14}$, $—OC(=O)R_{14}$, $—C(=NR_{14})NR_{14}R_{14}$, $—NHC(=NR_{14})NR_{14}R_{14}$, $—S(=O)R_{14}$, $—S(O)_2R_{14}$, $=O$, $—NR_{14}C(=O)OR_{14}$ and $—NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $—NH_2$, $—CN$, $—NO_2$, $—C(=O)OH$, $—C(=O)OR_{14}$, $—OCF_3$, $—OR_{14}$, $—OH$, $—SH$, $—SR_{14}$, $—S(O)_3H$, $—P(O)_3H_2$, $—C(=O)NR_{14}R_{14}$, $—NR_{14}R_{14}$, $—S(O)_2NR_{14}R_{14}$, $—NR_{14}S(O)_2CF_3$, $—C(=O)NR_{14}S(O)_2R_{10}$, $—S(O)_2NR_{14}C(=O)OR_{10}$, $—S(O)_2NR_{14}C(=O)NR_{14}R_{14}$, $—C(=O)NR_{14}S(O)_2CF_3$, $—C(=O)R_{14}$, $—NR_{14}C(=O)H$, $—NR_{14}C(=O)R_{14}$, $—OC(=O)R_{14}$, $—C(=NR_{14})NR_{14}R_{14}$, $—NHC(=NR_{14})NR_{14}R_{14}$, $—S(=O)R_{14}$, $—S(O)_2R_{14}$, $—NR_{14}C(=O)OR_8$, $—NR_{14}S(O_2)R_8$, $=O$ and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $—NH_2$, $—CN$, $—NO_2$, $—C(=O)OH$, $—C(=O)OR_{14}$, $—OCF_3$, $—OR_{14}$, $—OH$, $—SH$, $—SR_{14}$, $—S(O)_3H$, $—P(O)_3H_2$, $—C(=O)NR_{14}R_{14}$, $—NR_{14}R_{14}$, $—S(O)_2NR_{14}R_{14}$, $—NR_{14}S(O)_2CF_3$, $—C(=O)NR_{14}S(O)_2R_9$, $—S(O)_2NR_{14}C(=O)OR_9$, $—S(O)_2NR_{14}C(=O)NR_{14}R_{14}$, $—C(=O)NR_{14}S(O)_2CF_3$, $—C(=O)R_{14}$, $—NR_{14}C(=O)H$, $—NR_{14}C(=O)R_{14}$, $—OC(=O)R_{14}$, $—C(=NR_{14})NR_{14}R_{14}$, $—NHC(=NR_{14})NR_{14}R_{14}$, $—S(=O)R_{14}$, $—S(O)_2R_{14}$, $—NR_{14}C(=O)OR_8$, $—NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $—NH_2$, $—CN$, $—NO_2$, $—C(=O)OH$, $—C(=O)OR_{14}$, $—OCF_3$, $—OR_{14}$; $—OH$, $—SH$, $—SR_{14}$, $—S(O)_3H$, $—P(O)_3H_2$, $—C(=O)NR_{14}R_{14}$, $—NR_{14}R_{14}$, $—S(O)_2NR_{14}R_{14}$; $—NR_{14}S(O)_2CF_3$, $—C(=O)NR_{14}S(O)_2R_9$, $—S(O)_2NR_{14}C(=O)OR_9$; $—S(O)_2NR_{14}C(=O)NR_{14}R_{14}$, $—C(=O)NR_{14}S(O)_2CF_3$, $—C(=O)R_{14}$, $—NR_{14}C(=O)H$, $—NR_{14}C(=O)R_{14}$, $—OC(=O)R_{14}$, $—C(=NR_{14})NR_{14}R_{14}$, $—NHC(=NR_{14})NR_{14}R_{14}$; $—S(=O)R_{14}$, $—S(O)_2R_{14}$, $—NR_{14}C(=O)OR_8$, $—NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, $—CN$, $—C(=O)OH$, $—C(=O)OR_{10}$, $—OCF_3$, $—OR_{10}$, $—OH$, $—C(=O)NR_9R_9$; $—C(=O)R_{10}$ and $—OC(=O)R_{10}$.

In a seventeenth embodiment, compounds of Formula I and Formula IA are provided wherein:

ring A is optionally substituted with one or more R's shown as $R_{20}$ and $R_{21}$;

G is CH or N;

Q is C or N;

X is CH;

Y is $CH_2$, $N(R_3)$, $C(=O)$, $O$, $OCR_9R_9$, $S$, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, $—NH_2$, $—CN$, $—NO_2$, $—C(=O)OH$, $—C(=O)OR_{10}$, $—OCF_3$, $—OR_{11}$, $—OH$, $—SH$, $—SR_{11}$, $—S(O)_3H$, $—P(O)_3H_2$, $—C(=O)NR_9R_9$, $—NR_{12}R_{12}$, $—S(O)_2NR_9R_9$, $—NR_9S(O)_2CF_3$, $—C(=O)NR_9S(O)_2R_9$, $—S(O)_2NR_9C(=O)OR_9$, $—S(O)_2NR_9C(=O)NR_9R_9$, $—C(=O)NR_9S(O)_2CF_3$, $—C(=O)R_{11}$, $—NR_9C(=O)H$, $—NR_9C(=O)R_{10}$, $—OC(=O)R_{10}$, $—OC(=O)NR_9R_9$, $—C(=NR_{14})NR_9R_9$, $—NHC(=NR_{14})NR_{14}R_{14}$, $—S(=O)R_{11}$, $—S(O)_2R_{11}$, $—NR_9C(=O)OR_8$ and $—NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is cycloalkyl, aryl, heteroaryl, heterocyclyl, $—S(O)_2R_5$, $—C(=O)NR_3R_5$, $—C(=O)R_5$ or $—C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)R_9$, —$S(O)_2NR_9C(=O)NR_9R_9$, —C(=O)$NR_9S(O)_2CF_3$, —C(=O)$R_{10}$, —$NR_9C(=O)H$, —$NR_9C(=O)R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —$NH_2$, —CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(=O)$R_{10}$, —$NR_9C(=O)H$, —$NR_9C(=O)R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$; —$OCF_3$, —$OR_{14}$; —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{14}$, —$S(O)_2NR_{14}C(=O)OR_{14}$; —$S(O)_2NR_{14}C(=O)NR_{14}R_{14}$; —C(=O)$NR_{14}S(O)_2CF_3$, —C(=O)$R_{14}$, —$NR_{14}C(=O)H$, —$NR_{14}C(=O)R_{14}$, —OC(=O)$R_{14}$; —C(=$NR_{14}$)$NR_{14}R_{14}$, —NHC(=$NR_{14}$)$NR_{14}R_{14}$; —S(=O)$R_{14}$, —$S(O)_2R_{14}$, =O, —$NR_{14}C(=O)OR_{14}$ and —$NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$; —$OCF_3$, —$OR_{14}$; —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$; —$NR_{14}S(O)_2CF_3$, —C(=O)$NR_{14}S(O)_2R_{10}$, —$S(O)_2NR_{14}C(=O)OR_{10}$; —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$; —S(=O)$R_{14}$, —$S(O)_2R_{14}$, —$NR_{14}C(=O)OR_8$, —$NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_9$, —$S(O)_2NR_{14}C(=O)OR_9$, —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C(=O)OR_8$, —$NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_9$, —$S(O)_2NR_{14}C(=O)OR_9$, —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}C(=O)OR_8$, —$NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In an eighteenth embodiment, compounds of Formula I and Formula IA are provided wherein:

ring A is optionally substituted with one or more R's shown as $R_{20}$ and $R_{2i}$;

G is CH or N;

Q is C;

X is CH;

Y is $CH_2$, N($R_3$), C(=O), O, $OCR_9R_9$, S, S(=O) or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —$NH_2$, —CN, —$NO_2$, —C(=O)OH, —C(=O)$OR_{10}$, —$OCF_3$, —$OR_{11}$, —OH, —SH, —$SR_{11}$, —$S(O)_3H$, —$P(O)_3H_2$, —C(=O)

$NR_9R_9$, $-NR_{12}R_{12}$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{11}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{11}$, $-S(O)_2R_{11}$, $-NR_9C(=O)OR_8$ and $-NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of VS;

$R_2$ is cycloalkyl, aryl, heteroaryl, heterocyclyl, $-S(O)_2R_5$, $-C(=O)NR_3R_5$, $-C(=O)R_5$ or $-C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $=O$, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$, $=O$ and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, $-CN$, $-C(=O)OH$, $-C(=O)OR_{10}$, $-OCF_3$, $-OR_{10}$, $-OH$, $-C(=O)NR_9R_9$, $-C(=O)R_{10}$ and $-OC(=O)R_{10}$.

In a nineteenth embodiment, compounds of Formula IA are provided wherein:

ring A is optionally substituted with one or more R's shown as $R_{20}$ and $R_{21}$;

G is CH or N;

Q is C;

X is CH;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, $-NH_2$, $-CN$, $-NO_2$, $-C(=O)OH$, $-C(=O)OR_{10}$, $-OCF_3$, $-OR_{11}$, $-OH$, $-SH$, $-SR_{11}$, $-S(O)_3H$, $-P(O)_3H_2$, $-C(=O)NR_9R_9$, $-NR_{12}R_{12}$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{11}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{11}$, $-S(O)_2R_{11}$, $-NR_9C(=O)OR_8$ and $-NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is cycloalkyl, aryl, heteroaryl, heterocyclyl, $-S(O)_2R_5$, $-C(=O)NR_3R_5$, $-C(=O)R_5$ or $-C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $=O$, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$, $=O$ and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twentieth embodiment, compounds of Formula I are provided wherein:

ring A is optionally substituted with one or more R's shown as R$_{20}$ and R$_{2i}$;

G is CH or N;

Q is C;

X is CH;

Y is CH$_2$, N(R$_3$), C(=O), O, OCR$_9$R$_9$, S, S(=O) or S(O)$_2$;

n$_1$ is 0-2;

n$_2$ is 0-2;

n$_3$ is 2;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'S;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)

OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-first embodiment, compounds of Formula IA are provided wherein:

ring A is optionally substituted with one or more R's shown as R$_{20}$ and R$_{21}$;

G is CH or N;

Q is C;

X is CH;

Y is CH$_2$, N(R$_3$), C(=O), O, OCR$_9$R$_9$, S, S(=O) or S(O)$_2$;

n$_1$ is 1;

n$_2$ is 1;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$; —OCF$_3$, —OR$_{14}$; —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$; —S(O)$_2$NR$_{14}$C(=O)NR$_{14}$R$_{14}$; —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$; —C(=NR$_{14}$)NR$_{14}$R$_{14}$, —NHC(=NR$_{14}$)NR$_{14}$R$_{14}$; —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$; —$OCF_3$, —$OR_{14}$; —OH, —SH, —$SR_{14}$, —S(O)$_3$H, —P(O)$_3H_2$, —C(=O)$NR_{14}R_{14}$, —$NR_{14}R_{14}$, —S(O)$_2NR_{14}R_{14}$; —$NR_{14}S(O)_2CF_3$, —C(=O)$NR_{14}$S(O)$_2R_{10}$, —S(O)$_2NR_{14}$C(=O)$OR_{10}$, —S(O)$_2NR_{14}$C(=O)$NR_{14}R_{14}$, —C(=O)$NR_{14}$S(O)$_2CF_3$, —C(=O)$R_{14}$, —$NR_{14}$C(=O)H, —$NR_{14}$C(=O)$R_{14}$, —OC(=O)$R_{14}$, —C(=$NR_{14}$)$NR_{14}R_{14}$, —NHC(=$NR_{14}$)$NR_{14}R_{14}$; —S(=O)$R_{14}$, —S(O)$_2R_{14}$, —$NR_{14}$C(=O)$OR_8$, —$NR_{14}$S(O$_2$)$R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}$S(O)$_2R_9$, —S(O)$_2NR_{14}$C(=O)$OR_9$, —S(O)$_2NR_{14}$C(=O)$NR_{14}R_{14}$, —C(=O)$NR_{14}$S(O)$_2CF_3$, —C(=O)$R_{14}$, —$NR_{14}$C(=O)H, —$NR_{14}$C(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —S(O)$_2R_{14}$, —$NR_{14}$C(=O)$OR_8$, —$NR_{14}$S(O$_2$)$R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2CF_3$, —C(=O)$NR_{14}$S(O)$_2R_9$, —S(O)$_2NR_{14}$C(=O)$OR_9$, —S(O)$_2NR_{14}$C(=O)$NR_{14}R_{14}$, —C(=O)$NR_{14}$S(O)$_2CF_3$, —C(=O)$R_{14}$, —$NR_{14}$C(=O)H, —$NR_{14}$C(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —S(O)$_2R_{14}$, —$NR_{14}$C(=O)$OR_8$, —$NR_{14}$S(O$_2$)$R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a twenty-second embodiment, compounds of Formula I are provided wherein:

ring A is optionally substituted with one or more R's shown as $R_{20}$ and $R_{21}$;

G is CH or N;

Q is C;

X is CH;

Y is $CH_2$, N($R_3$), C(=O), O, OCR$_9R_9$, S, S(=O) or S(O)$_2$;

$n_1$ is 1;

$n_2$ is 1;

$n_3$ is 2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —$NH_2$, —CN, —$NO_2$, —C(=O)OH, —C(=O)$OR_{10}$, —$OCF_3$, —$OR_{11}$, —OH, —SH, —$SR_{11}$, —S(O)$_3$H, —P(O)$_3H_2$, —C(=O)$NR_9R_9$, —$NR_{12}R_{12}$, —S(O)$_2NR_9R_9$, —$NR_9S(O)_2CF_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2CF_3$, —C(=O)$R_{11}$, —$NR_9$C(=O)H, —$NR_9$C(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{11}$, —S(O)$_2R_{11}$, —$NR_9$C(=O)$OR_8$ and —$NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'S;

$R_2$ is cycloalkyl, aryl, heteroaryl, heterocyclyl, —S(O)$_2R_5$, —C(=O)$NR_3R_5$, —C(=O)$R_5$ or —C(=O)$OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3H_2$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2CF_3$, —C(=O)$R_{10}$, —$NR_9$C(=O)H, —$NR_9$C(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, =O, —$NR_9$C(=O)$OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3H_2$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2CF_3$, —C(=O)$R_{10}$, —$NR_9$C(=O)H, —$NR_9$C(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, =O, —$NR_9$C(=O)$OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)

$OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, =O, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and arylalkyl;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, $-CN$, $-C(=O)OH$, $-C(=O)OR_{10}$, $-OCF_3$, $-OR_{10}$, $-OH$, $-C(=O)NR_9R_9$, $-C(=O)R_{10}$ and $-OC(=O)R_{10}$.

In a twenty-third embodiment, compounds of Formula IA are provided wherein:

ring A is optionally substituted with one or more R's shown as $R_{20}$ and $R_{21}$;

G is CH or N;

Q is C;

X is CH;

Y is $CH_2$, $N(R_3)$, $C(=O)$, O, $OCR_9R_9$, S, $S(=O)$ or $S(O)_2$;

$n_1$ is 1;

$n_2$ is 1;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, $-NH_2$, $-CN$, $-NO_2$, $-C(=O)OH$, $-C(=O)OR_{10}$, $-OCF_3$, $-OR_{11}$, $-OH$, $-SH$, $-SR_{11}$, $-S(O)_3H$, $-P(O)_3H_2$, $-C(=O)NR_9R_9$, $-NR_{12}R_{12}$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{11}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{11}$, $-S(O)_2R_{11}$, $-NR_9C(=O)OR_8$ and $-NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is cycloalkyl, aryl, heteroaryl, heterocyclyl, $-S(O)_2R_5$, $-C(=O)NR_3R_5$, $-C(=O)R_5$ or $-C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, =O, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, $-NH_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)R$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$, =O;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-fourth embodiment, compounds of Formula I are provided wherein:

ring A is optionally substituted with one or more R's shown as R$_{20}$ and R$_{21}$;

G is CH or N;

Q is C;

X is CH;

Y is CH$_2$, N(R$_3$), C(=O), O, OCR$_9$R$_9$, S, S(=O) or S(O)$_2$;

n$_1$ is 1;

n$_2$ is 1;

n$_3$ is 2;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$, =O;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-fifth embodiment, compounds of Formula IA are provided wherein:

ring A is optionally substituted with one or more R's shown as R$_{20}$ and R$_{21}$;

G is CH or N;

Q is C;

X is CH;

Y is O, OCR$_9$R$_9$, or S;

n$_1$ is 1;

n$_2$ is 1;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$, =O;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-sixth embodiment, compounds of Formula I are provided wherein:

ring A is optionally substituted with one or more R's shown as R$_{20}$ and R$_{21}$;

G is CH or N;

Q is C;

X is CH;

Y is O, OCR$_9$R$_9$ or S;

n$_1$ is 1;

n$_2$ is 1;

n$_3$ is 2;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)$R_{10}$, —$NR_9$C(=O)H, —$NR_9$C(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, =O, —$NR_9$C(=O)$OR_8$ and —$NR_9$S(O$_2$)$R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)$OR_{14}$, —OCF$_3$, —$OR_{14}$, —OH, —C(=O)$NR_{14}R_{14}$, —$NR_{14}R_{14}$, —S(O)$_2NR_{14}R_{14}$, —$NR_{14}$S(O)$_2$CF$_3$, —C(=O)$R_{14}$, —$NR_{14}$C(=O)H, —$NR_{14}$C(=O)$R_{14}$, —OC(=O)$R_{14}$, —S(=O)$R_{14}$, —S(O)$_2R_{14}$, =O, —$NR_{14}$C(=O)$OR_{14}$ and —$NR_{14}$S(O$_2$)$R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)$OR_{14}$, —OCF$_3$, —$OR_{14}$, —OH, —C(=O)$NR_{14}R_{14}$, —$NR_{14}R_{14}$, —S(O)$_2NR_{14}R_{14}$, —$NR_{14}$S(O)$_2$CF$_3$, —C(=O)$R_{14}$, —$NR_{14}$C(=O)H, —$NR_{14}$C(=O)$R_{14}$, —OC(=O)$R_{14}$, —S(=O)$R_{14}$, —S(O)$_2R_{14}$, —$NR_{14}$C(=O)$OR_8$, —$NR_{14}$S(O$_2$)$R_8$, =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)$OR_{14}$, —OCF$_3$, —$OR_{14}$, —OH, —C(=O)$NR_{14}R_{14}$, —$NR_{14}R_{14}$, —S(O)$_2NR_{14}R_{14}$, —$NR_{14}$S(O)$_2$CF$_3$, —C(=O)$R_{14}$, —$NR_{14}$C(=O)H, —$NR_{14}$C(=O)$R_{14}$, —OC(=O)$R_{14}$, —S(=O)$R_{14}$, —S(O)$_2R_{14}$, —$NR_{14}$C(=O)$OR_8$, —$NR_{14}$S(O$_2$)$R_8$;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)$OR_{14}$, —OCF$_3$, —$OR_{14}$, —OH, —C(=O)$NR_{14}R_{14}$, —$NR_{14}R_{14}$, —S(O)$_2NR_{14}R_{14}$, —$NR_{14}$S(O)$_2$CF$_3$, —C(=O)$R_{14}$, —$NR_{14}$C(=O)H, —$NR_{14}$C(=O)$R_{14}$, —OC(=O)$R_{14}$, —S(=O)$R_{14}$, —S(O)$_2R_{14}$, —$NR_{14}$C(=O)$OR_8$ and —$NR_{14}$S(O$_2$)$R_8$;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —OCF$_3$, —$OR_{10}$, —OH, —C(=O)$NR_9R_9$, —C(=O)$R_{10}$ and —OC(=O)$R_{10}$.

In a twenty-seventh embodiment, compounds of Formula IA are provided wherein:

ring A is optionally substituted with one or more R's shown as $R_{20}$ and $R_{21}$;

G is CH or N;

Q is C;

X is CH;

Y is O, OCR$_9R_9$ or S;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)$OR_{10}$, —OCF$_3$, —$OR_{11}$, —OH, —SH, —$SR_{11}$, —S(O)$_3$H, —P(O)$_3$H$_2$, —C(=O)$NR_9R_9$, —$NR_{12}R_{12}$, —S(O)$_2NR_9R_9$, —$NR_9$S(O)$_2$CF$_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2$CF$_3$, —C(=O)$R_{11}$, —$NR_9$C(=O)H, —$NR_9$C(=O)$R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{11}$, —S(O)$_2R_{11}$, —$NR_9$C(=O)$OR_8$ and —$NR_9$S(O$_2$)$R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)$OR_{10}$, —OCF$_3$, —$OR_{10}$, —OH, —SH, —$SR_{10}$, —S(O)$_3$H, —P(O)$_3$H$_2$, —C(=O)$NR_9R_9$, —$NR_9R_9$, —S(O)$_2NR_9R_9$, —$NR_9$S(O)$_2$CF$_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2$CF$_3$, —C(=O)$R_{10}$, —$NR_9$C(=O)H, —$NR_9$C(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, =O, —$NR_9$C(=O)$OR_8$ and —$NR_9$S(O$_2$)$R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)$OR_{10}$, —OCF$_3$, —$OR_{10}$, —OH, —SH, —$SR_{10}$, —S(O)$_3$H, —P(O)$_3$H$_2$, —C(=O)$NR_9R_9$, —$NR_9R_9$, —S(O)$_2NR_9R_9$, —$NR_9$S(O)$_2$CF$_3$, —C(=O)$NR_9$S(O)$_2R_9$, —S(O)$_2NR_9$C(=O)$OR_9$, —S(O)$_2NR_9$C(=O)$NR_9R_9$, —C(=O)$NR_9$S(O)$_2$CF$_3$, —C(=O)$R_{10}$, —$NR_9$C(=O)H, —$NR_9$C(=O)$R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, =O, —$NR_9$C(=O)$OR_8$ and —$NR_9$S(O$_2$)$R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$, =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{10}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-eighth embodiment, compounds of Formula I are provided wherein:

ring A is optionally substituted with one or more R's shown as $R_{20}$ and $R_{2i}$;

G is CH or N;

Q is C;

X is CH;

Y is O, OCR$_9$R$_9$ or S;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heterocyclyl, halo, —NH$_2$, —CN, —NO$_2$, —C(=O)OH, —C(=O)OR$_{10}$, —OCF$_3$, —OR$_{11}$, —OH, —SH, —SR$_{11}$, —S(O)$_3$H, —P(O)$_3$H$_2$, —C(=O)NR$_9$R$_9$, —NR$_{12}$R$_{12}$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is heteroaryl or —C(=O)OR$_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{11a}$;

R$_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 R$_{10a}$;

R$_{10}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-ninth embodiment, compounds of Formula IA are provided wherein:
ring A is optionally substituted with one or more R's shown as R$_{20}$ and R$_{2i}$;
G is CH or N;
Q is C;
X is CH;
Y is O, OCR$_9$R$_9$, or S;
n$_1$ is 1;
n$_2$ is 1;

R$_1$ is phenyl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1d}$ and R$_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

R$_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is heteroaryl or —C(=O)OR$_5$, wherein the heteroaryl may be optionally substituted with one or more R$_6$'s;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirtieth embodiment, compounds of Formula I are provided wherein:

ring A is optionally substituted with one or more R's shown as $R_{20}$ and $R_{21}$;

G is CH or N;

Q is C;

X is CH;

Y is O, OCR$_9$R$_9$, or S;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is heteroaryl or —C(=O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more R$_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{11}$, at each occurrence, is independently selected from alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{11a}$;

$R_{11a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{12}$, at each occurrence, is independently selected from hydrogen, alkyl, alkenyl, alkynyl, cycloalkyl, aryl, arylalkyl, heterocyclyl and heterocyclylalkyl, wherein the cycloalkyl, aryl, arylalkyl, heterocyclyl and heterocyclylalkyl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirty-first embodiment, compounds of Formula IA are provided wherein:

ring A is optionally substituted with one or more R's shown as $R_{20}$ and $R_{21}$;

G is CH or N;

Q is C;

X is CH;

Y is O, OCR$_9R_9$ or S;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —$OCF_3$, —$OR_{11}$, —OH, —C(=O)$NR_9R_9$, —$NR_{12}R_{12}$, —S(O)$_2NR_9R_9$, —$NR_9S(O)_2CF_3$, —C(=O)$R_{11}$, —$NR_9C(=O)H$, —$NR_9C(=O)R_{10}$, —OC(=O)$R_{10}$, —OC(=O)$NR_9R_9$, —S(=O)$R_{11}$, —S(O)$_2R_{11}$, —$NR_9C(=O)OR_8$ and —$NR_9S(O_2)R_8$, wherein: (a) the alkenyl, alkynyl and cycloalkyl may each be optionally substituted with one or more $R_6$'s; and (b) the alkyl may optionally be substituted by one or more of $R_7$'s;

$R_{1c}$ is selected from the group consisting of hydrogen, alkyl, alkenyl, alkynyl, cycloalkyl, aryl, heterocyclyl, halo, —CN, —$OCF_3$, —$OR_{11}$, —OH, —$SR_{11}$, —C(=O)$NR_9R_9$, —$NR_{12}R_{12}$, —S(O)$_2NR_9R_9$, —$NR_9S(O)_2CF_3$, —C(=O)$R_{11}$, —$NR_9C(=O)H$, —$NR_9C(=O)R_{10}$, —OC(=O)$R_{10}$, —OC(=O)$NR_9R_9$, —S(=O)$R_{11}$, —S(O)$_2R_{11}$, —$NR_9C(=O)OR_8$ and —$NR_9S(O_2)R_8$, wherein: (a) the alkenyl, alkynyl, aryl and heterocyclyl may each be optionally substituted with one or more $R_6$'s; and (b) the alkyl may optionally be substituted by one or more of $R_7$'s;

$R_2$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may optionally be substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$R_{10}$, —$NR_9C(=O)H$, —$NR_9C(=O)R_{10}$, —OC(=O)$R_{10}$, —S(=O)$R_{10}$, —S(O)$_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$R_{10}$, —$NR_9C(=O)H$, —$NR_9C(=O)R_{10}$, —OC(=O)$R_{10}$, —S(=O)$R_{10}$, —S(O)$_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl and cycloalkyl, each of which may be optionally substituted with one or more $R_{8a}$s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, =O, —$NR_{14}C(=O)OR_{14}$ and —$NR_{14}S(O_2)R_{14}$;

$R_9$, at each occurrence, is independently selected from hydrogen, alkyl, cycloalkyl, and aryl, wherein the alkyl, cycloalkyl, and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$, —$NR_{14}S(O_2)R_8$ and =O;

$R_{10}$, at each occurrence, is independently selected from alkyl, cycloalkyl, and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{11}$, at each occurrence, is independently selected from alkyl, cycloalkyl and aryl, which may each be optionally substituted with 0-3 $R_{11a}$;

$R_{11a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C$ (=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{12}$, at each occurrence, is independently selected from hydrogen, alkyl, cycloalkyl and aryl, wherein the alkyl, cycloalkyl and aryl may each be optionally substituted with 0-3 R$_{10a}$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirty-second embodiment, compounds of Formula I are provided wherein:

ring A is optionally substituted with one or more R's shown as R$_{20}$ and R$_{2i}$;

G is CH or N;

Q is C;

X is CH;

Y is O, OCR$_9$R$_9$ or S;

n$_1$ is 1;

n$_2$ is 1;

n$_3$ is 2;

R$_1$ is phenyl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1d}$ and R$_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

R$_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

R$_2$ is heteroaryl or —C(=O)OR$_5$, wherein the heteroaryl may be optionally substituted with one or more R$_6$'s;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

R$_8$, at each occurrence, is independently selected from the group consisting of alkyl and cycloalkyl, each of which may be optionally substituted with one or more R$_{8a}$s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, cycloalkyl and aryl, wherein the alkyl, cycloalkyl and aryl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

R$_{10}$, at each occurrence, is independently selected from alkyl, cycloalkyl and aryl, which may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{11}$, at each occurrence, is independently selected from alkyl, cycloalkyl and aryl, which may each be optionally substituted with 0-3 R$_{11a}$;

R$_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

R$_{12}$, at each occurrence, is independently selected from hydrogen, alkyl, cycloalkyl and aryl, wherein the alkyl, cycloalkyl and aryl may each be optionally substituted with 0-3 R$_{10a}$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirty-third embodiment, compounds of Formula IA are provided wherein:

ring A is optionally substituted with one or more R's shown as R$_{20}$ and R$_{21}$;

G is N;

Q is C;

X is CH;

Y is O, OCR$_9$R$_9$ or S;

n$_1$ is 1;

n$_2$ is 1

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is heteroaryl or —C(=O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl and cycloalkyl, each of which may be optionally substituted with one or more R$_{8a}$ s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ —NR$_{14}$S(O$_2$)R$_8$ and =O;

$R_{10}$, at each occurrence, is independently selected from alkyl, cycloalkyl, and aryl, which may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, cycloalkyl and aryl, which may each be optionally substituted with 0-3 R$_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, cycloalkyl and aryl, wherein the alkyl, cycloalkyl and aryl may each be optionally substituted with 0-3 R$_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirty-fourth embodiment, compounds of Formula I are provided wherein:

ring A is optionally substituted with one or more R's shown as $R_{20}$ and $R_{2i}$;

G is N;

Q is C;

X is CH;

Y is O, OCR$_9$R$_9$ or S;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is heteroaryl or —C(=O)OR$_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl, and aryl, which may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, cycloalkyl and aryl, which may each be optionally substituted with 0-3 $R_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, cycloalkyl and aryl, wherein the alkyl, cycloalkyl and aryl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirty-fifth embodiment, compounds of Formula IA are provided wherein:

ring A is optionally substituted with one or more R's shown as $R_{20}$ and $R_{21}$;

G is N;

Q is C;

X is CH;

Y is O;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl, may each be optionally substituted with one or more $R_6$'s; and (b) the alkyl may optionally be substituted by one or more of $R_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is heteroaryl or —C(=O)OR$_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl and cycloalkyl, each of which may be optionally substituted with one or more R$_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl, and aryl, which may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, cycloalkyl and aryl, which may each be optionally substituted with 0-3 R$_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, cycloalkyl and aryl, wherein the alkyl, cycloalkyl and aryl may each be optionally substituted with 0-3 R$_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirty-sixth embodiment, compounds of Formula I are provided wherein:

ring A is optionally substituted with one or more R's shown as $R_{20}$ and $R_{21}$;

G is N;
Q is C;
X is CH;
Y is O;
$n_1$ is 1;
$n_2$ is 1;
$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl, may each be optionally substituted with one or more R$_6$'s; and (b) the alkyl may optionally be substituted by one or more of R$_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is heteroaryl or —C(=O)OR$_5$, wherein the heteroaryl may optionally be substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl and cycloalkyl, each of which may be optionally substituted with one or more R$_{8a}$s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, which may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, cycloalkyl and aryl, which may each be optionally substituted with 0-3 $R_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, cycloalkyl and aryl, wherein the alkyl, cycloalkyl and aryl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirty-seventh embodiment, compounds of Formula IA are provided wherein:

ring A is optionally substituted with one or more R's shown as $R_{20}$ and $R_{21}$;

G is N;

Q is C;

X is CH;

Y is O;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O)$_2$R$_8$, wherein: (a) the alkenyl, alkynyl and cycloalkyl may be optionally substituted with one or more $R_6$'s; and (b) the alkyl may optionally be substituted by one or more of $R_7$'s;

$R_{1c}$ is selected from the group consisting of hydrogen, alkyl, alkenyl, alkynyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O)$_2$R$_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is heteroaryl or —C(=O)OR$_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl and cycloalkyl, each of which may be optionally substituted with one or more $R_{8a}$ s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, cycloalkyl and aryl, which may each be optionally substituted with 0-3 $R_{11a}$;

$R_{11a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{12}$, at each occurrence, is independently selected from hydrogen, alkyl, cycloalkyl and aryl, wherein the alkyl cycloalkyl and aryl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a thirty-eighth embodiment, compounds of Formula I are provided wherein:

ring A is optionally substituted with one or more R's shown as $R_{20}$ and $R_{21}$;

G is N;

Q is C;

X is CH;

Y is O;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —$OCF_3$, —$OR_{11}$, —OH, —C(=O)$NR_9R_9$, —$NR_{12}R_{12}$, —S(O)$_2NR_9R_9$, —$NR_9S(O)_2CF_3$, —C(=O)$R_{11}$, —$NR_9C(=O)H$, —$NR_9C(=O)R_{10}$, —OC(=O)$R_{10}$, —OC(=O)$NR_9R_9$, —S(=O)$R_{11}$, —S(O)$_2R_{11}$, —$NR_9C(=O)OR_8$ and —$NR_9S(O_2)R_8$, wherein: (a) the alkenyl, alkynyl and cycloalkyl may each be optionally substituted with one or more $R_6$'s; and (b) the alkyl may optionally be substituted by one or more of $R_7$'s;

$R_{1c}$ is selected from the group consisting of hydrogen, alkyl, alkenyl, alkynyl, cycloalkyl, aryl, heterocyclyl, halo, —CN, —$OCF_3$, —$OR_{11}$, —OH, —$SR_{11}$, —C(=O)$NR_9R_9$, —$NR_{12}R_{12}$, —S(O)$_2NR_9R_9$, —$NR_9S(O)_2CF_3$, —C(=O)$R_{11}$, —$NR_9C(=O)H$, —$NR_9C(=O)R_{10}$, —OC(=O)$R_{10}$, —OC(=O)$NR_9R_9$, —S(=O)$R_{11}$, —S(O)$_2R_{11}$, —$NR_9C(=O)OR_8$ and —$NR_9S(O_2)R_8$, wherein: (a) the alkenyl, alkynyl, cycloalkyl, aryl and heterocyclyl may each be optionally substituted with one or more $R_6$'s; and (b) the alkyl may optionally be substituted by one or more of $R_7$'s;

$R_2$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$R_{10}$, —$NR_9C(=O)H$, —$NR_9C(=O)R_{10}$, —OC(=O)$R_{10}$, —S(=O)$R_{10}$, —S(O)$_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$R_{10}$, —$NR_9C(=O)H$, —$NR_9C(=O)R_{10}$, —OC(=O)$R_{10}$, —S(=O)$R_{10}$, —S(O)$_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl and heterocyclyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, =O, —$NR_{14}C(=O)OR_{14}$ and —$NR_{14}S(O_2)R_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$, —$NR_{14}S(O_2)R_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{11}$, at each occurrence, is independently selected from alkyl, cycloalkyl and aryl, which may each be optionally substituted with 0-3 $R_{11a}$;

$R_{11a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{12}$, at each occurrence, is independently selected from hydrogen, alkyl, cycloalkyl and aryl, wherein the alkyl, cycloalkyl and aryl may each be optionally substituted with 0-3 $R_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a thirty-ninth embodiment, compounds of Formula IA are provided wherein:
ring A is optionally substituted with one or more R's shown as $R_{20}$ and $R_{21}$;
G is N;
Q is C;
X is CH;
Y is O;
$n_1$ is 1;
$n_2$ is 1;
$R_1$ is

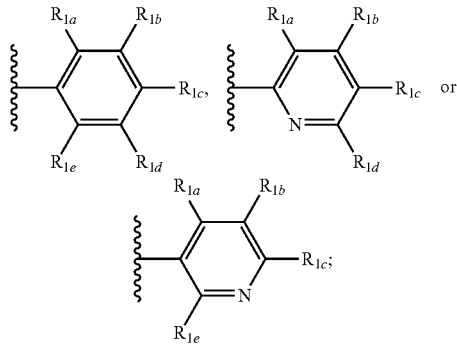

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is heteroaryl or —C(=O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl and cycloalkyl, each of which may be optionally substituted with one or more R$_{8a}$s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl and aryl, which may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, cycloalkyl and aryl, which may each be optionally substituted with 0-3 R$_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, cycloalkyl and aryl, wherein the alkyl, cycloalkyl and aryl may each be optionally substituted with 0-3 R$_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a fortieth embodiment, compounds of Formula I are provided wherein:
ring A is optionally substituted with one or more R's shown as $R_{20}$ and $R_{21}$;
G is N;
Q is C;
X is CH;
Y is O;
$n_1$ is 1;
$n_2$ is 1;
$n_3$ is 2;

R₁ is

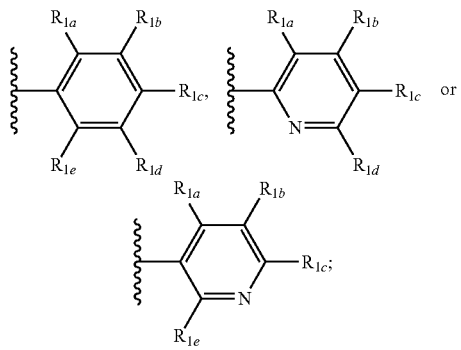

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF₃, —OR₁₁, —OH, —C(=O)NR₉R₉, —NR₁₂R₁₂, —S(O)₂NR₉R₉, —NR₉S(O)₂CF₃, —C(=O)R₁₁, —NR₉C(=O)H, —NR₉C(=O)R₁₀, —OC(=O)R₁₀, —OC(=O)NR₉R₉, —S(=O)R₁₁, —S(O)₂R₁₁, —NR₉C(=O)OR₈ and —NR₉S(O₂)R₈, wherein: (a) the alkenyl, alkynyl and cycloalkyl may each be optionally substituted with one or more R₆'s; and (b) the alkyl may optionally be substituted by one or more of R₇'s;

$R_{1c}$ is selected from the group consisting of hydrogen, alkyl, alkenyl, alkynyl, cycloalkyl, aryl, heterocyclyl, halo, —CN, —OCF₃, —OR₁₁, —OH, —SR₁₁, —C(=O)NR₉R₉, —NR₁₂R₁₂, —S(O)₂NR₉R₉, —NR₉S(O)₂CF₃, —C(=O)R₁₁, —NR₉C(=O)H, —NR₉C(=O)R₁₀, —OC(=O)R₁₀, —OC(=O)NR₉R₉, —S(=O)R₁₁, —S(O)₂R₁₁, —NR₉C(=O)OR₈ and —NR₉S(O₂)R₈, wherein: (a) the alkenyl, alkynyl, cycloalkyl, aryl and heterocyclyl may each be optionally substituted with one or more R₆'s; and (b) the alkyl may optionally be substituted by one or more of R₇'s;

R₂ is heteroaryl or —C(=O)OR₅, wherein the heteroaryl may be optionally substituted with one or more R₆'s;

R₅ is alkyl, alkenyl, aryl, cycloalkyl, heteroaryl or heterocyclyl, each of which may be optionally substituted with one or more R₆'s;

R₆, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR₁₀, —OCF₃, —OR₁₀, —OH, —SH, —SR₁₀, —C(=O)NR₉R₉, —NR₉R₉, —S(O)₂NR₉R₉, —NR₉S(O)₂CF₃, —C(=O)R₁₀, —NR₉C(=O)H, —NR₉C(=O)R₁₀, —OC(=O)R₁₀, —S(=O)R₁₀, —S(O)₂R₁₀, =O, —NR₉C(=O)OR₈ and —NR₉S(O₂)R₈, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R₉ₐ;

R₇, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR₁₀, —OCF₃, —OR₁₀, —OH, —SH, —SR₁₀, —C(=O)NR₉R₉, —NR₉R₉, —S(O)₂NR₉R₉, —NR₉S(O)₂CF₃, —C(=O)R₁₀, —NR₉C(=O)H, —NR₉C(=O)R₁₀, —OC(=O)R₁₀, —S(=O)R₁₀, —S(O)₂R₁₀, =O, —NR₉C(=O)OR₈ and —NR₉S(O₂)R₈, wherein the alkyl, alkenyl, alkynyl, aryl, cycloalkyl, cycloalkylalkyl and heterocyclyl may each be optionally substituted with 0-5 R₉ₐ;

R₈, at each occurrence, is independently selected from the group consisting of alkyl and cycloalkyl, each of which may be optionally substituted with one or more R₈ₐ's;

R₈ₐ, at each occurrence, is independently selected from alkyl, haloalkyl, aryl, alkenyl, alkynyl, cycloalkyl, halo, —NH₂, —CN, —C(=O)OH, —C(=O)OR₁₄, —OCF₃, —OR₁₄, —OH, —C(=O)NR₁₄R₁₄, —NR₁₄R₁₄, —S(O)₂NR₁₄R₁₄, —NR₁₄S(O)₂CF₃, —C(=O)R₁₄, —NR₁₄C(=O)H, —NR₁₄C(=O)R₁₄, —OC(=O)R₁₄, —S(=O)R₁₄, —S(O)₂R₁₄, =O, —NR₁₄C(=O)OR₁₄ and —NR₁₄S(O₂)R₁₄;

R₉, at each occurrence, is independently selected from hydrogen, alkyl, cycloalkyl and aryl, wherein the alkyl, cycloalkyl and aryl may each be optionally substituted with 0-5 R₉ₐ;

R₉ₐ, at each occurrence, is independently selected from alkyl, haloalkyl, aryl, alkenyl, alkynyl, cycloalkyl, halo, —NH₂, —CN, —C(=O)OH, —C(=O)OR₁₄, —OCF₃, —OR₁₄, —OH, —C(=O)NR₁₄R₁₄, —NR₁₄R₁₄, —S(O)₂NR₁₄R₁₄, —NR₁₄S(O)₂CF₃, —C(=O)R₁₄, —NR₁₄C(=O)H, —NR₁₄C(=O)R₁₄, —OC(=O)R₁₄, —S(=O)R₁₄, —S(O)₂R₁₄, —NR₁₄C(=O)OR₈ and —NR₁₄S(O₂)R₈, =O;

R₁₀, at each occurrence, is independently selected from alkyl, cycloalkyl and aryl, which may each be optionally substituted with 0-3 R₁₀ₐ;

R₁₀ₐ, at each occurrence, is independently selected from alkyl, haloalkyl, aryl, alkenyl, alkynyl, halo, —NH₂, —CN, —C(=O)OR₁₄, —OCF₃, —OR₁₄, —OH, —C(=O)NR₁₄R₁₄, —NR₁₄R₁₄, —S(O)₂NR₁₄R₁₄, —NR₁₄S(O)₂CF₃, —C(=O)R₁₄, —NR₁₄C(=O)H, —NR₁₄C(=O)R₁₄, —OC(=O)R₁₄, —S(=O)R₁₄, —S(O)₂R₁₄, —NR₁₄C(=O)OR₈, and —NR₁₄S(O₂)R₈;

R₁₁, at each occurrence, is independently selected from alkyl, cycloalkyl and aryl, which may each be optionally substituted with 0-3 R₁₁ₐ;

R₁₁ₐ, at each occurrence, is independently selected from alkyl, haloalkyl, aryl, alkenyl, alkynyl, cycloalkyl, halo, —NH₂, —CN, —C(=O)OH, —C(=O)OR₁₄, —OCF₃, —OR₁₄, —OH, —C(=O)NR₁₄R₁₄, —NR₁₄R₁₄, —S(O)₂NR₁₄R₁₄, —NR₁₄S(O)₂CF₃, —C(=O)R₁₄, —NR₁₄C(=O)H, —NR₁₄C(=O)R₁₄, —OC(=O)R₁₄, —S(=O)R₁₄, —S(O)₂R₁₄, —NR₁₄C(=O)OR₈ and —NR₁₄S(O₂)R₈;

R₁₂, at each occurrence, is independently selected from hydrogen, alkyl, cycloalkyl and aryl, wherein the alkyl, cycloalkyl and aryl may each be optionally substituted with 0-3 R₁₀ₐ;

R₁₄, at each occurrence, is independently selected from hydrogen, alkyl, cycloalkyl and aryl;

R₂₀ is hydrogen; and

R₂₁ is selected from the group consisting of hydrogen, alkyl, haloalkyl, halo and —CN.

In a forty-first embodiment, compounds of Formula IA are provided wherein:

ring A is optionally substituted with one or more R's shown as R₂₀ and R₂₁;

G is N;

Q is C;

X is CH;

Y is O;

n₁ is 1;

n₂ is 1:

R₁ is

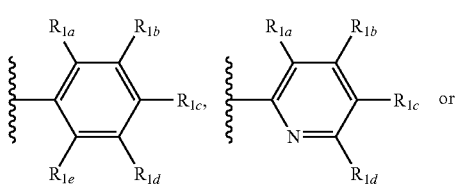

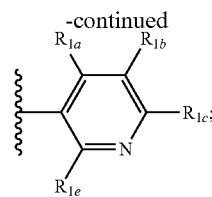

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(═O)NR$_9$R$_9$, —NR$_{12}$R$_{12}$, —S(O)$_2$NR$_9$R$_9$, —NR$_9$S(O)$_2$CF$_3$, —C(═O)R$_{11}$, —NR$_9$C(═O)H, —NR$_9$C(═O)R$_{10}$, —OC(═O)R$_{10}$, —OC(═O)NR$_9$R$_9$, —S(═O)R$_{11}$, —S(O)$_2$R$_{11}$, —NR$_9$C(═O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(═O)NR$_9$R$_9$, —NR$_{12}$R$_{12}$, —S(O)$_2$NR$_9$R$_9$, —NR$_9$S(O)$_2$CF$_3$, —C(═O)R$_{11}$, —NR$_9$C(═O)H, —NR$_9$C(═O)R$_{10}$, —OC(═O)R$_{10}$, —OC(═O)NR$_9$R$_9$, —S(═O)R$_{11}$, —S(O)$_2$R$_{11}$, —NR$_9$C(═O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is pyridinyl, pyrimidinyl or —C(═O)OR$_5$, wherein the pyridinyl and pyrimidinyl may each be optionally substituted with one or more R$_6$'s;

$R_5$ is alkyl, aryl or cycloalkyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(═O)OR$_{10}$, —OCF$_3$, —OR$_{10}$, —OH, —SH, —SR$_{10}$, —C(═O)NR$_9$R$_9$, —NR$_9$R$_9$, —S(O)$_2$NR$_9$R$_9$, —NR$_9$S(O)$_2$CF$_3$, —C(═O)R$_{10}$, —NR$_9$C(═O)H, —NR$_9$C(═O)R$_{10}$, —OC(═O)R$_{10}$, —S(═O)R$_{10}$, —S(O)$_2$R$_{10}$, ═O, —NR$_9$C(═O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(═O)OR$_{10}$, —OCF$_3$, —OR$_{10}$, —OH, —SH, —SR$_{10}$, —C(═O)NR$_9$R$_9$, —NR$_9$R$_9$, —S(O)$_2$NR$_9$R$_9$, —NR$_9$S(O)$_2$CF$_3$, —C(═O)R$_{10}$, —NR$_9$C(═O)H, —NR$_9$C(═O)R$_{10}$, —OC(═O)R$_{10}$, —S(═O)R$_{10}$, —S(O)$_2$R$_{10}$, ═O, —NR$_9$C(═O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl and cycloalkyl, each of which may be optionally substituted with one or more R$_8$'s;

$R_{8a}$, at each occurrence, is independently selected from alkyl, haloalkyl, aryl, alkenyl, alkynyl, cycloalkyl, halo, —NH$_2$, —CN, —C(═O)OH, —C(═O)OR$_{14}$, —OCF$_3$, —OR$_{14}$, —OH, —C(═O)NR$_{14}$R$_{14}$, —NR$_{14}$R$_{14}$, —S(O)$_2$NR$_{14}$R$_{14}$, —NR$_{14}$S(O)$_2$CF$_3$, —C(═O)R$_{14}$, —NR$_{14}$C(═O)H, —NR$_{14}$C(═O)R$_{14}$, —OC(═O)R$_{14}$, —S(═O)R$_{14}$, —S(O)$_2$R$_{14}$, ═O, —NR$_{14}$C(═O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(═O)OH, —C(═O)OR$_{14}$, —OCF$_3$, —OR$_{14}$, —OH, —C(═O)NR$_{14}$R$_{14}$, —NR$_{14}$R$_{14}$, —S(O)$_2$NR$_{14}$R$_{14}$, —NR$_{14}$S(O)$_2$CF$_3$, —C(═O)R$_{14}$, —NR$_{14}$C(═O)H, —NR$_{14}$C(═O)R$_{14}$, —OC(═O)R$_{14}$, —S(═O)R$_{14}$, —S(O)$_2$R$_{14}$, —NR$_{14}$C(═O)OR$_8$, —NR$_{14}$S(O$_2$)R$_8$ and ═O;

$R_{10}$, at each occurrence, is independently selected from alkyl, cycloalkyl and aryl, which may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(═O)OR$_{14}$, —OCF$_3$, —OR$_{14}$, —OH, —C(═O)NR$_{14}$R$_{14}$, —NR$_{14}$R$_{14}$, —S(O)$_2$NR$_{14}$R$_{14}$, —NR$_{14}$S(O)$_2$CF$_3$, —C(═O)R$_{14}$, —NR$_{14}$C(═O)H, —NR$_{14}$C(═O)R$_{14}$, —OC(═O)R$_{14}$, —S(═O)R$_{14}$, —S(O)$_2$R$_{14}$, —NR$_{14}$C(═O)OR$_8$ and —NR$_{14}$S(O$_2$)R$_8$;

$R_{11}$, at each occurrence, is independently selected from alkyl, cycloalkyl and aryl, which may each be optionally substituted with 0-3 R$_{11a}$;

$R_{11a}$, at each occurrence, is independently selected from alkyl, haloalkyl, aryl, alkenyl, alkynyl, cycloalkyl, halo, —NH$_2$, —CN, —C(═O)OH, —C(═O)OR$_{14}$, —OCF$_3$, —OR$_{14}$, —OH, —C(═O)NR$_{14}$R$_{14}$, —NR$_{14}$R$_{14}$, —S(O)$_2$NR$_{14}$R$_{14}$, —NR$_{14}$S(O)$_2$CF$_3$, —C(═O)R$_{14}$, —NR$_{14}$C(═O)H, —NR$_{14}$C(═O)R$_{14}$, —OC(═O)R$_{14}$, —S(═O)R$_{14}$, —S(O)$_2$R$_{14}$, —NR$_{14}$C(═O)OR$_8$ and —NR$_{14}$S(O$_2$)R$_8$;

$R_{12}$, at each occurrence, is independently selected from hydrogen, alkyl, cycloalkyl and aryl, wherein the alkyl, cycloalkyl and aryl may each be optionally substituted with 0-3 R$_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a forty-second embodiment, compounds of Formula I are provided wherein:

ring A is optionally substituted with one or more R's shown as $R_{20}$ and $R_{2i}$;

G is N;

Q is C;

X is CH;

Y is O;

$n_1$ is 1;

$n_2$ is 1;

$n_3$ is 2;

$R_1$ is

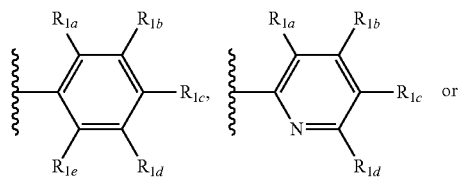

-continued

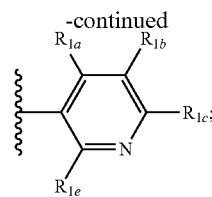

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{11}$, —OH, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl and cycloalkyl may each be optionally substituted with one or more R$_6$'s; and (b) the alkyl may optionally be substituted by one or more of R$_7$'s;

$R_{1c}$ is selected from the group consisting of hydrogen, alkyl, alkenyl, alkynyl, cycloalkyl, aryl, heterocyclyl, halo, —CN, —OCF$_3$, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —OC(=O)R$_{10}$, —OC(=O)NR$_9$R$_9$, —S(=O)R$_{11}$, —S(O)$_2$R$_{11}$, —NR$_9$C(=O)OR$_8$ and —NR$_9$S(O$_2$)R$_8$, wherein: (a) the alkenyl, alkynyl, cycloalkyl, aryl and heterocyclyl may each be optionally substituted with one or more R$_6$'s; and (b) the alkyl may optionally be substituted by one or more of R$_7$'s;

$R_2$ is pyridinyl, pyrimidinyl or —C(=O)OR$_5$, wherein the pyridinyl and pyrimidinyl may each be optionally substituted with one or more R$_6$'s;

$R_5$ is alkyl, aryl or cycloalkyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_7$, at each occurrence, is independently selected from the group consisting of alkyl, haloalkyl, aryl, alkenyl, alkynyl, cycloalkyl, cycloalkylalkyl, heterocyclyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl and heterocyclyl may each be optionally substituted with 0-5 R$_{9a}$;

$R_8$, at each occurrence, is independently selected from the group consisting of alkyl and cycloalkyl, each of which may be optionally substituted with one or more R$_{8a}$ s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl and aryl, which may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{11}$, at each occurrence, is independently selected from alkyl, cycloalkyl and aryl, which may each be optionally substituted with 0-3 R$_{11a}$;

$R_{11a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{12}$, at each occurrence, is independently selected from hydrogen, alkyl, cycloalkyl and aryl, wherein the alkyl, cycloalkyl and aryl may each be optionally substituted with 0-3 R$_{10a}$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

One particular group of compounds is the group of embodiments of Formula I.

Another particular group of compounds is the group of embodiments of Formula IA (noting that for Formula IA there is no n$_3$ in the formula).

For each of the embodiments described in this application, further and more particular values of the terms used in each of the embodiments may be selected from the following definitions; these values may be used individually in any of the embodiments or in any combination. It is noted that for any occurrences of "=O", these may be used with suitable accommodation in the bond structure at that site as will be appreciated by those skilled in the art.

The heteroaryl, heteroarylalkyl, heterocyclyl and heterocyclylalkyl used in each occurrence may each contain 1-4 heteroatoms selected from N, O and S.

$R_1$ may be selected from phenyl and a 6 membered monocyclic heteroaryl having 1 or 2 N's wherein:
a) phenyl and heteroaryl may each be substituted with 1-3 of R$_{1a}$, R$_{1b}$, R$_{1c}$, R$_{1d}$ and R$_{1e}$; and
b) R$_{1a}$, R$_{1b}$, R$_{1c}$, R$_{1d}$ and R$_{1e}$ are each independently selected from hydrogen, C$_{1-3}$ alkyl, C$_{3-6}$ cycloalkyl, phenyl, halo, —CN, —OR$_{11}$, —OH, —SR$_{11}$, —C(=O)NR$_9$R$_9$, —NR$_{12}$R$_{12}$, —S(O)$_2$NR$_9$R$_9$, —NR$_9$S(O)$_2$CF$_3$, —C(=O)R$_{11}$, —NR$_9$C(=O)H, —NR$_9$C(=O)R$_{10}$, —S(=O)R$_{11}$, —S(O)$_2$R$_{11}$, —NR$_9$C(=O)OR$_8$, NR$_9$C(=O)NR$_9$R$_9$ and —NR$_9$S(O$_2$)R$_8$ wherein:

i) $R_8$ is selected from the group consisting of $C_{1-6}$ straight and branched chain alkyl and $C_{3-6}$ cycloalkyl each of which may be optionally substituted with one or more $R_{8a}$, where $R_{8a}$ is selected from halo, $C_{1-3}$ haloalkyl, $C_{3-6}$ cycloalkyl, OH, $C_{1-3}$ alkoxy and CN;

ii) $R_9$ is selected from the group consisting of $C_{1-6}$ straight and branched chain alkyl and $C_{3-6}$ cycloalkyl each of which may be optionally substituted with one or more $R_{9a}$, where $R_{9a}$ is selected from halo, $C_{1-3}$ haloalkyl, $C_{3-6}$ cycloalkyl, OH, $C_{1-3}$ alkoxy and CN;

iii) $R_{10}$ is selected from the group consisting of $C_{1-6}$ straight and branched chain alkyl and $C_{3-6}$ cycloalkyl each of which may be optionally substituted with one or more $R_{10a}$ where $R_{10a}$ is selected from halo, $C_{1-3}$ haloalkyl, $C_{3-6}$ cycloalkyl, OH, $C_{1-3}$ alkoxy and CN;

iv) $R_{11}$ is selected from the group consisting of $C_{1-6}$ straight and branched chain alkyl and $C_{3-6}$ cycloalkyl each of which may be optionally substituted with one or more $R_{11a}$, where $R_{11a}$ is selected from halo, $C_{1-3}$ haloalkyl, $C_{3-6}$ cycloalkyl, OH, $C_{1-3}$ alkoxy and CN; and v) $R_{12}$ is selected from the group consisting of $C_{1-6}$ straight and branched chain alkyl and $C_{3-6}$ cycloalkyl each of which may be optionally substituted with one or more $R_{10a}$, where $R_{10a}$ is selected from halo, $C_{1-3}$ haloalkyl, $C_{3-6}$ cycloalkyl, OH, $C_{1-3}$ alkoxy and CN.

$R_2$ may be selected from —C(=O)OR$_5$, a 5-6 membered monocyclic heteroaryl having 1-3 heteroatoms selected from O and N; and an 8-10 bicyclic heteroaryl having 1-3 heteroatoms selected from O and N, wherein:

i) the heteroaryls may be each be substituted with 1 or 2 of $R_6$, where $R_6$ is selected from $C_{1-6}$ alkyl, $C_{1-3}$ haloalkyl, phenyl, $C_{3-6}$ cycloalkyl, halo, —CN, —OCF$_3$ and —OC$_{1-5}$alkyl, wherein the alkyl, phenyl, and cycloalkyl values for $R_6$ may each be optionally substituted with 0-2 $R_{9a}$ where $R_{9a}$ is selected from halo, $C_{1-3}$ haloalkyl, $C_{3-6}$ cycloalkyl, OH, $C_{1-3}$ alkoxy and CN; and ii) $R_5$ is selected from the group consisting of $C_{1-6}$ straight and branched chain alkyl, $C_{3-6}$ cycloalkyl and phenyl wherein the alkyl, phenyl, and cycloalkyl, may each be optionally substituted with 0-2 $R_6$ wherein $R_6$ is as defined in i).

$R_5$ may be selected from the group consisting of $C_{1-6}$ straight and branched chain alkyl, $C_{3-6}$ cycloalkyl and phenyl wherein:

i) the alkyl, phenyl, and cycloalkyl, may each be optionally substituted with 0-2 $R_6$;

ii) $R_6$ is selected from $C_{1-6}$ straight and branched chain alkyl; $C_{3-6}$ cycloalkyl; $C_{2-6}$ alkenyl; $C_{2-6}$ alkynyl; OH; phenyl; halo; $C_{1-6}$ haloalkyl; 5-6 membered heteroaryl having carbon atoms and 1-2 heteroatoms selected from O, S and N; 5-6 membered heterocycle having carbon atoms and 1-2 heteroatoms selected from O and N; OCF$_3$; OR$_{10}$ where $R_{10}$ is $C_{1-3}$ alkyl or $C_{3-6}$ cycloalkyl; and SR$_{10}$ where $R_{10}$ is $C_{1-3}$ alkyl or $C_{3-6}$ cycloalkyl; and iii) the alkyl, alkenyl, alkynyl, phenyl, cycloalkyl, heteroaryl and heterocyclyl values of $R_6$ may each be optionally substituted with 0-3 $R_{9a}$, where $R_{9a}$ is selected from the group consisting of halo, $C_{1-3}$ haloalkyl, $C_{3-6}$ cycloalkyl, OH, $C_{1-3}$ alkoxy CN and =O.

$R_6$ may be selected from $C_{1-6}$ straight and branched chain alkyl; $C_{3-6}$ cycloalkyl; $C_{2-6}$ alkenyl; $C_{2-6}$ alkynyl; OH; phenyl; halo; $C_{1-6}$ haloalkyl; 5-6 membered heteroaryl having carbon atoms and 1-2 heteroatoms selected from O, S and N; 5-6 membered heterocycle having carbon atoms and 1-2 heteroatoms selected from O and N; OCF$_3$; OR$_{10}$ where $R_{10}$ is $C_{1-3}$ alkyl or $C_{3-6}$ cycloalkyl; and SR$_{10}$ where $R_{10}$ is $C_{1-3}$ alkyl or $C_{3-6}$ cycloalkyl; and further wherein the alkyl, alkenyl, alkynyl, phenyl, cycloalkyl, heteroaryl and heterocyclyl values of $R_6$ may each be optionally substituted with 0-3 $R_{9a}$, where $R_{9a}$ is selected from the group consisting of halo, $C_{1-3}$ haloalkyl, $C_{3-6}$ cycloalkyl, OH, $C_{1-3}$ alkoxy, CN and =O.

$R_7$ may be selected from the group consisting of $C_{1-6}$ straight and branched chain alkyl; $C_{3-6}$ cycloalkyl; $C_{2-6}$ alkenyl; $C_{2-6}$ alkynyl; OH; phenyl; halo; $C_{1-6}$ haloalkyl; 5-6 membered heterocycle having carbon atoms and 1-2 heteroatoms selected from O and N; OCF$_3$; OR$_{10}$ where $R_{10}$ is $C_{1-3}$ alkyl or $C_{3-6}$ cycloalkyl; and SR$_{10}$ where $R_{10}$ is $C_{1-3}$ alkyl or $C_{3-6}$ cycloalkyl; and further, where the alkyl, alkenyl, alkynyl, phenyl, cycloalkyl and heterocyclyl values of $R_7$ may each be optionally substituted with 0-3 $R_{9a}$, where $R_{9a}$ is selected from the group consisting of halo, $C_{1-3}$ haloalkyl, $C_{3-6}$ cycloalkyl, OH, $C_{1-3}$ alkoxy, CN and =O.

$R_8$ is selected from the group consisting of $C_{1-6}$ straight and branched chain alkyl and $C_{3-6}$ cycloalkyl each of which may be optionally substituted with one or more $R_{8a}$'s where $R_{8a}$ is selected from halo, $C_{1-3}$ haloalkyl, $C_{3-6}$ cycloalkyl, OH, $C_{1-3}$ alkoxy, CN and =O.

$R_{8a}$ is selected from halo, $C_{1-3}$ haloalkyl, $C_{3-6}$ cycloalkyl, OH, $C_{1-3}$ alkoxy, CN and =O.

$R_9$ is selected from H, $C_{1-3}$ straight and branched chain alkyl and $C_{3-6}$ cycloalkyl.

$R_{9a}$ is selected from halo, $C_{1-3}$ haloalkyl, $C_{3-6}$ cycloalkyl, OH, $C_{1-3}$ alkoxy, CN and =O.

$R_{10}$ is selected from $C_{1-3}$ straight and branched chain alkyl and $C_{3-6}$ cycloalkyl.

$R_{10a}$ is selected from halo, $C_{1-3}$ haloalkyl, $C_{3-6}$ cycloalkyl, OH, $C_{1-3}$ alkoxy, CN and =O.

$R_{11}$ is selected from $C_{1-3}$ straight and branched chain alkyl and $C_{3-6}$ cycloalkyl.

$R_{11a}$ is selected from halo, $C_{1-3}$ haloalkyl, $C_{3-6}$ cycloalkyl, OH, $C_{1-3}$ alkoxy, CN and =O.

$R_{12}$ is selected from the group consisting of $C_{1-3}$ straight and branched chain alkyl and $C_{3-6}$ cycloalkyl.

$R_{14}$ is H.

$R_{20}$ is H.

$R_{21}$ is selected from H, $C_{1-3}$ alkyl, $C_{3-6}$ cycloalkyl, halo and CN.

In a forty-third embodiment, compounds of the present invention are selected from the group of compounds exemplified in the Examples.

In a forty-fourth embodiment, the present invention relates to pharmaceutical compositions comprised of a therapeutically effective amount of a compound of the present invention, alone or, optionally, in combination with a pharmaceutically acceptable carrier and/or one or more other agent(s), for example, a glucagon-like peptide-1 receptor agonist or fragment thereof.

In a forty-fifth embodiment, the present invention relates to methods of modulating the activity of the GPR119 G protein-coupled receptor comprising administering to a mammalian patient, for example, a human patient, in need thereof a therapeutically effective amount of a compound of the present invention, alone, or optionally, in combination with another compound of the present invention and/or at least one other type of therapeutic agent.

In a forty-sixth embodiment, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In a forty-seventh embodiment, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a forty-eighth embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a forty-ninth embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fiftieth embodiment, the present invention relates to a method for preventing, modulating, or treating the progression or onset of obesity comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fifty-first embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fifty-second embodiment, the present invention relates to a method for preventing, modulating, or treating the progression or onset of hypertension comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fifty-third embodiment, the present invention relates to a formulated product wherein the selected formulation is made by combining (a) a compound of Formula I or IA (using any of the compound embodiments listed above) and (b) a dipeptidyl peptidase-IV (DPP4) inhibitor (for example a member selected from saxagliptin, sitagliptin, vildagliptin and alogliptin).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I or Formula IA may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Young, S. D. et al., *Antimicrobial Agents and Chemotherapy*, 2602-2605 (1995).

To the extent that compounds of Formula I and IA, and salts thereof, may exist in their tautomeric form, all such tautomeric forms are contemplated herein as part of the present invention.

The term "substituted", as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

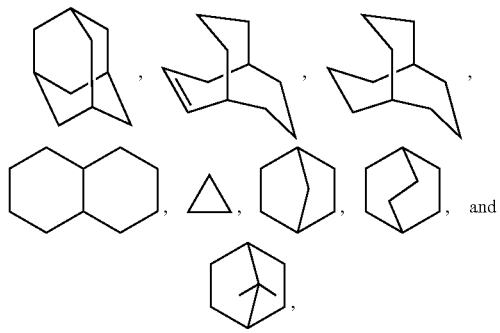

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl or cycloheteroalkyl rings for example

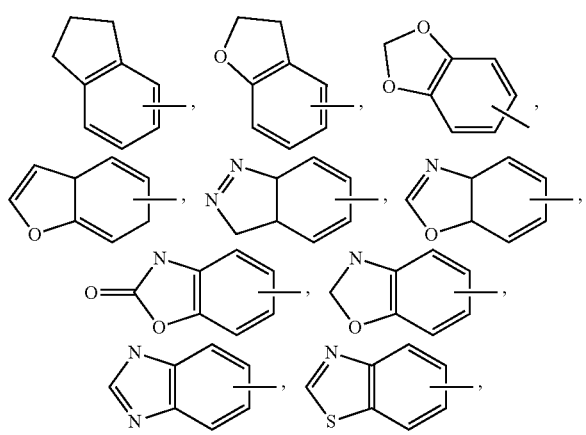

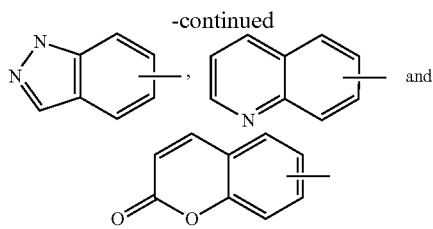

and may be optionally substituted through available carbon atoms with 1, 2 or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino" or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, pyrrolidonyl, 4-piperidonyl, chromanyl, decahydroquinolinyl, dihydrofuro[2,3-b]tetrahydrofuran, indolinyl, isochromanyl, isoindolinyloctahydroisoquinolinyl, piperazinyl, piperidinyl, piperidonyl, 4-piperidonyl, tetrahydrofuranyl, tetrahydroisoquinolinyl, tetrahydroquinolinyl, morpholinyl, dihydrofuranyl, tetrahydrothiophenyl, pyranyl, dihydropyranyl, 1,4-dioxanyl and 1,3-dioxanyl. Also included are fused ring and spiro compounds containing, for example, the above heterocycles.

As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heteroaryls are 1H-indazole, 2H,6H-1,5,2-dithiazinyl, indolyl, 4aH-carbazole, 4H-quinolizinyl, 6H-1,2, 5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinolinyl, 4H-quinolizinyl, quinoxalinyl, quinuclidinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl and tetrazolyl.

The term "heterocyclylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene or alkenylene as defined above.

The term "cyano" as used herein refers to a —CN group.

The term "nitro" as used herein refers to an —NO$_2$ group.

The term "hydroxy" as used herein refers to an —OH group.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Any compound that can be converted in vivo to provide the bioactive agent (i.e., a compound of Formula I or IA) is a prodrug within the scope and spirit of the invention.

The term "prodrug(s)" as employed herein includes esters and carbonates formed by reacting one or more hydroxyls of compounds of Formula I or IA with alkyl, alkoxy or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch. 5, pp. 113-191 (Harwood Academic Publishers, 1991); and
d) *Hydrolysis in Drug and Prodrug Metabolism*, Bernard Testa and Joachim M. Mayer, (Wiley-VCH, 2003).

Said references are incorporated herein by reference, particularly as to the description of prodrugs.

In addition, compounds of Formula I and IA are, subsequent to their preparation, preferably isolated and purified to obtain a composition containing an amount by weight equal to or greater than 99% of a compound of Formula I or IA ("substantially pure" compound), which is then used or formulated as described herein. Such "substantially pure" compounds of Formula I and IA are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of Formula I and IA can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders.

As used herein, "treating" or "treatment" covers the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I and IA may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I and IA falling into a given class may be compatible with some of the reaction conditions required in some of the methods described. Such restrictions to the substituents, which are compatible with the reaction conditions, will be readily apparent to one skilled in the art and alternate methods must be used.

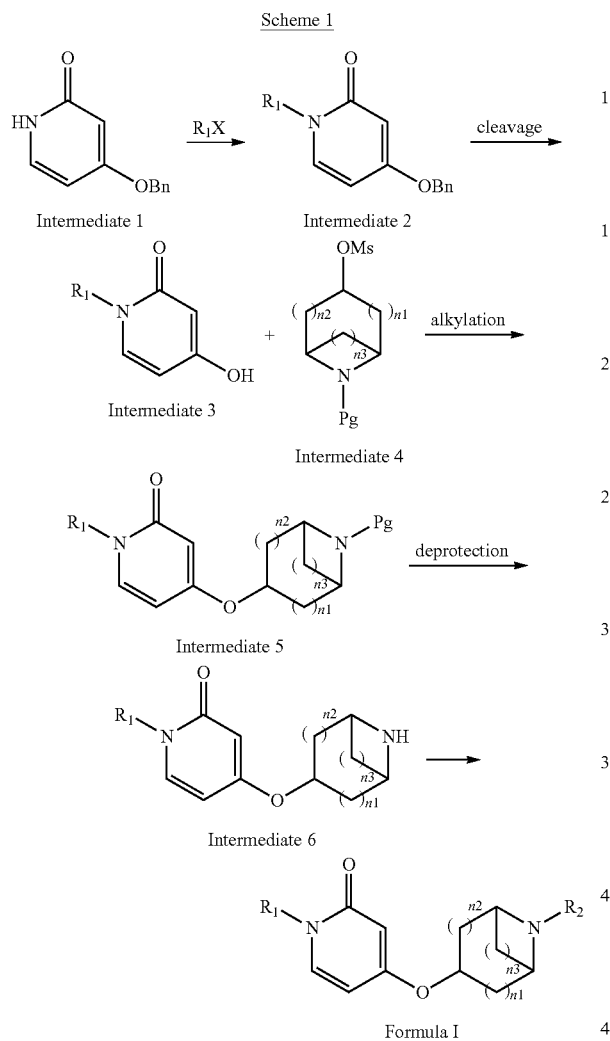

Compounds of Formula I and IA may be prepared by procedures depicted in Scheme 1. Intermediate 1, obtained from commercial sources, can be reacted with $R_1X$ (where $R_1$ other than H is as defined with respect to Formula I and IA and X is a halide) in the presence of a ligand such as 8-hydroxyquinoline, CuI (I) and a base such as $K_2CO_3$ in a suitable solvent such as DMF, DMSO etc. at an elevated temperature to yield intermediate 2. Cleavage of the benzyl group of intermediate 2 can be performed using the methods known in the art such as hydrogenolysis catalyzed by palladium. Intermediate 3 can then be alkylated with intermediate 4, which can be prepared by reaction of the corresponding alcohols with methanesulfonyl chloride, in the presence of a base such as $K_2CO_3$ at an elevated temperature. The above alcohols are commercially available or can be prepared by many methods well known to one skilled in the art (typical examples may be found in Sandler, S. et al., *Organic Functional Group Preparations*, Vol. I (Academic Press, Inc., 1983)). Removal of the protecting group of intermediate 5 can be carried out with appropriate reagents well known to those skilled in the art (for specific details see Greene et al., *Protecting Groups in Organic Synthesis* (John Wiley & Sons Inc., 1991)). The deprotected product can then be treated with $R_2X$ (where $R_2$ is defined as in Formula I and IA and X is a leaving group such as halide, mesylate, triflate, etc.), which are commercially available or can be prepared by many methods known in the art, at a number of conditions that are routine for those skilled in the art of organic synthesis to afford compounds of Formula I and IA. Alternatively the intermediate 6 can also be reacted with isocyates or isothiocyanates in the presence of a base such as $Et_3N$ to provide the compounds of Formula I and IA.

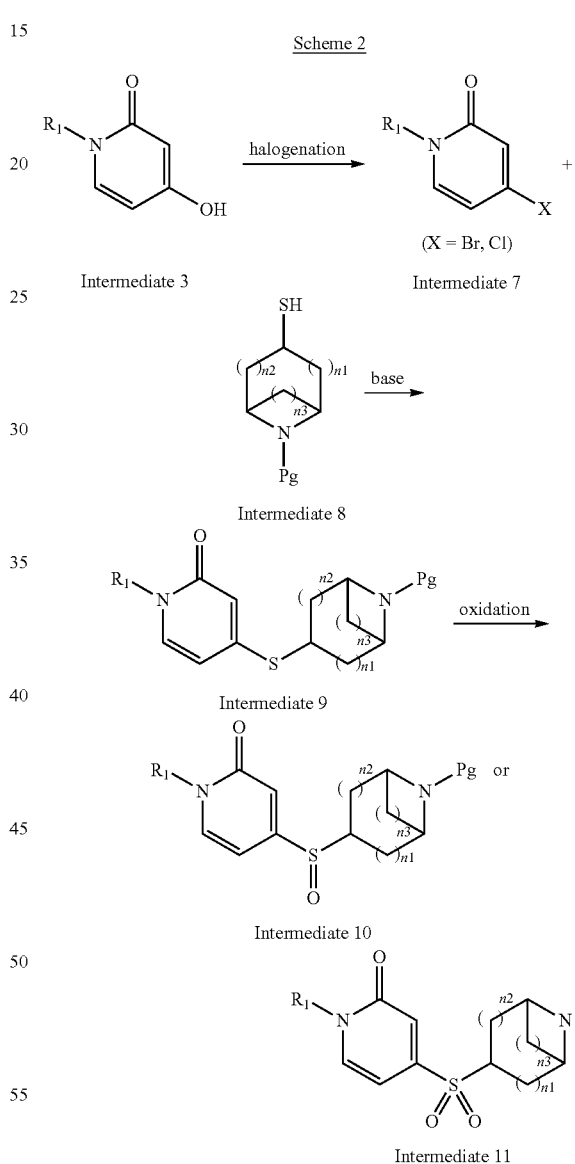

Compounds of Formula I and IA, wherein Y is defined as S, S(=O) or S(O)$_2$, may be prepared by procedures outlined in Scheme 2. Halogenation of intermediate 3 generated as described in Scheme I can be achieved with $POBr_3$, $PBr_3$ or $POCl_3$ using the conditions known to one skilled in the art. The halogenated pyridone can then be reacted with intermediate 8, which can be prepared according to the procedures described in U.S. Pat. No. 6,556,384 B1 (Owen, D. et al.)

incorporated by reference herein as to these preparations, in the presence of a base such as NaH to yield intermediate 9. Oxidation of intermediate 9 with an oxidant such as mCPBA in a suitable solvent such as $CH_2Cl_2$ affords intermediate 10 and intermediate 11. Intermediate 9, intermediate 10 or intermediate 11 can be carried forward to compounds of Formula I and IA following the procedures described above in Scheme 1 substituting intermediate 9, 10 or 11 for intermediate 5.

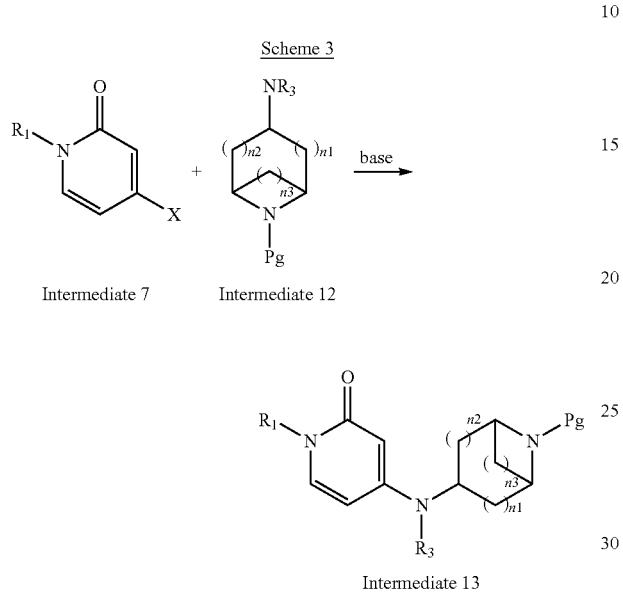

Compounds of Formula I and IA, wherein Y is defined as $NR_3$, may be prepared by procedures illustrated in Scheme 3. Intermediate 7 prepared as described in Scheme II can be reacted with intermediate 12, which are commercially available or can be prepared by the methods known to one skilled in the art, in the presence of a catalyst such as Pd $(P(tBu)_3)_2$ and a base such as NaOtBu in a suitable solvent such as toluene to yield intermediate 13. The products can then be further elaborated to compounds of Formula I and IA using the procedures described above in Scheme 1 substituting intermediate 13 for intermediate 5.

Alternatively, compounds of Formula I and IA, wherein Y is defined as N $R_3$, may also be prepared by the procedures similar to those provided in Scheme 3. Those invention compounds can be alternatively obtained by treatment of the compounds of Formula I and IA, wherein $R_3$=H, with a suitable electrophile $R_3X$ (where X is a halide, mesylate, triflate, etc.) in the presence of a base such as $K_2CO_3$, $CsCO_3$, NaOtBu, etc.

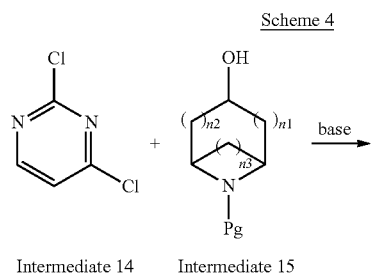

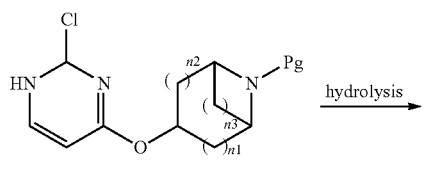

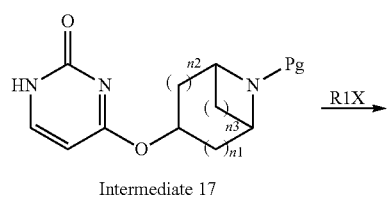

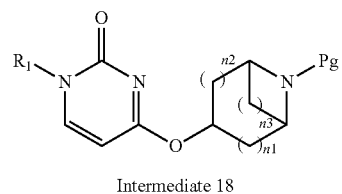

Alternatively, compounds of Formula I and IA can be synthesized by procedures outlined in Scheme 4. Intermediate 14, obtained from commercial sources, can be reacted with intermediate 15, which are commercially available or can be generated by many methods readily recognized by one skilled in the art (typical examples may be found in Sandler, S. et al., *Organic Functional Group Preparations*, Vol. I (Academic Press, Inc., 1983)), in the presence of a base such as NaH to yield intermediate 16. Hydrolysis of intermediate 16 can be achieved by treatment with DABCO in the presence of a base such as $K_2CO_3$ in dioxane/water at an elevated temperature. Intermediate 17 can then be reacted with $R_1X$ (where $R_1$ is defined with respect to Formula I or IA and X is a halide) in the presence of a ligand such as 8-hydroxyquinoline, CuI (I) and a base such as $K_2CO_3$ in a suitable solvent such as DMF, DMSO etc. at an elevated temperature to yield intermediate 18. The intermediate 18 can be carried forward to compounds of Formula I and IA following the procedures described above in Scheme 1 substituting intermediate 18 for intermediate 5.

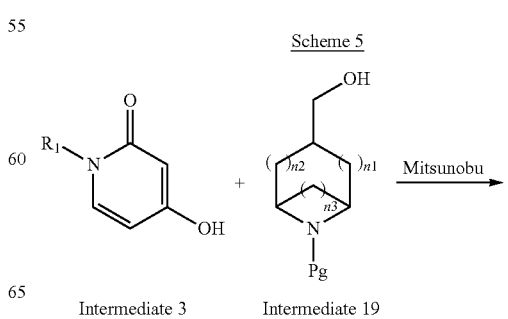

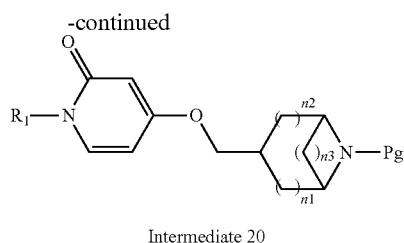

Intermediate 20

Compounds of Formula I and IA may be prepared by procedures illustrated in Scheme 5. Intermediate 3 generated as described in Scheme I can be reacted with intermediate 19, which are commercially available or can be made by many methods readily recognized by one skilled in the art (typical examples may be found in Sandler, S. et al., *Organic Functional Group Preparations*, Vol. I (Academic Press, Inc., 1983)), via Mitsunobo reaction to yield intermediate 20 which can be converted to Formula I or IA using the procedures described above in Scheme 1 substituting intermediate 20 for intermediate 5.

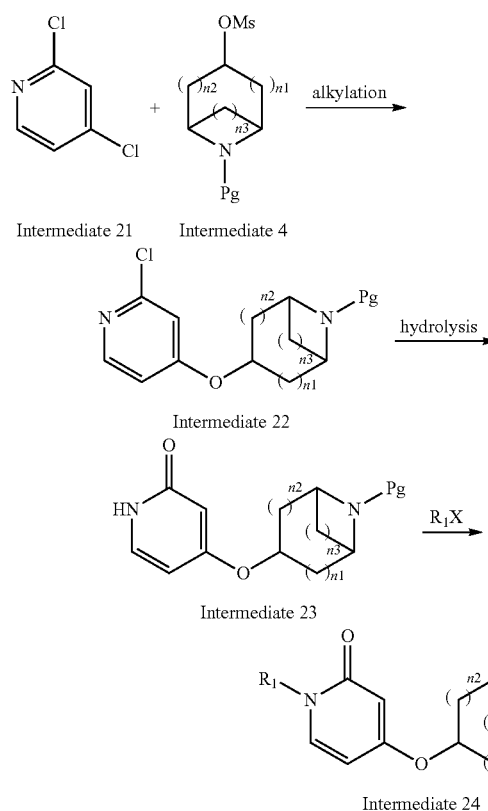

Alternatively, compounds of Formula I and IA may be synthesized as provided in Scheme 6. Intermediate 21, obtained from commercial sources, can be reacted with intermediate 4 prepared as described in Scheme I to give intermediate 22. Hydrolysis of intermediate 22 can be achieved by treatment with DABCO in the presence of a base such as $K_2CO_3$ in dioxane/water at an elevated temperature. Intermediate 23 can be treated with $R_1X$ (where $R_1$ is defined with respect to Formula I or IA and X is a halide) in the presence of a ligand such as 8-hydroxyquinoline, CuI (I) and a base such as $K_2CO_3$ in a suitable solvent such as DMF, DMSO etc at an elevated temperature to yield intermediate 24. The intermediate 24 can be carried forward to compounds of Formula I and IA following the procedures described above in Scheme 1 substituting intermediate 24 for intermediate 5.

Scheme 7

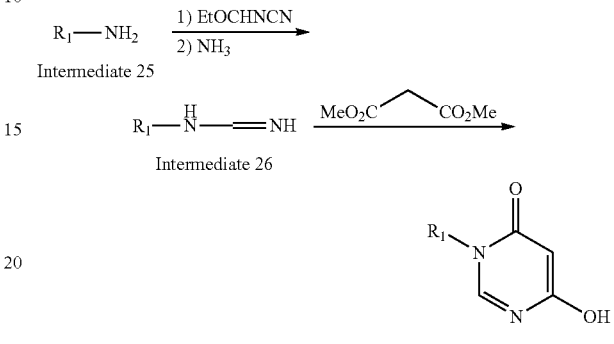

Intermediate 27

Compounds of Formula I and IA can also be prepared by procedures illustrated in Scheme 7. Intermediate 25 ($R_1$—$NH_2$, where $R_1$ is as defined in Formula I and IA), which are commercially available or can be made by methods recognized by one skilled in the art, can be converted to formamidine intermediate 26 in a two step procedure described by Donetti, A. et al. (*J. Med. Chem.*, 27:380 (1984)). Intermediate 26 can be reacted with dimethyl malonate to yield intermediate 27 using literature procedures (*J. Med. Chem.*, 45:3639 (2002)). The intermediate 27 can then be carried forward to compounds of Formula I and IA following the procedures described above in Scheme 1 substituting intermediate 28 for intermediate 3.

ABBREVIATIONS

The following abbreviations are employed in the Examples and elsewhere herein:

| | |
|---|---|
| EtOAc = | ethyl acetate |
| DMF = | dimethylformamide |
| THF = | tetrahydrofuran |
| $K_2CO_3$ = | potassiumm carbonate |
| $Na_2CO_3$ = | sodium carbonate |
| $MgSO_4$ = | magnesium sulfate |
| $SiO_2$ = | silicon dioxide |
| $CH_2Cl_2$ = | methylene chloride |
| MeOH = | methanol |
| HCl = | hydrochloric acid |
| $Cs_2CO_3$ = | cesium carbonate |
| KOH = | potassium hydroxide |
| DME = | 1,2-dimethoxyethane |
| $Pd(dppf)Cl_2$ = | [1,1'-bis(diphenylphosphino)ferrocene]dichloropalladium (II) |
| t-BuONa = | sodium tert-butoxide |
| $Pd_2(dba)_3$ = | tris(dibenzylideneacetone)dipalladium (0) |
| TFA = | trifluoroacetic acid |
| BINAP = | rac-2,2'-bis(diphenylphosphino)-1,1'-binaphthyl |
| DABCO = | 1,4-diazabicyclo[2.2.2]octane |
| mCPBA = | m-chloroperoxybenzoic acid |
| min = | minute(s) |
| h or hr = | hour(s) |
| mL or ml = | milliliter |
| g = | gram(s) |
| mg = | milligram(s) |

EXAMPLES mmol = millimole(s)
LRMS = low resolution mass spectrometry
NMR = nuclear magnetic resonance The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

Example 1

Preparation of tert-butyl 4-(1-(4-(methylsulfonyl)phenyl)-2-oxo-1,2-dihydropyridin-4-yloxy)piperidine-1-carboxylate

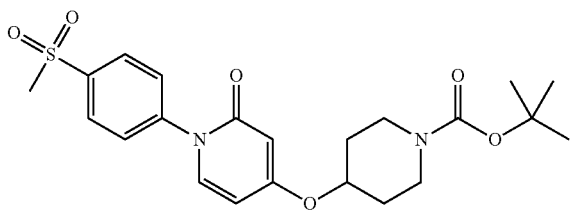

Step A. Preparation of 4-(benzyloxy)-1-(4-(methylsulfonyl)phenyl)pyridin-2(1H)-one A mixture of 4-benzyloxy-2(1H)-pyridone (6.87 g, 34.1 mmol, Aldrich), 4-bromophenyl methyl sulphone (8.01 g, 34.1 mmol, Combi-Blocks Inc.), copper(I) iodide (1.30 g, 6.82 mmol, Aldrich), 8-hydroxyquinoline (0.99 g, 6.82 mmol, Alfa Aesar) and potassium carbonate (6.12 g, 44.3 mmol, EMD) in DMSO (100 mL) was heated at 145° C. for 6 h, cooled to room temperature and then diluted with 10% NH$_4$OH aqueous solution (50 mL) and EtOAc (100 mL). The resulting mixture was filtered and the solid was washed with H$_2$O and EtOAc to give 8.0 g crude product as a greenish solid. MS (ESI) 356 (M+H).

Step B. Preparation of 4-hydroxy-1-(4-(methylsulfonyl)$_p$ h enyl)pyridin-2 (1H)-one A stirring suspension of 4-(benzyloxy)-1-(4-(methylsulfonyl)phenyl)pyridin-2(1H)-one (3.0 g, 8.44 mmol) and palladium on activated carbon (1.63 g, 10 wt. %, wet, Aldrich) in THF (150 mL) and methanol (250 mL) was placed under hydrogen (balloon) for 1 h. The resulting mixture was purged with nitrogen and then diluted with THF (150 mL) and methanol (50 mL). After stirring under nitrogen for 30 min, the mixture was filtered through a pad of CELITE® 545 filter aid and the filtrate was evaporated under reduced pressure to give 2.28 g crude product as a dark greenish solid. MS (ESI) 266 (M+H).

Step C. Preparation of tert-butyl 4-(methylsulfonyloxy)piperidine-1-carboxylate To a stirring solution of tert-butyl-4-hydroxy-1-piperidinecarboxylate (10.28 g, 51.08 mmol, Aldrich) and Et$_3$N (14.25 mL, 102.16 mmol, EMD) in CH$_2$Cl$_2$ (300 mL) at room temperature was added methanesulfonyl chloride (4.35 mL, 56.19 mmol, Aldrich) dropwise. The reaction mixture was stirred at room temperature for 4 h and washed with 0.1N HCl aqueous solution, H$_2$O and brine. The organic layer was dried with Na$_2$SO$_4$ and concentrate in vacuo to yield 14.3 g of the crude product as a light orange solid.

Step D

Example 1

A stirring mixture of 4-hydroxy-1-(4-(methylsulfonyl)phenyl)pyridin-2(1H)-one (2.27 g, 8.55 mmol), tert-butyl 4-(methylsulfonyloxy)piperidine-1-carboxylate (3.6 g, 12.83 mmol) and potassium carbonate (2.36 g, 17.1 mmol, EMD) in DMF (50 mL) was heated at 90° C. overnight and then cooled to room temperature. The resulting mixture was diluted with EtOAc and H$_2$O and the aqueous layer was extracted further with EtOAc (2×). The combined extracts were washed with H$_2$O/brine (1:1, 3×), dried (Na$_2$SO$_4$) and evaporated. The residual was purified by flash chromatography (0 to 10% MeOH/CH$_2$Cl$_2$) to yield 2.57 g (67%) of Example 1 as a yellow solid. $^1$H NMR (500 MHz, CDCl$_3$) δ 8.07 (d, J=8.80 Hz, 2 H), 7.62 (d, J=8.80 Hz, 2 H), 7.23 (d, J=7.70 Hz, 1 H), 6.06 (dd, J=7.42, 2.47 Hz, 1 H), 5.97 (d, J=2.75 Hz, 1 H), 4.38-4.57 (m, 1 H), 3.63-3.78 (m, 2 H), 3.22-3.45 (m, 2 H), 3.09 (s, 3 H), 1.93-2.03 (m, 2 H), 1.69-1.85 (m, 2 H), 1.48 (s, 9 H). MS (ESI) 449 (M+H).

Example 2

Preparation of 1,1,1-trifluoropropan-2-yl 4-(1-(2-fluoro-4-(methylsulfonyl)phenyl)-2-oxo-1,2-dihydropyridin-4-yloxy)piperidine-1-carboxylate

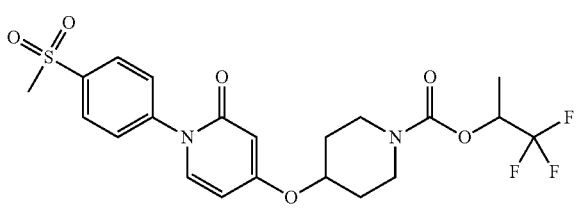 [SMILES: CC(OC(=O)N1CCC(Oc2ccn(-c3ccc(S(C)(=O)=O)cc3)c(=O)c2)CC1)C(F)(F)F]

Step A. Preparation of 1-(4-(methylsulfonyl)phenyl)-4-(piperidin-4-yloxy)pyridin-2(1H)-one hydrochloric acid salt A mixture of tert-butyl 4-(1-(4-(methylsulfonyl)phenyl)-2-oxo-1,2-dihydropyridin-4-yloxy)piperidine-1-carboxylate (2.515 g, 5.61 mmol) and hydrogen chloride (4.0 M in dioxane, 35.0 mL, Aldrich) in methanol (45 mL) was stirred for 1 h and then concentrated in vacuo. The obtained solid was dissolved in methanol and evaporated to give 2.28 g of the crude product as a dark yellow solid. MS (ESI) 349 (M+H).

Step B. Preparation of 1,1,1-trifluoropropan-2-yl chloroformate

To a mixture of 1,1,1-trifluoro-2-propanol (114.1 mg, 1.0 mmol, Matrix Scientific) and triphosgene (98 mg, 0.33 mmol, Aldrich) in ethyl ether (10 mL) at −40° C. was added pyridine (80 μL, 1.0 mmol, EMD) in ethyl ether (1.0 mL) dropwise. The reaction mixture was warmed to 0° C. and stirred for 6 h. The flask containing the above reaction mixture was put into a refrigerator overnight and then filtered. The filtrate was concentrated in vacuo in ice both to colorless oil which was used directly in the next step.

Step C

Example 2

To a suspension of 1-(4-(methylsulfonyl)phenyl)-4-(piperidin-4-yloxy)pyridin-2(1H)-one hydrochloric acid salt (30.8 mg, 0.08 mmol) in CH$_2$Cl$_2$ was added diisopropylethylamin (70 μL, 0.40 mmol, Aldrich) followed by addition of 1,1,1-trifluoropropan-2-yl chloroformate (⅓ of the material from Step B, 0.33 mmol) in CH$_2$Cl$_2$ (0.5 mL). The reaction mixture was stirred for 30 min and then evaporated under the reduced pressure to yield the crude product which was purified by preparative HPLC (C$_{18}$ column; 10-100% acetonitrile in water containing 0.05% trifluoroacetic acid) to give Example 2 (16.8 mg, off-white solid, 43%) upon lyophilization. $^1$H NMR (500 MHz, CDCl$_3$) δ 8.07 (d, J=8.80 Hz, 2 H), 7.59 (d, J=8.80 Hz, 2 H), 7.25 (d, J=7.70, 1 H), 6.03-6.22 (m, 2 H), 5.17-5.36 (m, 1 H), 4.57 (m, 1 H), 3.64-3.85 (m, 2 H), 3.37-3.56 (m, 2 H), 3.10 (s, 3 H), 1.95-2.08 (m, 2 H), 1.76-1.93 (m, 2 H), 1.42 (d, J=6.60 Hz, 3 H). MS (ESI) 489 (M+H).

Example 3

Preparation of isopropyl 4-(1-(4-(methylsulfonyl) phenyl)-2-oxo-1,2-dihydropyridin-4-yloxy)piperidine-1-carboxylate

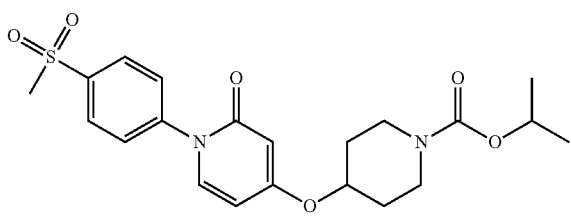 [SMILES: CC(C)OC(=O)N1CCC(Oc2ccn(-c3ccc(S(C)(=O)=O)cc3)c(=O)c2)CC1]

To a solution of tert-butyl 4-(1-(4-(methylsulfonyl)phenyl)-2-oxo-1,2-dihydropyridin-4-yloxy)piperidine-1-carboxylate (53 mg, 0.118 mmol) in CH$_2$Cl$_2$ (1.0 mL) was added TFA (0.5 mL) dropwise. The reaction mixture was stirred for 1 h and evaporated under reduced pressure. The residue was then dissolved in CH$_2$Cl$_2$ (1.5 mL) followed by addition of Et$_3$N (82 μL, 0.59 mmol) and isopropyl chloroformate (0.295 mL, 0.295 mmol). The resulting mixture was stirred at room temperature for 30 min, quenched with H$_2$O (0.2 mL) and then evaporated to dryness. The crude product was purified by preparative HPLC (C$_{18}$ column; 10-100% methanol in water containing 0.05% trifluoroacetic acid) to give Example 3 (44.5 mg, white solid, 87%) upon lyophilization. $^1$H NMR (500 MHz, CDCl$_3$) δ 8.09 (d, J=8.80 Hz, 2 H), 7.61 (d, J=8.25 Hz, 2 H), 7.30 (d, J=7.70 Hz, 1 H), 6.28 (d, J=2.20 Hz, 1 H), 6.19 (dd, J=7.70, 2.20 Hz, 1 H), 4.86-5.00 (m, 1 H), 4.51-4.63 (m, 1 H), 3.77 (app brs, 2 H), 3.33-3.44 (m, 2 H), 3.11 (s, 3 H), 1.96-2.11 (m, 2 H), 1.73-1.86 (m, J=7.15 Hz, 2 H), 1.26 (d, J=6.05 Hz, 6 H). MS (ESI) 435 (M+H).

Example 4

Preparation of tert-butyl 4-((1-(4-(methylsulfonyl) phenyl)-2-oxo-1,2-dihydropyridin-4-yloxy)methyl) piperidine-1-carboxylate

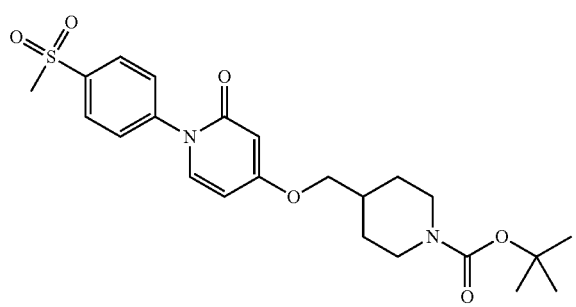 [SMILES: CC(C)(C)OC(=O)N1CCC(COc2ccn(-c3ccc(S(C)(=O)=O)cc3)c(=O)c2)CC1]

To a stirring solution of triphenylphosphine (86.6 mg, 0.33 mmol, Aldrich) in THF (1.5 mL) was added 4-hydroxy-1-(4-(methylsulfonyl)phenyl)pyridin-2(1H)-one (39.8 mg, 0.15 mmol), N-Boc-4-piperidinemethanol (71.0 mg, 0.33 mmol, Aldrich) and diisopropylazodicarboxylate (63.9 μL, 0.33 mmol, Aldrich). The reaction mixture was stirred for 1.5 h, quenched with methanol (1.5 mL) and then evaporated under reduced pressure. The residue was purified by flash chromatography (0-100% EtOAc/Hexanes) to give 33 mg (48%) of Example 4 as a white solid. $^1$H NMR (500 MHz, CDCl$_3$) δ 8.06 (d, J=8.80 Hz, 2 H), 7.61 (d, J=8.80 Hz, 2 H), 7.22 (d, J=7.70 Hz, 1 H), 6.06 (dd, J=7.70, 2.75 Hz, 1 H), 5.94 (d, J=2.20 Hz, 1 H), 4.18 (app brs, 2 H), 3.83 (d, J=6.05 Hz, 2 H), 3.09 (s, 3 H), 2.75 (app brs, 2 H), 1.91-2.09 (m, 1 H), 1.71-1.85 (m, 2 H), 1.47 (s, 9 H), 1.19-1.38 (m, 2 H). MS (ESI) 464 (M+H).

Example 5

Preparation of isopropyl 4-((1-(4-(methylsulfonyl) phenyl)-2-oxo-1,2-dihydropyridin-4-yloxy)methyl) piperidine-1-carboxylate

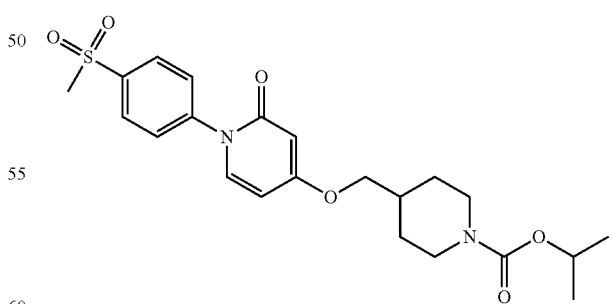

Example 5 was prepared according to procedures described in Example 3 substituting tert-butyl 4-((1-(4-(methylsulfonyl)phenyl)-2-oxo-1,2-dihydropyridin-4-yloxy) methyl)piperidine-1-carboxylate for tert-butyl 4-(1-(4-(methylsulfonyl)phenyl)-2-oxo-1,2-dihydropyridin-4-yloxy) piperidine-1-carboxylate. $^1$H NMR (500 MHz, CDCl$_3$) δ

8.07 (d, J=8.25 Hz, 2 H), 7.61 (d, J=8.80 Hz, 2 H), 7.23 (d, J=7.70 Hz, 1 H), 6.09 (dd, J=7.70, 2.75 Hz, 1 H), 6.01 (d, J=2.75 Hz, 1 H), 4.87-4.98 (m, 1 H), 4.23 (app brs, 2 H), 3.85 (d, J=6.05 Hz, 2 H), 3.09 (s, 3 H), 2.79 (t, J=12.65 Hz, 2 H), 1.87-2.06 (m, 1 H), 1.76-1.87 (d, J=12.10 Hz, 2 H), 1.18-1.37 (m, 6 H), 1.25 (d, J=6.05 Hz, 6 H). MS (ESI) 449 (M+H).

Example 6

Preparation of tert-butyl 4-(1-(4-(methylsulfonyl)phenyl)-2-oxo-1,2-dihydropyridin-4-yloxy)azepane-1-carboxylate

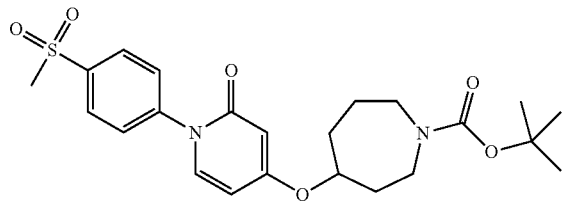 [SMILES: CC(C)(C)OC(=O)N1CCCC(Oc2ccn(-c3ccc(S(C)(=O)=O)cc3)c(=O)c2)CC1]

Example 6 was prepared according to procedures described in Example 1 substituting tert-butyl 4-hydroxyazepane-1-carboxylate (SynChem, Inc.) for tert-butyl-4-hydroxy-1-piperidinecarboxylate in Step C. $^1$H NMR (500 MHz, CDCl$_3$) δ 8.07 (d, J=8.80 Hz, 2 H), 7.61 (d, J=8.80 Hz, 2 H), 7.22 (d, J=7.70 Hz, 1 H), 6.03 (d, J=7.70 Hz, 1 H), 5.91 (s, 1 H), 4.40-4.51 (m, 1 H), 3.32-3.60 (m, 4 H), 3.09 (s, 3 H), 2.06-2.17 (m, 1 H), 1.87-2.03 (m, 4 H), 1.63-1.73 (m, 1 H), 1.48 (s, 9 H). MS (ESI) 463 (M+H).

Example 7

Preparation of isopropyl 4-(1-(4-(methylsulfonyl)phenyl)-2-oxo-1,2-dihydropyridin-4-yloxy)azepane-1-carboxylate

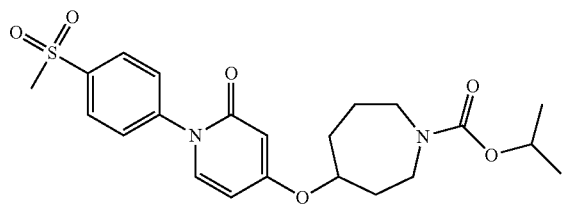 [SMILES: CC(C)OC(=O)N1CCCC(Oc2ccn(-c3ccc(S(C)(=O)=O)cc3)c(=O)c2)CC1]

Example 7 was prepared according to procedures described in Example 3 substituting tert-butyl 4-(1-(4-(methylsulfonyl)phenyl)-2-oxo-1,2-dihydropyridin-4-yloxy)azepane-1-carboxylate for tert-butyl 4-(1-(4-(methylsulfonyl)phenyl)-2-oxo-1,2-dihydropyridin-4-yloxy)piperidine-1-carboxylate. $^1$H NMR (500 MHz, CDCl$_3$) δ 8.08 (d, J=8.80 Hz, 2 H), 7.61 (d, J=8.80 Hz, 2 H), 7.29 (d, J=7.70 Hz, 1 H), 6.22 (s, 1 H), 6.17 (d, J=7.70 Hz, 1 H), 4.90-5.02 (m, 1 H), 4.48-4.56 (m, 1 H), 3.36-3.63 (m, 4 H), 3.11 (s, 3 H), 1.91-2.17 (m, 5 H), 1.64-1.77 (m, 1 H), 1.27 (d, J=6.05 Hz, 6 H). MS (ESI) 449 (M+H).

Example 8

Preparation of isopropyl 4-(1-(4-(cyanophenyl)-2-oxo-1,2-dihydropyridin-4-yloxy)piperidine-1-carboxylate

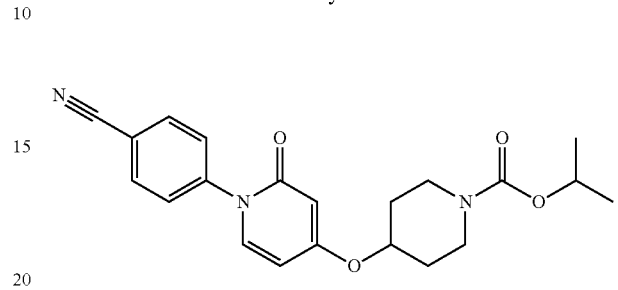

Step A. Preparation of 4-hydroxypyridin-2(1H)-one

A stirring mixture of 4-benzyloxy-2(1H)-pyridine (5.0 g, 24.85 mmol, Aldrich) and palladium on activated carbon (2.6 g, 10 wt. %, wet, Aldrich) in methanol (200 mL) was under hydrogen (balloon) for 2 h. The resulting mixture was purged with nitrogen and then diluted with methanol (50 mL) and CH$_2$Cl$_2$ (10 mL). After stirring under nitrogen for 30 min, the mixture was filtered through a pad of CELITE® 545 filter aid and the filtrate was evaporated under reduced pressure to give 2.73 g crude product as a light orange solid.

Step B. Preparation of isopropyl 4-(2-oxo-1,2-dihydropyridin-4-yloxy)piperidine-1-carboxylate A stirring mixture of 4-hydroxypyridin-2(1H)-one (1.5 g, 13.5 mmol), isopropyl 4-(methylsulfonyloxy)piperidine-1-carboxylate (5.0 g, 18.9 mmol, prepared according to the procedure described in Step C of Example 1) and potassium carbonate (3.7 g, 27.0 mmol, EMD) in DMF (80 mL) was heated at 140° C. for 2 h and then cooled to room temperature. The resulting mixture was diluted with EtOAc and H$_2$O and the aqueous layer was extracted further with EtOAc (7×). The combined extracts were washed with saturated NH$_4$Cl aqueous solution (2×), dried (Na$_2$SO$_4$) and evaporated. The residual was purified by flash chromatography (0 to 100% EtOAc/Hexanes and then 5% MeOH/CH$_2$Cl$_2$) to yield 1.67 g (44%) of the product as an off-white solid. MS (ESI) 281 (M+H).

Step C

Example 8

A mixture of isopropyl 4-(2-oxo-1,2-dihydropyridin-4-yloxy)piperidine-1-carboxylate (42 mg, 0.15 mmol,), 4-bromobenzonitrile (27.3 mg, 0.15 mmol, Aldrich.), copper(I) iodide (5.7 mg, 0.03 mmol, Aldrich), 8-hydroxyquinoline (4.4 mg, 0.03 mmol, Alfa Aesar) and potassium carbonate (26.9 mg, 0.195 mmol, EMD) in DMSO (0.6 mL) was heated under Microwave conditions (160° C., 30 min), then cooled to room temperature and finally purified by preparative HPLC (C$_{18}$ column; 0-100% methanol in water containing 0.05% trifluoroacetic acid) to give Example 8 (23.1 mg, off-white solid, 40%) upon lyophilization. $^1$H NMR (500 MHz, CDCl$_3$)

δ 7.79 (d, J=8.80 Hz, 2 H), 7.53 (d, J=8.80 Hz, 2 H), 7.21 (d, J=7.70 Hz, 1 H), 6.04 (dd, J=7.70, 2.75 Hz, 1 H), 5.96 (d, J=2.75 Hz, 1 H), 4.89-4.99 (m, 1 H), 4.44-4.55 (m, 1 H), 3.70-3.80 (m, 2 H), 3.33-3.43 (m, 2 H), 1.93-2.05 (m, 2 H), 1.72-1.85 (m, 2 H), 1.26 (d, J=6.05 Hz, 6 H). MS (ESI) 382 (M+H).

Example 9

Preparation of isopropyl 4-(1-(2-fluoro-4-(methylsulfonyl)phenyl)-2-oxo-1,2-dihydropyridin-4-yloxy)piperidine-1-carboxylate

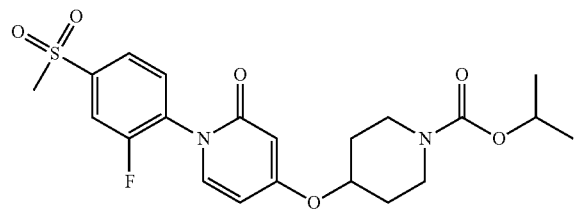 [SMILES: CC(C)OC(=O)N1CCC(Oc2ccn(-c3ccc(S(C)(=O)=O)cc3F)c(=O)c2)CC1]

Example 9 was prepared according to procedures described in Example 8 substituting 1-bromo-2-fluoro-4-(methylsulfonyl)benzene (prepared according to procedures described in International Patent Application No. WO 2004/089885) for 4-bromobenzonitrile in Step C except that the reaction was heated at 180° C. in a microwave for 1 h. $^1$H NMR (500 MHz, CDCl$_3$) δ 7.84-7.89 (m, 2 H), 7.62 (t, J=7.70 Hz, 1 H), 7.17 (d, J=7.70 Hz, 1 H), 6.11-6.20 (m, 2 H), 4.88-5.01 (m, 1 H), 4.47-4.61 (m, 1 H), 3.70-3.83 (m, 2 H), 3.35-3.48 (m, 2 H), 3.12 (s, 3 H), 1.96-2.06 (m, 2 H), 1.73-1.86 (m, 2 H), 1.26 (d, J=6.60 Hz, 6 H). MS (ESI) 453 (M+H).

Example 10

Preparation of isopropyl 4-(1-(4-methoxyphenyl)-2-oxo-1,2-dihydropyridin-4-yloxy)piperidine-1-carboxylate

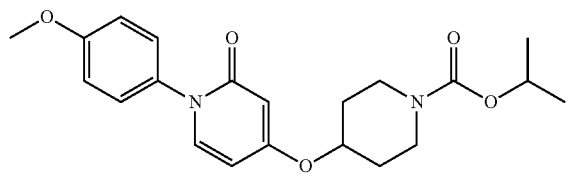 [SMILES: COc1ccc(-n2ccc(OC3CCN(C(=O)OC(C)C)CC3)cc2=O)cc1]

Example 10 was prepared according to procedures described in Example 8 substituting 1-bromo-4-methoxybenzene for 4-bromobenzonitrile in Step C. $^1$H NMR (500 MHz, CD$_3$OD). 7.50 (d, J=7.70 Hz, 1 H), 7.26 (d, J=8.80 Hz, 2 H), 7.04 (d, J=8.80 Hz, 2 H), 6.21 (dd, J=7.70, 2.75 Hz, 1 H), 6.04 (d, J=2.75 Hz, 1 H), 4.82-4.92 (m, 1 H), 4.64-4.74 (m, 1 H), 3.84 (s, 3 H), 3.69-3.80 (m, 2 H), 3.36-3.45 (m, 2 H), 1.96-2.07 (m, 2 H), 1.68-1.79 (m, 2 H), 1.26 (d, J=6.05 Hz, 6 H). MS (ESI) 387 (M+H).

Example 11

Preparation of isopropyl 4-(1-(3-cyanophenyl)-2-oxo-1,2-dihydropyridin-4-yloxy)piperidine-1-carboxylate

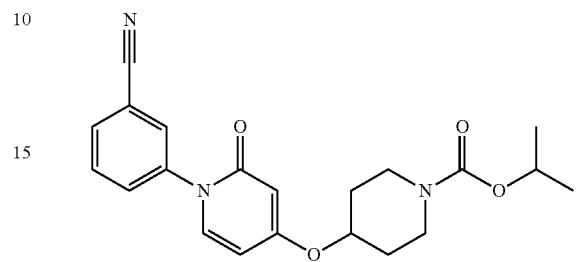

Example 11 was prepared according to procedures described in Example 8 substituting 3-bromobenzonitrile for 4-bromobenzonitrile in Step C. $^1$H NMR (500 MHz, CDCl$_3$) δ 7.56-7.81 (m, 4 H), 7.26 (d, J=7.70 Hz, 1 H), 6.26 (d, J=2.75 Hz, 1 H), 6.16 (dd, J=7.70, 2.75 Hz, 1 H), 4.89-5.05 (m, 1 H), 4.50-4.62 (m, 1 H), 3.77 (app brs, 2 H), 3.33-3.47 (m, 2 H), 1.93-2.09 (m, 2 H), 1.74-1.85 (m, 2 H), 1.26 (d, J=6.05 Hz, 6 H). MS (ESI) 382 (M+H).

Example 12

Preparation of isopropyl 4-(1-(3-methoxyphenyl)-2-oxo-1,2-dihydropyridin-4-yloxy)piperidine-1-carboxylate

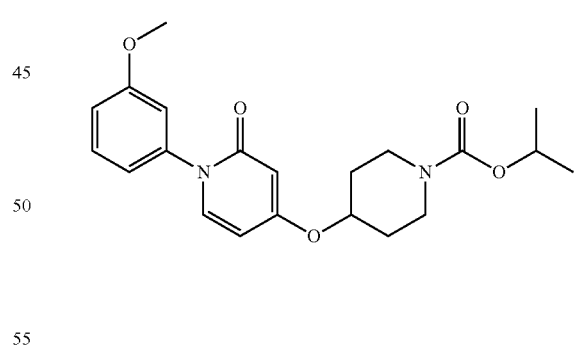

Example 12 was prepared according to procedures described in Example 8 substituting 1-bromo-3-methoxybenzene for 4-bromobenzonitrile in Step C. $^1$H NMR (500 MHz, CDCl$_3$) δ 7.39 (t, J=7.97 Hz, 1 H), 7.33 (d, J=7.70 Hz, 1 H), 6.98 (dd, J=8.25, 2.20 Hz, 1 H), 6.91 (d, J=8.25 Hz, 1 H), 6.89 (t, J=2.20 Hz, 1 H), 6.41 (d, J=2.20 Hz, 1 H), 6.16 (dd, J=7.70, 2.75 Hz, 1 H), 4.89-4.98 (m, 1 H), 4.51-4.60 (m, 1 H), 3.83 (s, 3 H), 3.77 (app brs, 2 H), 3.33-3.44 (m, 2 H), 1.96-2.06 (m, 2 H), 1.79 (app brs, 2 H), 1.26 (d, J=6.05 Hz, 6 H). MS (ESI) 387 (M+H).

Example 13

Preparation of isopropyl 4-(2-oxo-1-(4-(trifluoromethyl)phenyl)-1,2-dihydropyridin-4-yloxy)piperidine-1-carboxylate

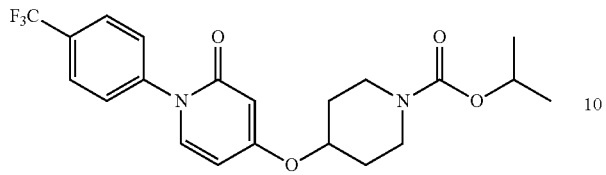

Example 13 was prepared according to procedures described in Example 8 substituting 1-bromo-4-(trifluoromethyl)benzene for 4-bromobenzonitrile in Step C. $^1$H NMR (500 MHz, CDCl$_3$) δ 7.76 (d, J=8.25 Hz, 2 H), 7.52 (d, J=8.25 Hz, 2 H), 7.25 (d, J=7.1 Hz, 1 H), 6.01-6.17 (m, 2 H), 4.83-5.03 (m, 1 H), 4.44-4.59 (m, 1 H), 3.76 (app brs, 2 H), 3.29-3.47 (m, 2 H), 1.90-2.11 (m, 2 H), 1.80 (app brs, 2 H), 1.26 (d, J=6.05 Hz, 6 H).). MS (ESI) 425 (M+H).

Example 14

Preparation of isopropyl 4-(1-(3-(methylsulfonyl)phenyl)-2-oxo-1,2-dihydropyridin-4-yloxy)piperidine-1-carboxylate

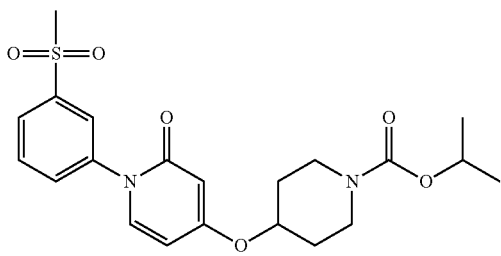 [SMILES: CC(C)OC(=O)N1CCC(Oc2ccn(-c3cccc(S(C)(=O)=O)c3)c(=O)c2)CC1]

Example 14 was prepared according to procedures described in Example 8 substituting 1-bromo-3-(methylsulfonyl)benzene (available from Oakwood Product Inc.) for 4-bromobenzonitrile in Step C. $^1$H NMR (500 MHz, CDCl$_3$) δ 8.01 (m, 1 H), 7.95 (s, 1 H), 7.72 (m, 2 H), 7.30 (d, J=7.70 Hz, 1 H), 6.11-6.23 (m, 2 H), 4.88-5.02 (m, 1 H), 4.47-4.62 (m, 1 H), 3.72-3.82 (m, 2 H), 3.31-3.47 (m, 2 H), 3.11 (s, 3 H), 1.95-2.08 (m, 2 H), 1.81 (app brs, 2 H), 1.26 (d, J=6.60 Hz, 6 H). MS (ESI) 435 (M+H).

Example 15

Preparation of isopropyl 4-(2-oxo-1-(pyridin-4-yl)-1,2-dihydropyridin-4-yloxy)piperidine-1-carboxylate, TFA salt

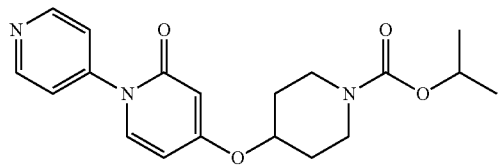 [SMILES: CC(C)OC(=O)N1CCC(Oc2ccn(-c3ccncc3)c(=O)c2)CC1]

Example 15 was prepared according to procedures described in Example 8 substituting 4-bromopyridine hydrochloride for 4-bromobenzonitrile in Step C. $^1$H NMR (500 MHz, CDCl$_3$) 14.50 (brs, 2 H), 8.34 (brs, 2 H), δ 7.32 (d, J=7.15 Hz, 1 H), 6.18 (d, J=7.15 Hz, 1 H), 6.06 (s, 1 H), 4.88-4.99 (m, 1 H), 4.53 (app brs, 1 H), 3.76 (app brs, 2 H), 3.34-3.44 (m, 2 H), 2.00 (app brs, 2 H), 1.80 (app brs, 2 H), 1.26 (d, J=6.05 Hz, 6 H). MS (ESI) 358 (M+H).

Example 16

Preparation of isopropyl 4-(2-oxo-1-(pyridin-3-yl)-1,2-dihydropyridin-4-yloxy)piperidine-1-carboxylate

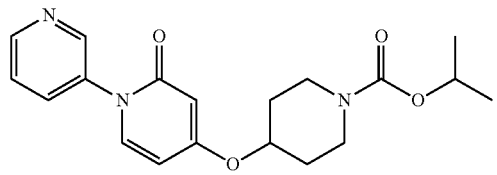 [SMILES: CC(C)OC(=O)N1CCC(Oc2ccn(-c3cccnc3)c(=O)c2)CC1]

Example 16 was prepared according to procedures described in Example 8 substituting 3-bromopyridine for 4-bromobenzonitrile in Step C. $^1$H NMR (500 MHz, CDCl$_3$) δ 8.74 (brs, 2 H), 8.08 (d, J=8.25 Hz, 1 H), 7.69 (brs, 1 H), 7.29 (d, J=8.25 Hz, 1 H), 6.13-6.18 (m, 2 H), 4.88-5.01 (m, 1 H), 4.46-4.62 (m, 1 H), 3.70-3.83 (m, 2 H), 3.31-3.46 (m, 2 H), 1.93-2.07 (m, 2 H), 1.74-1.86 (m, 2 H), 1.26 (d, J=6.60 Hz, 6 H). MS (ESI) 358 (M+H).

Example 17

Preparation of tert-butyl 3-((1-(4-(methylsulfonyl)phenyl)-2-oxo-1,2-dihydropyridin-4-yloxy)methyl)pyrrolidine-1-carboxylate

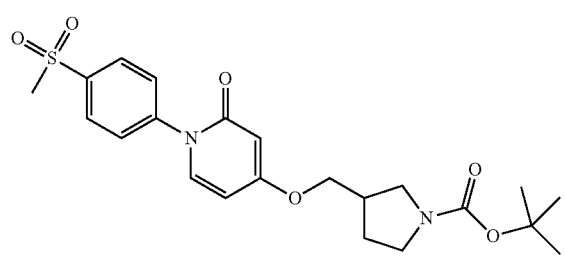 [SMILES: CC(C)(C)OC(=O)N1CCC(COc2ccn(-c3ccc(S(C)(=O)=O)cc3)c(=O)c2)C1]

Example 17 was prepared according to procedures described in Example 1 substituting tert-butyl 3-(hydroxymethyl)pyrrolidine-1-carboxylate for tert-butyl 4-hydroxy-1-piperidinecarboxylate in Step C. $^1$H NMR (500 MHz, CDCl$_3$) δ 8.07 (d, J=8.25 Hz, 2 H), 7.61 (d, J=8.80 Hz, 2 H), 7.22 (d, J=7.70 Hz, 1 H), 6.02-6.11 (m, 1 H), 5.95 (d, J=2.75 Hz, 1 H), 3.86-4.02 (m, 2 H), 3.32-3.67 (m, 3 H), 3.12-3.30 (m, 1 H), 3.09 (s, 3 H), 2.65-2.75 (m, 1 H), 2.03-2.15 (m, 1 H), 1.72-1.83 (m, 1 H), 1.48 (s, 9 H). MS (ESI) 449 (M+H).

Example 18

Preparation of 4-chlorophenyl 3-((1-(4-(methylsulfonyl)phenyl)-2-oxo-1,2-dihydropyridin-4-yloxy)methyl)pyrrolidine-1-carboxylate

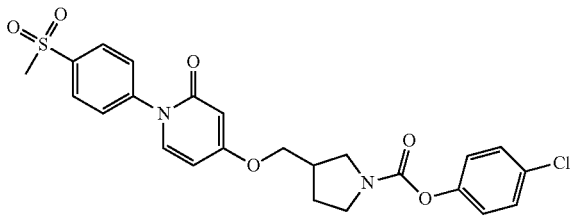 [SMILES: CS(=O)(=O)c1ccc(-n2ccc(OCC3CCN(C(=O)Oc4ccc(Cl)cc4)C3)cc2=O)cc1]

Example 18 was prepared according to procedures described in Example 2, Step A and Step C, substituting tert-butyl 3-((1-(4-(methylsulfonyl)phenyl)-2-oxo-1,2-dihydropyridin-4-yloxy)methyl)pyrrolidine-1-carboxylate for tert-butyl 4-(1-(4-(methylsulfonyl)phenyl)-2-oxo-1,2-dihydropyridin-4-yloxy)piperidine-1-carboxylate in Step A and 4-chlorophenyl chloroformate for 1,1,1-trifluoropropan-2-yl chloroformate in Step C. $^1$H NMR (500 MHz, CDCl$_3$) δ 8.07 (d, J=8.25 Hz, 2 H), 7.61 (d, J=8.25 Hz, 2 H), 7.32 (d, J=8.80 Hz, 2 H), 7.25 (dd, J=7.70, 3.30 Hz, 1 H), 7.09 (d, J=8.80 Hz, 2 H), 6.06-6.12 (m, 1 H), 5.98-6.03 (m, 1 H), 3.92-4.09 (m, 2 H), 3.49-3.92 (m, 3 H), 3.34-3.48 (m, 1 H), 3.09 (s, 3 H), 2.73-2.89 (m, 1 H), 2.12-2.29 (m, 1 H), 1.79-1.97 (m, 1 H). MS (ESI) 503 (M+H).

Example 19

Preparation of 2-chlorophenyl 3-((1-(4-(methylsulfonyl)phenyl)-2-oxo-1,2-dihydropyridin-4-yloxy)methyl)pyrrolidine-1-carboxylate

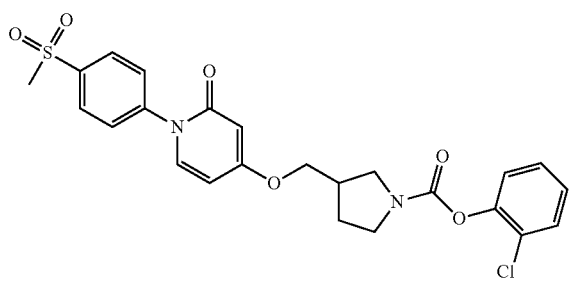 [SMILES: CS(=O)(=O)c1ccc(-n2ccc(OCC3CCN(C(=O)Oc4ccccc4Cl)C3)cc2=O)cc1]

Example 19 was prepared according to procedures described in Example 2, Step A and Step C, substituting tert-butyl 3-((1-(4-(methylsulfonyl)phenyl)-2-oxo-1,2-dihydropyridin-4-yloxy)methyl)pyrrolidine-1-carboxylate for tert-butyl 4-(1-(4-(methylsulfonyl)phenyl)-2-oxo-1,2-dihydropyridin-4-yloxy)piperidine-1-carboxylate in Step A and 2-chlorophenyl chloroformate for 1,1,1-trifluoropropan-2-yl chloroformate in Step C. $^1$H NMR (500 MHz, CDCl$_3$) δ 8.08 (d, J=8.80 Hz, 2 H), 7.61 (d, J=8.80 Hz, 2 H), 7.43 (d, J=8.25 Hz, 1 H), 7.23-7.31 (m, 3 H), 7.14-7.19 (m, 1 H), 6.10-6.21 (m, 2 H), 3.38-4.14 (m, 6 H), 3.10 (s, 3 H), 2.77-2.93 (m, 1 H), 2.15-2.32 (m, 1 H), 1.83-2.00 (m, 1 H). MS (ESI) 503 (M+H).

Example 20

Preparation of tert-butyl 3-((1-(4-(methylsulfonyl)phenyl)-2-oxo-1,2-dihydropyridin-4-yloxy)methyl)azetidine-1-carboxylate

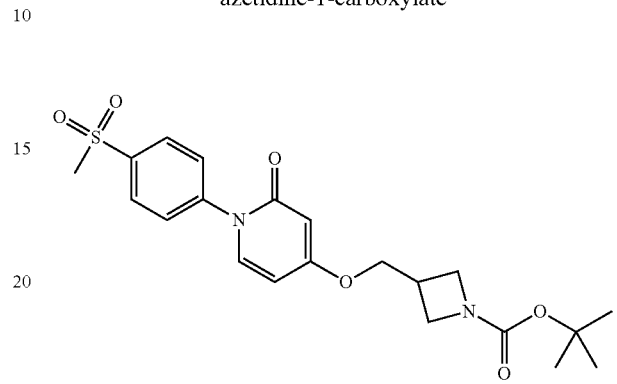

Example 20 was prepared according to procedures described in Example 1 substituting tert-butyl 3-(hydroxymethyl)azetidine-1-carboxylate for tert-butyl 4-hydroxy-1-piperidinecarboxylate in Step C. $^1$H NMR (500 MHz, CDCl$_3$) δ 8.07 (d, J=8.80 Hz, 2 H), 7.62 (d, J=8.80 Hz, 2 H), 7.23 (d, J=7.70 Hz, 1 H), 6.07 (dd, J=7.70, 2.75 Hz, 1 H), 5.97 (d, J=2.75 Hz, 1 H), 4.06-4.14 (m, 4 H), 3.79 (dd, J=8.80, 4.95 Hz, 2 H), 3.09 (s, 3 H), 2.94-3.05 (m, 1 H), 1.46 (s, 9 H). MS (ESI) 435 (M+H).

Example 21

Preparation of 4-chlorophenyl 3-((1-(4-(methylsulfonyl)phenyl)-2-oxo-1,2-dihydropyridin-4-yloxy)methyl)azetidine-1-carboxylate

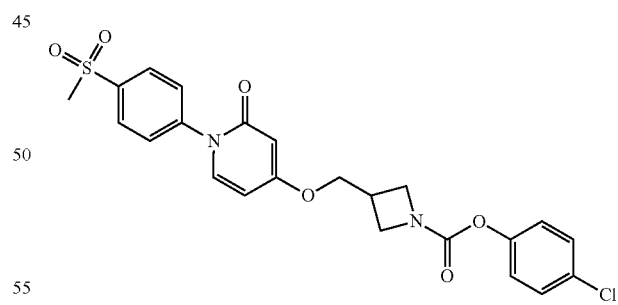

Example 21 was prepared according to procedures described in Example 2, Step A and Step C, substituting tert-butyl 3-((1-(4-(methylsulfonyl)phenyl)-2-oxo-1,2-dihydropyridin-4-yloxy)methyl)azetidine-1-carboxylate for tert-butyl 4-(1-(4-(methylsulfonyl)phenyl)-2-oxo-1,2-dihydropyridin-4-yloxy)piperidine-1-carboxylate in Step A and 4-chlorophenyl chloroformate for 1,1,1-trifluoropropan-2-yl chloroformate in Step C. $^1$H NMR (500 MHz, CDCl$_3$) δ 8.09 (d, J=8.25 Hz, 2 H), 7.62 (d, J=8.80 Hz, 2 H), 7.29-7.36 (m, 3 H), 7.05-7.12 (m, 2 H), 6.16-6.25 (m, 2 H), 4.38 (app br. s, 1

H), 4.28 (app br. s, 1 H), 4.21 (d, J=6.05 Hz, 2 H), 4.09 (app br. s, 1 H), 4.00 (app br. s, 1 H), 3.14-3.23 (m, 1 H), 3.11 (s, 3 H). MS (ESI) 489 (M+H).

Example 22

Preparation of 2-chlorophenyl 3-((1-(4-(methylsulfonyl)phenyl)-2-oxo-1,2-dihydropyridin-4-yloxy)methyl)azetidine-1-carboxylate

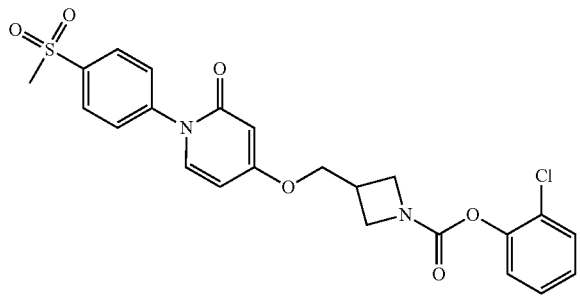 [SMILES: CS(=O)(=O)c1ccc(-n2ccc(OCC3CN(C(=O)Oc4ccccc4Cl)C3)cc2=O)cc1]

Example 22 was prepared according to procedures described in Example 2, Step A and Step C, substituting tert-butyl 3-((1-(4-(methylsulfonyl)phenyl)-2-oxo-1,2-dihydropyridin-4-yloxy)methyl)azetidine-1-carboxylate for tert-butyl 4-(1-(4-(methylsulfonyl)phenyl)-2-oxo-1,2-dihydropyridin-4-yloxy)piperidine-1-carboxylate in Step A and 2-chlorophenyl chloroformate for 1,1,1-trifluoropropan-2-yl chloroformate in Step C. $^1$H NMR (500 MHz, CDCl$_3$) δ 8.09 (d, J=8.25 Hz, 2 H), 7.62 (d, J=8.25 Hz, 2 H), 7.43 (dd, J=7.97, 1.37 Hz, 1 H), 7.32 (d, J=7.70 Hz, 1 H), 7.16-7.31 (m, 3 H), 6.28 (d, J=2.20 Hz, 1 H), 6.25 (dd, J=7.70, 2.75 Hz, 1 H), 4.41 (app brs, 1 H), 4.31 (app brs, 1 H), 4.23 (d, J=6.05 Hz, 2 H), 4.20 (app brs, 1 H), 4.04 (app brs, 1 H) 3.15-3.26 (m, 1 H), 3.11 (s, 3 H). MS (ESI) 489 (M+H).

Example 23

Preparation of 1-methyl-5-(trifluoromethyl)-1H-pyrazol-3-yl 4-(1-(4-(methylsulfonyl)phenyl)-2-oxo-1,2-dihydropyridin-4-yloxy)piperidine-1-carboxylate

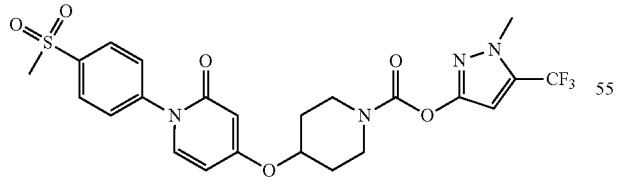

Example 23 was prepared according to procedures described in Example 2 substituting 1-methyl-5-(trifluoromethyl)-1H-pyrazol-3-ol for 1,1,1-trifluoro-2-propanol in Step B. $^1$H NMR (500 MHz, CDCl$_3$) δ 8.08 (d, J=8.80 Hz, 2 H), 7.62 (d, J=8.80 Hz, 2 H), 7.26 (d, J=7.70 Hz, 1 H), 6.50 (s, 1 H), 6.09 (dd, J=7.70, 2.75 Hz, 1 H), 6.02 (d, J=2.75 Hz, 1 H), 4.55-4.63 (m, 1 H), 3.91 (s, 3 H), 3.82-3.92 (m, 1 H), 3.73- 3.83 (m, 1 H), 3.63-3.73 (m, 1 H), 3.54-3.63 (m, 1 H), 3.10 (s, 3 H), 2.01-2.12 (m, 2 H), 1.86-1.98 (m, 2 H). MS (ESI) 489 (M+H).

Example 24

Preparation of (3-exo)-tert-butyl 3-(1-(4-(methylsulfonyl)phenyl)-2-oxo-1,2-dihydropyridin-4-yloxy)-8-azabicyclo[3.2.1]octane-8-carboxylate Example 24 was prepared according to procedures described in Example 1 substituting (3-endo)-tert-butyl 3-hydroxy-8-azabicyclo[3.2.1]octane-8-carboxylate for tert-butyl 4-hydroxy-1-piperidinecarboxylate in Step C. $^1$H NMR (500 MHz, CDCl$_3$) δ 8.07 (d, J=8.80 Hz, 2 H), 7.61 (d, J=8.80 Hz, 2 H), 7.20 (d, J=7.70 Hz, 1 H), 5.97-6.02 (m, 2 H), 4.66-4.81 (m, 1 H), 4.37 (app brs, 1 H), 4.28 (app brs, 1 H), 3.09 (s, 3 H), 1.99-2.19 (m, 4 H), 1.65-1.90 (m, 4 H), 1.49 (s, 9 H). MS (ESI) 475 (M+H).

Example 25

Preparation of (3-endo)-tert-butyl 3-(1-(4-(methylsulfonyl)phenyl)-2-oxo-1,2-dihydropyridin-4-yloxy)-8-azabicyclo[3.2.1]octane-8-carboxylate Example 25 was prepared according to procedures described in Example 1 substituting (3-exo)-tert-butyl 3-hydroxy-8-azabicyclo[3.2.1]octane-8-carboxylate for tert-butyl 4-hydroxy-1-piperidinecarboxylate in Step C. $^1$H NMR (500 MHz, CDCl$_3$) δ 8.07 (d, J=8.25 Hz, 2 H), 7.61 (d, J=8.25 Hz, 2 H), 7.24 (d, J=7.70 Hz, 1 H), 6.03 (dd, J=7.70, 2.75 Hz, 1 H), 5.85 (d, J=2.20 Hz, 1 H), 4.62 (t, J=4.40 Hz, 1 H), 4.29

(app brs, 1 H), 4.21 (app brs, 1 H), 3.09 (s, 3 H), 1.92-2.29 (m, 8 H), 1.48 (s, 9 H). MS (ESI) 475 (M+H).

Example 26

Preparation of (3-exo)-isopropyl 3-(1-(4-(methylsulfonyl)phenyl)-2-oxo-1,2-dihydropyridin-4-yloxy)-8-azabicyclo[3.2.1]octane-8-carboxylate

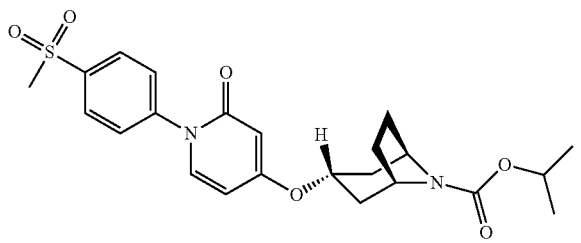

Example 26 was prepared according to procedures described in Example 3 substituting (3-exo)-tert-butyl 3-(1-(4-(methylsulfonyl)phenyl)-2-oxo-1,2-dihydropyridin-4-yloxy)-8-azabicyclo[3.2.1]octane-8-carboxylate for tert-butyl 4-(1-(4-(methylsulfonyl)phenyl)-2-oxo-1,2-dihydropyridin-4-yloxy)piperidine-1-carboxylate. $^1$H NMR (500 MHz, CDCl$_3$) δ 8.07 (d, J=8.25 Hz, 2 H), 7.61 (d, J=8.80 Hz, 2 H), 7.22 (d, J=7.70 Hz, 1 H), 6.06 (d, J=2.75 Hz, 1 H), 6.03 (dd, J=7.70, 2.75 Hz, 1 H), 4.91-5.03 (m, 1 H), 4.70-4.81 (m, 1 H), 4.41 (app brs, 1 H), 4.36 (app brs, 1 H), 3.10 (s, 3 H), 1.99-2.23 (m, 4 H), 1.66-1.92 (m, 4 H), 1.27 (d, J=6.05 Hz, 6 H). MS (ESI) 461 (M+H).

Example 27

Preparation of (3-endo)-isopropyl 3-(1-(4-(methylsulfonyl)phenyl)-2-oxo-1,2-dihydropyridin-4-yloxy)-8-azabicyclo[3.2.1]octane-8-carboxylate

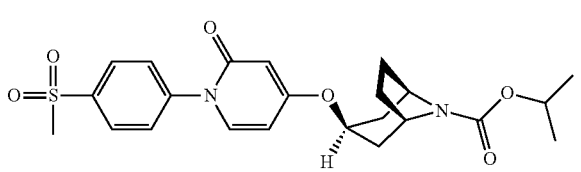

Example 27 was prepared according to procedures described in Example 3 substituting (3-endo)-tert-butyl 3-(1-(4-(methylsulfonyl)phenyl)-2-oxo-1,2-dihydropyridin-4-yloxy)-8-azabicyclo[3.2.1]octane-8-carboxylate for tert-butyl 4-(1-(4-(methylsulfonyl)phenyl)-2-oxo-1,2-dihydropyridin-4-yloxy)piperidine-1-carboxylate. $^1$H NMR (500 MHz, CDCl$_3$) δ 8.08 (d, J=8.25 Hz, 2 H), 7.61 (d, J=8.80 Hz, 2 H), 7.26 (d, J=7.70 Hz, 1 H), 6.09 (dd, J=7.70, 2.75 Hz, 1 H), 5.97 (d, J=2.75 Hz, 1 H), 4.92-5.00 (m, 1 H), 4.63 (t, J=4.67 Hz, 1 H), 4.30 (app brs, 2 H), 3.10 (s, 3 H), 1.96-2.35 (m, 8 H), 11.27 (d, J=6.60 Hz, 6 H). MS (ESI) 461 (M+H).

Example 28

Preparation of (3-exo)-1-(4-(methylsulfonyl)phenyl)-4-(8-(pyrimidin-2-yl)-8-azabicyclo[3.2.1]octan-3-yloxy)pyridin-2(1H)-one, TFA salt

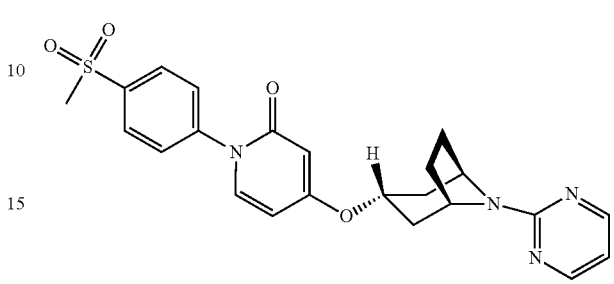

Step A. Preparation of (3-exo)-4-(8-azabicyclo[3.2.1]octan-3-yloxy)-1-(4-(methylsulfonyl)phenyl)pyridin-2(1H)-one hydrochloric acid salt (3-Exo)-4-(8-azabicyclo[3.2.1]octan-3-yloxy)-1-(4-(methylsulfonyl)phenyl)pyridin-2(1H)-one hydrochloric acid salt was prepared according to procedures described in Example 2, Step A, substituting (3-exo)-tert-butyl 3-(1-(4-(methylsulfonyl)phenyl)-2-oxo-1,2-dihydropyridin-4-yloxy)-8-azabicyclo[3.2.1]octane-8-carboxylate for tert-butyl 4-(1-(4-(methylsulfonyl)phenyl)-2-oxo-1,2-dihydropyridin-4-yloxy)piperidine-1-carboxylate. MS (ESI) 375 (M+H).

Step B

Example 28

A mixture of (3-exo)-4-(8-azabicyclo[3.2.1]octan-3-yloxy)-1-(4-(methylsulfonyl)phenyl)pyridin-2(1H)-one hydrochloric acid salt (41 mg, 0.10 mmol,), 2-bromopyrimidine (31.8 mg, 0.20 mmol, Alfa Aesar) and potassium carbonate (55.2 mg, 0.40 mmol, EMD) in DMF (0.8 mL) was under Microwave conditions (160° C., 30 min) and then cooled to room temperature. The reaction mixture was purified by preparative HPLC (C$_{18}$ column; 0-100% methanol in water containing 0.05% trifluoroacetic acid) to give Example 28 (17.0 mg, yellow solid, TFA salt, 30%) upon lyophilization. $^1$H NMR (500 MHz, CDCl$_3$) δ 8.53 (d, J=4.95 Hz, 2 H), 8.08 (d, J=8.80 Hz, 2 H), 7.60 (d, J=8.25 Hz, 2 H), 7.23 (d, J=7.70 Hz, 1 H), 6.70 (t, J=5.22 Hz, 1 H), 6.25 (d, J=2.20 Hz, 1 H), 6.03 (dd, J=7.70, 2.75 Hz, 1 H), 4.98 (m, 2 H), 4.86-4.97 (m, 1 H), 3.10 (s, 3 H), 2.26-2.40 (m, 2 H), 2.14-2.27 (m, 2 H), 1.92-2.03 (m, 2 H), 1.79-1.92 (m, 2 H). MS (ESI) 461 (M+H).

Example 29

Preparation of (3-exo)-4-(8-(5-ethylpyrimidin-2-yl)-8-azabicyclo[3.2.1]octan-3-yloxy)-1-(4-(methylsulfonyl)phenyl)pyridin-2(1H)-one. TFA salt

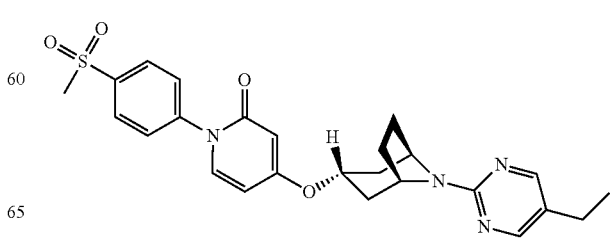

Example 29 was prepared according to procedures described in Example 28 substituting 2-chloro-5-ethylpyrimidine for 2-bromopyrimidine in Step B except that the reaction was heated in a microwave at 160° C. for 1 h. $^{1}$H NMR (500 MHz, CDCl$_{3}$) δ 8.35 (s, 2 H), 8.07 (d, J=8.80 Hz, 2 H), 7.61 (d, J=8.25 Hz, 2 H), 7.19 (d, J=7.70 Hz, 1 H), 6.07 (d, J=2.20 Hz, 1 H), 5.96 (dd, J=7.70, 2.75 Hz, 1 H), 4.81-4.97 (m, 2 H), 3.09 (s, 3 H), 2.54 (q, J=7.33 Hz, 2 H), 2.14-2.30 (m, 4 H), 1.78-1.98 (m, 4 H), 1.24 (t, J=7.70 Hz, 3 H). MS (ESI) 481 (M+H).

Example 30

Preparation of (3-exo)-cyclopentyl 3-(1-(4-(methylsulfonyl)phenyl)-2-oxo-1,2-dihydropyridin-4-yloxy)-8-azabicyclo[3.2.1]octane-8-carboxylate

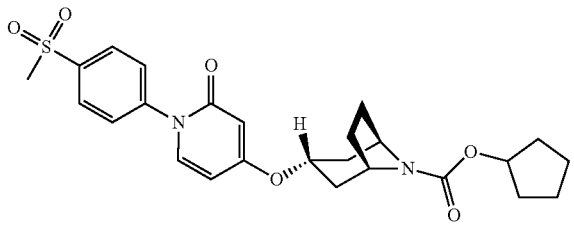

Example 30 was prepared according to procedures described in Example 2, Step C, substituting (3-exo)-4-(8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt and cyclopentyl chloroformate for 1,1,1-trifluoropropan-2-yl chloroformate. $^{1}$H NMR (500 MHz, CDCl$_{3}$) δ 8.08 (d, J=8.80 Hz, 2 H), 7.61 (d, J=8.80 Hz, 2 H), 7.26 (d, J=7.70 Hz, 1 H), 6.25 (d, J=2.75 Hz, 1 H), 6.10 (dd, J=7.70, 2.75 Hz, 1 H), 5.15-5.19 (m, 1 H), 4.71-4.83 (m, 1 H), 4.42 (app brs, 1 H), 4.32 (app brs, 1 H), 3.10 (s, 3 H), 2.03-2.21 (m, 4 H), 1.51-1.94 (m, 12 H). MS (ESI) 487 (M+H).

Example 31

Preparation of (3-exo)-4-chlorophenyl 3-(1-(4-(methylsulfonyl)phenyl)-2-oxo-1,2-dihydropyridin-4-yloxy)-8-azabicyclo[3.2.1]octane-8-carboxylate

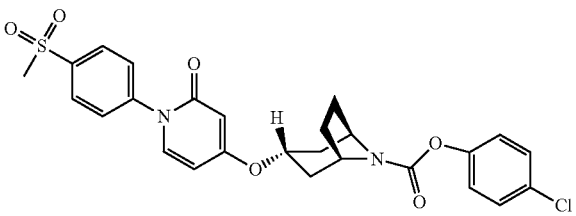

Example 31 was prepared according to procedures described in Example 2, Step C, substituting (3-exo)-4-(8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt and 4-chlorophenyl chloroformate for 1,1,1-trifluoropropan-2-yl chloroformate. $^{1}$H NMR (500 MHz, CDCl$_{3}$) δ 8.08 (d, J=8.80 Hz, 2 H), 7.62 (d, J=8.25 Hz, 2 H), 7.34 (d, J=8.80 Hz, 2 H), 7.22 (d, J=7.15 Hz, 1 H), 7.10 (d, J=8.80 Hz, 2 H), 5.98-6.06 (m, 2 H), 4.75-4.85 (m, 1 H), 4.58 (app brs, 1 H), 4.51 (app brs, 1 H), 3.10 (s, 3 H), 2.08-2.36 (m, 4 H), 1.77-2.00 (m, 4 H). MS (ESI) 529 (M+H).

Example 32

Preparation of (3-exo)-1,1,1-trifluoro-2-methylpropan-2-yl 3-(1-(4-(methylsulfonyl)phenyl)-2-oxo-1,2-dihydropyridin-4-yloxy)-8-azabicyclo[3.2.1]octane-8-carboxylate

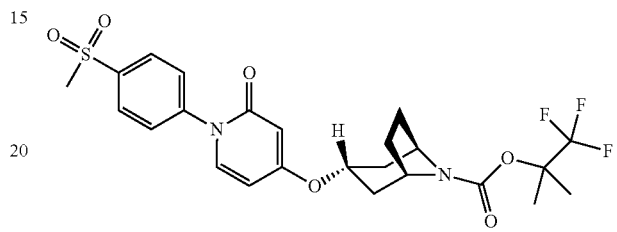

Example 32 was prepared according to procedures described in Example 2, Step B-C, substituting 2-(trifluoromethyl)propan-2-ol for 1,1,1-trifluoro-2-propanol in Step B and (3-exo)-4-(8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt in Step C. $^{1}$H NMR (500 MHz, CDCl$_{3}$) δ 8.07 (d, J=8.25 Hz, 2 H), 7.61 (d, J=8.80 Hz, 2 H), 7.21 (d, J=7.70 Hz, 1 H), 6.01 (dd, J=7.70, 2.75 Hz, 1 H), 5.97 (d, J=2.75 Hz, 1 H), 4.69-4.79 (m, 1 H), 4.38 (app brs, 1 H), 4.30 (app brs, 1 H), 3.09 (s, 3 H), 2.00-2.26 (m, 4 H), 1.67-1.90 (m, 4 H), 1.73 (d, J=16.50 Hz, 6 H). MS (ESI) 529 (M+H).

Example 33

Preparation of (3-exo)-1,3-difluoro-2-methylpropan-2-yl 3-(1-(4-(methylsulfonyl)phenyl)-2-oxo-1,2-dihydropyridin-4-yloxy)-8-azabicyclo[3.2.1]octane-8-carboxylate

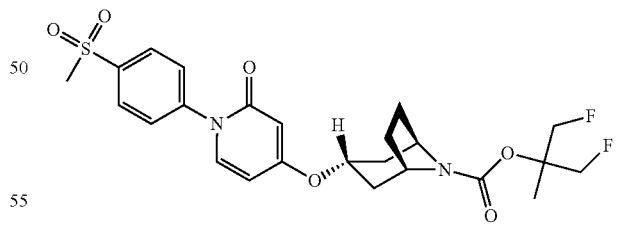

Example 33 was prepared according to procedures described in Example 2, Step B-C, substituting 1,3-difluoro-2-methylpropan-2-ol for 1,1,1-trifluoro-2-propanol in Step B and (3-exo)-4-(8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt in Step C. $^{1}$H NMR (500 MHz, CDCl$_{3}$) δ 8.07 (d, J=8.80 Hz, 2 H), 7.61 (d, J=8.80 Hz, 2 H), 7.21 (d, J=7.70 Hz, 1 H), 6.01 (dd, J=7.42, 2.47 Hz, 1 H), 5.97 (d, J=2.75 Hz, 1 H), 4.69-4.78 (m, 2 H), 4.63 (dd, J=9.35, 2.20 Hz, 1 H), 4.54 (dd, J=9.35, 2.20 Hz, 1 H), 4.37 (app brs, 1 H), 4.32 (app brs, 1 H), 3.09 (s, 3 H), 2.03-2.23 (m, 4 H), 1.69-1.89 (m, 4 H), 1.56 (t, J=2.20 Hz, 3 H). MS (ESI) 511 (M+H).

Example 34

Preparation of (3-exo)-1,1,1-trifluoropropan-2-yl 3-(1-(4-(methylsulfonyl)phenyl)-2-oxo-1,2-dihydropyridin-4-yloxy)-8-azabicyclo[3.2.1]octane-8-carboxylate

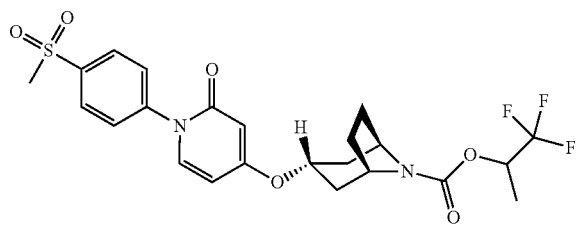

Example 34 was prepared according to procedures described in Example 2, StepC, substituting (3-exo)-4-(8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt. $^1$H NMR (500 MHz, CDCl$_3$) δ 8.08 (d, J=8.80 Hz, 2 H), 7.61 (d, J=8.80 Hz, 2 H), 7.24 (d, J=7.70 Hz, 1 H), 6.16 (s, 1 H), 6.01-6.11 (m, 1 H), 5.23-5.36 (m, 1 H), 4.72-4.83 (m, 1 H), 4.38-4.49 (m, 2 H), 3.10 (s, 3 H), 1.65-2.31 (m, 8 H), 1.38-1.51 (m, 3 H). MS (ESI) 515 (M+H).

Example 35

Preparation of (3-exo)-sec-butyl 3-(1-(4-(methylsulfonyl)phenyl)-2-oxo-1,2-dihydropyridin-4-yloxy)-8-azabicyclo[3.2.1]octane-8-carboxylate

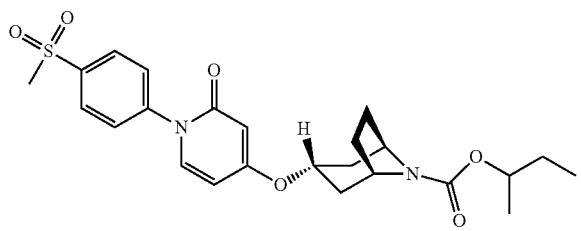

Example 35 was prepared according to procedures described in Example 2, Step B-C, substituting 2-butanol for 1,1,1-trifluoro-2-propanol in Step B and (3-exo)-4-(8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt in Step C. $^1$H NMR (500 MHz, CDCl$_3$) δ 8.08 (d, J=8.80 Hz, 2 H), 7.61 (d, J=8.25 Hz, 2 H), 7.25 (d, J=7.70 Hz, 1 H), 6.22 (d, J=2.75 Hz, 1 H), 6.09 (dd, J=7.42, 2.47 Hz, 1 H), 4.72-4.84 (m, 2 H), 4.33-4.46 (m, 2 H), 3.10 (s, 3 H), 2.00-2.23 (m, 4 H), 1.50-1.95 (m, 6 H), 1.25 (d, J=6.05 Hz, 3 H), 0.94 (app brs, 3 H). MS (ESI) 475 (M+H).

Example 36

Preparation of (3-exo)-1-methyl-5-(trifluoromethyl)-1H-pyrazol-3-yl 3-(1-(4-(methylsulfonyl)phenyl)-2-oxo-1,2-dihydropyridin-4-yloxy)-8-azabicyclo[3.2.1]octane-8-carboxylate

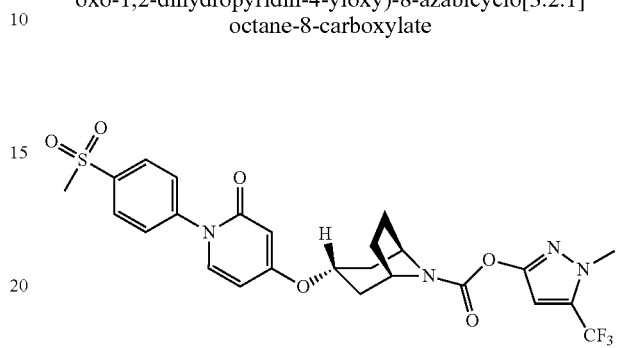

Example 36 was prepared according to procedures described in Example 2, Step B-C, substituting 1-methyl-5-(trifluoromethyl)-1H-pyrazol-3-ol for 1,1,1-trifluoro-2-propanol in Step B and (3-exo)-4-(8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt in Step C. $^1$H NMR (500 MHz, CDCl$_3$) δ 8.10 (d, J=8.25 Hz, 2 H), 7.61 (d, J=8.80 Hz, 2 H), 7.32 (d, J=7.70 Hz, 1 H), 6.61 (d, J=2.75 Hz, 1 H), 6.54 (s, 1 H), 6.22 (dd, J=7.70, 2.75 Hz, 1 H), 4.82-4.94 (m, 1 H), 4.58-4.65 (m, 1 H), 4.48-4.57 (m, 1 H), 3.93 (s, 3 H), 3.12 (s, 3 H), 2.07-2.35 (m, 4 H), 1.84-2.00 (m, 4 H). MS (ESI) 567 (M+H).

Example 37

Preparation of (3-exo)-4-methoxyphenyl 3-(1-(4-(methylsulfonyl)phenyl)-2-oxo-1,2-dihydropyridin-4-yloxy)-8-azabicyclo[3.2.1]octane-8-carboxylate

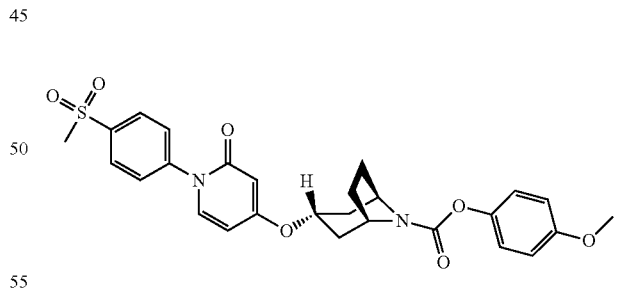

Example 37 was prepared according to procedures described in Example 2, Step C, substituting (3-exo)-4-(-8-azabicyclo[3.2.1]octan-3-yloxy)-1-(4-(methylsulfonyl)phenyl)pyridin-2(1H)-one hydrochloric acid salt for 1-(4-(methylsulfonyl)phenyl)-4-(piperidin-4-yloxy)pyridin-2(1H)-one hydrochloric acid salt and 4-methoxyphenyl chloroformate for 1,1,1-trifluoropropan-2-yl chloroformate. $^1$H NMR (500 MHz, CDCl$_3$) δ 8.09 (d, J=8.25 Hz, 2 H), 7.61 (d, J=8.80 Hz, 2 H), 7.28 (d, J=7.70 Hz, 1 H), 7.06 (d, J=8.80 Hz, 2 H), 6.89 (d, J=8.80 Hz, 2 H), 6.35 (d, J=2.75 Hz, 1 H), 6.14 (dd, J=7.70, 2.20 Hz, 1 H), 4.79-4.92 (m, 1 H), 4.60 (app brs, 1 H), 4.51

(app brs, 1 H), 3.80 (s, 3 H), 3.11 (s, 3 H), 2.08-2.35 (m, 4 H), 1.77-2.01 (m, 4 H). MS (ESI) 525 (M+H).

Example 38

Preparation of tert-butyl 4-(1-(4-(methylsulfonyl) phenyl)-2-oxo-1,2-dihydropyridin-4-ylthio)piperidine-1-carboxylate

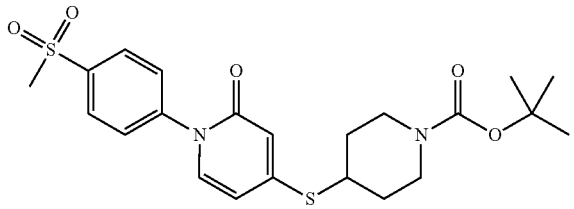

Step A. Preparation of 4-bromo-1-(4-(methylsulfonyl)phenyl)pyridin-2(1H)-one A mixture of 4-hydroxy-1-(4-(methylsulfonyl)phenyl)pyridin-2(1H)-one (106.1 mg, 0.4 mmol) and phosphorous oxybromide (573.4 mg, 2.0 mmol, Alfa Aesar) was heated at 100° C. for 45 min and then cooed to room temperature. To the above residue was added saturated NaHCO$_3$ aqueous solution at 0° C. followed by extraction with CH$_2$Cl$_2$ (3×). The combined extracts were washed with saturated NaHCO$_3$ aqueous solution and brine, dried (Na$_2$SO$_4$) and evaporated. The residual was purified by flash chromatography (0 to 100% EtOAc/hexanes) to yield 60.7 mg (46%) of the product as a yellow solid. MS (ESI) 328 (M+H).

Step B. Example 38

To a solution of tert-butyl 4-mercaptopiperidine-1-carboxylate (65.2 mg, 0.3 mmol, prepared according to procedures described in U.S. Pat. No. 6,566,384 B1) in DMF (1.5 mL) at 0° C. was added sodium hydride (37 mg, 1.0 mmol, 65% dispersion in mineral oil, Aldrich). After stirring at 0° C. for 30 min, 4-bromo-1-(4-(methylsulfonyl)phenyl)pyridin-2 (1H)-one (82 mg, 0.25 mmol) in DMF (1.2 mL) was added. The resulting mixture was stirred at room temperature for 50 min and then quenched with saturated NH$_4$Cl aqueous solution (0.5 mL). The reaction mixture was diluted with EtOAc and H$_2$O and the aqueous layer was extracted further with EtOAc (3×). The combined extracts were washed with brine/H$_2$O (1:1, 3×), dried (Na$_2$SO$_4$) and evaporated. The residual was purified by flash chromatography (0 to 100% EtOAc/hexanes) to yield 100.6 mg (72%) of Example 38 as a light yellow solid. $^1$H NMR (500 MHz, CDCl$_3$) δ ppm 8.08 (d, J=8.25 Hz, 2 H), 7.62 (d, J=8.25 Hz, 2 H), 7.18 (d, J=7.15 Hz, 1 H), 6.41 (d, J=2.20 Hz, 1 H), 6.14 (dd, J=7.15, 2.20 Hz, 1 H), 3.98 (app brs, 2 H), 3.43-3.52 (m, 1 H), 3.03-3.16 (m, 2 H), 3.10 (s, 3 H), 2.06-2.16 (m, 2 H), 1.61-1.73 (m, 2 H), 1.47 (s, 9 H). MS (ESI) 465 (M+H).

Example 39

Preparation of isopropyl 4-(1-(4-(methylsulfonyl) phenyl)-2-oxo-1,2-dihydropyridin-4-ylthio)piperidine-1-carboxylate

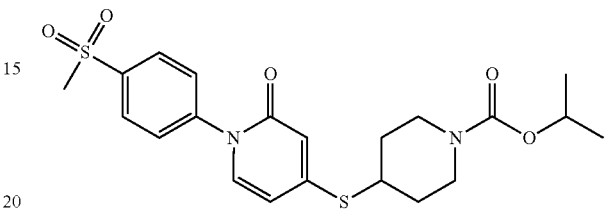

Example 39 was prepared according to procedures described in Example 3 substituting tert-butyl 4-(1-(4-(methylsulfonyl)phenyl)-2-oxo-1,2-dihydropyridin-4-ylthio)piperidine-1-carboxylate for tert-butyl 4-(1-(4-(methylsulfonyl) phenyl)-2-oxo-1,2-dihydropyridin-4-yloxy)piperidine-1-carboxylate. $^1$H NMR (500 MHz, CDCl$_3$) δ 8.09 (d, J=8.80 Hz, 2 H), 7.62 (d, J=8.80 Hz, 2 H), 7.22 (d, J=7.70 Hz, 1 H), 6.66 (d, J=1.65 Hz, 1 H), 6.27 (dd, J=7.42, 1.92 Hz, 1 H), 4.88-5.00 (m, 1 H), 4.04 (app brs, 2 H), 3.47-3.58 (m, 1 H), 3.12-3.17 (m, 2 H), 3.11 (s, 3 H), 2.08-2.16 (m, 2 H), 1.61-1.73 (m, 2 H), 1.26 (d, J=6.05 Hz, 6 H). MS (ESI) 451 (M+H).

Example 40

Preparation of tert-butyl 4-(1-(4-(methylsulfonyl) phenyl)-2-oxo-1,2-dihydropyrimidin-4-yloxy)piperidine-1-carboxylate

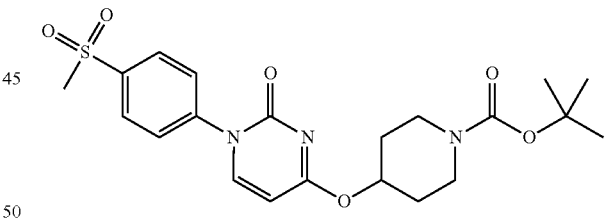

Step A. Preparation of tert-butyl 4-(2-chloropyrimidin-4-yloxy)piperidine-1-carboxylate To a solution of tert-butyl 4-hydroxypiperidine-1-carboxylate (1.0 g, 5.0 mmol, Aldrich) in DMF (15.0 mL) at 0° C. was added sodium hydride (0.55 g, 15.0 mmol, 65% dispersion in mineral oil, commercially available from Sigma-Aldrich Corporation). in several portions. After stirring at 0° C. for 10 min, 2,4-dichloropyrimidine (745 mg, 5.0 mmol, commercially available from Sigma-Aldrich Corporation) in DMF (10.0 mL) was added. The resulting mixture was stirred at 0° C. for 10 min and at room temperature for 2 h and then quenched with saturated NH$_4$Cl aqueous solution (1.5 mL). The reaction mixture was diluted with EtOAc and H$_2$O and the aqueous solution was extracted further with EtOAc (2×).

The combined organic extracts were washed with H$_2$O (3×) and brine, dried (Na$_2$SO$_4$) and evaporated. The residual was purified by flash chromatography (0 to 50% EtOAc/hexanes) to yield 409.3 mg (26%) of the product as an off-white semi-solid. MS (ESI) 314 (M+H).

Step B. Preparation of tert-butyl 4-(2-oxo-1,2-dihydropyrimidin-4-yloxy)piperidine-1-carboxylate A mixture of tert-butyl 4-(2-chloropyrimidin-4-yloxy)piperidine-1-carboxylate (341.5 mg, 0.90 mmol), potassium carbonate (225.6 mg, 1.64 mmol, EMD) and 1,4-diazacyclo[2,2,2]octane (48.8 mg, 0.44 mmol, commercially available from Alfa Aesar) in dioxane/H$_2$O (10 mL/10 mL) was heated at 70° C. for 6 h, cooled to room temperature and then evaporated. The residual was purified by flash chromatography (0 to 10% MeOH/CH$_2$Cl$_2$) to yield 275 mg (85%) of the product as an off-white solid.

Step C

Example 40

A mixture of tert-butyl 4-(2-oxo-1,2-dihydropyrimidin-4-yloxy)piperidine-1-carboxylate (266.5 mg, 0.90 mmol,), 4-bromophenyl methyl sulfone (212.2 mg, 0.90 mmol, commercially available from Sigma-Aldrich Corporation), copper(I) iodide (60.4 mg, 0.32 mmol, commercially available from Sigma-Aldrich Corporation), 8-hydroxyquinoline (47 mg, 0.32 mmol, commercially available from Alfa Aesar) and potassium carbonate (188 mg, 1.35 mmol, EMD) in DMSO (7.5 mL) was heated under Microwave conditions (160° C., 30 min) and cooled to room temperature. The reaction mixture was diluted with EtOAc and then filtered. The filtrate was washed with H$_2$O and the aqueous layer was back extracted with EtOAc (2×). The combined organic layers were washed with H$_2$O/brine (1:1, 4×), dried (Na$_2$SO$_4$) and evaporated. The residual was purified by flash chromatography (0 to 100% EtOAc/Hexanes, twice) to yield 168.5 mg (55%) of Example 40 as a yellow solid. $^1$H NMR (500 MHz, CDCl$_3$) δ 8.08 (d, J=8.25 Hz, 2 H), 7.63 (d, J=8.25 Hz, 2 H), 7.54 (d, J=7.15 Hz, 1 H), 6.05 (d, J=7.70 Hz, 1 H), 5.44-5.57 (m, 1 H), 3.80 (app brs, 2 H), 3.18-3.31 (m, 2 H), 3.10 (s, 3 H), 1.95-2.08 (m, 2 H), 1.65-1.85 (m, 2 H), 1.48 (s, 9 H). MS (ESI) 450 (M+H).

Example 41

Preparation of prop-1-en-2-yl 4-(1-(4-(methylsulfonyl)phenyl)-2-oxo-1,2-dihydropyridin-4-yloxy)piperidine-1-carboxylate

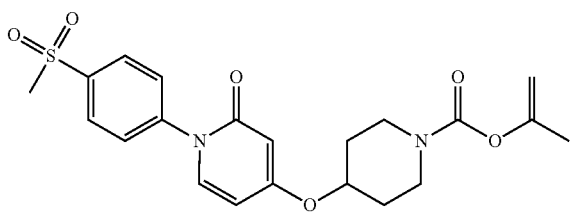 [SMILES: C=C(C)OC(=O)N1CCC(Oc2ccn(-c3ccc(S(C)(=O)=O)cc3)c(=O)c2)CC1]

Example 41 was prepared according to procedures described in Example 2, Step C, substituting isopropenyl chloroformate for 1,1,1-trifluoropropan-2-yl chloroformate. $^1$H NMR (500 MHz, CDCl$_3$) δ 8.07 (d, J=8.80 Hz, 2 H), 7.62 (d, J=8.25 Hz, 2 H), 7.24 (d, J=7.15 Hz, 1 H), 6.06 (dd, J=7.70, 2.75 Hz, 1 H), 5.98 (d, J=2.75 Hz, 1 H), 4.69 (d, J=5.50 Hz, 2 H), 4.50-4.59 (m, 1 H), 3.72-3.83 (m, 2 H), 3.43-3.53 (m, 2 H), 3.09 (s, 3 H), 1.99-2.08 (m, 2 H), 1.97 (s, 3 H), 1.86 (app brs, 2 H). MS (ESI) 433 (M+H).

Example 42

Preparation of N-tert-butyl-4-(1-(4-(methylsulfonyl)phenyl)-2-oxo-1,2-dihydropyridin-4-yloxy)piperidine-1-carboxamide

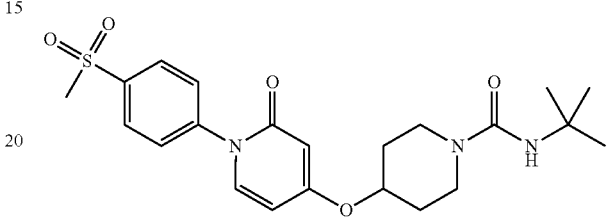

To a suspension of 1-(4-(methylsulfonyl)phenyl)-4-(piperidin-4-yloxy)pyridin-2(1H)-one hydrochloric acid salt (20 mg, 0.052 mmol) in CH$_2$Cl$_2$ (1.0 mL) was added Et$_3$N (36.2 μL, 0.26 mmol) followed by addition of tert-butyl isocyanate (14.8 μL, 0.13 mmol, commercially available from Sigma-Aldrich Corporation). The reaction mixture was stirred for 1.5 h and evaporated under reduced pressure. The crude product was purified by preparative HPLC (C$_{18}$ column; 0-100% methanol in water containing 0.05% trifluoroacetic acid) to give 15.4 mg (62%) of Example 42 as an off-white solid. $^1$H NMR (500 MHz, CDCl$_3$) δ 8.10 (d, J=8.80 Hz, 2 H), 7.61 (d, J=8.25 Hz, 2 H), 7.36 (d, J=7.70 Hz, 1 H), 6.51 (d, J=2.75 Hz, 1 H), 6.30 (dd, J=7.42, 2.47 Hz, 1 H), 4.54-4.68 (m, 1 H), 3.55-3.70 (m, 2 H), 3.26-3.39 (m, 2 H), 3.12 (s, 3 H), 2.01-2.13 (m, 2 H), 1.80-1.95 (m, 2 H), 1.37 (s, 9 H). MS (ESI) 448 (M+H).

Example 43

Preparation of 4-chlorophenyl 4-(1-(4-(methylsulfonyl)phenyl)-2-oxo-1,2-dihydropyridin-4-yloxy)piperidine-1-carboxylate

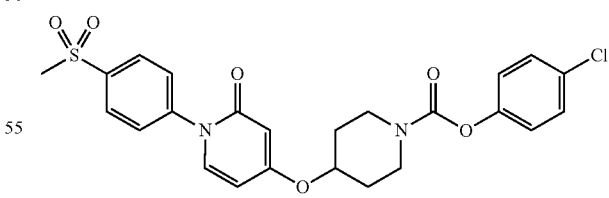

Example 43 was prepared according to procedures described in Example 2 substituting 4-chlorophenyl chloroformate for 1,1,1-trifluoropropan-2-yl chloroformate at Step C. $^1$H NMR (400 MHz, CDCl$_3$) δ 8.01 (d, J=8.3 Hz, 2 H), 7.55 (d, J=8.3 Hz, 2 H), 7.25 (d, J=7.5 Hz, 2 H), 7.20 (d, J=7.5 Hz, 1 H), 7.00 (d, J=7.5 Hz, 2 H), 6.07-6.09 (m, 2 H), 4.55 (app brs, 1 H), 3.70-3.89 (m, 2 H), 3.47-3.63 (m, 2 H), 3.04 (s, 3 H), 1.94-2.09 (m, 2 H), 1.89-1.91 (m, 2 H). MS (ESI) 503 (M+H).

Example 44

Preparation of 4-fluorophenyl 4-(1-(4-(methylsulfonyl)phenyl)-2-oxo-1,2-dihydropyridin-4-yloxy)piperidine-1-carboxylate

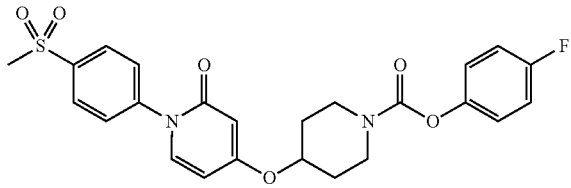 [SMILES: CS(=O)(=O)c1ccc(-n2ccc(OC3CCN(C(=O)Oc4ccc(F)cc4)CC3)cc2=O)cc1]

Example 44 was prepared according to procedures described in Example 2 substituting 4-fluorophenyl chloroformate for 1,1,1-trifluoropropan-2-yl chloroformate at Step C. $^1$H NMR (400 MHz, CDCl$_3$) δ 8.02 (d, J=7.5 Hz, 2 H), 7.55 (d, J=7.5 Hz, 2 H), 7.20 (d, J=7.5 Hz, 1 H), 7.09 (d, J=8.5 Hz, 2 H), 6.93 (d, J=8.5 Hz, 2 H), 6.15-6.20 (m, 2 H), 4.57 (app brs, 1 H), 3.70-3.89 (m, 2 H), 3.45-3.63 (m, 2 H), 3.05 (s, 3 H), 1.92-2.06 (m, 2 H), 1.79-1.89 (m, 2 H). MS (ESI) 487 (M+H).

Example 45

Preparation of 4-methylphenyl 4-(1-(4-(methylsulfonyl)phenyl)-2-oxo-1,2-dihydropyridin-4-yloxy)piperidine-1-carboxylate

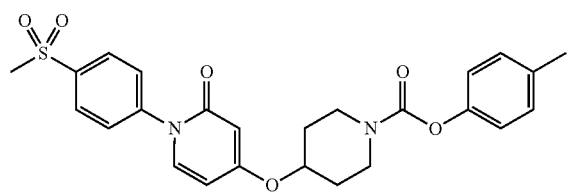

Example 45 was prepared according to procedures described in Example 2 substituting 4-methylphenyl chloroformate for 1,1,1-trifluoropropan-2-yl chloroformate at Step C. $^1$H NMR (400 MHz, CDCl$_3$) δ 8.02 (d, J=7.5 Hz, 2 H), 7.56 (d, J=7.5 Hz, 2 H), 7.20 (d, J=7.5 Hz, 1 H), 6.98-7.02 (m, 4 H), 6.15-6.20 (m, 2 H), 4.57 (app brs, 1 H), 3.70-3.89 (m, 2 H), 3.45-3.63 (m, 2 H), 3.05 (s, 3 H), 2.27 (s, 3 H), 1.92-2.06 (m, 2 H), 1.79-1.89 (m, 2 H). MS (ESI) 483 (M+H).

Example 46

Preparation of 4-methoxyphenyl 4-(1-(4-(methylsulfonyl)phenyl)-2-oxo-1,2-dihydropyridin-4-yloxy)piperidine-1-carboxylate

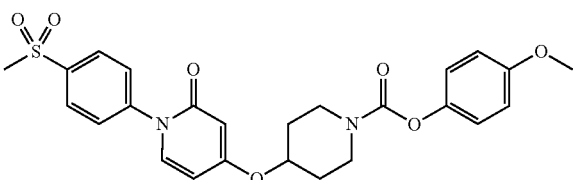

Example 46 was prepared according to procedures described in Example 2 substituting 4-methoxyphenyl chloroformate for 1,1,1-trifluoropropan-2-yl chloroformate at Step C. $^1$H NMR (400 MHz, CDCl$_3$) δ 8.02 (d, J=7.5 Hz, 2 H), 7.55 (d, J=7.5 Hz, 2 H), 7.20 (d, J=7.5 Hz, 1 H), 6.95 (d, J=8.5 Hz, 2 H), 6.81 (d, J=8.5 Hz, 2 H), 6.07-6.10 (m, 2 H), 4.55 (app brs, 1 H), 3.74-3.89 (m, 2 H), 3.73 (s, 3 H), 3.44-3.59 (m, 2 H), 3.03 (s, 3 H), 1.92-2.06 (m, 2 H), 1.79-1.89 (m, 2 H). MS (ESI) 499 (M+H).

Example 47

Preparation of 3-trifluoromethylphenyl 4-(1-(4-(methylsulfonyl)phenyl)-2-oxo-1,2-dihydropyridin-4-yloxy)piperidine-1-carboxylate

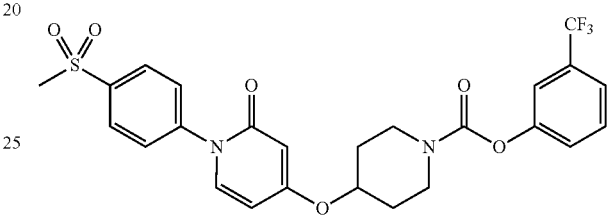

Example 47 was prepared according to procedures described in Example 2 substituting 3-trifluoromethylphenyl chloroformate for 1,1,1-trifluoropropan-2-yl chloroformate at Step C. $^1$H NMR (400 MHz, CDCl$_3$) δ 8.02 (d, J=7.5 Hz, 2 H), 7.55 (d, J=7.5 Hz, 2 H), 7.40-7.47 (m, 2H) 7.34 (s, 1H) 7.25-7.30 (m, 1H), 7.22 (d, J=7.5 Hz, 1 H), 6.07-6.10 (m, 2 H), 4.57 (app brs, 1 H), 3.70-3.89 (m, 2 H), 3.47-3.64 (m, 2 H), 3.03 (s, 3 H), 1.92-2.06 (m, 2 H), 1.79-1.89 (m, 2 H). MS (ESI) 537 (M+H).

Example 48

Preparation of 2-chlorophenyl 4-(1-(4-(methylsulfonyl)phenyl)-2-oxo-1,2-dihydropyridin-4-yloxy)piperidine-1-carboxylate

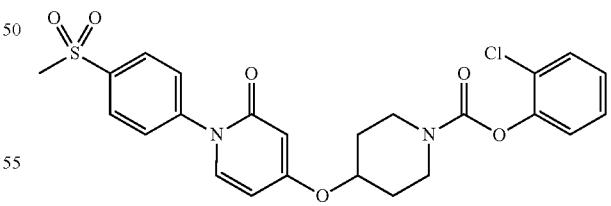

Example 48 was prepared according to procedures described in Example 2 substituting 2-chlorophenyl chloroformate for 1,1,1-trifluoropropan-2-yl chloroformate at Step C. $^1$H NMR (400 MHz, CDCl$_3$) δ 8.02 (d, J=7.5 Hz, 2 H), 7.55 (d, J=7.5 Hz, 2 H), 7.37 (d, J=7.5 Hz, 1 H), 7.06-7.22 (m, 4 H), 6.07-6.09 (m, 2 H), 4.56 (app brs, 1 H), 3.89-3.95 (m, 1 H), 3.72-3.82 (m, 1 H), 3.61-3.69 (m, 1 H), 3.45-3.55 (m, 1 H), 3.03 (s, 3 H), 1.92-2.06 (m, 2 H), 1.79-1.89 (m, 2 H). MS (ESI) 503 (M+H).

Example 49

Preparation of (±)-4-chlorophenyl 3-(1-(4-(methylsulfonyl)phenyl)-2-oxo-1,2-dihydropyridin-4-yloxy)pyrrolidine-1-carboxylate

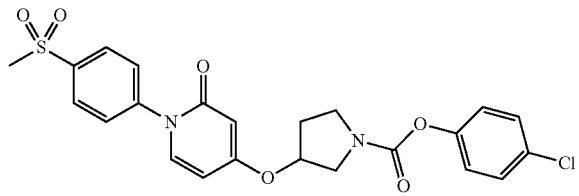 [SMILES: CS(=O)(=O)c1ccc(-n2ccc(OC3CCN(C(=O)Oc4ccc(Cl)cc4)C3)cc2=O)cc1]

Example 49 was prepared according to procedures described in Examples 1 and 2 substituting tert-butyl 3-(methylsulfonyloxy)pyrrolidine-1-carboxylate for tert-butyl 4-(methylsulfonyloxy)piperidine-1-carboxylate in Example 1 at Step C, and 4-chlorophenyl chloroformate for 1,1,1-trifluoropropan-2-yl chloroformate in Example 2 at Step C. $^1$H NMR (400 MHz, CDCl$_3$) δ 8.01 (d, J=8.3 Hz, 2 H), 7.55 (d, J=8.3 Hz, 2 H), 7.26 (d, J=7.5 Hz, 2 H), 7.20 (d, J=7.5 Hz, 1 H), 7.04 (d, J=7.5 Hz, 2 H), 6.00-6.05 (m, 1 H), 5.95 (s, 1H) 4.92 (app brs, 1 H), 3.70-3.89 (m, 2 H), 3.53-3.86 (m, 2 H), 3.04 (s, 3 H), 2.13-2.35 (m, 2 H). MS (ESI) 489 (M+H).

Example 50

Preparation of (±)-benzyl 3-(1-(4-(methylsulfonyl)phenyl)-2-oxo-1,2-dihydropyridin-4-yloxy)pyrrolidine-1-carboxylate

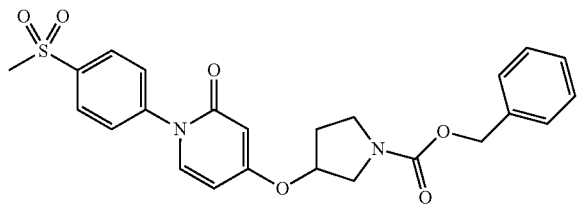 [SMILES: CS(=O)(=O)c1ccc(-n2ccc(OC3CCN(C(=O)OCc4ccccc4)C3)cc2=O)cc1]

Example 50 was prepared according to procedures described in Example 49 substituting benzyl chloroformate for 4-chlorophenyl chloroformate. $^1$H NMR (400 MHz, CDCl$_3$) δ 8.00 (d, J=8.3 Hz, 2 H), 7.53 (d, J=8.3 Hz, 2 H), 7.22-7.35 (m, 5 H), 7.18 (d, J=7.5 Hz, 1 H), 5.98 (d, J=7.8 Hz, 2 H), 5.88 (d, J=7.8 Hz, 2 H), 5.09 (s, 2H) 4.84 (app brs, 1 H), 3.45-3.79 (m, 4 H), 3.02 (s, 3 H), 2.06-2.25 (m, 2 H). MS (ESI) 469 (M+H).

Example 51

Preparation of 4-(1-(benzo[d]oxazol-2-yl)piperidin-4-yloxy)-1-(4-(methylsulfonyl)phenyl)pyridin-2(1H)-one

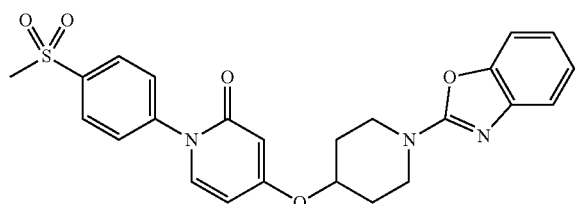

Example 51 was prepared according to procedures described in Example 2 substituting 2-chlorobenzoxazole for 1,1,1-trifluoropropan-2-yl chloroformate at Step C and the reaction was heated at 100° C. for 10 min. $^1$H NMR (400 MHz, CDCl$_3$) δ 8.00 (d, J=7.5 Hz, 2 H), 7.55 (d, J=7.5 Hz, 2 H), 7.35 (d, J=7.5 Hz, 1 H), 7.20 (app t, J=8.5 Hz, 2 H), 7.14 (t, J=8.5 Hz, 1 H), 7.01 (t, J=8.5 Hz, 1 H), 6.01 (d, J=7.5 Hz, 1 H), 5.94 (s, 1H), 4.56 (app brs, 1 H), 3.87-3.95 (m, 2 H), 3.68-3.75 (m, 2 H), 3.02 (s, 3 H), 2.03-2.12 (m, 2 H), 1.89-1.97 (m, 2 H). MS (ESI) 466 (M+H).

Example 52

Preparation of 4-(1-(5-methylbenzo[d]oxazol-2-yl)piperidin-4-yloxy)-1-(4-(methylsulfonyl)phenyl)pyridin-2(1H)-one

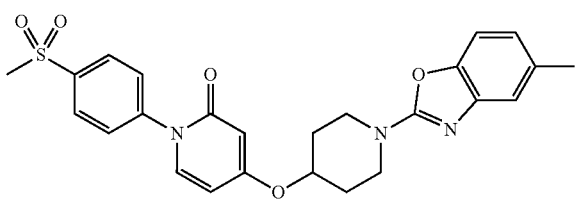

Example 52 was prepared according to procedures described in Example 51 substituting 2-chloro-5-methylbenzoxazole for 2-chlorobenzoxazole. $^1$H NMR (400 MHz, CDCl$_3$) δ 8.07 (d, J=7.5 Hz, 2 H), 7.61 (d, J=7.5 Hz, 2 H), 7.22-7.26 (m, 2 H), 7.15 (d, J=8.5 Hz, 1 H), 6.88 (d, J=8.0 Hz, 1 H), 6.08 (d, J=7.5 Hz, 1 H), 5.99 (s, 1H), 4.62 (app brs, 1 H), 3.91-3.98 (m, 2 H), 3.68-3.85 (m, 2 H), 3.09 (s, 3 H), 2.10-2.28 (m, 2 H), 1.98-2.07 (m, 2 H). MS (ESI) 480 (M+H).

Example 53

Preparation of cyclopropyl 4-(1-(4-(methylsulfonyl)phenyl)-2-oxo-1,2-dihydropyridin-4-yloxy)piperidine-1-carboxylate

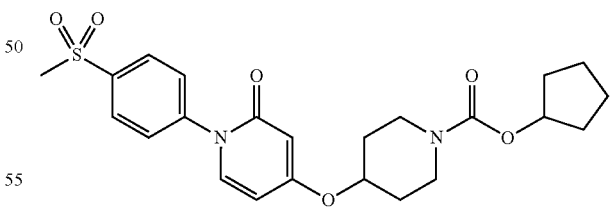

Example 53 was prepared according to procedures described in Example 2 substituting cyclopropyl chloroformate for 1,1,1-trifluoropropan-2-yl chloroformate at Step C. $^1$H NMR (400 MHz, CDCl$_3$) δ 8.05 (d, J=8.5 Hz, 2 H), 7.60 (d, J=8.5 Hz, 2 H), 7.23 (d, J=7.5 Hz, 1 H), 6.04 (d, J=7.5 Hz, 1 H), 5.98 (s, 1 H), 5.09-5.13 (m, 1 H), 4.47-4.50 (m, 1 H), 3.69-3.76 (m, 2 H), 3.34-3.40 (m, 2 H), 3.08 (s, 3 H), 1.55-2.06 (m, 12 H). MS (ESI) 461 (M+H).

Example 54

Preparation of 1-(4-(methylsulfonyl)phenyl)-4-(1-(pyrimidin-2-yl)piperidin-4-yloxy)pyridin-2(1H)-one

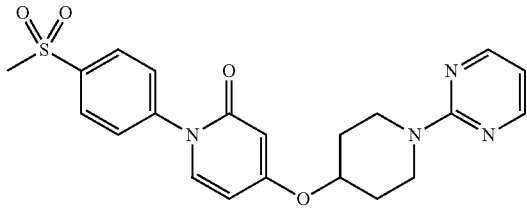 [SMILES: CS(=O)(=O)c1ccc(-n2ccc(OC3CCN(c4ncccn4)CC3)cc2=O)cc1]

Example 54 was prepared according to procedures described in Example 51 substituting 2-chloropyrimidine for 2-chlorobenzoxazole. $^1$H NMR (400 MHz, CDCl$_3$) δ 8.29 (d, J=4.8 Hz, 2 H), 8.00 (d, J=8.5 Hz, 2 H), 7.55 (d, J=8.5 Hz, 2 H), 7.17 (d, J=7.5 Hz, 1 H), 6.49 (d, J=4.8 Hz, 1 H), 6.00 (d, J=7.5 Hz, 1 H), 5.95 (s, 1 H), 4.52-4.55 (m, 1 H), 4.10-4.19 (m, 2 H), 3.65-3.76 (m, 2 H), 3.03 (s, 3 H), 1.98-2.06 (m, 2 H), 1.77-1.89 (m, 2 H). MS (ESI) 427 (M+H).

Example 55

Preparation of 4-(1-(5-ethylpyrimidin-2-yl)piperidin-4-yloxy)-1-(4-(methylsulfonyl)phenyl)pyridin-2(1H)-one

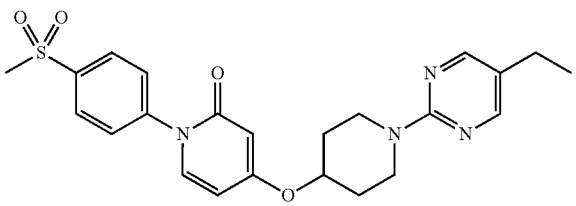 [SMILES: CCc1cnc(N2CCC(Oc3ccn(-c4ccc(S(C)(=O)=O)cc4)c(=O)c3)CC2)nc1]

Example 55 was prepared according to procedures described in Example 51 substituting 2-chloro-5-ethylpyrimidine for 2-chlorobenzoxazole. $^1$H NMR (400 MHz, CDCl$_3$) δ 8.27 (s, 2 H), 8.05 (d, J=8.5 Hz, 2 H), 7.61 (d, J=8.5 Hz, 2 H), 7.23 (d, J=7.5 Hz, 1 H), 6.09 (d, J=7.5 Hz, 1 H), 5.99 (s, 1 H), 4.60-4.64 (m, 1 H), 4.10-4.19 (m, 2 H), 3.85-4.02 (m, 2 H), 3.08 (s, 3 H), 2.51 (q, J=7.1 Hz, 2 H), 2.03-2.14 (m, 2 H), 1.89-1.98 (m, 2 H), 1.23 (t, J=7.1 Hz, 3 H). MS (ESI) 455 (M+H).

Example 56

Preparation of 4-(1-(5-fluoropyrimidin-2-yl)piperidin-4-yloxy)-1-(4-(methylsulfonyl)phenyl)pyridin-2(1H)-one

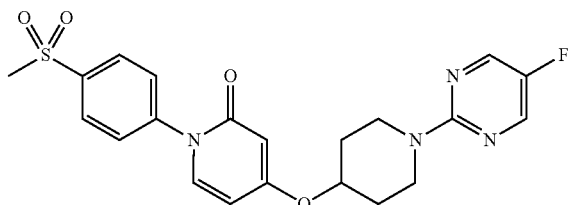

Example 56 was prepared according to procedures described in Example 51 substituting 2-chloro-5-fluoropyrimidine for 2-chlorobenzoxazole. $^1$H NMR (400 MHz, CDCl$_3$) δ 8.23 (s, 2 H), 8.05 (d, J=8.5 Hz, 2 H), 7.60 (d, J=8.5 Hz, 2 H), 7.23 (d, J=7.5 Hz, 1 H), 6.08 (d, J=7.5 Hz, 1 H), 6.01 (s, 1 H), 4.56-4.61 (m, 1 H), 4.10-4.19 (m, 2 H), 3.69-4.76 (m, 2 H), 3.08 (s, 3 H), 2.03-2.11 (m, 2 H), 1.80-1.92 (m, 2 H). MS (ESI) 445 (M+H).

Example 57

Preparation of 4-(1-(5-bromopyrimidin-2-yl)piperidin-4-yloxy)-1-(4-(methylsulfonyl)phenyl)pyridin-2(1H)-one

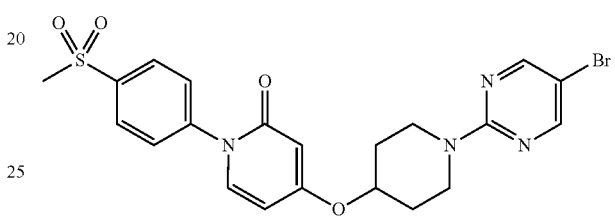

Example 57 was prepared according to procedures described in Example 51 substituting 2-chloro-5-bromopyrimidine for 2-chlorobenzoxazole. $^1$H NMR (400 MHz, CDCl$_3$) δ 8.33 (s, 2 H), 8.07 (d, J=8.5 Hz, 2 H), 7.62 (d, J=8.5 Hz, 2 H), 7.24 (d, J=7.5 Hz, 1 H), 6.08 (d, J=7.5 Hz, 1 H), 6.03 (s, 1 H), 4.58-4.64 (m, 1 H), 4.08-4.15 (m, 2 H), 3.72-4.82 (m, 2 H), 3.09 (s, 3 H), 1.99-2.12 (m, 2 H), 1.82-1.94 (m, 2 H). MS (ESI) 505 (M+H).

Example 58

Preparation of 4-(1-(4-methylpyrimidin-2-yl)piperidin-4-yloxy)-1-(4-(methylsulfonyl)phenyl)pyridin-2(1H)-one

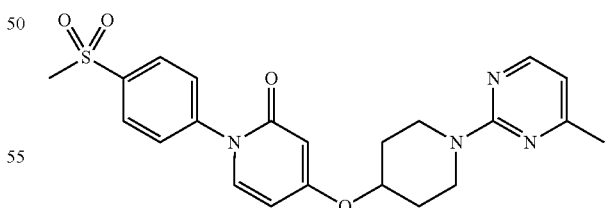

Example 58 was prepared according to procedures described in Example 51 substituting 2-chloro-4-methylpyrimidine for 2-chlorobenzoxazole. $^1$H NMR (400 MHz, CDCl$_3$) δ 8.16 (d, J=6.1 Hz, 1 H), 8.10 (d, J=8.5 Hz, 2 H), 7.55 (d, J=8.5 Hz, 2 H), 7.19 (d, J=7.5 Hz, 1 H), 6.45 (d, J=6.1 Hz, 1 H), 6.00 (d, J=7.5 Hz, 1 H), 5.94 (s, 1 H), 4.55-4.60 (m, 1 H), 4.11-4.18 (m, 2 H), 3.87-4.96 (m, 2 H), 3.03 (s, 3 H), 2.39 (s, 3 H), 2.01-2.12 (m, 2 H), 1.82-1.94 (m, 2 H). MS (ESI) 441 (M+H).

Example 59

Preparation of 1-(4-(methylsulfonyl)phenyl)-4-(1-(pyridin-2-yl)piperidin-4-yloxy)pyridin-2(1H)-one

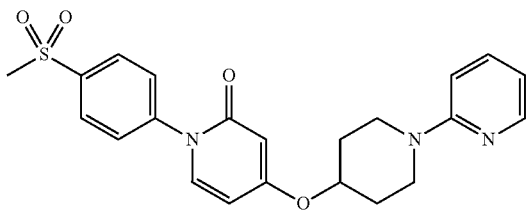 [SMILES: CS(=O)(=O)c1ccc(-n2ccc(OC3CCN(c4ccccn4)CC3)cc2=O)cc1]

Example 59 was prepared according to procedures described in Example 51 substituting 2-chloro-pyridine for 2-chlorobenzoxazole. $^1$H NMR (400 MHz, CDCl$_3$) δ 8.10 (d, J=8.5 Hz, 2 H), 8.09 (d, J=8.1 Hz, 1 H), 7.68 (d, J=8.5 Hz, 2H), 7.55-7.61 (m, 2 H), 6.92 (d, J=8.1 Hz, 1 H), 6.87 (t, J=8.1 Hz, 1 H), 6.26 (d, J=7.5 Hz, 1 H), 6.09 (s, 1 H), 4.83-4.89 (m, 1 H), 3.88-3.96 (m, 2 H), 3.43-3.51 (m, 2 H), 3.07 (s, 3 H), 2.09-2.17 (m, 2 H), 1.80-1.90 (m, 2 H). MS (ESI) 426 (M+H).

Examples 60 and 61

Preparation of trans-ethyl 4-(1-(4-(methylsulfonyl)phenyl)-2-oxo-1,2-dihydropyridin-4-yloxy)cyclohexanecarboxylate and cis-ethyl 4-(1-(4-(methylsulfonyl)phenyl)-2-oxo-1,2-dihydropyridin-4-yloxy)cyclohexanecarboxylate

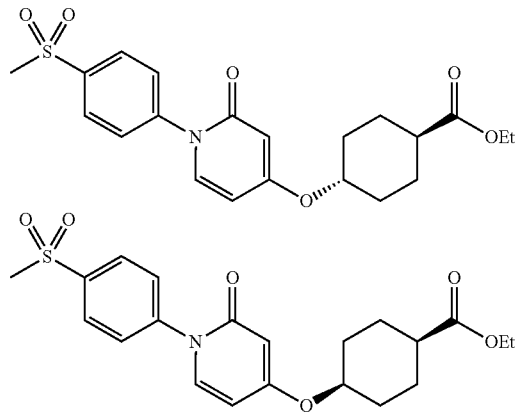

Examples 60 and 61 were prepared according to procedures described in Example 1 substituting a mixture of cis and trans ethyl 4-hydroxycyclohexane-carboxylate for t-tert-butyl-4-hydroxy-1-piperidinecarboxylate to yield separated products by flash chromatography (0 to 100% EtOAc in hexanes). Example 60: $^1$H NMR (400 MHz, CDCl$_3$) δ 8.06 (d, J=8.5 Hz, 2 H), 7.60 (d, J=8.5 Hz, 2 H), 7.23 (d, J=7.5 Hz, 1 H), 6.09 (s, 1 H), 6.06 (d, J=7.5 Hz, 1 H), 4.24-4.31 (m, 1 H), 4.13 (q, J=7.2 Hz, 2 H), 3.08 (s, 3 H), 2.31-2.46 (m, 2 H), 2.10-2.25 (m, 2 H), 1.47-1.70 (m, 5 H), 1.26 (t, J=7.2 Hz, 3 H). MS (ESI) 420 (M+H); and Example 61: $^1$H NMR (400 MHz, CDCl$_3$) δ 8.06 (d, J=8.5 Hz, 2 H), 7.60 (d, J=8.5 Hz, 2 H), 7.29 (d, J=7.5 Hz, 1 H), 6.35 (s, 1 H), 6.21 (d, J=7.5 Hz, 1 H), 4.54-4.61 (m, 1 H), 4.13 (q, J=7.2 Hz, 2 H), 3.08 (s, 3 H), 2.31-2.46 (m, 2 H), 2.10-2.25 (m, 2 H), 1.47-1.70 (m, 5 H), 1.25 (t, J=7.2 Hz, 3 H). MS (ESI) 420 (M+H).

Example 62

Preparation of 4-((trans)-4-(3-isopropyl-1,2,4-oxadiazol-5-yl)cyclohexyloxy)-1-(4-(methylsulfonyl)phenyl)pyridin-2(1H)-one

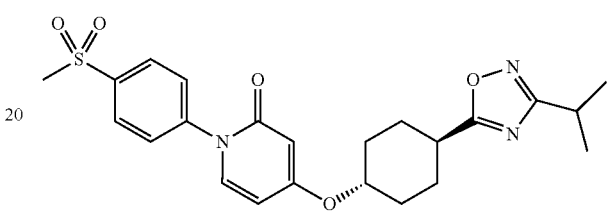

Step A. Preparation of trans-4-(1-(4-(methylsulfonyl)phenyl)-2-oxo-1,2-dihydropyridin-4-yloxy)cyclohexanecarboxylate To a stirring solution of trans-ethyl 4-(1-(4-(methylsulfonyl)phenyl)-2-oxo-1,2-dihydropyridin-4-yloxy)cyclohexanecarboxylate (500 mg, 1.19 mmol) in MeOH (10 mL), water (1 mL), and DMF (1 mL) at room temperature was added sodium hydroxide (120 mg, 3.0 mmol, commercially available from EM Science). The reaction mixture was stirred overnight and then concentrated in vacuo to dryness. The residue was portioned between EtOAc and water. The reaction was then acidified to pH 2 with concentrated HCl and stirred for 20 min. The solid was filtered and washed with EtOAc. The solid was dried in vacuo at to yield 454 mg of desired product as a white solid. MS (ESI) 392 (M+H).

Step B

Example 62

To a stirring solution of trans-4-(1-(4-(methylsulfonyl)phenyl)-2-oxo-1,2-dihydropyridin-4-yloxy)cyclohexanecarboxylate (100 mg, 0.26 mmol) in dry DMF (2 mL) at room temperature was added carbonyl diimidazole (41 mg, 0.26 mmol, commercially available from Sigma-Aldrich Corporation). The reaction was heated to 100° C. for 30 min and the isopropyl oxime (27 mg, 0.26 mmol) was added. The reaction was stirred overnight and then quenched with brine. The reaction was extracted with EtOAc. The organic layers were combined, dried over Na$_2$SO$_4$, and concentrated in vacuo to a pale yellow oil. The oil was purified by flash chromatography (0 to 100% EtOAc in hexanes) to yield 52 mg of Example 62 as a white solid. $^1$H NMR (400 MHz, CDCl$_3$) δ 8.06 (d, J=8.5 Hz, 2 H), 7.60 (d, J=8.5 Hz, 2 H), 7.25 (d, J=7.5 Hz, 1 H), 6.26 (s, 1 H), 6.15 (d, J=7.5 Hz, 1 H), 4.31-4.42 (m, 1 H), 3.09 (s, 3 H), 2.96-3.08 (m, 2 H), 2.21-2.45 (m, 5 H), 1.76-1.88 (m, 3 H), 1.61-1.73 (m, 2 H), 1.31 (d, J=6.9 Hz, 6 H). MS (ESI) 458 (M+H).

Example 63

Preparation of 4-((cis)-4-(3-isopropyl-1,2,4-oxadiazol-5-yl)cyclohexyloxy)-1-(4-(methylsulfonyl)phenyl)pyridin-2(1H)-one

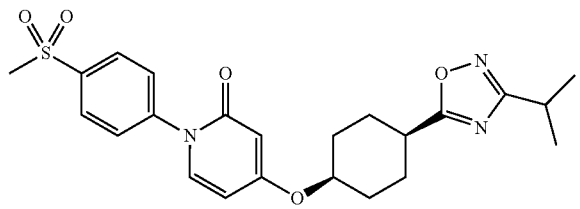 [SMILES: CC(C)c1noc([C@H]2CC[C@@H](Oc3ccn(-c4ccc(S(C)(=O)=O)cc4)c(=O)c3)CC2)n1]

Example 63 was prepared according to procedures described in Example 62 substituting cis-ethyl 4-(1-(4-(methylsulfonyl)phenyl)-2-oxo-1,2-dihydropyridin-4-yloxy)cyclohexanecarboxylate for of trans-ethyl 4-(1-(4-(methylsulfonyl)phenyl)-2-oxo-1,2-dihydropyridin-4-yloxy)cyclohexanecarboxylate. $^1$H NMR (400 MHz, CDCl$_3$) δ 8.04 (d, J=8.5 Hz, 2 H), 7.59 (d, J=8.5 Hz, 2 H), 7.20 (d, J=7.5 Hz, 1H), 6.05 (d, J=7.5 Hz, 1 H), 5.94 (s, 1 H), 4.52-4.58 (m, 1 H), 3.09 (s, 3 H), 2.99-3.08 (m, 2 H), 1.95-2.19 (m, 6 H), 1.73-1.85 (m, 2 H), 1.32 (d, J=7.0 Hz, 6 H). MS (ESI) 458 (M+H).

Example 64

Preparation of trans-isopropyl 4-(1-(4-(methylsulfonyl)phenyl)-2-oxo-1,2-dihydropyridin-4-yloxy)cyclohexanecarboxylate

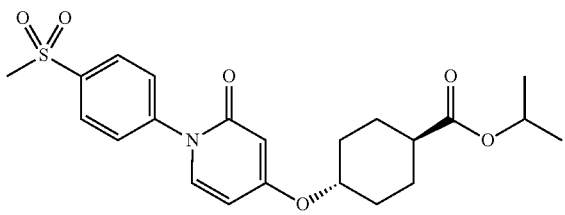 [SMILES: CC(C)OC(=O)[C@H]1CC[C@H](Oc2ccn(-c3ccc(S(C)(=O)=O)cc3)c(=O)c2)CC1]

To a stirring solution of trans-4-(1-(4-(methylsulfonyl)phenyl)-2-oxo-1,2-dihydropyridin-4-yloxy)cyclohexanecarboxylate (100 mg, 0.26 mmol) and diiopropylethylamine (65 mg, 0.5 mmol, commercially available from Sigma-Aldrich Corporation) in dry DMF (2 mL) at room temperature was added isopropyl iodide (85 mg, 0.5 mmol, commercially available from Sigma-Aldrich Corporation). The reaction was heated to 100° C. overnight. The reaction was cooled to room temperature and then concentrated in vacuo to a brown solid. The solid was purified by flash chromatography (30 to 100% EtOAc in hexanes) to yield 65 mg of Example 64 as a white solid. $^1$H NMR (400 MHz, CDCl$_3$) δ 8.06 (d, J=8.5 Hz, 2 H), 7.60 (d, J=8.5 Hz, 2 H), 7.24 (d, J=7.5 Hz, 1 H), 6.08 (s, 1 H), 6.06 (d, J=7.5 Hz, 1 H), 5.01 (sept, J=6.0 Hz, 1 H), 4.24-4.28 (m, 1 H), 3.09 (s, 3 H), 2.28-2.35 (m, 1 H), 2.18-2.25 (m, 2 H), 2.06-2.11 (m, 2 H), 1.47-1.73 (m, 4 H), 1.23 (d, J=6.0 Hz, 6 H). MS (ESI) 434 (M+H).

Example 65

Preparation of cis-isopropyl 4-(1-(4-(methylsulfonyl)phenyl)-2-oxo-1,2-dihydropyridin-4-yloxy)cyclohexanecarboxylate

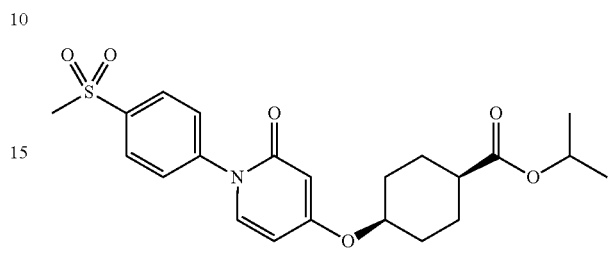

Example 65 was prepared according to procedures described in Example 66 substituting cis-ethyl 4-(1-(4-(methylsulfonyl)phenyl)-2-oxo-1,2-dihydropyridin-4-yloxy)cyclohexanecarboxylate for trans-ethyl 4-(1-(4-(methylsulfonyl)phenyl)-2-oxo-1,2-dihydropyridin-4-yloxy)cyclohexanecarboxylate. $^1$H NMR (400 MHz, CDCl$_3$) δ 8.03 (d, J=8.5 Hz, 2 H), 7.59 (d, J=8.5 Hz, 2 H), 7.20 (d, J=7.5 Hz, 1H), 6.05 (d, J=7.5 Hz, 1 H), 5.96 (s, 1 H), 5.00 (sept, J=6.2 Hz, 1 H), 4.44-4.48 (m, 1 H), 3.08 (s, 3 H), 2.36-2.41 (m, 1 H), 1.99-2.08 (m, 2 H), 1.83-1.95 (m, 2 H), 1.63-1.79 (m, 4 H), 1.21 (d, J=6.2 Hz, 6 H). MS (ESI) 434 (M+H).

Example 66

Preparation of phenyl 4-(1-(4-(methylsulfonyl)phenyl)-2-oxo-1,2-dihydropyridin-4-yloxy)piperidine-1-carboxylate

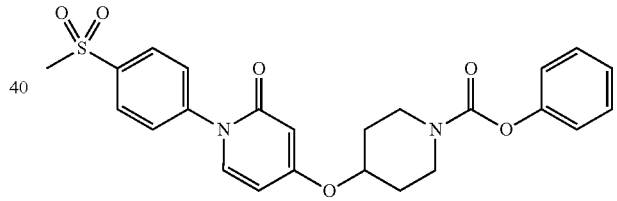

Example 66 was prepared according to procedures described in Example 3 substituting phenyl chloroformate for isopropyl chloroformate. MS (ESI) 469 (M+H).

Example 67

Preparation of 4-(1-benzoylpiperidin-4-yloxy)-1-(4-(methylsulfonyl)phenyl)pyridin-2(1H)-one

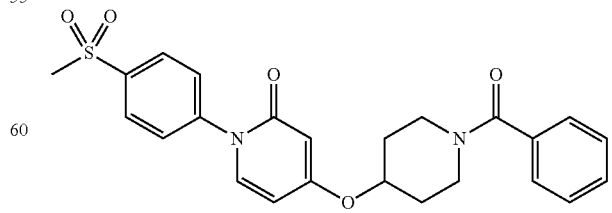

Example 67 was prepared according to procedures described in Example 3 substituting benzoyl chloride for isopropyl chloroformate. MS (ESI) 453 (M+H).

Example 68

Preparation of 4-(1-(2-chlorobenzoyl)piperidin-4-yloxy)-1-(4-(methylsulfonyl)phenyl)pyridin-2(1H)-one

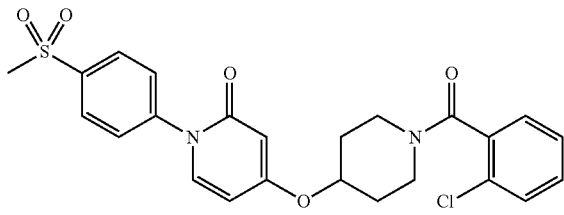 [SMILES: CS(=O)(=O)c1ccc(-n2ccc(OC3CCN(C(=O)c4ccccc4Cl)CC3)cc2=O)cc1]

Example 68 was prepared according to procedures described in Example 3 substituting 2-chlorobenzoyl chloride for isopropyl chloroformate. MS (ESI) 488 (M+H).

Example 69

Preparation of 4-(1-(3-chlorobenzoyl)piperidin-4-yloxy)-1-(4-(methylsulfonyl)phenyl)pyridin-2(1H)-one

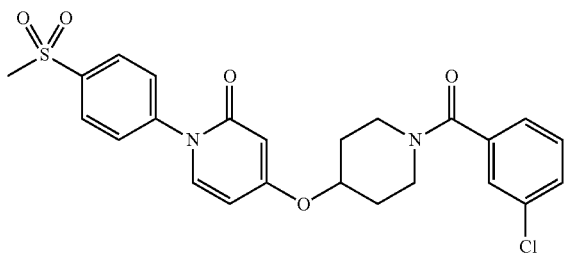 [SMILES: CS(=O)(=O)c1ccc(-n2ccc(OC3CCN(C(=O)c4cccc(Cl)c4)CC3)cc2=O)cc1]

Example 69 was prepared according to procedures described in Example 3 substituting 3-chlorobenzoyl chloride for isopropyl chloroformate. MS (ESI) 488 (M+H).

Example 70

Preparation of 4-(1-(4-chlorobenzoyl)piperidin-4-yloxy)-1-(4-(methylsulfonyl)phenyl)pyridin-2(1H)-one

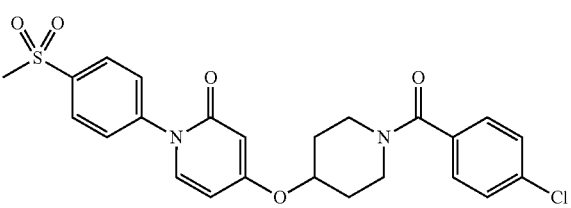 [SMILES: CS(=O)(=O)c1ccc(-n2ccc(OC3CCN(C(=O)c4ccc(Cl)cc4)CC3)cc2=O)cc1]

Example 70 was prepared according to procedures described in Example 3 substituting 4-chlorobenzoyl chloride for isopropyl chloroformate. MS (ESI) 488 (M+H).

Example 71

Preparation of 4-(1-(4-methoxybenzoyl)piperidin-4-yloxy)-1-(4-(methylsulfonyl)phenyl)pyridin-2(1H)-one

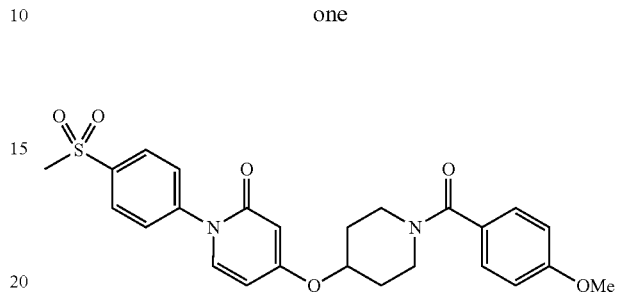

Example 71 was prepared according to procedures described in Example 3 substituting 4-methoxybenzoyl chloride for isopropyl chloroformate. MS (ESI) 483 (M+H).

Example 72

Preparation of 4-(1-(3,3-dimethylbutanoyl)piperidin-4-yloxy)-1-(4-(methylsulfonyl)phenyl)pyridin-2(1H)-one

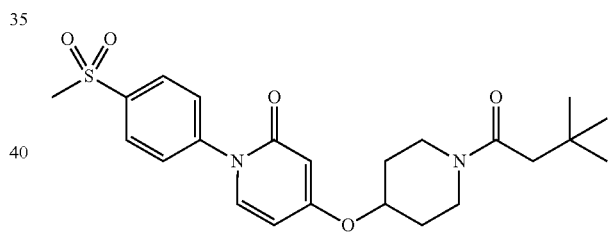

Example 72 was prepared according to procedures described in Example 3 substituting 3,3-dimethylbutanoyl chloride for isopropyl chloroformate. MS (ESI) 447 (M+H).

Example 73

Preparation of 4-(1-(3-methylbutanoyl)piperidin-4-yloxy)-1-(4-(methylsulfonyl)phenyl)pyridin-2(1H)-one

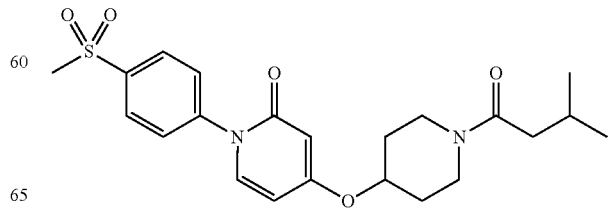

Example 73 was prepared according to procedures described in Example 3 substituting 3-methylbutanoyl chloride for isopropyl chloroformate. MS (ESI) 433 (M+H).

Example 74

Preparation of 1-(4-(methylsulfonyl)phenyl)-4-(1-(3-phenylpropanoyl)piperidin-4-yloxy)pyridin-2(1H)-one

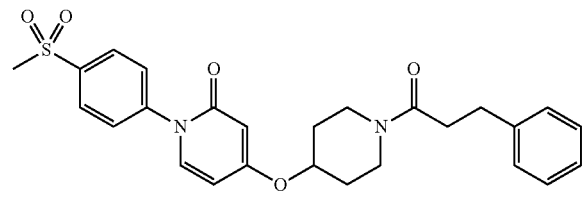 [SMILES: CS(=O)(=O)c1ccc(-n2ccc(OC3CCN(C(=O)CCc4ccccc4)CC3)cc2=O)cc1]

Example 74 was prepared according to procedures described in Example 3 substituting 3-phenylpropanoyl chloride for isopropyl chloroformate. MS (ESI) 481 (M+H).

Example 75

Preparation of 4-(1-(cyclobutanecarbonyl)piperidin-4-yloxy)-1-(4-(methylsulfonyl)phenyl)pyridin-2(1H)-one

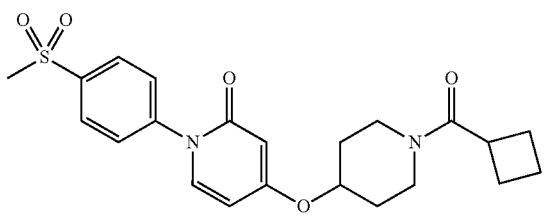 [SMILES: CS(=O)(=O)c1ccc(-n2ccc(OC3CCN(C(=O)C4CCC4)CC3)cc2=O)cc1]

Example 75 was prepared according to procedures described in Example 3 substituting cyclobutanecarbonyl chloride for isopropyl chloroformate. MS (ESI) 431 (M+H).

Example 76

Preparation of 4-(1-(cyclopentanecarbonyl)piperidin-4-yloxy)-1-(4-(methylsulfonyl)phenyl)pyridin-2(1H)-one

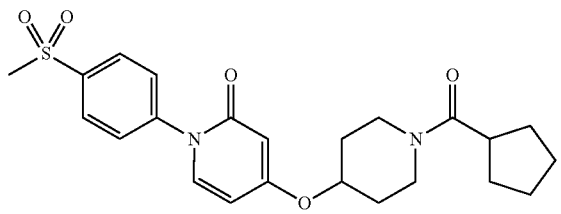 [SMILES: CS(=O)(=O)c1ccc(-n2ccc(OC3CCN(C(=O)C4CCCC4)CC3)cc2=O)cc1]

Example 76 was prepared according to procedures described in Example 3 substituting cyclopentanecarbonyl chloride for isopropyl chloroformate. MS (ESI) 445 (M+H).

Example 77

Preparation of 1-(4-(methylsulfonyl)phenyl)-4-(1-(thiophene-2-carbonyl)piperidin-4-yloxy)pyridin-2(1H)-one

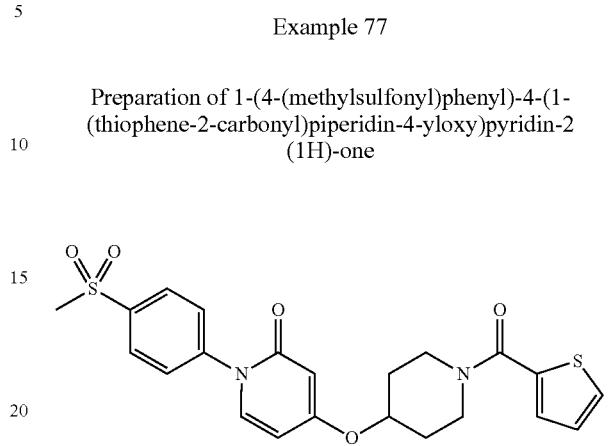

Example 77 was prepared according to procedures described in Example 3 substituting thiophene-2-carbonyl chloride for isopropyl chloroformate. MS (ESI) 459 (M+H).

Example 78

Preparation of 1-(4-(methylsulfonyl)phenyl)-4-(1-(quinoxaline-2-carbonyl)piperidin-4-yloxy)pyridin-2(1H)-one, TFA salt

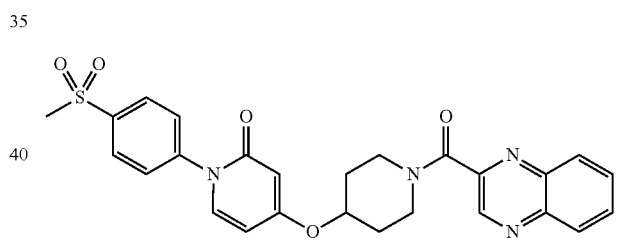

Example 78 was prepared according to procedures described in Example 3 substituting quinoxaline-2-carbonyl chloride for isopropyl chloroformate. MS (ESI) 505 (M+H).

Example 79

Preparation of 1-(4-(methylsulfonyl)phenyl)-4-(1-(quinolin-8-ylsulfonyl)piperidin-4-yloxy)pyridin-2(1H)-one, TFA salt

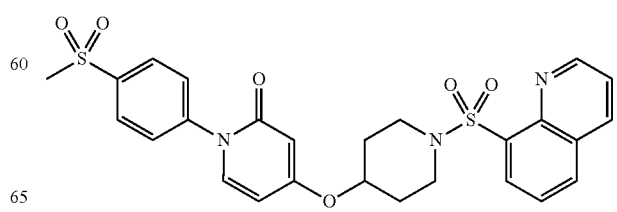

Example 79 was prepared according to procedures described in Example 3 substituting quinolin-8-ylsulfonyl chloride for isopropyl chloroformate. MS (ESI) 540 (M+H).

Example 80

Preparation of 4-(1-(benzylsulfonyl)piperidin-4-yloxy)-1-(4-(methylsulfonyl)phenyl)pyridin-2(1H)-one

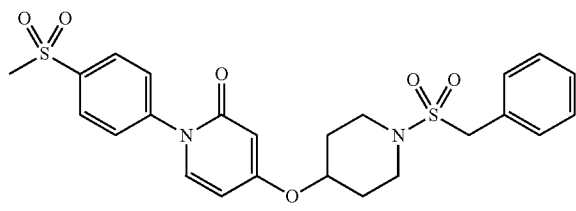 [SMILES: CS(=O)(=O)c1ccc(-n2ccc(OC3CCN(S(=O)(=O)Cc4ccccc4)CC3)cc2=O)cc1]

Example 80 was prepared according to procedures described in Example 3 substituting benzylsulfonyl chloride for isopropyl chloroformate. MS (ESI) 503 (M+H).

Example 81

Preparation of 1-(4-(methylsulfonyl)phenyl)-4-(1-(propylsulfonyl)piperidin-4-yloxy)pyridin-2(1H)-one

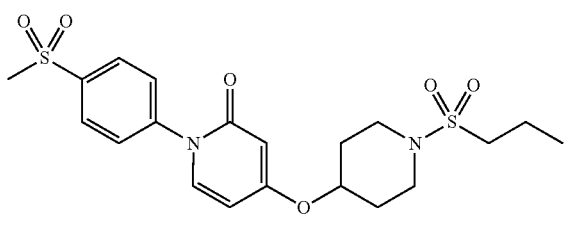 [SMILES: CCCS(=O)(=O)N1CCC(Oc2ccn(-c3ccc(S(C)(=O)=O)cc3)c(=O)c2)CC1]

Example 81 was prepared according to procedures described in Example 3 substituting propylsulfonyl chloride for isopropyl chloroformate. MS (ESI) 455 (M+H).

Example 82

Preparation of 1-(4-(methylsulfonyl)phenyl)-4-(1-(2,2,2-trifluoroethylsulfonyl)piperidin-4-yloxy)pyridin-2(1H)-one

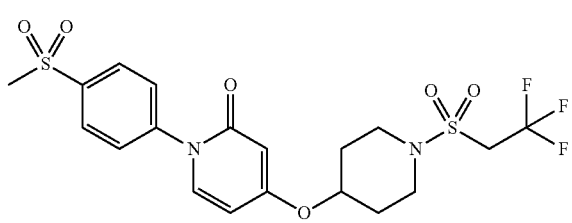 [SMILES: CS(=O)(=O)c1ccc(-n2ccc(OC3CCN(S(=O)(=O)CC(F)(F)F)CC3)cc2=O)cc1]

Example 82 was prepared according to procedures described in Example 3 substituting 2,2,2-trifluoroethylsulfonyl chloride for isopropyl chloroformate. MS (ESI) 495 (M+H).

Example 83

Preparation of 1-(4-(methylsulfonyl)phenyl)-4-(1-(methylsulfonyl)piperidin-4-yloxy)pyridin-2(1H)-one

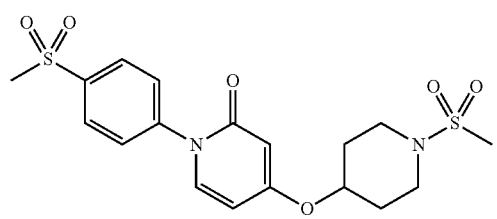

Example 83 was prepared according to procedures described in Example 3 substituting methylsulfonyl chloride for isopropyl chloroformate. MS (ESI) 427 (M+H).

Example 84

Preparation of 4-(1-(cyclopropylsulfonyl)piperidin-4-yloxy)-1-(4-(methylsulfonyl)phenyl)pyridin-2(1H)-one

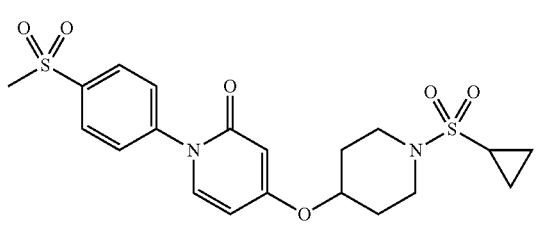 [SMILES: CS(=O)(=O)c1ccc(-n2ccc(OC3CCN(S(=O)(=O)C4CC4)CC3)cc2=O)cc1]

Example 84 was prepared according to procedures described in Example 3 substituting cyclopropylsulfonyl chloride for isopropyl chloroformate. MS (ESI) 453 (M+H).

Example 85

Preparation of 1-(4-(methylsulfonyl)phenyl)-4-(1-(4-phenoxyphenylsulfonyl)piperidin-4-yloxy)pyridin-2(1H)-one

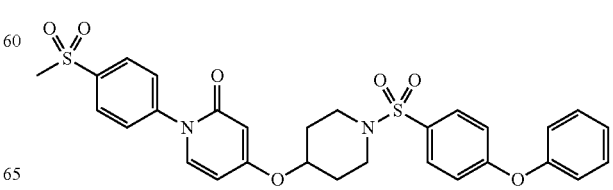

Example 85 was prepared according to procedures described in Example 3 substituting phenoxyphenylsulfonyl chloride for isopropyl chloroformate. MS (ESI) 581 (M+H).

Example 86

Preparation of 1-(4-(methylsulfonyl)phenyl)-4-(1-(pyridin-2-ylsulfonyl)piperidin-4-yloxy)pyridin-2(1H)-one, TFA salt

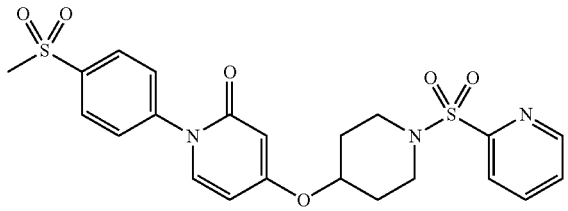 [SMILES: CS(=O)(=O)c1ccc(-n2ccc(OC3CCN(S(=O)(=O)c4ccccn4)CC3)cc2=O)cc1]

Example 86 was prepared according to procedures described in Example 3 substituting pyridin-2-ylsulfonyl chloride for isopropyl chloroformate. MS (ESI) 490 (M+H).

Example 87

Preparation of 1-(4-(methylsulfonyl)phenyl)-4-(1-(thiophen-3-ylsulfonyl)piperidin-4-yloxy)pyridin-2(1H)-one

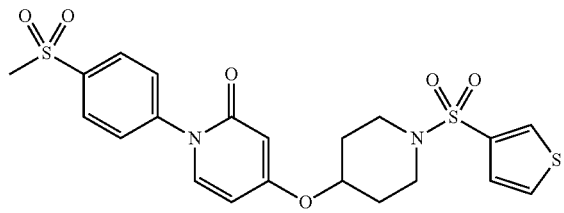 [SMILES: CS(=O)(=O)c1ccc(-n2ccc(OC3CCN(S(=O)(=O)c4ccsc4)CC3)cc2=O)cc1]

Example 87 was prepared according to procedures described in Example 3 substituting thiophen-3-ylsulfonyl chloride for isopropyl chloroformate. MS (ESI) 495 (M+H).

Example 88

Preparation of 1-(4-(methylsulfonyl)phenyl)-4-(1-picolinoylpiperidin-4-yloxy)pyridin-2(1H)-one

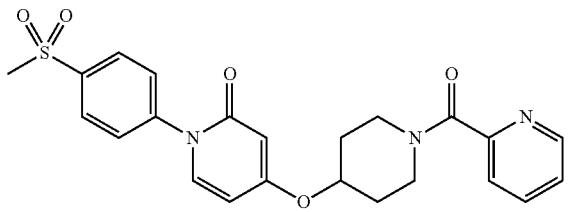 [SMILES: CS(=O)(=O)c1ccc(-n2ccc(OC3CCN(C(=O)c4ccccn4)CC3)cc2=O)cc1]

Example 88 was prepared according to procedures described in Example 3 substituting picolinoyl chloride for isopropyl chloroformate. MS (ESI) 454 (M+H).

Example 89

Preparation of 2-methoxyethyl 4-(1-(4-(methylsulfonyl)phenyl)-2-oxo-1,2-dihydropyridin-4-yloxy)piperidine-1-carboxylate

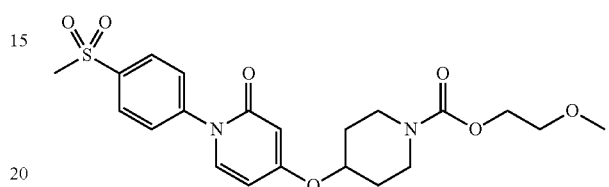

Example 89 was prepared according to procedures described in Example 3 substituting 2-methoxyethyl chloroformate for isopropyl chloroformate. MS (ESI) 451 (M+H).

Example 90

Preparation of methyl 4-(1-(4-(methylsulfonyl)phenyl)-2-oxo-1,2-dihydropyridin-4-yloxy)piperidine-1-carboxylate

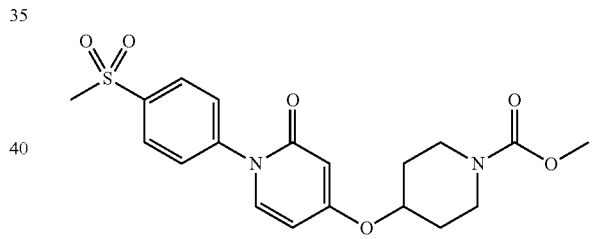

Example 90 was prepared according to procedures described in Example 3 substituting methyl chloroformate for isopropyl chloroformate. MS (ESI) 407 (M+H).

Example 91

Preparation of propyl 4-(1-(4-(methylsulfonyl)phenyl)-2-oxo-1,2-dihydropyridin-4-yloxy)piperidine-1-carboxylate

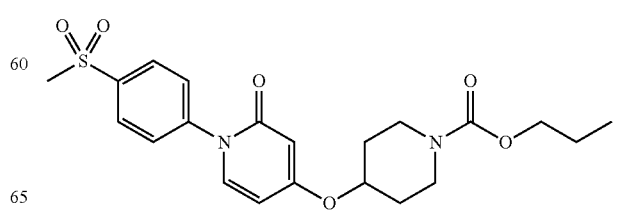

Example 91 was prepared according to procedures described in Example 3 substituting propyl chloroformate for isopropyl chloroformate. MS (ESI) 435 (M+H).

Example 92

Preparation of prop-2-ynyl 4-(1-(4-(methylsulfonyl)phenyl)-2-oxo-1,2-dihydropyridin-4-yloxy)piperidine-1-carboxylate

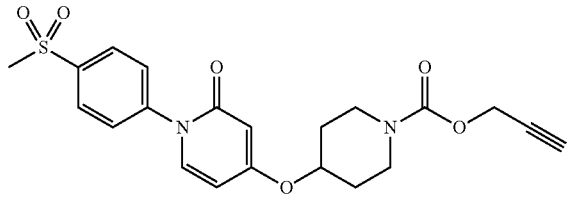 [SMILES: C#CCOC(=O)N1CCC(Oc2ccn(-c3ccc(S(C)(=O)=O)cc3)c(=O)c2)CC1]

Example 92 was prepared according to procedures described in Example 3 substituting prop-2-ynyl chloroformate for isopropyl chloroformate. MS (ESI) 431 (M+H).

Example 93

Preparation of 2,2-dimethylpropyl 4-(1-(4-(methylsulfonyl)phenyl)-2-oxo-1,2-dihydropyridin-4-yloxy)piperidine-1-carboxylate

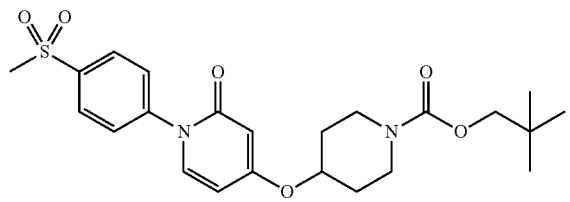 [SMILES: CC(C)(C)COC(=O)N1CCC(Oc2ccn(-c3ccc(S(C)(=O)=O)cc3)c(=O)c2)CC1]

Example 93 was prepared according to procedures described in Example 3 substituting 2,2-dimethylpropyl chloroformate for isopropyl chloroformate. MS (ESI) 463 (M+H).

Example 94

Preparation of N-isopropyl 4-(1-(4-(methylsulfonyl)phenyl)-2-oxo-1,2-dihydropyridin-4-yloxy)piperidine-1-carboxamide

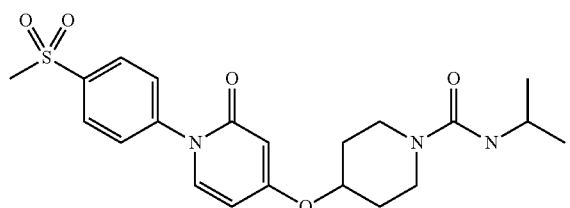

Example 94 was prepared according to procedures described in Example 3 substituting isopropyl isocyanate for isopropyl chloroformate. MS (ESI) 434 (M+H).

Example 95

Preparation of N-methyl 4-(1-(4-(methylsulfonyl)phenyl)-2-oxo-1,2-dihydropyridin-4-yloxy)piperidine-1-carboxamide

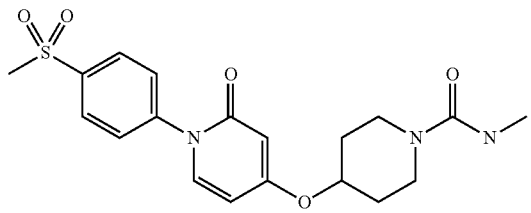

Example 95 was prepared according to procedures described in Example 3 substituting methyl isocyanate for isopropyl chloroformate. MS (ESI) 406 (M+H).

Example 96

Preparation of N-ethyl 4-(1-(4-(methylsulfonyl)phenyl)-2-oxo-1,2-dihydropyridin-4-yloxy)piperidine-1-carboxamide

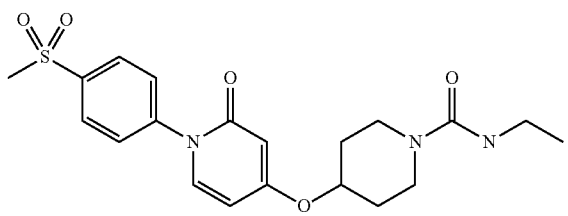 [SMILES: CCNC(=O)N1CCC(Oc2ccn(-c3ccc(S(C)(=O)=O)cc3)c(=O)c2)CC1]

Example 96 was prepared according to procedures described in Example 3 substituting ethyl isocyanate for isopropyl chloroformate. MS (ESI) 420 (M+H).

Example 97

Preparation of N-propyl 4-(1-(4-(methylsulfonyl)phenyl)-2-oxo-1,2-dihydropyridin-4-yloxy)piperidine-1-carboxamide

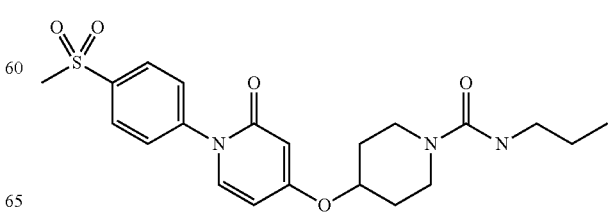

Example 97 was prepared according to procedures described in Example 3 substituting propyl isocyanate for isopropyl chloroformate. MS (ESI) 434 (M+H).

Example 98

Preparation of N-cyclohexyl 4-(1-(4-(methylsulfonyl)phenyl)-2-oxo-1,2-dihydropyridin-4-yloxy)piperidine-1-carboxamide

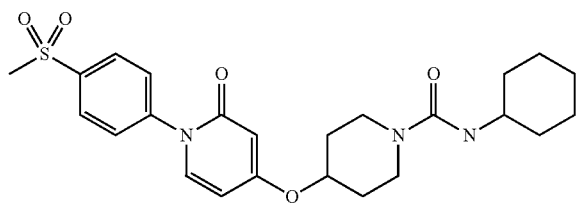 [SMILES: CS(=O)(=O)c1ccc(-n2ccc(OC3CCN(C(=O)NC4CCCCC4)CC3)cc2=O)cc1]

Example 98 was prepared according to procedures described in Example 3 substituting cyclohexyl isocyanate for isopropyl chloroformate. MS (ESI) 474 (M+H).

Example 99

Preparation of N-benzyl 4-(1-(4-(methylsulfonyl)phenyl)-2-oxo-1,2-dihydropyridin-4-yloxy)piperidine-1-carboxamide

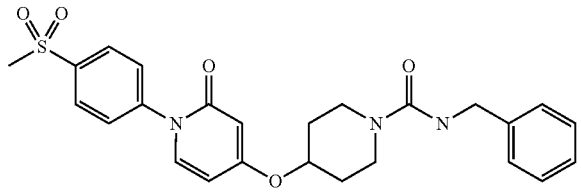 [SMILES: CS(=O)(=O)c1ccc(-n2ccc(OC3CCN(C(=O)NCc4ccccc4)CC3)cc2=O)cc1]

Example 99 was prepared according to procedures described in Example 3 substituting benzyl isocyanate for isopropyl chloroformate. MS (ESI) 481 (M+H).

Example 100

Preparation of N-4-methoxybenzyl 4-(1-(4-(methylsulfonyl)phenyl)-2-oxo-1,2-dihydropyridin-4-yloxy)piperidine-1-carboxamide

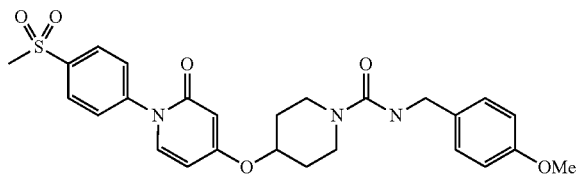 [SMILES: COc1ccc(CNC(=O)N2CCC(Oc3ccn(-c4ccc(S(C)(=O)=O)cc4)c(=O)c3)CC2)cc1]

Example 100 was prepared according to procedures described in Example 3 substituting 4-methoxybenzyl isocyanate for isopropyl chloroformate. MS (ESI) 512 (M+H).

Example 101

Preparation of N-cyclopentyl 4-(1-(4-(methylsulfonyl)phenyl)-2-oxo-1,2-dihydropyridin-4-yloxy)piperidine-1-carboxamide

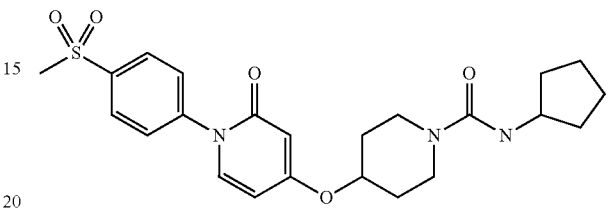

Example 101 was prepared according to procedures described in Example 3 substituting cyclopentyl isocyanate for isopropyl chloroformate. MS (ESI) 460 (M+H).

Example 102

Preparation of N-cyclohexylmethyl 4-(1-(4-(methylsulfonyl)phenyl)-2-oxo-1,2-dihydropyridin-4-yloxy)piperidine-1-carboxamide

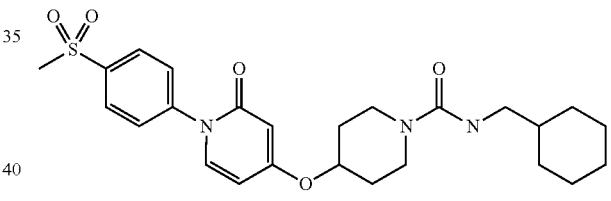

Example 102 was prepared according to procedures described in Example 3 with substitution of cyclohexylmethyl isocyanate for isopropyl chloroformate. MS (ESI) 488 (M+H).

Example 103

Preparation of 4-tert-butylphenyl 4-(1-(4-(methylsulfonyl)phenyl)-2-oxo-1,2-dihydropyridin-4-yloxy)piperidine-1-carboxylate

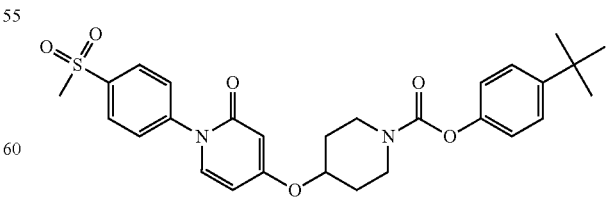

Example 103 was prepared according to procedures described in Example 2 substituting 4-tert-butylphenol for 1,1,1-trifluoro-2-propanol at Step B. $^1$H NMR (500 MHz, CDCl$_3$) δ 8.08 (d, J=8.80 Hz, 2 H), 7.63 (d, J=8.80 Hz, 2 H), 7.38 (d, J=8.80 Hz, 2 H), 7.19-7.30 (m, 1 H), 7.03 (d, J=8.80 Hz, 2 H), 6.09 (dd, J=7.70, 2.75 Hz, 1 H), 6.02 (d, J=2.75 Hz, 1 H), 4.52-4.66 (m, 1 H), 3.90 (app brs, 1 H), 3.77-3.89 (m, 1 H), 3.59-3.72 (m, 1 H), 3.56 (app brs, 1 H), 3.10 (s, 9 H), 2.08 (m, 2 H), 1.83-1.99 (m, 2 H), 1.32 (s, 9 H). MS (ESI) 525 (M+H).

Example 104

Preparation of 4-isopropylphenyl 4-(1-(4-(methylsulfonyl)phenyl)-2-oxo-1,2-dihydropyridin-4-yloxy)piperidine-1-carboxylate

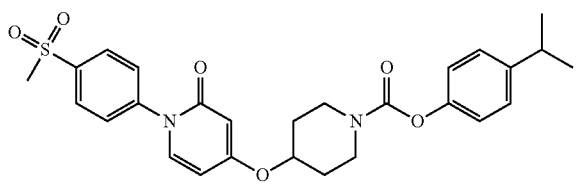 [SMILES: CC(C)c1ccc(OC(=O)N2CCC(Oc3ccn(-c4ccc(S(C)(=O)=O)cc4)c(=O)c3)CC2)cc1]

Example 104 was prepared according to procedures described in Example 2 substituting 4-isopropylphenol for 1,1,1-trifluoro-2-propanol at step B. $^1$H NMR (500 MHz, CDCl$_3$) δ 8.09 (d, J=8.25 Hz, 2 H), 7.62 (d, J=8.80 Hz, 2 H), 7.29 (d, J=7.70 Hz, 1 H), 7.22 (d, J=8.80 Hz, 2 H), 7.02 (d, J=8.25 Hz, 2 H), 6.13-6.21 (m, 2 H), 4.57-4.66 (m, 1 H), 3.91 (app brs, 1 H), 3.79-3.89 (m, 1 H), 3.59-3.69 (m, 1 H), 3.55 (app brs, 1 H), 3.10 (s, 3 H), 2.85-2.96 (m, 1 H), 2.09 (app brs, 2 H), 1.84-2.00 (m, 2 H), 0.24 (d, J=6.60 Hz, 6 H). MS (ESI) 511 (M+H).

Example 105

Preparation of 4-(1-(5-cyclopropylpyrimidin-2-yl)piperidin-4-yloxy)-1-(4-(methylsulfonyl)phenyl)pyridin-2(1H)-one

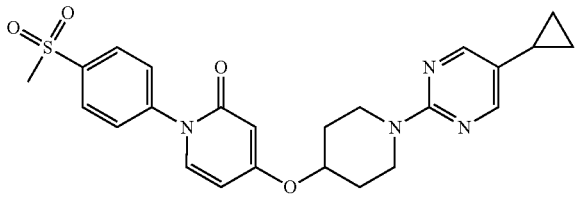 [SMILES: CS(=O)(=O)c1ccc(-n2ccc(OC3CCN(c4ncc(C5CC5)cn4)CC3)cc2=O)cc1]

A mixture of 4-(1-(5-bromopyrimidin-2-yl)piperidin-4-yloxy)-1-(4-(methylsulfonyl)phenyl)pyridin-2(1H)-one (47.0 mg, 0.093 mmol), potassium carbonate (64 mg, 0.47 mmol, EMD) and cyclopropylboronic acid (24 mg, 0.28 mmol, Aldrich) in THF (0.8 mL) and Water (0.1 mL) was degassed by vacuum and purged with Argon. To the resulting mixture was added 1,1'-Bis(diphenylphosphino)ferrocene-palladium(II)dichloride dichloromethane complex (7.65 mg, 9.30 μmol, Aldrich) and then stirred under Argon at 66° C. for 3 h. The reaction mixture was cooled to room temperature followed by addition of another portion of cyclopropylboronic acid (24 mg, 0.28 mmol, Aldrich) and 1,1'-Bis(diphenylphosphino)ferrocene-palladium(II)dichloride dichloromethane complex (7.65 mg, 9.30 μmol, Aldrich). Reaction mixture was stirred under Argon at 66° C. for another 3 hours and then concentrated in vacuo to a brown solid. The solid was purified by flash chromatography (SiO$_2$, 0 to 100% EtOAc in hexanes) to yield 18 mg of Example 105 as an off-white solid. $^1$H NMR (400 MHz, CDCl$_3$) δ ppm 8.13 (s, 2 H) 8.07 (d, J=8.31 Hz, 2 H), 7.62 (d, J=8.31 Hz, 2 H), 7.23 (d, J=7.83 Hz, 1 H), 6.06 (d, J=7.82 Hz, 1 H), 6.00 (s, 1 H), 4.55-4.59 (m, 1 H), 4.15-4.21 (m, 2 H), 3.59-3.66 (m, 2 H), 3.09 (s, 3 H), 2.03-2.10 (m, 2 H), 1.79-1.88 (m, 2 H), 1.68-1.75 (m, 1 H), 0.88-0.94 (m, 2 H), 0.56-0.62 (m, 2 H). MS (ESI) 467 (M+H).

Example 106

Preparation of 1-(4-(methylsulfonyl)phenyl)-4-(1-(5-propylpyrimidin-2-yl)piperidin-4-yloxy)pyridin-2(1H)-one, TFA salt

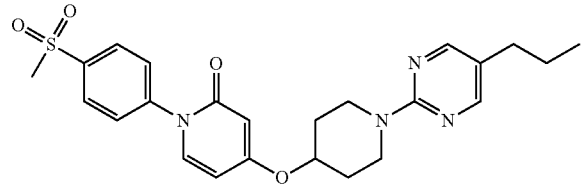 [SMILES: CCCc1cnc(N2CCC(Oc3ccn(-c4ccc(S(C)(=O)=O)cc4)c(=O)c3)CC2)nc1]

Step A. Preparation of 1-(4-(methylsulfonyl)phenyl)-4-(piperidin-4-yloxy)pyridin-2(1H)-one hydrochloric acid salt A mixture of tert-butyl 4-(1-(4-(methylsulfonyl)phenyl)-2-oxo-1,2-dihydropyridin-4-yloxy)piperidine-1-carboxylate (5.279 g, 11.77 mmol) and hydrogen chloride (37% in H$_2$O, 40 mL, EMD) was stirred for 20 min and then concentrated in vacuo. The obtained solid was dissolved in methanol (80 mL) and diethyl ether (300 mL) was added. The resulting solid was filtered to give 4.52 g of the desired product as an off-white solid. MS (ESI) 349 (M+H).

Step B

Example 106

To a stirring suspension of 1-(4-(methylsulfonyl)phenyl)-4-(piperidin-4-yloxy)pyridin-2(1H)-one hydrochloric acid salt (4.50 g, 11.7 mmol) and potassium carbonate (6.46 g, 46.8 mmol, EMD) in dry DMF (180 mL) at room temperature was added 2-chloro-5-propylpyrimidine (2.75 g, 17.54 mmol, WAKO). The reaction mixture was heated to 100° C. for 12 hours and then concentrated in vacuo to a brown solid. The solid was purified by flash chromatography (SiO$_2$, 0 to 15% MeOH in CH$_2$Cl$_2$ and SiO$_2$, 0 to 100% EtOAc in CH$_2$Cl$_2$) to yield 3.988 g of Example 106 as a light yellow solid. $^1$H NMR (400 MHz, CDCl$_3$) δ ppm 8.17 (s, 2 H), 8.07 (d, J=8.31 Hz, 2 H), 7.62 (d, J=8.80 Hz, 2 H), 7.23 (d, J=7.83 Hz, 1 H), 6.07 (dd, J=7.83, 2.45 Hz, 1 H), 6.02 (d, J=2.45 Hz, 1 H), 4.54-4.61 (m, 1 H), 4.15-4.23 (m, 2 H), 3.59-3.69 (m, 2

H), 3.09 (s, 3 H), 2.41 (t, J=7.58 Hz, 2 H), 2.04-2.12 (m, 2 H), 1.79-1.90 (m, 2 H), 1.53-1.62 (m, 2 H), 0.94 (t, J=7.34 Hz, 3 H). MS (ESI) 469 (M+H).

Example 107

Preparation of 4-propylphenyl 4-(1-(4-(methylsulfonyl)phenyl)-2-oxo-1,2-dihydropyridin-4-yloxy)piperidine-1-carboxylate

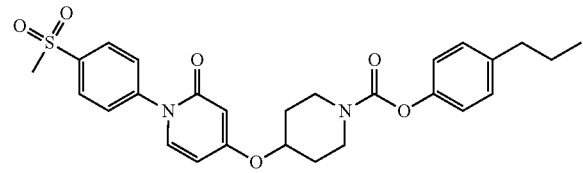

Example 107 was prepared according to procedures described in Example 2 substituting 4-propylphenol for 1,1,1-trifluoro-2-propanol at Step B. $^1$H NMR (500 MHz, CDCl$_3$) δ 8.08 (d, J=8.80 Hz, 2 H), 7.62 (d, J=8.25 Hz, 2 H), 7.24-7.29 (m, 1 H), 7.17 (d, J=8.25 Hz, 2 H), 7.01 (d, J=8.80 Hz, 2 H), 6.11 (dd, J=7.70, 2.20 Hz, 1 H), 6.07 (d, J=2.75 Hz, 1 H), 4.53-4.66 (m, 1 H), 3.91 (app brs, 1 H), 3.78-3.88 (m, 1 H), 3.59-3.71 (m, 1 H), 3.52-3.60 (m, 1 H), 3.10 (s, 3 H), 2.50-2.64 (m, 2 H), 2.09 (app brs, 2 H), 1.80-1.98 (m, 2 H), 1.55-1.72 (m, 2 H), 0.94 (t, J=7.42 Hz, 3 H). MS (ESI) 511 (M+H).

Example 108

Preparation of 4-(1-(5-methylpyrimidin-2-yl)piperidin-4-yloxy)-1-(4-(methylsulfonyl)phenyl)pyridin-2(1H)-one, TFA salt

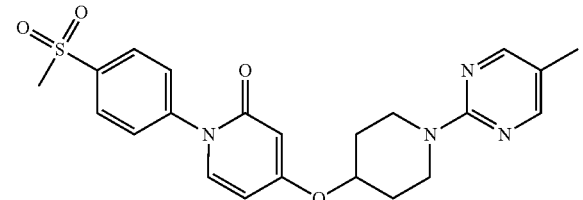

Example 108 was prepared according to procedures described in Example 105 substituting methylboronic acid (Aldrich) for cyclopropylboronic acid except that the crude product was purified by preparative HPLC (C$_{18}$ column, 10-100% MeOH in water containing 0.1% trifluoroacetic acid) to give Example 108 upon lyophilization. $^1$H NMR (400 MHz, CD$_3$OD) δ ppm 8.30 (s, 2 H), 8.12 (d, J=8.31 Hz, 2 H), 7.69 (d, J=8.80 Hz, 2 H), 7.60 (d, J=7.83 Hz, 1 H), 6.28 (dd, J=7.58, 2.69 Hz, 1 H), 6.10 (d, J=2.45 Hz, 1 H), 4.78-4.85 (m, 1 H), 4.12-4.20 (m, 2 H), 3.68-3.77 (m, 2 H), 3.18 (s, 3 H), 2.19 (s, 3 H), 2.05-2.17 (m, 2 H), 1.80-1.90 (m, 2 H). MS (ESI) 441 (M+H).

Example 109

Preparation of 1-(4-(methylsulfonyl)phenyl)-4-(1-(5-phenylpyrimidin-2-yl)piperidin-4-yloxy)pyridin-2(1H)-one, TFA salt

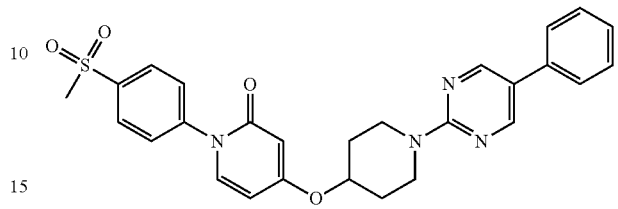

Example 109 was prepared according to procedures described in Example 105 substituting phenylboronic acid (Aldrich) for cyclopropylboronic acid and substituting DMF for THF. Reaction was heated under microwave condition at 120° C. for 10 min. $^1$H NMR (400 MHz, CDCl$_3$) δ ppm 8.56 (s, 2 H), 8.06 (d, J=8.80 Hz, 2H), 7.62 (d, J=8.80 Hz, 2 H), 7.40-7.50 (m, 4 H), 7.31-7.38 (m, 1 H), 7.23 (d, J=7.34 Hz, 1 H), 6.07 (dd, J=7.83, 2.45 Hz, 1 H), 6.02 (d, J=2.93 Hz, 1 H), 4.57-4.66 (m, 1 H), 4.19-4.28 (m, 2 H), 3.70-3.80 (m, 2 H), 3.08 (s, 3 H), 2.05-2.15 (m, 2 H), 1.83-1.94 (m, 2 H). MS (ESI) 503 (M+H).

Example 110

Preparation of 4-cyanophenyl 4-(1-(4-(methylsulfonyl)phenyl)-2-oxo-1,2-dihydropyridin-4-yloxy)piperidine-1-carboxylate

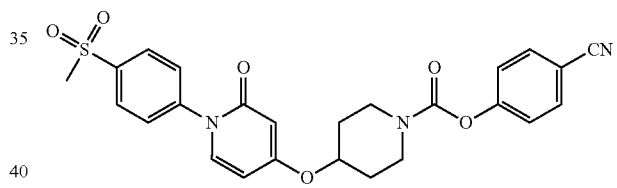

Example 110 was prepared according to procedures described in Example 2 substituting 4-hydroxybenzonitrile for 1,1,1-trifluoro-2-propanol at Step B. $^1$H NMR (500 MHz, CDCl$_3$) δ 8.08 (d, J=8.25 Hz, 2 H), 7.69 (d, J=8.80 Hz, 2 H), 7.62 (d, J=8.80 Hz, 2 H), 7.22-7.35 (m, 3 H), 6.11 (dd, J=7.42, 2.47 Hz, 1 H), 6.05 (d, J=2.75 Hz, 1 H), 4.57-4.65 (m, 1 H), 3.86-3.95 (m, 1 H), 3.76-3.86 (m, 1 H), 3.63-3.72 (m, 1 H), 3.55-3.64 (m, 1 H), 3.10 (s, 3 H), 2.09 (app brs, 2 H), 1.89-1.99 (m, 2 H). MS (ESI) 494 (M+H).

Example 111

Preparation of 2,2,2-trifluoroethyl 4-(1-(4-(methylsulfonyl)phenyl)-2-oxo-1,2-dihydropyridin-4-yloxy)piperidine-1-carboxylate

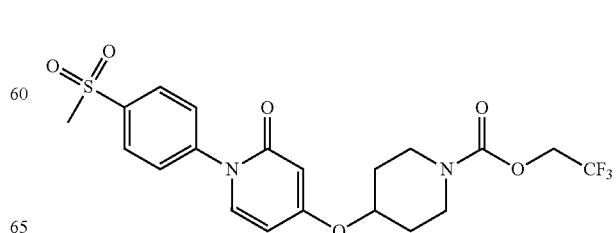

Example 111 was prepared according to procedures described in Example 2 substituting 2,2,2-trifluoroethanol for 1,1,1-trifluoro-2-propanol at Step B. ¹H NMR (500 MHz, CDCl₃) δ 8.09 (d, J=8.80 Hz, 2 H), 7.61 (d, J=8.80 Hz, 2 H), 7.31 (d, J=7.70 Hz, 1 H), 6.29 (d, J=2.20 Hz, 1 H), 6.20 (dd, J=7.70, 2.75 Hz, 1 H), 4.56-4.65 (m, 1 H), 4.44-4.57 (m, 2 H), 3.71-3.83 (m, 2 H), 3.46-3.58 (m, 2 H), 3.11 (s, 3 H), 2.02 (d app brs, 2 H), 1.86 (app brs, 2 H). MS (ESI) 475 (M+H).

Example 112

Preparation of (1R,5R)-2,2,2-trifluoroethyl 3-(1-(4-(methylsulfonyl)phenyl)-2-oxo-1,2-dihydropyridin-4-yloxy)-8-azabicyclo[3.2.1]octane-8-carboxylate

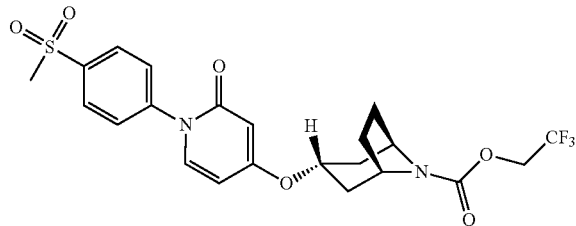

Example 112 was prepared according to procedures described in Example 2 substituting (3-exo)-tert-butyl 3-(1-(4-(methylsulfonyl)phenyl)-2-oxo-1,2-dihydropyridin-4-yloxy)-8-azabicyclo[3.2.1]octane-8-carboxylate (Example 25) for tert-butyl 4-(1-(4-(methylsulfonyl)phenyl)-2-oxo-1,2-dihydropyridin-4-yloxy)piperidine-1-carboxylate at Step A and 2,2,2-trifluoroethanol for 1,1,1-trifluoro-2-propanol at Step B. ¹H NMR (500 MHz, CDCl₃) δ 8.08 (d, J=8.80 Hz, 2 H), 7.61 (d, J=8.80 Hz, 2 H), 7.20-7.32 (m, 1 H), 6.24 (d, J=2.75 Hz, 1 H), 6.09 (dd, J=7.70, 2.75 Hz, 1 H), 4.73-4.87 (m, 1 H), 4.54-4.67 (m, 1 H), 4.39-4.55 (m, 3 H), 3.10 (s, 3 H), 2.17-2.30 (m, 2 H), 2.04-2.19 (m, 2 H), 1.68-1.94 (m, 4 H). MS (ESI) 501 (M+H).

Example 113

Preparation of 4-(1-(5,5'-bipyrimidin-2-yl)piperidin-4-yloxy)-1-(4-(methylsulfonyl)phenyl)pyridin-2(1H)-one

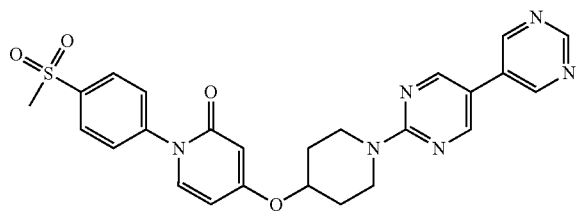 [SMILES: CS(=O)(=O)c1ccc(-n2ccc(OC3CCN(c4ncc(-c5cncnc5)cn4)CC3)cc2=O)cc1]

Example 113 was prepared according to procedures described in Example 109 substituting pyrimidin-5-ylboronic acid (Maybridge) for phenylboronic acid except that the crude solid was purified by flash chromatography (SiO₂, 0 to 10% MeOH in CH₂Cl₂) ¹H NMR (400 MHz, DMSO-d6) δ ppm 9.13 (s, 3 H), 8.84 (s, 2 H), 8.03 (d, J=8.31 Hz, 2 H), 7.69 (d, J=8.80 Hz, 2 H), 7.65 (d, J=7.34 Hz, 1 H), 6.05-6.14 (m, 2 H), 4.76-4.86 (m, 1 H), 4.25-4.35 (m, 2 H), 3.55-3.65 (m, 2 H), 3.28 (s, 3 H), 2.00-2.11 (m, 2 H), 1.58-1.69 (m, 2 H). MS (ESI) 505 (M+H).

Example 114

Preparation of 4-(1-(5-(4-chlorophenyl)pyrimidin-2-yl)piperidin-4-yloxy)-1-(4-(methylsulfonyl)phenyl)pyridin-2(1H)-one

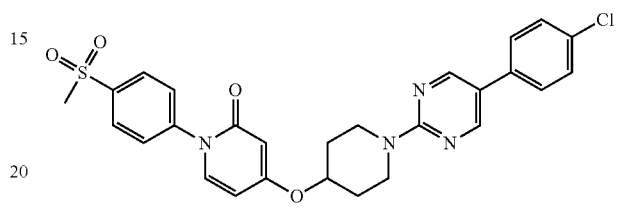

Example 114 was prepared according to procedures described in Example 106 substituting 2-chloro-5-(4-chlorophenyl)pyrimidine (Peakdale) for 2-chloro-5-propylpyrimidine in Step B. The reaction was heated under microwave conditions at 140-160° C. for 50 min. The crude solid was purified by flash chromatography (SiO₂, 0 to 100% EtOAc in Hexanes). ¹H NMR (400 MHz, DMSO-d6) δ ppm 8.72 (s, 2 H), 8.00-8.05 (m, 2 H), 7.67-7.71 (m, 4 H), 7.65 (d, J=7.82 Hz, 1 H), 7.40-7.55 (m, 2H), 6.07-6.13 (m, 2 H), 4.76-4.83 (m, 1 H), 4.24-4.33 (m, 2 H), 3.53-3.62 (m, 2 H), 3.28 (s, 3 H), 2.01-2.09 (m, 2 H), 1.58-1.68 (m, 2 H). MS (ESI) 537 (M+H).

Example 115

Preparation of 4-(1-(5-bromopyridin-2-yl)piperidin-4-yloxy)-1-(4-(methylsulfonyl)phenyl)pyridin-2(1H)-one

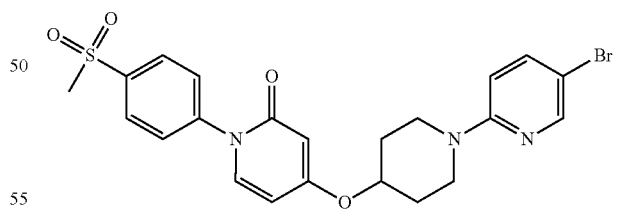

Example 115 was prepared according to procedures described in Example 114 substituting 5-bromo-2-fluoropyridine (Aldrich) for 2-chloro-5-(4-chlorophenyl)pyrimidine. ¹H NMR (400 MHz, CDCl₃) δ ppm 8.20 (d, J=2.45 Hz, 1H), 8.04-8.09 (m, 2 H), 7.59-7.64 (m, 2 H), 7.56 (dd, J=9.05, 2.20 Hz, 1 H), 7.23 (d, J=7.82 Hz, 1 H), 6.62 (d, J=9.29 Hz, 1 H), 6.06 (dd, J=7.58, 2.69 Hz, 1 H), 6.00 (d, J=2.45 Hz, 1 H), 4.53-4.60 (m, 1 H), 3.84-3.92 (m, 2 H), 3.41-3.52 (m, 2 H), 3.09 (s, 3 H), 2.05-2.14 (m, 2 H), 1.84-1.94 (m, 2 H). MS (ESI) 504 (M+H).

Example 116

Preparation of 1-(4-(methylsulfonyl)phenyl)-4-(1-(5-phenylpyridin-2-yl)piperidin-4-yloxy)pyridin-2(1H)-one

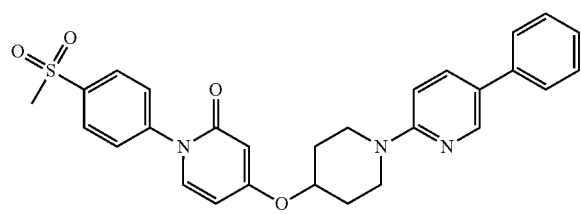 [SMILES: CS(=O)(=O)c1ccc(-n2ccc(OC3CCN(c4ccc(-c5ccccc5)cn4)CC3)cc2=O)cc1]

Example 116 was prepared according to procedures described in Example 105 substituting 4-(1-(5-bromopyridin-2-yl)piperidin-4-yloxy)-1-(4-(methylsulfonyl)phenyl) pyridin-2(1H)-one for 4-(1-(5-bromopyrimidin-2-yl)piperidin-4-yloxy)-1-(4-(methylsulfonyl)phenyl)pyridin-2(1H)-one, substituting phenylboronic acid (Aldrich) for cyclopropylboronic acid and substituting DMF for THF. The reaction was heated under microwave conditions at 120° C. for 10 min. $^1$H NMR (400 MHz, DMSO-d6) δ ppm 8.37 (d, J=2.45 Hz, 1 H), 7.95 (d, J=8.31 Hz, 2 H), 7.77 (dd, J=9.05, 2.20 Hz, 1 H), 7.51-7.63 (m, 5 H), 7.34 (t, J=7.58 Hz, 2 H), 7.21 (t, J=7.82 Hz, 1 H), 6.90 (d, J=8.80 Hz, 1 H), 5.98-6.04 (m, 2 H), 4.65-4.73 (m, 1 H), 3.92-4.00 (m, 2 H), 3.26-3.34 (m, 2 H), 3.20 (s, 3 H), 1.92-2.00 (m, 2 H), 1.51-1.61 (m, 2 H). MS (ESI) 502 (M+H).

Example 117

Preparation of isopropyl 4-(2-oxo-1-(4-(2,2,2-trifluoroacetamido)phenyl)-1,2-dihydropyridin-4-yloxy)piperidine-1-carboxylate

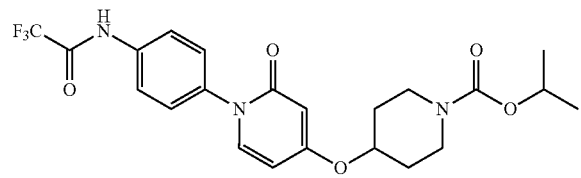 [SMILES: CC(C)OC(=O)N1CCC(Oc2ccn(-c3ccc(NC(=O)C(F)(F)F)cc3)c(=O)c2)CC1]

Step A. Preparation of isopropyl 4-(1-(4-aminophenyl)-2-oxo-1,2-dihydropyridin-4-yloxy)piperidine-1-carboxylate Isopropyl 4-(1-(4-aminophenyl)-2-oxo-1,2-dihydropyridin-4-yloxy)piperidine-1-carboxylate was prepared according to procedures described in Example 8 substituting tert-butyl 4-iodophenylcarbamate for 4-bromobenzonitrile at Step C and the cleavage of BOC protecting group occurred during the course of the reaction. MS (ESI) 372 (M+H).

Step B

Example 117

A mixture of isopropyl 4-(1-(4-aminophenyl)-2-oxo-1,2-dihydropyridin-4-yloxy)piperidine-1-carboxylate (20 mg, 0.054 mmol), pyridine (0.022 mL, 0.269 mmol, EMD) and methanesulfonyl chloride (0.013 mL, 0.162 mmol, Aldrich) in CH$_2$Cl$_2$ (0.5 mL) was stirred at room temperature for 30 min and then evaporated under reduced pressure. The residue was purified by preparative HPLC (C$_{18}$ column; 20-100% methanol in water containing 0.05% trifluoroacetic acid) to give Example 117 (12.4 mg, off-white solid, 49%) upon lyophilization. $^1$H NMR (500 MHz, CDCl$_3$) δ 9.72 (s, 1 H), 7.55 (d, J=8.80 Hz, 2 H), 7.24-7.29 (m, 1 H), 7.18 (d, J=8.80 Hz, 2 H), 6.05-6.24 (m, 2 H), 4.86-5.01 (m, 1 H), 4.52-4.64 (m, 1 H), 3.76 (app brs, 2 H), 3.37-3.52 (m, 2 H), 1.93-2.12 (m, 2 H), 1.76-1.88 (m, 2 H), 1.27 (d, J=6.05 Hz, 6 H). MS (ESI) 468 (M+H).

Example 118

Preparation of isopropyl 4-(1-(4-acetamidophenyl)-2-oxo-1,2-dihydropyridin-4-yloxy)piperidine-1-carboxylate

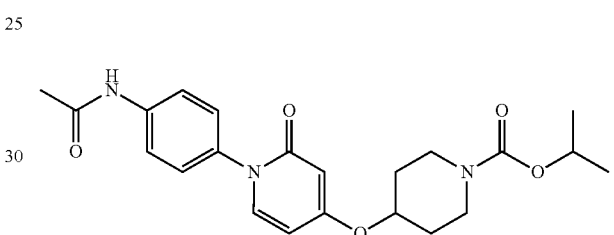

Example 118 was prepared according to procedures described in Example 117 substituting acetyl chloride for methanesulfonyl chloride at Step B. $^1$H NMR (500 MHz, CDCl$_3$) δ 8.44 (d, J=7.70 Hz, 1 H), 7.48 (d, J=8.25 Hz, 2 H), 7.29 (d, J=7.70 Hz, 1 H), 7.18 (d, J=8.25 Hz, 2 H), 6.25 (d, J=2.75 Hz, 1 H), 6.15 (dd, J=7.42, 2.47 Hz, 1 H), 4.90-5.02 (m, 1 H), 4.49-4.62 (m, 1 H), 3.76 (app brs, 2 H), 3.34-3.48 (m, 2 H), 2.14 (s, 3 H), 1.93-2.07 (m, 2 H), 1.80 (app brs, 2 H). MS (ESI) 449 (M+H).

Example 119

Preparation of isopropyl 4-(1-(4-(3-methylureido)phenyl)-2-oxo-1,2-dihydropyridin-4-yloxy)piperidine-1-carboxylate

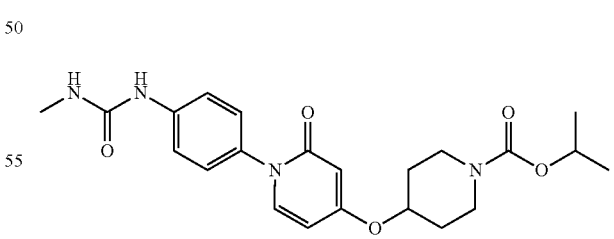

Example 118 was prepared according to procedures described in Example 117 substituting methylisocyanate for methanesulfonyl chloride at Step B. $^1$H NMR (500 MHz, CDCl$_3$) δ 7.78 (brs, 1 H), 7.23-7.29 (m, 1 H), 7.11-7.18 (m, 2 H), 7.05-7.11 (m, 1 H), 6.05-6.17 (m, 2 H), 4.88-5.00 (m, 1 H), 4.51-4.60 (m, 1 H), 3.68-3.81 (m, 2 H), 3.36-3.50 (m, 2 H), 2.79 (s, 3 H), 1.99 (app brs, 2 H), 1.82 (app brs, 2 H), 1.27 (d, J=6.60 Hz, 6 H). MS (ESI) 429 (M+H).

Example 120

Preparation of 4-(1-(5-isopropylpyrimidin-2-yl)piperidin-4-yloxy)-1-(4-(methylsulfonyl)phenyl)pyridin-2(1H)-one, TFA salt

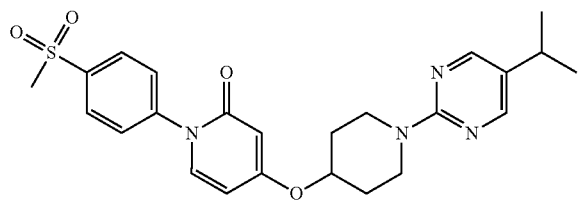 [SMILES: CC(C)c1cnc(N2CCC(Oc3ccn(-c4ccc(S(C)(=O)=O)cc4)c(=O)c3)CC2)nc1]

Step A. Preparation of prop-1-en-2-ylboronic acid

To a stirring solution of prop-1-en-2-ylmagnesium bromide (0.5 N in THF, 20 mL, 10.00 mmol, Aldrich) in THF (12.00 mL) at room temperature was added trimethyl borate (3.34 mL, 30.0 mmol, Aldrich). The reaction was stirred at room temperature for 2.5 h and then cooled to 0° C. To the reaction was added hydrogen chloride (1 N in H$_2$O, 12 mL) and stirred for 10 min. The resulting mixture was extracted with diethyl ether (2×20 mL). The organic layers were combined, dried over Na$_2$SO$_4$, and concentrated in vacuo to yield 600 mg of crude product as a white solid.

Step B. Preparation of 1-(4-(methylsulfonyl)phenyl)-4-(1-(5-(prop-1-en-2-yl)pyrimidin-2-yl)piperidin-4-yloxy)pyridin-2(1H)-one A mixture of 4-(1-(5-bromopyrimidin-2-yl)piperidin-4-yloxy)-1-(4-(methylsulfonyl)phenyl)pyridin-2(1H)-one (103 mg, 0.20 mmol), potassium carbonate (140 mg, 1.02 mmol, EMD) and prop-1-en-2-ylboronic acid (52.4 mg, 0.610 mmol) in DMF (1.8 mL) and Water (0.2 mL) was degassed by vacuum and purged with Argon. To the resulting mixture was added 1,1'-Bis(diphenylphosphino)ferrocene-palladium(II)dichloride dichloromethane complex (16.72 mg, 0.020 mmol, Aldrich) and then heated under microwave conditions at 120° C. for 20 min. The reaction mixture was concentrated in vacuo to a brown solid. The solid was purified by flash chromatography (SiO$_2$, 0 to 100% EtOAc in hexanes) to yield 25 mg of desired product as a light yellow solid. MS (ESI) 467 (M+H).

Step C. Example 120

A stirring suspension of 1-(4-(methylsulfonyl)phenyl)-4-(1-(5-(prop-1-en-2-yl)pyrimidin-2-yl)piperidin-4-yloxy)pyridin-2(1H)-one (25 mg, 0.054 mmol) and palladium on activated carbon (20 mg, 10 wt. %, wet, Aldrich) in MeOH (10 mL) was placed under hydrogen (1 Atm) for 1 h. The resulting mixture was purged with Argon and then filtered through a 45 μM syringe filter. The filtrate was concentrated in vacuo to a yellow oil. The oil was purified by preparative HPLC (C$_{18}$ column, 10-100% MeOH in water containing 0.1% trifluoroacetic acid) to yield 12.3 mg of Example 120 as a white solid upon lyophilization $^1$H NMR (400 MHz, CDCl$_3$) δ ppm 8.22 (s, 2 H), 7.97-8.04 (m, 2 H), 7.52-7.59 (m, 2 H), 7.17 (d, J=7.34 Hz, 1 H), 6.02 (dd, J=7.82, 2.45 Hz, 1 H), 5.98 (d, J=2.45 Hz, 1 H), 4.48-4.60 (m, 1 H), 4.04-4.15 (m, 2 H), 3.59-3.72 (m, 2 H), 3.03 (s, 3 H), 2.68-2.81 (m, 1 H), 1.95-2.09 (m, 2 H), 1.75-1.90 (m, 2 H), 1.18 (d, J=6.85 Hz, 6 H). MS (ESI) 469 (M+H).

Example 121

Preparation of 4-butylphenyl 4-(1-(4-(methylsulfonyl)phenyl)-2-oxo-1,2-dihydropyridin-4-yloxy)piperidine-1-carboxylate

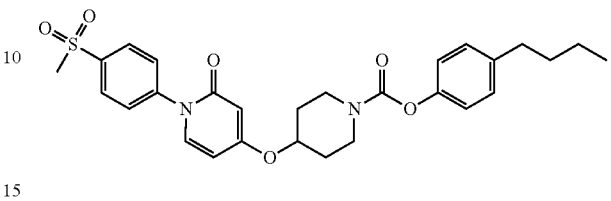

Example 110 was prepared according to procedures described in Example 2 substituting 4-n-butylphenol for 1,1,1-trifluoro-2-propanol at Step B. $^1$H NMR (500 MHz, CDCl$_3$) δ 8.09 (d, J=8.25 Hz, 2 H), 7.61 (d, J=8.80 Hz, 2 H), 7.37 (d, J=7.15 Hz, 1 H), 7.17 (d, J=8.80 Hz, 2 H), 7.00 (d, J=8.25 Hz, 2 H), 6.52 (d, J=2.75 Hz, 1 H), 6.31 (dd, J=7.70, 2.20 Hz, 1 H), 4.62-4.72 (m, 1 H), 3.89-4.00 (m, 1 H), 3.87 (app brs, 1 H), 3.66 (app brs, 1 H), 3.56 (app brs, 1 H), 3.11 (s, 3 H), 2.53-2.66 (m, 2 H), 2.12 (app brs, 2 H), 1.88-1.98 (m, 2 H), 1.52-1.64 (m, 2 H), 1.27-1.42 (m, 2 H), 0.92 (t, J=7.42 Hz, 3 H). MS (ESI) 525 (M+H).

Example 122

Preparation of 4-(1-(5-cyclohexenylpyrimidin-2-yl)piperidin-4-yloxy)-1-(4-(methylsulfonyl)phenyl)pyridin-2(1H)-one

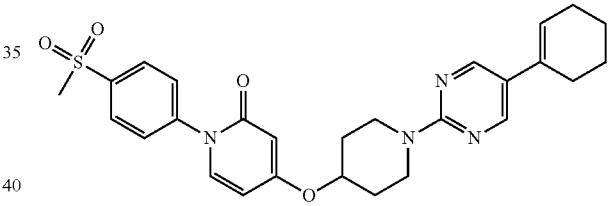

Example 122 was prepared according to procedures described in Example 109 substituting cyclohexenylboronic acid (Combi-Phos) for phenylboronic acid. $^1$H NMR (400 MHz, DMSO-d6) δ ppm 8.43 (s, 2 H), 8.03 (d, J=8.31 Hz, 2 H), 7.68 (d, J=8.31 Hz, 2 H), 7.64 (d, J=7.82 Hz, 1 H), 6.02-6.15 (m, 3 H), 4.70-4.84 (m, 1 H), 4.16-4.29 (m, 2 H), 3.44-3.57 (m, 2 H), 3.28 (s, 3 H), 2.25-2.35 (m, 2 H), 2.09-2.19 (m, 2 H), 1.93-2.07 (m, 2 H), 1.65-1.76 (m, 2 H), 1.53-1.64 (m, 4 H). MS (ESI) 507 (M+H).

Example 123

Preparation of biphenyl-4-yl 4-(1-(4-(methylsulfonyl)phenyl)-2-oxo-1,2-dihydropyridin-4-yloxy)piperidine-1-carboxylate

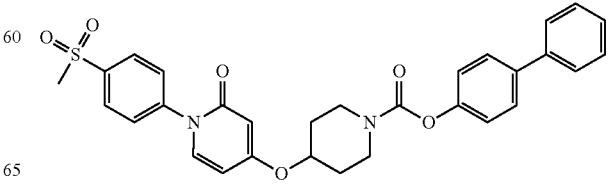

Example 123 was prepared according to procedures described in Example 2 substituting biphenyl-4-ol for 1,1,1-trifluoro-2-propanol at Step B. $^1$H NMR (500 MHz, CDCl$_3$) δ 8.08 (d, J=8.25 Hz, 2 H), 7.63 (d, J=7.70 Hz, 2 H), 7.58 (t, J=7.97 Hz, 4 H), 7.44 (t, J=7.42 Hz, 2 H), 7.35 (t, J=6.87 Hz, 1 H), 7.24-7.28 (m, 1 H), 7.19 (d, J=8.25 Hz, 2 H), 6.09 (dd, 1 H), 6.01 (d, J=2.75 Hz, 1 H), 4.54-4.66 (m, 1 H), 3.94 (app brs, 1 H), 3.84 (app brs, 1 H), 3.67 (app brs, 1 H), 3.69 (app brs, 1 H), 3.10 (s, 3 H), 2.10 (app brs, 2 H), 1.95 (app brs, 2 H). MS (ESI) 555 (M+H).

Example 124

Preparation of 4-pentylphenyl 4-(1-(4-(methylsulfonyl)phenyl)-2-oxo-1,2-dihydropyridin-4-yloxy)piperidine-1-carboxylate

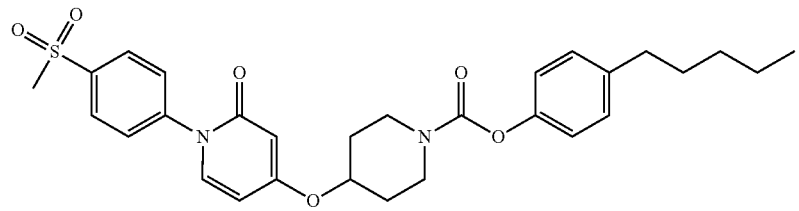 [SMILES: CCCCCc1ccc(OC(=O)N2CCC(Oc3ccn(-c4ccc(S(C)(=O)=O)cc4)c(=O)c3)CC2)cc1]

Example 124 was prepared according to procedures described in Example 2 substituting 4-pentylphenol (Alfa Aesar) for 1,1,1-trifluoro-2-propanol at Step B. $^1$H NMR (500 MHz, CDCl$_3$) δ d 8.10 (d, J=8.25 Hz, 2 H), 7.61 (d, J=8.80 Hz, 2 H), 7.38 (d, J=7.15 Hz, 1 H), 7.17 (d, J=8.80 Hz, 2 H), 7.00 (d, J=8.25 Hz, 2 H), 6.57 (d, J=2.20 Hz, 1 H), 6.34 (dd, J=7.42, 2.47 Hz, 1 H), 4.62-4.75 (m, 1 H), 3.79-4.03 (m, 2 H), 3.62 (m, 2 H), 3.12 (s, 3 H), 2.46-2.71 (m, 2 H), 2.13 (app brs, 2 H), 1.93 (m, 2 H), 1.52-1.69 (m, 2 H), 1.22-1.44 (m, 4 H), 0.89 (t, J=6.87 Hz, 3 H). MS (ESI) 539 (M+H).

Example 125

Preparation of 4-ethoxyphenyl 4-(1-(4-(methylsulfonyl)phenyl)-2-oxo-1,2-dihydropyridin-4-yloxy)piperidine-1-carboxylate

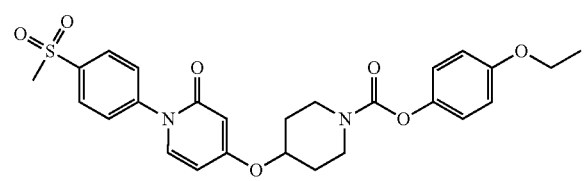 [SMILES: CCOc1ccc(OC(=O)N2CCC(Oc3ccn(-c4ccc(S(C)(=O)=O)cc4)c(=O)c3)CC2)cc1]

Example 125 was prepared according to procedures described in Example 2 substituting 4-ethoxyphenol for 1,1,1-trifluoro-2-propanol at Step B. $^1$H NMR (500 MHz, CDCl$_3$) δ 8.09 (d, J=8.80 Hz, 2 H), 7.61 (d, J=8.80 Hz, 2 H), 7.35 (d, J=7.70 Hz, 1 H), 7.01 (d, J=8.80 Hz, 2 H), 6.87 (d, J=8.80 Hz, 2 H), 6.48 (d, J=2.20 Hz, 1 H), 6.29 (dd, J=7.70, 2.75 Hz, 1 H), 4.61-4.72 (m, 1 H), 4.01 (q, J=6.78 Hz, 2 H), 3.93 (app brs, 1 H), 3.80-3.89 (m, 1 H), 3.60-3.70 (m, 1 H), 3.55 (app brs, 1 H), 3.11 (s, 3 H), 2.12 (app brs, 2 H), 1.86-1.98 (m, 2 H), 1.41 (t, J=6.87 Hz, 3 H). MS (ESI) 513 (M+H).

Example 126

Preparation of 4-(trifluoromethoxy)phenyl 4-(1-(4-(methylsulfonyl)phenyl)-2-oxo-1,2-dihydropyridin-4-yloxy)piperidine-1-carboxylate

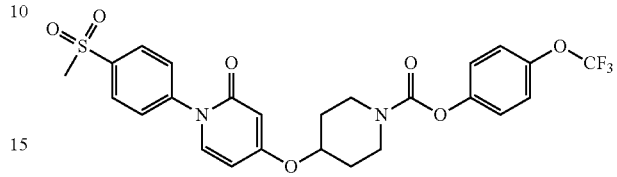

Example 126 was prepared according to procedures described in Example 2 substituting 4-(trifluoromethoxy)phenol (Aldrich) for 1,1,1-trifluoro-2-propanol at Step B. $^1$H NMR (500 MHz, CDCl$_3$) 8.10 (d, J=8.25 Hz, 2 H), 7.61 (d, J=8.80 Hz, 2 H), 7.38 (d, J=7.70 Hz, 1 H), 7.23 (d, J=8.80 Hz, 2 H), 7.15 (d, J=8.80 Hz, 2 H), 6.56 (d, J=2.75 Hz, 1 H), 6.33 (dd, J=7.70, 2.20 Hz, 1 H), 4.61-4.78 (m, 1 H), 3.90-4.01 (m, 1 H) 3.85 (app brs, 1 H), 3.68 (app brs, 1 H), 3.57 (app brs, 1 H), 3.12 (s, 3 H), 2.13 (app brs, 2 H), 1.87-1.99 (m, 2 H). MS (ESI) 553 (M+H).

Example 127

Preparation of 4-(1-(5-isobutylpyrimidin-2-yl)piperidin-4-yloxy)-1-(4-(methylsulfonyl)phenyl)pyridin-2(1H)-one

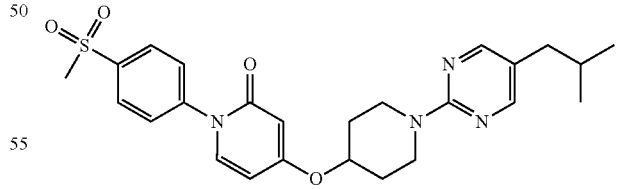

Example 127 was prepared according to procedures described in Example 120 Step B and C substituting 2-methylprop-1-enylboronic acid (Synthonix) for prop-1-en-2-ylboronic acid in Step B. The crude product was purified by flash chromatography (SiO$_2$, 0 to 100% EtOAc in CH$_2$Cl$_2$) $^1$H NMR (400 MHz, CDCl$_3$) δ ppm 8.14 (s, 2 H), 8.07 (d, J=8.31 Hz, 2 H), 7.62 (d, J=8.80 Hz, 2 H), 7.23 (d, J=7.82 Hz, 1 H), 6.07 (dd, J=7.82, 2.45 Hz, 1 H), 6.02 (d, J=2.45 Hz, 1 H), 4.53-4.62 (m, 1 H), 4.14-4.24 (m, 2 H), 3.60-3.71 (m, 2 H), 3.09 (s, 3 H), 2.30 (d, J=7.34 Hz, 2 H), 2.03-2.13 (m, 2 H), 1.81-1.90 (m, 2 H), 1.70-1.80 (m, 1 H), 0.91 (d, J=6.85 Hz, 6 H). MS (ESI) 483 (M+H).

Example 128

Preparation of isopropyl 4-(2-oxo-1-(pyridin-2-yl)-1,2-dihydropyridin-4-yloxy)piperidine-1-carboxylate, TFA salt

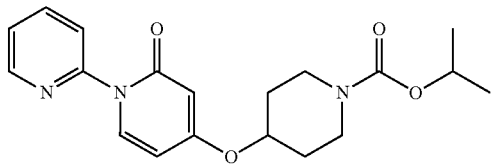 [SMILES: CC(C)OC(=O)N1CCC(Oc2ccn(-c3ccccn3)c(=O)c2)CC1]

Example 128 was prepared according to procedures described in Example 8 substituting 2-iodopyridine (TCI) for 4-bromobenzonitrile at Step C. $^1$H NMR (400 MHz, DMSO-$d_6$). δ 8.56 (d, J=4.0 Hz, 1 H), 7.94 (td, J=7.7, 1.7 Hz, 1 H), 7.82 (d, J=7.8 Hz, 1 H), 7.74 (d, J=8.2 Hz, 1 H), 7.44 (dd, J=6.8, 5.1 Hz, 1 H), 6.09 (dd, J=7.8, 2.7 Hz, 1 H), 5.99 (d, J=2.5 Hz, 1 H), 4.77 (spt, J=6.3 Hz, 1 H), 4.63-4.71 (m, 1 H), 3.64-3.74 (m, 2 H), 3.22 (t, J=10.0 Hz, 2 H), 1.84-2.01 (m, 2 H), 1.44-1.65 (m, 2 H), 1.18 (d, J=6.3 Hz, 6 H). MS (ESI) 358 (M+H).

Example 129

Preparation of 4-(1-(5-ethylpyridin-2-yl)piperidin-4-yloxy)-1-(4-(methylsulfonyl)phenyl)pyridin-2(1H)-one, TFA salt

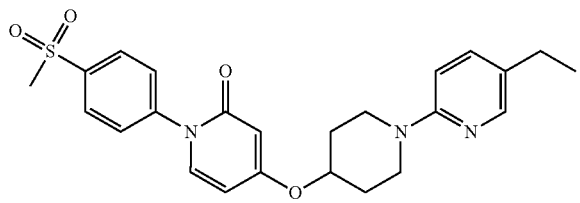 [SMILES: CCc1ccc(N2CCC(Oc3ccn(-c4ccc(S(C)(=O)=O)cc4)c(=O)c3)CC2)nc1]

Example 129 was prepared according to procedures described in Example 116 substituting ethylboronic acid (Alfa Aesar) for phenylboronic acid except that the reaction was heated under microwave conditions at 120-130° C. for 25 min and the crude product was purified by preparative HPLC ($C_{18}$ column, 10-100% MeOH in water containing 0.1% trifluoroacetic acid) to yield 4.7 mg of Example 129 upon lyophilization $^1$H NMR (400 MHz, DMSO-d6) δ ppm 8.02 (d, J=8.80 Hz, 2 H), 7.97 (s, 1 H), 7.69 (d, J=8.31 Hz, 1 H), 7.55 (d, J=8.80 Hz, 2 H), 7.22 (d, J=7.34 Hz, 1 H), 6.90 (d, J=8.80 Hz, 1 H), 6.06 (s, 1 H), 6.04 (s, 1 H), 4.59-4.70 (m, 1 H), 3.73-3.90 (m, 4 H), 3.03 (s, 3 H), 2.54 (q, J=7.66 Hz, 2 H), 1.99-2.19 (m, 4 H), 1.18 (t, J=7.58 Hz, 3 H). MS (ESI) 454 (M+H).

Example 130

Preparation of 1-(4-(methylsulfonyl)phenyl)-4-(1-(5-(pyridin-4-yl)pyrimidin-2-yl)piperidin-4-yloxy)pyridin-2(1H)-one

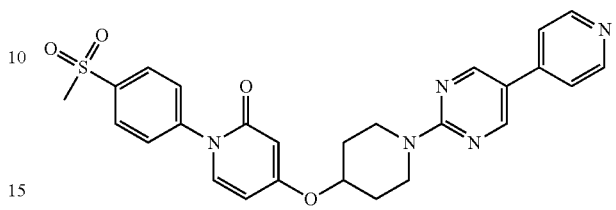

Example 130 was prepared according to procedures described in Example 113 substituting pyridin-4-ylboronic acid (Frontier Scientific) for pyrimidin-5-ylboronic acid. The resulting solid was washed with $CH_2Cl_2$ in a final purification step. $^1$H NMR (400 MHz, DMSO-d6) δ ppm 8.88 (s, 2 H), 8.56-8.62 (m, 2 H), 7.99-8.08 (m, 2 H), 7.67-7.75 (m, 4 H), 7.65 (d, J=7.82 Hz, 1 H), 6.10-6.14 (m, 1 H), 6.09 (d, J=2.45 Hz, 1 H), 4.78-4.86 (m, 1 H), 4.24-4.44 (m, 2 H), 3.55-3.72 (m, 2 H), 3.29 (s, 3 H), 1.99-2.15 (m, 2 H), 1.58-1.75 (m, 2 H). MS (ESI) 504 (M+H).

Example 131

Preparation of 1-(4-(methylsulfonyl)phenyl)-4-(1-(5-(pyridin-3-yl)pyrimidin-2-yl)piperidin-4-yloxy)pyridin-2(1H)-one

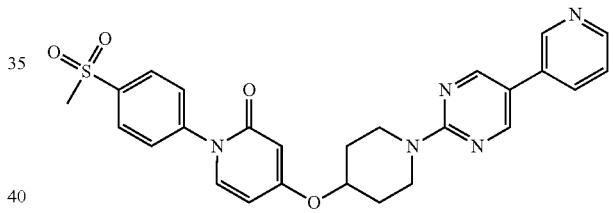

Example 131 was prepared according to procedures described in Example 113 substituting pyridin-3-ylboronic acid (Frontier Scientific) for pyrimidin-5-ylboronic acid. $^1$H NMR (400 MHz, DMSO-d6) δ ppm 8.89 (d, J=2.45 Hz, 1 H), 8.78 (s, 2 H), 8.53 (dd, J=4.65, 1.71 Hz, 1 H), 8.05-8.10 (m, 1 H), 8.00-8.05 (m, 2 H), 7.67-7.73 (m, 2 H), 7.65 (d, J=7.34 Hz, 1 H), 7.43-7.49 (m, 1 H), 6.10-6.15 (m, 1H), 6.09 (d, J=2.93 Hz, 1 H), 4.76-4.86 (m, 1 H), 4.24-4.35 (m, 2 H), 3.55-3.66 (m, 2 H), 3.29 (s, 3 H), 2.00-2.12 (m, 2 H), 1.57-1.71 (m, 2 H). MS (ESI) 504 (M+H).

Example 132

Preparation of 4-(1-(5-propylpyrimidin-2-yl)piperidin-4-yloxy)-1-(pyridin-3-yl)pyridin-2(1H)-one, TFA salt

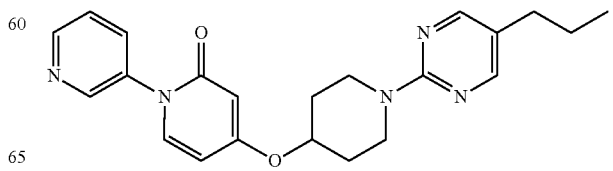

Step A. Preparation of tert-butyl 4-(2-oxo-1,2-dihydropyridin-4-yloxy)piperidine-1-carboxylate A stirring mixture of 4-hydroxypyridin-2(1H)-one (1.2 g, 10.8 mmol, prepared according to the procedure described at Step A of Example 8), tert-butyl 4-(methylsulfonyloxy)piperidine-1-carboxylate (4.83 g, 17.3 mmol, prepared according to the procedure described at Step C of Example 1) and potassium carbonate (3.13 g, 22.7 mmol) in DMF (45 mL) was heated at 90° C. for 14 hrs and then cooled to room temperature. The resulting mixture was diluted with EtOAc and H₂O and the aqueous layer was extracted further with EtOAc (5×). The combined extracts were washed with brine, dried (Na₂SO₄) and evaporated under reduced pressure. The residual was purified by flash chromatography on silica gel (0 to 10% MeOH/CH₂Cl₂) to yield 1.23 g (38.7%) of the product as a pinkish solid. MS (ESI) 295 (M+H).

Step B. Preparation of tert-butyl 4-(2-oxo-1-(pyridin-3-yl)-1,2-dihydropyridin-4-yloxy)piperidine-1-carboxylate A mixture of 3-iodopyridine (287 mg, 1.400 mmol, TCI), tert-butyl 4-(2-oxo-1,2-dihydropyridin-4-yloxy)piperidine-1-carboxylate (206 mg, 0.7 mmol), quinolin-8-ol (40.6 mg, 0.280 mmol, Alfa Aesar), copper(I) iodide (9.49 μL, 0.280 mmol, Aldrich) and cesium carbonate (296 mg, 0.910 mmol, Aldrich) in DMSO (0.8 mL) was heated at 125° C. for 3 hrs. The reaction mixture was diluted with EtOAC and water and filtrated. The filtrate was separated and the aqueous layer was extracted further with EtOAc. The combined organic layers were washed with brine, dried (Na₂SO₄) and evaporated under reduced pressure. The residue was purified by flash chromatography on silica gel (0-10% MeOH/CH₂Cl₂) to give the title compound (165.7 mg, 64%) as a yellow solid. MS (ESI) 372 (M+H).

Step C. Preparation of 4-(piperidin-4-yloxy)-1-(pyridin-3-yl)pyridin-2(1H)-one hydrochloric acid salt A mixture of tert-butyl 4-(2-oxo-1-(pyridin-3-yl)-1,2-dihydropyridin-4-yloxy)piperidine-1-carboxylate (142 mg, 0.382 mmol), hydrogen chloride (4.0 M in 1,4-dioaxne, 1.5 mL, Aldrich) in MeOH (1.5 mL) was stirred at room temperature for 45 min and then concentrated to give the product (115 mg) as a light orange solid. The material was used in the next step without further purification. MS (ESI) 272 (M+H).

Step D

Example 132

A mixture of 4-(piperidin-4-yloxy)-1-(pyridin-3-yl)pyridin-2(1H)-one hydrochloride (30.8 mg, 0.1 mmol), 2-chloro-5-propylpyrimidine (31.3 mg, 0.200 mmol, Maybridge) and cesium carbonate (81 mg, 0.25 mmol, Aldrich) in DMF (0.6 mL) was heated under microwave conditions (160° C., 30 min). The reaction mixture was purified by preparative HPLC (C₁₈ column; 0-85% methanol in water containing 0.05% trifluoroacetic acid) to give Example 132 (4.1 mg, off-white sticky solid, 10.5%) upon lyophilization. ¹H NMR (500 MHz, CDCl₃) δ 8.86 (s, 1 H), 8.78 (d, J=4.40 Hz, 1 H), 8.43 (s, 2 H), 8.22 (d, J=8.25 Hz, 1 H), 7.78 (dd, J=7.97, 5.22 Hz, 1 H), 7.37 (d, J=7.70 Hz, 1 H), 6.34 (d, J=2.20 Hz, 1 H), 6.26 (dd, J=7.70, 2.75 Hz, 1H), 4.67-4.82 (m, 1 H), 3.95-4.19 (m, 4 H), 2.55 (t, J=7.70 Hz, 2 H), 2.01-2.22 (m, 4 H), 1.57-1.73 (m, 2 H), 0.99 (t, J=7.42 Hz, 3 H). MS (ESI) 292 (M+H).

Example 133

Preparation of 4-(1-(5-ethylpyrimidin-2-yl)piperidin-4-yloxy)-1-(pyridin-3-yl)pyridin-2(1H)-one, TFA salt

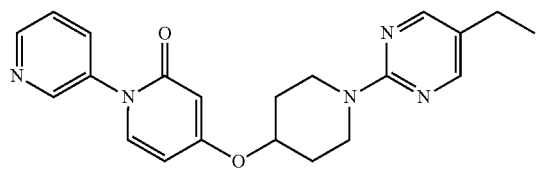 [SMILES: CCc1cnc(N2CCC(Oc3ccn(-c4cccnc4)c(=O)c3)CC2)nc1]

Example 133 was prepared according to procedures described in Example 132 substituting 2-chloro-5-ethylpyrimidine (Aldrich) for 2-chloro-5-propylpyrimidine at Step D. ¹H NMR (500 MHz, CDCl₃) δ 8.94 (s, 1 H), 8.81 (d, J=4.40 Hz, 1 H), 8.43 (s, 2 H), 8.31 (d, J=8.25 Hz, 1 H), 7.86 (dd, J=7.70, 5.50 Hz, 1 H), 7.42 (d, J=7.70 Hz, 1 H), 6.38 (s, 1 H), 6.30 (dd, J=7.70, 2.75 Hz, 2 H), 4.74-4.81 (m, 1 H), 3.94-4.18 (m, 4 H), 2.63 (q, J=7.70 Hz, 2 H), 2.01-2.23 (m, 4 H), 1.28 (t, J=7.70 Hz, 3 H). MS (ESI) 378 (M+H).

Example 134

Preparation of 4-tert-pentylphenyl 4-(1-(4-(methylsulfonyl)phenyl)-2-oxo-1,2-dihydropyridin-4-yloxy)piperidine-1-carboxylate

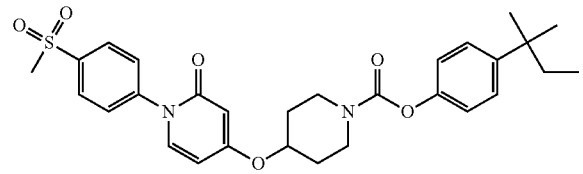 [SMILES: CCC(C)(C)c1ccc(OC(=O)N2CCC(Oc3ccn(-c4ccc(S(C)(=O)=O)cc4)c(=O)c3)CC2)cc1]

Example 134 was prepared according to procedures described in Example 2 substituting 4-tert-pentylphenol (Aldrich) for 1,1,1-trifluoro-2-propanol at Step B. ¹H NMR (500 MHz, CDCl₃) δ 8.09 (d, J=8.25 Hz, 2 H), 7.62 (d, J=8.80 Hz, 2 H), 7.29-7.33 (m, 3 H), 7.03 (d, J=8.80 Hz, 2 H), 6.25 (d, J=2.20 Hz, 1 H), 6.19 (dd, J=7.70, 2.75 Hz, 1 H), 4.54-4.68 (m, 1 H), 3.93 (app brs, 1 H), 3.84 (app brs, 1 H), 3.64 (app brs, 1 H), 3.55 (app brs, 1 H), 3.11 (s, 3 H), 2.10 (app brs, 2 H), 1.85-1.98 (m, 2 H), 1.63 (q, J=7.70 Hz, 2 H), 1.27 (s, 6 H), 0.68 (t, J=7.42 Hz, 3 H). MS (ESI) 539 (M+H).

Example 135

Preparation of 4-(trifluoromethyl)phenyl 4-(1-(4-(methylsulfonyl)phenyl)-2-oxo-1,2-dihydropyridin-4-yloxy)piperidine-1-carboxylate

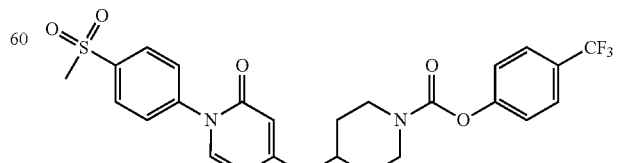

Example 135 was prepared according to procedures described in Example 2 substituting 4-(trifluoromethyl)phenol (Janssen) for 1,1,1-trifluoro-2-propanol at Step B. ¹H NMR (500 MHz, CDCl₃) δ 8.09 (d, J=8.25 Hz, 2 H), 7.63 (dd, J=14.30, 8.80 Hz, 4 H), 7.35 (d, J=7.70 Hz, 1 H), 7.25 (d, J=8.25 Hz, 2 H), 6.45 (d, J=2.75 Hz, 1 H), 6.27 (dd, J=7.70, 2.75 Hz, 1 H), 4.63-4.72 (m, 1 H), 3.89-3.99 (m, 1 H), 3.85 (app brs, 1 H), 3.68 (app brs, 1 H), 3.51-3.63 (m, 1 H), 3.11 (s, 3 H), 2.13 (app brs, 2 H), 1.88-2.01 (m, 2 H). MS (ESI) 537 (M+H).

Example 136

Preparation of 4-cyclopropylphenyl 4-(1-(4-(methylsulfonyl)phenyl)-2-oxo-1,2-dihydropyridin-4-yloxy)piperidine-1-carboxylate

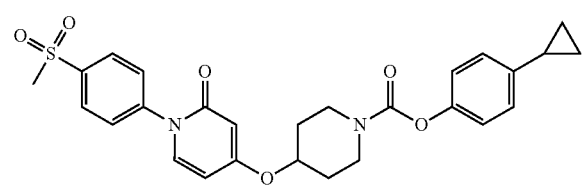 [SMILES: CS(=O)(=O)c1ccc(-n2ccc(OC3CCN(C(=O)Oc4ccc(C5CC5)cc4)CC3)cc2=O)cc1]

Step A. Preparation of 4-bromophenyl 4-(1-(4-(methylsulfonyl)phenyl)-2-oxo-1,2-dihydropyridin-4-yloxy)piperidine-1-carboxylate To a mixture of 1-(4-(methylsulfonyl)phenyl)-4-(piperidin-4-yloxy)pyridin-2(1H)-one hydrochloric acid (154 mg, 0.40 mmol) and diisopropylethylamine (0.35 mL, 0.20 mmol) in CH₂Cl₂ (1.5 mL) at room temperature was added 4-bromophenyl chloroformate (prepared according to procedures described at Step B of Example 2 substituting 4-bromophenol for 1,1,1-trifluoro-2-propanol) in CH₂Cl₂ (1.0 mL). The resulting mixture was stirred at room temperature for 3 hrs, diluted with CH₂Cl₂ and washed with water and brine. The organic layer was dried (Na₂SO₄) and evaporated under reduced pressure. The crude product was purified by flash chromatography on silica gel (0-100% EtOAc/Hexanes) to give the title compound (159 mg, 73%) as a light yellow solid. MS (ESI) 547, 549 (M+H).

Step B

Example 136

A mixture of 4-bromophenyl 4-(1-(4-(methylsulfonyl)phenyl)-2-oxo-1,2-dihydropyridin-4-yloxy)piperidine-1-carboxylate (38.3 mg, 0.07 mmol), 1,1'-bis(diphenylphosphino)ferrocene-palladium(II)dichloride dichloromethane complex (5.76 mg, 7.00 µmol, Combiphos Catalysts, Inc.), cyclopropylboronic acid (18.04 mg, 0.210 mmol, Aldrich) and cesium carbonate (114 mg, 0.350 mmol, Aldrich) in DMF (0.5 mL) and water (0.1 mL) was heated under microwave conditions (120° C., 20 min). The reaction mixture was purified by preparative HPLC (C₁₈ column; 30-100% methanol in water containing 0.05% trifluoroacetic acid) to give Example 136 (4.1 mg, beige color solid, 19%) upon lyophilization. ¹H NMR (500 MHz, CDCl₃) δ 8.08 (d, J=8.80 Hz, 2 H), 7.62 (d, J=8.25 Hz, 2 H), 7.28 (d, J=7.15 Hz, 1 H), 7.06 (d, J=8.80 Hz, 2 H), 6.99 (d, J=8.80 Hz, 2 H), 6.12-6.19 (m, 2 H), 4.53-4.67 (m, 1 H), 3.91 (app brs, 1 H), 3.83 (app brs, 1 H), 3.63 (app brs, 1 H), 3.49-3.57 (m, 1 H), 3.10 (s, 3 H), 2.09 (app brs, 2 H), 1.81-1.99 (m, 3 H), 0.94 (q, J=6.60 Hz, 2 H), 0.59-0.73 (m, 2 H). MS (ESI) 509 (M+H).

Example 137

Preparation of 4-(2-methylprop-1-enyl)phenyl 4-(1-(4-(methylsulfonyl)phenyl)-2-oxo-1,2-dihydropyridin-4-yloxy)piperidine-1-carboxylate

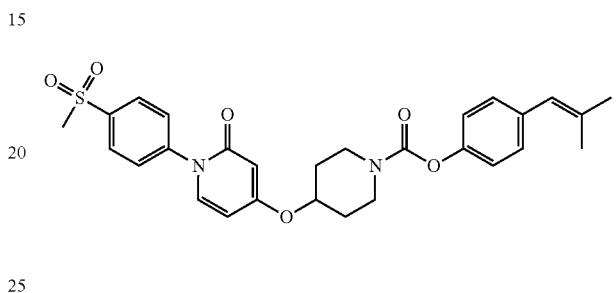

Example 137 was prepared according to procedures described in Example 136 substituting 2-methylprop-1-enylboronic acid (Synthonix) for cyclopropylboronic acid at Step B. ¹H NMR (500 MHz, CDCl₃) δ 8.09 (d, J=8.25 Hz, 2 H), 7.62 (d, J=8.25 Hz, 2 H), 7.32 (d, J=7.70 Hz, 1 H), 7.21 (d, J=8.80 Hz, 2 H), 7.05 (d, J=8.80 Hz, 2 H), 6.33 (s, 1 H), 6.19-6.26 (m, 2 H), 4.65 (d, J=3.30 Hz, 1 H), 3.94 (app brs, 1 H), 3.85 (app brs, 1 H), 3.65 (app brs, 1 H), 3.56 (app brs, 1 H), 3.11 (s, 3 H), 2.11 (app brs, 2 H), 1.88-1.96 (m, 2 H), 1.90 (s, 3 H), 1.85 (s, 3 H). MS (ESI) 523 (M+H).

Example 138

Preparation of 4-sec-butylphenyl 4-(1-(4-(methylsulfonyl)phenyl)-2-oxo-1,2-dihydropyridin-4-yloxy)piperidine-1-carboxylate

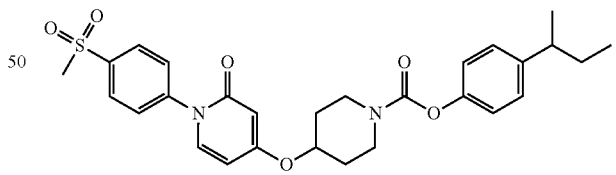

Example 138 was prepared according to procedures described in Example 2 substituting 4-sec-butylphenol (Aldrich) for 1,1,1-trifluoro-2-propanol at Step B. ¹H NMR (500 MHz, CDCl₃) δ 8.09 (d, J=8.25 Hz, 2 H), 7.61 (d, J=8.25 Hz, 2 H), 7.37 (d, J=7.70 Hz, 1 H), 7.17 (d, J=8.25 Hz, 2 H), 7.02 (d, J=8.25 Hz, 2 H), 6.52 (d, J=2.20 Hz, 1 H), 6.31 (dd, J=7.70, 2.20 Hz, 1 H), 4.64-4.72 (m, 1 H), 3.97 (app brs, 1 H), 3.85 (app brs, 1 H), 3.66 (app brs, 1 H), 3.56 (app brs, 1 H), 3.11 (s, 3 H), 2.54-2.65 (m, 1 H), 2.12 (app brs, 2 H), 1.86-1.96 (m, 2

H), 1.53-1.63 (m, 2 H), 1.22 (d, J=7.15 Hz, 3 H), 0.82 (t, J=7.42 Hz, 3 H). MS (ESI) 525 (M+H).

Example 139

Preparation of 4-ethyl-2-methoxyphenyl 4-(1-(4-(methylsulfonyl)phenyl)-2-oxo-1,2-dihydropyridin-4-yloxy)piperidine-1-carboxylate

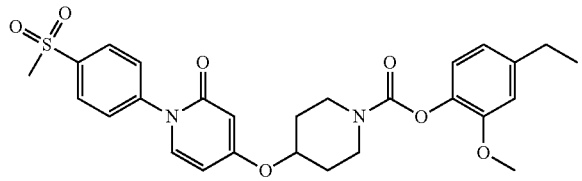 [SMILES: CCc1ccc(OC(=O)N2CCC(Oc3ccn(-c4ccc(S(C)(=O)=O)cc4)c(=O)c3)CC2)c(OC)c1]

Example 139 was prepared according to procedures described in Example 2 substituting 4-ethyl-2-methoxyphenol (Alfa Aesar) for 1,1,1-trifluoro-2-propanol at Step B. ¹H NMR (500 MHz, CDCl₃) δ 8.08 (d, J=8.25 Hz, 2 H), 7.62 (d, J=8.80 Hz, 2H), 7.33 (d, J=7.70 Hz, 1 H), 6.98 (d, J=7.70 Hz, 1 H), 6.74-6.80 (m, 2 H), 6.36 (d, J=2.75 Hz, 1 H), 6.24 (dd, J=7.70, 2.75 Hz, 1 H), 4.61-4.69 (m, 1 H), 3.98 (app brs, 1 H), 3.79-3.87 (m, 1 H), 3.84 (s, 3 H), 3.67 (app brs, 1 H), 3.55 (app brs, 1 H), 3.10 (s, 3 H), 2.64 (q, J=7.70 Hz, 2 H), 2.11 (app brs, 2 H), 1.92 (app brs, 2 H), 1.24 (t, J=7.70 Hz, 3 H). MS (ESI) 527 (M+H).

Example 141

Preparation of 4-(1-(5-methoxypyrimidin-2-yl)piperidin-4-yloxy)-1-(4-(methylsulfonyl)phenyl)pyridin-2(1H)-one

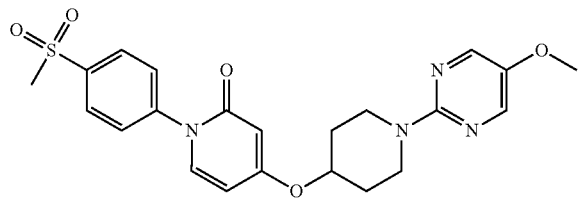 [SMILES: COc1cnc(N2CCC(Oc3ccn(-c4ccc(S(C)(=O)=O)cc4)c(=O)c3)CC2)nc1]

Example 141 was prepared according to procedures described in Example 106 substituting 2-chloro-5-methoxy-pyrimidine (Aldrich) for 2-chloro-5-propylpyrimidine in Step B except that the reaction was stirred at 100° C. for 3 days and the crude solid was purified by flash chromatography (SiO₂, 0 to 100% EtOAc in Hexanes). ¹H NMR (400 MHz, DMSO-d6) δ ppm 8.20 (s, 2 H), 7.98-8.06 (m, 2 H), 7.65-7.73 (m, 2 H), 7.63 (d, J=7.34 Hz, 1 H), 6.06-6.13 (m, 1 H), 6.04 (d, J=2.45 Hz, 1 H), 4.67-4.79 (m, 1 H), 4.07-4.20 (m, 2 H), 3.76 (s, 3 H), 3.35-3.47 (m, 2 H), 3.27 (s, 3 H), 1.94-2.04 (m, 2 H), 1.49-1.64 (m, 2 H). MS (ESI) 457 (M+H).

Example 142

Preparation of 1-(2-fluoro-4-(methylsulfonyl)phenyl)-4-(1-(5-propylpyrimidin-2-yl)piperidin-4-yloxy)pyridin-2(1H)-one, hydrochloride salt

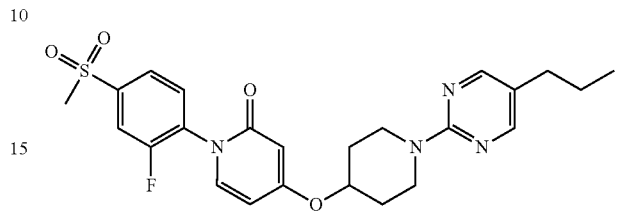

Step A. Preparation of 1-(5-propylpyrimidin-2-yl)piperidin-4-ol

A suspension of piperidin-4-ol (12 g, 119 mmol), 2-chloro-5-propylpyrimidine (20.44 g, 131 mmol) and potassium carbonate (49.2 g, 356 mmol) in DMF (100 mL) was heated at 110° C. for 12 h. The mixture was diluted with EtOAc (250 ml) and washed three times with water, dried over Na₂SO₄, and concentrated to give a yellow oil. The oil was purified by flash chromatography (SiO₂, O-10% MeOH/CH₂Cl₂) to yield product (19 g, 86 mmol, 72.4% yield) as yellow solid. MS (ESI) 222.2 (M+1).

Step B. Preparation of 1-(5-propylpyrimidin-2-yl)piperidin-4-yl methanesulfonate To a mixture of 1-(5-propylpyrimidin-2-yl)piperidin-4-ol (16.1 g, 72.8 mmol) and triethylamine (10.14 mL, 72.8 mmol) in CH₂Cl₂ (150 mL) at 0° C. was added methanesulfonyl chloride (4.76 mL, 80 mmol) slowly. After stirring at rt for 1.5 h, the mixture was quenched with 15 ml water followed by 15 ml 1N HCl. The organic layer was collected and the aqueous layer was extracted with CH₂Cl₂. The combined organic layers were then washed with saturated aqueous NaHCO₃ and brine. After drying over Na₂SO₄, the organic layer was concentrated to give the desired product 1-(5-propylpyrimidin-2-yl)piperidin-4-yl methanesulfonate (21 g, 70.1 mmol, 96% yield) as yellow solid. MS (ESI) 300.2 (M+1).

Step C. Preparation of 4-(benzyloxy)-1-(2-fluoro-4-(methylsulfonyl)phenyl)-pyridin-2(1H)-one To 4-(benzyloxy)pyridin-2(1H)-one (6.12 g, 30.4 mmol) in a 500 mL recovery flask was applied vacuum for 5 minutes then placed under an atmosphere of nitrogen and added DMF (100 mL) to produce a suspension. Added NaH (60% in oil) (1.271 g, 31.8 mmol) over 10 minutes as a slow evolution of gas was observed. By 60 minutes, the tan suspension had become thicker and lighter in color. After 60 minutes added 1,2-difluoro-4-(methylsulfonyl)benzene (5.31 g, 27.6 mmol) and placed the reaction mixture in a 110° C. oil bath under nitrogen for 70 minutes to produce a tan suspension. Added 400 mL of water and 400 mL of EtOAc to the reaction, removed aqueous layer, washed organic layer with 400 mL of brine, dried with MgSO₄, filtered and concentrated to give 12 g pale yellow powder. This was purified by flash chromatography (0.75-1.00% MeOH/CH₂Cl₂) followed by recrystallization from EtOAc to yield 5.39 g (14.4 mmol, 52% yield) of product as a white powder. MS (ESI) 374.4 (M+1).

Step D. Preparation of 1-(2-fluoro-4-(methylsulfonyl)phenyl)-4-hydroxypyridin-2(1H)-one To a 1 liter recovery flask added 10% palladium on carbon (1.75 g, 16.44 mmol), applied vacuum for 5 minutes then vented to nitrogen. Added 20 mL each of CH$_2$Cl$_2$/MeOH/THF to wet solid, then added a suspension of 4-(benzyloxy)-1-(2-fluoro-4-(methylsulfonyl)phenyl)pyridin-2(1H)-one (5.38 g, 14.41 mmol) in ~80 mL each of CH$_2$Cl$_2$/MeOH/THF (total of 100 mL each solvent), all while keeping a nitrogen flow over mixture. Applied vacuum briefly then placed under an atmosphere of hydrogen for 105 minutes, filtered through a 60×60 mm pad of CELITE® 545 filter aid using an additional 200 mL each of MeOH and CH$_2$Cl$_2$, and concentrated the filtrate to give 4.4 g of crude product as an off-white powder. MS (ESI) 284.3 (M+1).

Step E. Example 142

To 1-(2-fluoro-4-(methylsulfonyl)phenyl)-4-hydroxypyridin-2(1H)-one (4.4 g, 15.53 mmol) in a 200 mL recovery flask added 75 mL DMF, the mixture was stirred 5 minutes to effect a partial solubilization, then 1-(5-propylpyrimidin-2-yl)piperidin-4-yl methanesulfonate (6.9 g, 23.05 mmol) was added and appeared to completely dissolve while some of the pyridone appeared to remain insoluble. Added cesium carbonate (15.18 g, 46.6 mmol) and placed in a 90° C. oil bath under nitrogen for 225 minutes to produce a brown-tan slurry. Added reaction mixture to 500 mL EtOAc then washed with water (250 mL then 3×150 mL), dried organic layer with magnesium sulfate, filtered and then concentrated to give 8.7 g yellow solids which were purified by flash chromatography (50-100% EtOAc in hexane then 0-50% MeOH in EtOAc) to give 5.3 g (10.9 mmol) of off-white solid which were then recrystallized from EtOAc/hexane to give an electrostatic white solid. To this material were added 100 mL of ethanol to give a slurry to which was added 7.33 mL of 6 N aqueous HCl (44 mmol=4 equiv). Nearly all dissolved then a white precipitate began to form. Stirred for 45 minutes then solvent was removed in vacuo to give 5.2 g of an off-white powder. Added 100 mL of ethanol and heated to reflux. The solids were only partially soluble. Let cool to rt with stirring. Filtered after 10 minutes at rt and washed the solids with 2×10 mL of ethanol and 2×20 mL of hexane. Dried in vacuo to give Example 142 (4.8 g, 9.1 mmol, 59%) as an off-white powder. $^1$H NMR (500 MHz, CDCl$_3$) δ 0.98 (t, J=7.42 Hz, 3 H) 1.60-1.70 (m, 2 H) 2.07-2.20 (m, 4 H) 2.55 (t, J=7.42 Hz, 2 H) 3.12 (s, 3 H) 4.05-4.22 (m, 2 H) 4.28-4.43 (m, 2 H) 4.73 (br. s., 1 H) 6.06 (s, 1 H) 6.11 (d, J=7.70 Hz, 1 H) 7.18 (d, J=7.70 Hz, 1 H) 7.64 (t, J=7.15 Hz, 1 H) 7.87 (t, J=8.80 Hz, 2 H) 8.42 (s, 2 H). MS (ESI) 487.6 (M+1).

Example 143

Preparation of 4-bromo-2-methylphenyl 4-(1-(4-(methylsulfonyl)phenyl)-2-oxo-1,2-dihydropyridin-4-yloxy)piperidine-1-carboxylate

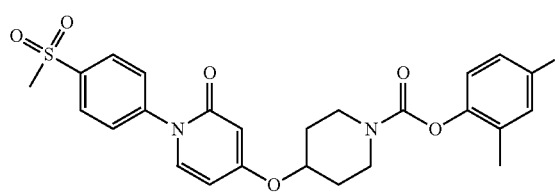

Example 143 was prepared according to procedures described in Example 2 substituting 4-bromo-2-methylphenol for 1,1,1-trifluoro-2-propanol at Step B. $^1$H NMR (500 MHz, CDCl$_3$) δ 8.11 (d, J=8.80 Hz, 2 H), 7.68 (d, J=8.80 Hz, 2 H), 7.60 (d, J=7.70 Hz, 1 H), 7.43 (d, J=1.65 Hz, 1 H), 7.35 (dd, J=8.52, 2.47 Hz, 1 H), 6.98 (d, J=8.25 Hz, 1 H), 6.29 (dd, J=7.70, 2.75 Hz, 1 H), 6.10 (d, J=2.75 Hz, 1 H), 4.77-4.84 (m, 1 H), 4.00 (app brs, 1 H), 3.83 (app brs, 1 H), 3.70 (app brs, 1 H), 3.49-3.57 (m, 1 H), 3.18 (s, 3 H), 2.06-2.22 (m, 2 H), 2.19 (s, 3 H), 1.81-1.94 (m, 2 H). MS (ESI) 561, 563 (M+H).

Example 144

Preparation of 4-isobutylphenyl 4-(1-(4-(methylsulfonyl)phenyl)-2-oxo-1,2-dihydropyridin-4-yloxy)piperidine-1-carboxylate

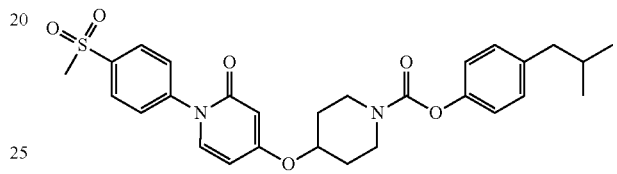

A suspension of 4-(2-methylprop-1-enyl)phenyl 4-(1-(4-(methylsulfonyl)phenyl)-2-oxo-1,2-dihydropyridin-4-yloxy)piperidine-1-carboxylate (30 mg, 0.057 mmol) and palladium on carbon (10 wt. %, wet) (20 mg, 0.188 mmol, Aldrich) in MeOH (4.0 mL) and DMF (0.5 mL) was placed under hydrogen (balloon) for 2 hrs and additional palladium on carbon (20 mg) was added. The resulting mixture was continuously stirred under hydrogen (balloon) for 1.5 hrs, diluted with CH$_2$Cl$_2$, filtrated through a pad of CELITE® 545 filter aid and concentrated in vacuo. The residue was purified by preparative HPLC (C$_{18}$ column; 30-100% methanol in water containing 0.05% trifluoroacetic acid) to give Example 144 (21.4 mg, yellow solid, 71%) upon lyophilization. $^1$H NMR (500 MHz, CDCl$_3$) 8.10 (d, J=8.25 Hz, 2 H), 7.61 (d, J=8.25 Hz, 2 H), 7.38 (d, J=7.70 Hz, 1 H), 7.14 (d, J=8.80 Hz, 2 H), 7.00 (d, J=8.25 Hz, 2 H), 6.56 (d, J=2.20 Hz, 1 H), 6.33 (dd, J=7.42, 2.47 Hz, 1 H), 4.62-4.74 (m, 1 H), 3.89-4.04 (m, 1 H), 3.85 (app brs, 1 H), 3.85 (app brs, 1 H), 3.57 (app brs, 1 H), 3.12 (s, 3 H), 2.46 (d, J=7.15 Hz, 2 H), 2.13 (app brs, 2 H), 1.89-1.98 (m, 2 H), 1.80-1.89 (m, 1 H), 0.90 (d, J=6.60 Hz, 6 H). MS (ESI) 525 (M+H).

Example 145

Preparation of 4-bromo-2-fluorophenyl 4-(1-(4-(methylsulfonyl)phenyl)-2-oxo-1,2-dihydropyridin-4-yloxy)piperidine-1-carboxylate

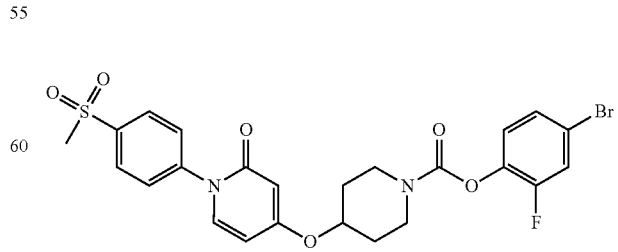

Example 145 was prepared according to procedures described in Example 2 substituting 4-bromo-2-fluorophenol (Aldrich) for 1,1,1-trifluoro-2-propanol at Step B. $^1$H NMR (500 MHz, CDCl$_3$) δ 8.07 (d, J=8.80 Hz, 2 H), 7.62 (d, J=8.25 Hz, 2 H), 7.33 (dd, J=9.35, 2.20 Hz, 1 H), 7.25-7.30 (m, 2 H), 7.08 (t, J=8.52 Hz, 1 H), 6.08 (dd, J=7.70, 2.75 Hz, 1 H), 5.99 (d, J=2.75 Hz, 1 H), 4.56-4.65 (m, 1 H), 3.84-3.96 (m, 1 H), 3.74-3.84 (m, 1 H), 3.64-3.74 (m, 1 H), 3.54-3.64 (m, 1 H), 3.10 (s, 3 H), 2.08 (app brs, 2 H), 1.95 (app brs, 2 H). MS (ESI) 565, 567 (M+H).

Example 146

Preparation of 2-methoxy-4-propylphenyl 4-(1-(4-(methylsulfonyl)phenyl)-2-oxo-1,2-dihydropyridin-4-yloxy)piperidine-1-carboxylate

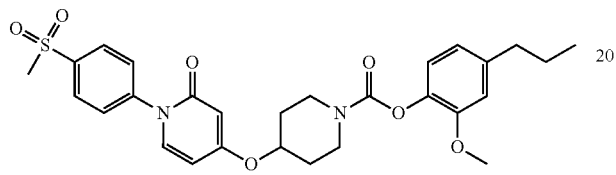

Example 146 was prepared according to procedures described in Example 2 substituting 2-methoxy-4-propylphenol (SAFC) for 1,1,1-trifluoro-2-propanol at Step B. $^1$H NMR (500 MHz, CDCl$_3$) δ 8.09 (d, J=8.80 Hz, 2 H), 7.62 (d, J=8.25 Hz, 2 H), 7.33 (d, J=7.15 Hz, 1 H), 6.97 (d, J=7.70 Hz, 1 H), 6.71-6.79 (m, 2 H), 6.37 (d, J=2.75 Hz, 1 H), 6.25 (dd, J=7.42, 2.47 Hz, 1 H), 4.58-4.70 (m, 1 H), 3.91-4.02 (m, 1 H), 3.83 (s, 3 H), 3.77-3.88 (m, 1 H), 3.61-3.71 (m, 1 H), 3.55 (app brs, 1 H), 3.11 (s, 3 H), 2.57 (t, J=7.70 Hz, 2 H)), 2.12 (app brs, 2 H), 1.93 (app brs, 2 H), 1.58-1.69 (m, 2 H), 0.95 (t, J=7.42 Hz, 3 H). MS (ESI) 541 (M+H).

Example 147

Preparation of 6-bromopyridin-3-yl 4-(1-(4-(methylsulfonyl)phenyl)-2-oxo-1,2-dihydropyridin-4-yloxy)piperidine-1-carboxylate

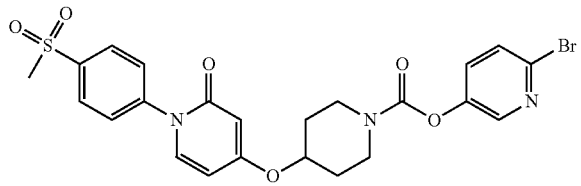 [SMILES: CS(=O)(=O)c1ccc(-n2ccc(OC3CCN(C(=O)Oc4ccc(Br)nc4)CC3)cc2=O)cc1]

Example 147 was prepared according to procedures described in Example 2 substituting 6-bromopyridin-3-ol (Synchem OHG) for 1,1,1-trifluoro-2-propanol at Step B except that the title compound was purified by flash chromatography on silica gel. $^1$H NMR (500 MHz, CDCl$_3$) δ 8.23 (d, J=3.30 Hz, 1 H), 8.08 (d, J=8.80 Hz, 2 H), 7.62 (d, J=8.25 Hz, 2 H), 7.50 (d, J=8.25 Hz, 1 H), 7.41 (dd, J=8.80, 2.75 Hz, 1 H), 7.25 (d, J=7.24 Hz, 1 H)), 6.09 (dd, J=7.70, 2.20 Hz, 1 H), 6.00 (d, J=2.20 Hz, 1 H), 4.55-4.65 (m, 1 H), 3.85-3.93 (m, 1 H), 3.75-3.83 (m, 1 H), 3.65-3.73 (m, 1 H), 3.55-3.63 (m, 1 H), 3.10 (s, 3 H), 2.02-2.14 (m, 2 H), 1.91-2.00 (m, 2 H). MS (ESI) 548, 550 (M+H).

Example 148

Preparation of 2-methyl-4-propylphenyl 4-(1-(4-(methylsulfonyl)phenyl)-2-oxo-1,2-dihydropyridin-4-yloxy)piperidine-1-carboxylate

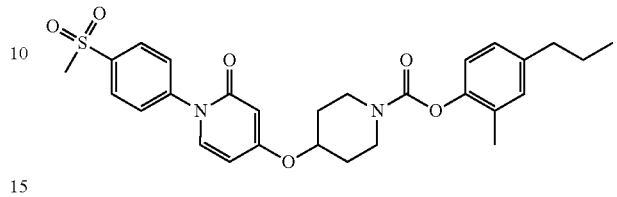

Step A. Preparation of (Z)-2-methyl-4-(prop-1-enyl)phenyl 4-(1-(4-(methylsulfonyl)phenyl)-2-oxo-1,2-dihydropyridin-4-yloxy)piperidine-1-carboxylate A mixture of 4-bromo-2-methylphenyl 4-(1-(4-(methylsulfonyl)phenyl)-2-oxo-1,2-dihydropyridin-4-yloxy)piperidine-1-carboxylate (32.5 mg, 0.058 mmol, Example 143), 1,1'-bis(diphenylphosphino)ferrocene-palladium(II)dichloride dichloromethane complex (4.76 mg, 5.79 μmol, Combiphos Catalysts, Inc.), (Z)-prop-1-enylboronic acid (14.92 mg, 0.174 mmol, Aldrich) and cesium carbonate (94 mg, 0.289 mmol, Aldrich) in DMF (0.6 mL) and water (0.12 mL) was heated under microwave conditions (100° C., 20 min). The reaction mixture was purified by preparative HPLC (C$_{18}$ column; 40-100% methanol in water containing 0.05% trifluoroacetic acid) to give the title compound (21.8 mg, yellow solid, 72%) upon lyophilization. MS (ESI) 523 (M+H).

Step B

Example 148

Example 148 was prepared according to procedures described in Example 144 substituting (Z)-2-methyl-4-(prop-1-enyl)phenyl 4-(1-(4-(methylsulfonyl)phenyl)-2-oxo-1,2-dihydropyridin-4-yloxy)piperidine-1-carboxylate for 4-(2-methylprop-1-enyl)phenyl 4-(1-(4-(methylsulfonyl)phenyl)-2-oxo-1,2-dihydropyridin-4-yloxy)piperidine-1-carboxylate. $^1$H NMR (500 MHz, CDCl$_3$) δ 8.10 (d, J=8.80 Hz, 2 H), 7.62 (d, J=8.80 Hz, 2 H), 7.35 (d, J=7.70 Hz, 1 H), 6.93-7.04 (m, 3 H), 6.48 (d, J=2.75 Hz, 1 H), 6.29 (dd, J=7.70, 2.20 Hz, 1 H), 4.64-4.71 (m, 1 H), 3.92-4.04 (m, 1 H), 3.81-3.92 (m, 1 H), 3.68 (app brs, 1 H), 3.56 (app brs, 1 H), 3.12 (s, 3 H), 2.54 ((t, J=7.70 Hz, 2 H), 2.07-2.22 (m, 2 H), 2.19 (s, 3 H), 1.93 (app brs, 2 H), 1.56-1.68 (m, 2 H), 0.94 (t, J=7.15 Hz, 3 H). MS (ESI) 525 (M+H).

Example 149

Preparation of 2-fluoro-4-propylphenyl 4-(1-(4-(methylsulfonyl)phenyl)-2-oxo-1,2-dihydropyridin-4-yloxy)piperidine-1-carboxylate

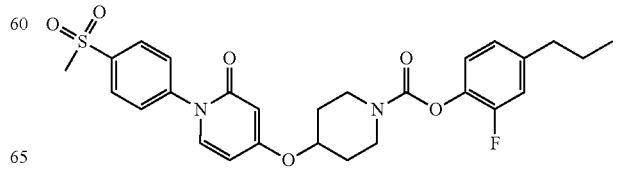

Example 149 was prepared according to procedures described in Example 148 substituting 4-bromo-2-fluorophenyl 4-(1-(4-(methylsulfonyl)phenyl)-2-oxo-1,2-dihydropyridin-4-yloxy)piperidine-1-carboxylate for 4-bromo-2-methylphenyl 4-(1-(4-(methylsulfonyl)phenyl)-2-oxo-1,2-dihydropyridin-4-yloxy)piperidine-1-carboxylate at Step A. $^1$H NMR (500 MHz, CDCl$_3$) δ 8.09 (d, J=8.80 Hz, 2 H), 7.62 (d, J=8.25 Hz, 2 H), 7.32 (d, J=7.70 Hz, 1 H), 7.07 (t, J=8.25 Hz, 1 H), 6.91-7.00 (m, 2 H), 6.31 (d, J=2.47 Hz, 2 H), 6.22 (dd, J=7.70, 2.20 Hz, 1 H), 4.60-4.72 (m, 1 H), 3.88-3.99 (m, 1 H), 3.83 (app brs, 1 H), 3.68 (app brs, 1 H), 3.57 (app brs, 1 H), 3.11 (s, 3 H), 2.50-2.61 (m, 2 H), 2.11 (app brs, 2 H), 1.94 (app brs, 2 H), 1.57-1.69 (m, 2 H), 0.94 (t, J=7.15 Hz, 3 H). MS (ESI) 529 (M+H).

Example 150

Preparation of (Z)-1-(4-(methylsulfonyl)phenyl)-4-(1-(5-(prop-1-enyl)pyrimidin-2-yl)piperidin-4-yloxy)pyridin-2(1H)-one

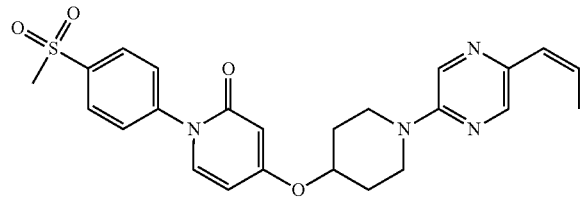 [SMILES: C/C=C\c1cnc(N2CCC(Oc3ccn(-c4ccc(S(C)(=O)=O)cc4)c(=O)c3)CC2)cn1]

Example 150 was prepared according to procedures described in Example 109 substituting (Z)-prop-1-enylboronic acid (Aldrich) for phenylboronic acid except that the crude solid was purified by flash chromatography (SiO$_2$, 0 to 100% EtOAc in CH$_2$Cl$_2$). $^1$H NMR (400 MHz, CDCl$_3$) δ ppm 8.31 (s, 2 H) 8.07 (d, J=8.31 Hz, 2 H) 7.62 (d, J=8.31 Hz, 2 H) 7.23 (d, J=7.34 Hz, 1 H) 6.17 (d, J=10.76 Hz, 1 H) 6.05-6.10 (m, 1 H) 6.02 (d, J=2.45 Hz, 1 H) 5.72-5.83 (m, 1 H) 4.55-4.63 (m, 1 H) 4.16-4.25 (m, 2 H) 3.65-3.76 (m, 2 H) 3.09 (s, 3 H) 2.02-2.14 (m, 2 H) 1.88 (d, J=7.34 Hz, 3 H) 1.80-1.86 (m, 2 H). MS (ESI) 467 (M+H).

Example 151

Preparation of 4-(1-(5-cyclopropylpyrimidin-2-yl)piperidin-4-yloxy)-1-(2-fluoro-4-(methylsulfonyl)phenyl)pyridin-2(1H)-one, TFA salt

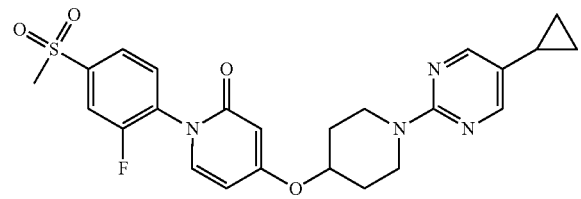

Step A. Preparation of 4-(1-(5-bromopyrimidin-2-yl)piperidin-4-yloxy)-1-(2-fluoro-4-(methylsulfonyl)phenyl)pyridin-2(1H)-one A mixture of 1-(2-fluoro-4-(methylsulfonyl)phenyl)-4-(piperidin-4-yloxy)pyridin-2(1H)-one hydrochloride (100 mg, 0.248 mmol, prepared according to the procedures described in Example 9), 5-bromo-2-chloropyrimidine (144 mg, 0.745 mmol) and cesium carbonate (324 mg, 0.993 mmol) in DMF (3 mL) was placed in a microwave and heated at 160° C. for 20 min. The reaction mixture was diluted with EtOAc (30 mL) and washed with water 3 times. The organic layer was dried over Na$_2$SO$_4$ and concentrated under reduced pressure to give a crude yellow solid. The residue was purified by flash chromatography (SiO$_2$, O-100% EtOAc/Hexanes) to give a white solid (70 mg, 53.9%). MS (ESI) 523 (M+H).

Step B

Example 151

To a microwave vial was added 4-(1-(5-bromopyrimidin-2-yl)piperidin-4-yloxy)-1-(2-fluoro-4-(methylsulfonyl)phenyl)pyridin-2(1H)-one (70 mg, 0.134 mmol), cyclopropylboronic acid (34.5 mg, 0.401 mmol), 1,1'-bis(diphenylphosphino)ferrocene-palladium(II)dichloride dichloromethane complex (11.00 mg, 0.013 mmol) and K$_2$CO$_3$ (55.5 mg, 0.401 mmol), DMF (2 mL) and water (0.5 mL). The mixture was heated at 125° C. in a microwave for 20 min. The mixture was diluted with EtOAc (20 mL) and washed with water (3×). The organic layer was collected and evaporated to give a yellow oil. The crude was purified by preparative HPLC (C$_{18}$ column; 20-90% MeOH in water containing 0.1% trifluoroacetic acid) to give Example 151 (4.5 mg, 7%) as a white oil. $^1$H NMR (500 MHz, CDCl$_3$) δ ppm 8.36 (s, 2 H), 7.75-7.93 (m, 2 H), 7.56-7.67 (m, 1 H), 7.18-7.25 (m, 1 H), 6.43 (d, J=2.75 Hz, 1 H), 6.25 (dd, J=7.70, 2.20 Hz, 1 H), 4.75-4.79 (m, 1 H), 3.90-4.15 (m, 4H), 3.13 (s, 3 H), 1.97-2.23 (m, 4 H), 1.73-1.92 (m, 1 H), 0.97-1.16 (m, 2 H), 0.57-0.83 (m, 2 H). MS (ESI) 485 (M+H).

Example 152

Preparation of 2-chloro-4-propylphenyl 4-(1-(4-(methylsulfonyl)phenyl)-2-oxo-1,2-dihydropyridin-4-yloxy)piperidine-1-carboxylate

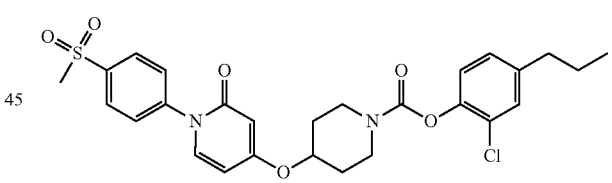

Step A. Preparation of 4-bromo-2-chlorophenyl 4-(1-(4-(methylsulfonyl)phenyl)-2-oxo-1,2-dihydropyridin-4-yloxy)piperidine-1-carboxylate 4-Bromo-2-chlorophenyl 4-(1-(4-(methylsulfonyl)phenyl)-2-oxo-1,2-dihydropyridin-4-yloxy)piperidine-1-carboxylate was prepared according to procedures described in Example 2 substituting 4-bromo-2-chlorophenol (Aldrich) for 1,1,1-trifluoro-2-propanol at Step B. MS (ESI) 581, 583 (M+H).

Step B

Example 152

Example 152 was prepared according to procedures described in Example 148 substituting 4-bromo-2-chlorophenyl 4-(1-(4-(methylsulfonyl)phenyl)-2-oxo-1,2-dihydropyridin-4-yloxy)piperidine-1-carboxylate for 4-bromo-2-methylphenyl 4-(1-(4-(methylsulfonyl)phenyl)-2-oxo-1,2-dihydropyridin-4-yloxy)piperidine-1-carboxylate at Step A. $^1$H NMR (500 MHz, CDCl$_3$) δ 8.08 (d, J=8.80 Hz, 2 H), 7.62 (d, J=8.80 Hz, 2 H), 7.21-7.29 (m, 1 H), 7.02-7.15 (m, 2 H), 6.11 (dd, J=7.70, 2.75 Hz, 1 H), 6.04 (d, J=2.75 Hz, 1 H), 4.55-4.68 (m, 1 H), 3.96 (app brs, 1 H), 3.82 (app brs, 1 H), 3.70 (app brs, 1 H), 3.58 (app brs, 1 H), 3.10 (s, 3 H), 2.49-2.62 (m, 2 H), 2.04-2.19 (m, 2 H), 1.94 (app brs, 2 H), 1.55-1.70 (m, 2 H), 0.94 (t, J=7.42 Hz, 3 H). MS (ESI) 545 (M+H).

Example 153

Preparation of 6-propylpyridin-3-yl 4-(1-(4-(methylsulfonyl)phenyl)-2-oxo-1,2-dihydropyridin-4-yloxy)piperidine-1-carboxylate, TFA salt

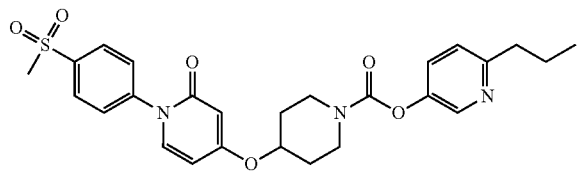

Example 153 was prepared according to procedures described in Example 148 substituting 6-bromopyridin-3-yl 4-(1-(4-(methylsulfonyl)phenyl)-2-oxo-1,2-dihydropyridin-4-yloxy)piperidine-1-carboxylate (Example 147) for 4-bromo-2-methylphenyl 4-(1-(4-(methylsulfonyl)phenyl)-2-oxo-1,2-dihydropyridin-4-yloxy)piperidine-1-carboxylate at Step A. $^1$H NMR (500 MHz, CDCl$_3$) δ 8.63 (d, J=2.75 Hz, 1 H), 8.08 (d, J=8.80 Hz, 2 H), 7.76 (dd, J=8.80, 2.20 Hz, 1 H), 7.62 (d, J=8.25 Hz, 2 H), 7.38 (d, J=8.80 Hz, 1 H), 7.26 (d, J=7.70, 1 H), 6.10 (dd, J=7.70, 2.75 Hz, 1 H), 6.02 (d, J=2.20 Hz, 1 H), 4.57-4.68 (m, 1 H), 3.84-3.95 (m, 1 H), 3.74-3.81 (m, 1 H), 3.65-3.74 (m, 1 H), 3.57-3.65 (m, 1 H), 3.10 (s, 3 H), 2.92 (t, J=7.70 Hz, 2 H), 2.04-2.15 (m 2 H), 1.91-2.02 (m, 2 H), 1.73-1.86 (m, 2 H), 1.00 (t, J=7.15 Hz, 3 H). MS (ESI) 512 (M+H).

Example 154

Preparation of 4-(3,3,3-trifluoropropyl)phenyl 4-(1-(4-(methylsulfonyl)phenyl)-2-oxo-1,2-dihydropyridin-4-yloxy)piperidine-1-carboxylate

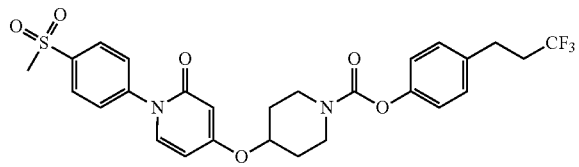 [SMILES: CS(=O)(=O)c1ccc(-n2ccc(OC3CCN(C(=O)Oc4ccc(CCC(F)(F)F)cc4)CC3)cc2=O)cc1]

Step A. Preparation of (E)-1-(benzyloxy)-4-(3,3,3-trifluoroprop-1-enyl)benzene

A mixture of 4-(benzyloxy)phenylboronic acid (1026 mg, 4.50 mmol, Alfa Aesar), (E)-1-bromo-3,3,3-trifluoroprop-1-ene (262 mg, 1.5 mmol, SynQuest), 1,1'-bis(diphenylphosphino)ferrocene-palladium(II)dichloride dichloromethane complex (122 mg, 0.15, Combiphos Catalysts, Inc.) and cesium carbonate (2444 mg, 7.50 mmol, Aldrich) in Water (0.5 mL) and DMF (3.0 mL) was heated under microwave conditions (90° C., 20 min). The reaction mixture was diluted with EtOAc and filtered. The filtrate was washed with water and brine, dried (Na$_2$SO$_4$) and concentrated in vacuo. The residual was purified by flash chromatography on silica gel (0 to 100% EtOAc/hexanes) to yield the title compound (310 mg, 74%) as a pale yellow solid.

Step B. Preparation of 4-(3,3,3-trifluoropropyl)phenol

A solution of (E)-1-(benzyloxy)-4-(3,3,3-trifluoroprop-1-enyl)benzene (305 mg, 1.096 mmol) and palladium on carbon (305 mg, 10 wt. %, wet, Aldrich) in MeOH (15 mL) and THF (5 mL) was placed under hydrogen (1 Atm) for 4 hrs. The resulting mixture was diluted with CH$_2$Cl$_2$ and filtered through a pad of CELITE® 545 filter aid. The filtrate was evaporated under reduced pressure and then purified by flash chromatography on silica gel (0 to 30% EtOAc/hexanes) to yield the title compound (151 mg, 72%) as a colorless oil. MS (ESI) 189 (M–H).

Step C

Example 154

Example 154 was prepared according to procedures described in Example 2 substituting 4-(3,3,3-trifluoropropyl)phenol for 1,1,1-trifluoro-2-propanol at Step B. $^1$H NMR (500 MHz, CDCl$_3$) δ 8.10 (d, J=8.80 Hz, 2 H), 7.62 (d, J=8.80 Hz, 2 H), 7.33 (d, J=7.70 Hz, 1 H), 7.20 (d, J=8.25 Hz, 2 H), 7.06 (d, J=8.25 Hz, 2 H), 6.40 (d, J=2.75 Hz, 1 H), 6.25 (dd, J=7.70, 2.75 Hz, 1 H), 4.59-4.71 (m, 1 H), 3.94 (app brs, 1 H), 3.79-3.91 (m, 1 H), 3.60-3.71 (m, 1 H), 3.51-3.60 (m, 1 H), 3.11 (s, 3 H), 2.81-2.94 (m, 2 H), 2.29-2.47 (m, 2 H), 2.11 (app brs, 2 H), 1.84-1.98 (m, 2 H). MS (ESI) 565 (M+H).

Example 155

Preparation of 1-(4-(methylthio)phenyl)-4-(1-(5-propylpyrimidin-2-yl)piperidin-4-yloxy)pyridin-2(1H)-one

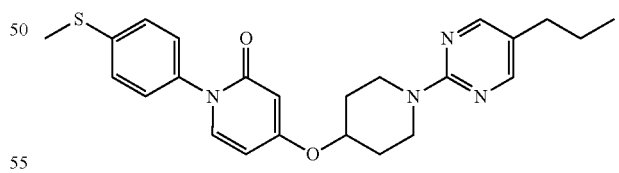

Step A. Preparation of benzyl 4-(methylsulfonyloxy)piperidine-1-carboxylate

To a stirring solution of benzyl 4-hydroxy-1-piperidinecarboxylate (3.55 mL, 23.4 mmol, Aldrich) and Et$_3$N (7.18 mL, 51.5 mmol, Aldrich) in CH$_2$Cl$_2$ (25 mL) at room temperature was added a solution of methanesulfonyl chloride (1.99 mL, 25.8 mmol, Acros) in CH$_2$Cl$_2$ (25 mL) dropwise. The reaction mixture was stirred at room temperature for 1 h and washed with 1N HCl aqueous solution, H$_2$O and brine. The organic layer was dried over Na$_2$SO$_4$ and concentrated in vacuo to yield 7.43 g of the desired product as a yellow oil. MS (ESI) 314 (M+H).

Step B. Preparation of benzyl 4-(2-oxo-1,2-dihydropyridin-4-yloxy)piperidine-1-carboxylate A stirring suspension of benzyl 4-(methylsulfonyloxy)piperidine-1-carboxylate (1.97 g, 6.30 mmol), 4-hydroxypyridin-2(1H)-one (0.50 g, 4.5 mmol, Aldrich), potassium carbonate (1.43 g, 10.6 mmol, EMD) and DMF (25 mL) was heated at 140° C. for 2.5 h and then cooled to room temperature. The resulting mixture was diluted with H$_2$O and extracted with EtOAc (2×). The organic layers were combined and washed with brine, dried over Na$_2$SO$_4$ and concentrated in vacuo to a light yellow oil. The oil was purified by flash chromatography (SiO$_2$, 0 to 10% MeOH in CH$_2$Cl$_2$) to yield 550 mg of desired product as a white solid. MS (ESI) 329 (M+H).

Step C. Preparation of benzyl 4-(1-(4-(methylthio)phenyl)-2-oxo-1,2-dihydropyridin-4-yloxy)piperidine-1-carboxylate A mixture of benzyl 4-(2-oxo-1,2-dihydropyridin-4-yloxy)piperidine-1-carboxylate (697 mg, 2.12 mmol), (4-bromophenyl)(methyl)sulfane (431 mg, 2.12 mmol, Aldrich), quinolin-8-ol (61.6 mg, 0.425 mmol, Alfa Aesar), potassium carbonate (381 mg, 2.76 mmol, EMD), Copper(I) iodide (81 mg, 0.43 mmol, Alfa Aesar) in DMSO (6 mL) was stirred at 145° C. overnight under Argon. The resulting mixture was diluted with H$_2$O and extracted with EtOAc (2×). The combined organic layers were washed with brine, dried over Na$_2$SO$_4$ and concentrated in vacuo to a green solid. The solid was purified by flash chromatography (SiO$_2$, 0 to 5% MeOH in CH$_2$Cl$_2$) to yield 911 mg of desired product as a light green solid. MS (ESI) 451 (M+H).

Step D. Preparation of 1-(4-(methylthio)phenyl)-4-(piperidin-4-yloxy)pyridin-2(1H)-one To a stirring solution of benzyl 4-(1-(4-(methylthio)phenyl)-2-oxo-1,2-dihydropyridin-4-yloxy)piperidine-1-carboxylate (367 mg, 0.815 mmol) in CH$_2$Cl$_2$ (5 mL) at 0° C. was added iodotrimethylsilane (0.33 mL, 2.4 mmol, Aldrich). The reaction was stirred for 40 min and then quenched at 0° C. with HCl (1N in H$_2$O, 5 mL). To the resulting mixture was diluted with CH$_2$Cl$_2$ and extracted with H$_2$O. The H$_2$O layer was basified with NaOH (1N in H$_2$O, 10 mL) and extracted with CH$_2$Cl$_2$ (2×). The combined organic layers were washed with brine, dried over Na$_2$SO$_4$ and concentrated in vacuo to yield 189 mg crude product as an off-white solid. MS (ESI) 317 (M+H).

Step E

Example 155

To a stirring mixture of 1-(4-(methylthio)phenyl)-4-(piperidin-4-yloxy)pyridin-2(1H)-one (175 mg, 0.552 mmol) and potassium carbonate (305 mg, 2.21 mmol, EMD) in DMF (8.5 mL) was added at room temperature 2-chloro-5-propylpyrimidine (130 mg, 0.828 mmol, Wako). The reaction mixture heated at 100° C. for 9 h and then concentrated in vacuo. The obtained oil was purified by flash chromatography (SiO$_2$, 0 to 100% EtOAc in CH$_2$Cl$_2$) to yield 101 mg of example 155 as a white solid. $^1$H NMR (400 MHz, CDCl$_3$) δ ppm 8.14 (s, 2 H), 7.25-7.36 (m, 4 H,) 7.18 (d, J=7.34 Hz, 1H,) 5.82-6.18 (m, 2 H), 4.46-4.58 (m, 1 H), 4.12-4.23 (m, 2 H), 3.53-3.66 (m, 2 H), 2.49 (s, 3 H), 2.38 (t, J=7.58 Hz, 2 H), 2.00-2.14 (m, 2 H), 1.73-1.89 (m, 2 H), 1.46-1.63 (m, 2 H), 0.92 (t, J=7.34 Hz, 3 H). MS (ESI) 437 (M+H).

Example 156

Preparation of (±)-1-(4-(methylsulfinyl)phenyl)-4-(1-(5-propylpyrimidin-2-yl)piperidin-4-yloxy)pyridin-2(1H)-one

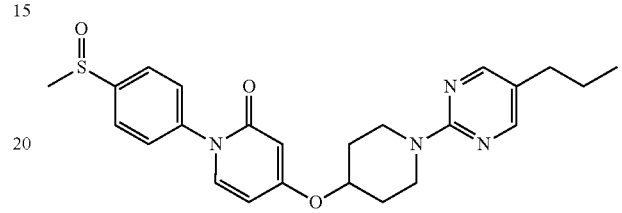

To a stirring solution of 1-(4-(methylthio)phenyl)-4-(1-(5-propylpyrimidin-2-yl)piperidin-4-yloxy)pyridin-2(1H)-one (51.4 mg, 0.118 mmol) in CH$_2$Cl$_2$ (15 mL) at 0° C. was added a solution of 3-Chloroperoxybenzoic acid (26.4 mg, 0.118 mmol) in 5 mL CH$_2$Cl$_2$. The reaction was stirred at 0° C. for 15 min and then quenched with Na$_2$SO$_3$ (sat. solution in H$_2$O). The organic layer was washed with H$_2$O, brine, dried over Na$_2$SO$_4$ and concentrated in vacuo to a white solid. The solid was purified by flash chromatography (SiO$_2$, 0 to 10% MeOH in CH$_2$Cl$_2$) to yield 50 mg of desired product as a white solid. $^1$H NMR (400 MHz, CDCl$_3$) δ ppm 8.16 (s, 2 H), 7.77 (d, J=8.31 Hz, 2 H), 7.57 (d, J=8.31 Hz, 2 H), 7.23 (d, J=7.34 Hz, 1 H), 5.94-6.11 (m, 2 H), 4.44-4.64 (m, 1 H), 4.07-4.31 (m, 2 H), 3.50-3.74 (m, 2 H), 2.77 (s, 3 H), 2.40 (t, J=7.58 Hz, 2 H), 1.98-2.17 (m, 2 H), 1.73-1.93 (m, 2 H), 1.50-1.64 (m, 2 H), 0.93 (t,=7.34 Hz, 3 H). MS (ESI) 453 (M+H).

Example 157

Preparation of 4-(2-fluoroethyl)phenyl 4-(1-(4-(methylsulfonyl)phenyl)-2-oxo-1,2-dihydropyridin-4-yloxy)piperidine-1-carboxylate

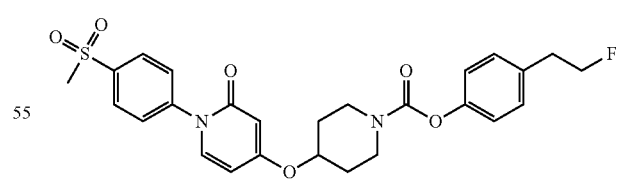

Example 157 was prepared according to procedures described in Example 154 substituting (E)-1-bromo-2-fluoroethene (SynQuest) for (E)-1-bromo-3,3,3-trifluoroprop-1-ene at Step A. $^1$H NMR (500 MHz, CDCl$_3$) δ 8.08 (d, J=8.80 Hz, 2 H), 7.62 (d, J=8.80 Hz, 2 H), 7.20-7.29 (m, 3 H), 7.06 (d, J=8.25 Hz, 2 H), 6.09 (dd, J=7.70, 2.20 Hz, 1 H), 6.00 (d, J=2.20 Hz, 1 H), 4.67 (t, J=6.32 Hz, 1 H), 4.62 4.65 (m, 2 H), 3.91 (app brs, 1 H), 3.78-3.85 (m, 1 H), 3.62-3.69 (m, 1 H), 3.53-3.60 (m, 1 H), 3.10 (s, 3 H), 3.04 (t, J=6.60 Hz, 1 H), 2.99 (t, J=6.32 Hz, 1 H), 2.03-2.13 (m, 2 H), 1.87-1.97 (m, 2 H). MS (ESI) 515 (M+H).

Example 158

Preparation of benzyl 4-(5-methyl-1-(4-(methylsulfonyl)phenyl)-2-oxo-1,2-dihydropyridin-4-yloxy)piperidine-1-carboxylate

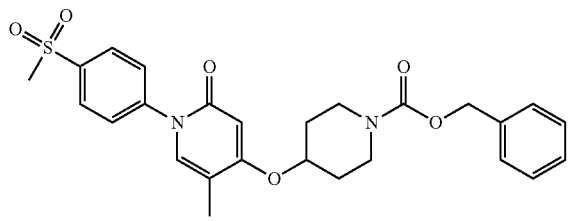 [SMILES: Cc1cn(-c2ccc(S(C)(=O)=O)cc2)c(=O)cc1OC1CCN(C(=O)OCc2ccccc2)CC1]

Step A. Preparation of benzyl 4-(methylsulfonyloxy)piperidine-1-carboxylate

To benzyl 4-hydroxypiperidine-1-carboxylate (48.8 g, 207 mmol) in CH$_2$Cl$_2$ (400 mL) was added triethylamine (57.8 mL, 415 mmol), the mixture was cooled to 0° C. under nitrogen and then methanesulfonyl chloride (17.78 mL, 228 mmol) was added over 15 minutes keeping internal temperature below 30° C. After 2 hours at 0° C., the reaction was quenched with 300 mL of 0.1 N aqueous HCl, the organic layer was washed with 300 mL of water, 300 mL of brine, dried with MgSO$_4$, filtered and concentrated to give the product (69.5 g) as an amber liquid which was used without further purification. MS (ESI) 314.4 (M+1).

Step B. Preparation of 6-chloro-4-hydroxy-5-methylpyridin-2(1H)-one

Malonyl dichloride (25 g, 177 mmol) was added to propiononitrile (30 mL, 420 mmol) at rt under argon. The reaction mixture was stirred at rt overnight. 1,4-dioxane (50 mL) was added to the above heterogeneous mixture to yield a precipitate which was collected by filtration, washed with 1,4-dioxane (2×20 mL) and dried in vacuum oven at 55° C. for 4 h to provide 6-chloro-4-hydroxy-5-methylpyridin-2(1H)-one, HCl, H$_2$O (15.6 g, 73 mmol, 34%) as an off-white solid. MS (ESI) 314.4 (M+1).

Step C. Preparation of 4-hydroxy-5-methylpyridin-2(1H)-one

6-Chloro-4-hydroxy-5-methylpyridin-2(1H)-one, HCl, H$_2$O (1 g, 4.67 mmol) was dissolved in 30 mL EtOH, and then triethylamine (0.473 g, 4.67 mmol) was added. The reaction was flushed with vacuum and then hydrogen three times, then placed under a balloon of hydrogen for 50 hours. The reaction mixture was passed through a 20×20 mm pad of CELITE® 545 filter aid using an additional 4×5 mL of EtOH and the eluant was concentrated to 1.62 g of a tan foam. Added 20 mL of water, heated to reflux causing nearly all to dissolve, then let cool to rt. Filtered the suspension from above and washed with 3×3 mL of water, and dried in vacuo to product (97 mg, 0.8 mmol, 17%) as a pale tan powder. MS (ESI) 126.1 (M+1).

Step D. Preparation of benzyl 4-(5-methyl-2-oxo-1,2-dihydropyridin-4-yloxy)piperidine-1-carboxylate 4-Hydroxy-5-methylpyridin-2(1H)-one (554 mg, 4.43 mmol), benzyl 4-(methylsulfonyloxy)piperidine-1-carboxylate (2081 mg, 6.64 mmol), and potassium carbonate (1224 mg, 8.86 mmol) were stirred in DMF (12 mL) at 100° C. under nitrogen for 14 hours. 100 mL water and 100 mL EtOAc was added and then washed the EtOAc layer with 2×100 mL additional water. The organic layer was dried with Na$_2$SO$_4$, filtered, and concentrated to give 1454 mg of a brown oil. The oil was purified by flash chromatography (0-5% MeOH/CH$_2$Cl$_2$) to give product (280 mg, 0.82 mmol, 18%) as a pale tan foam. MS (ESI) 343.4 (M+1).

Step E. Example 158

Benzyl 4-(5-methyl-2-oxo-1,2-dihydropyridin-4-yloxy)piperidine-1-carboxylate (34 mg, 0.099 mmol), 4-bromophenyl methylsulphone (23.35 mg, 0.099 mmol), potassium carbonate (20.59 mg, 0.149 mmol), and copper(I) iodide (3.78 mg, 0.020 mmol) were combined in 0.4 mL DMSO was degassed with bubbling nitrogen subsurface for 20 seconds and then heated in a 100° C. oil bath for 16 hours. To the reaction mixture was added 5 mL EtOAc which was then washed with 3 mL each of saturated aqueous NH$_4$Cl, NaHCO$_3$, NaCl, water, dried with MgSO$_4$ and filtered. The EtOAc filtrate was then purified directly with flash chromatography (EtOAc as eluant) to yield product (24 mg, 0.048 mmol, 49%) as a yellow foam. $^1$H NMR (500 MHz, CDCl$_3$) δ 1.81-1.93 (m, 2 H) 1.92-2.00 (m, 2 H) 2.02 (s, 3 H) 3.09 (s, 3 H) 3.48-3.63 (m, 2 H) 3.66-3.78 (m, 2 H) 4.58 (br. s., 1 H) 5.16 (s, 2 H) 5.96 (br. s., 1 H) 7.10 (br. s., 1 H) 7.30-7.45 (m, 5 H) 7.61 (d, J=8.25 Hz, 2 H) 8.06 (d, J=8.25 Hz, 2 H). MS (ESI) 497.6 (M+1).

Example 159

Preparation of (±)-4-(1-(5-cyclopropylpyrimidin-2-yl)piperidin-4-yloxy)-1-(4-(methylsulfinyl)phenyl)pyridin-2(1H)-one

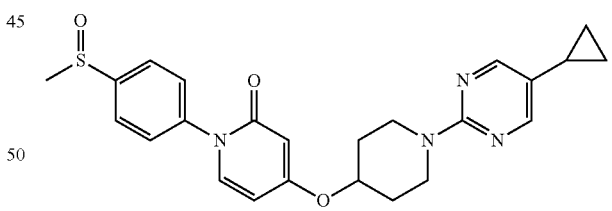

Step A. Preparation of 2-chloro-5-cyclopropylpyrimidine

A mixture of 5-bromo-2-chloropyrimidine (100 mg, 0.517 mmol, Aldrich), cyclopropylboronic acid (57.7 mg, 0.672 mmol, Aldrich), Tricyclohexylphosphine (14.50 mg, 0.052 mmol, Aldrich) and K$_3$PO$_4$ (384 mg, 1.81 mmol, EMD) in Toluene (2 mL) and Water (0.110 mL) was degassed by vacuum and purged with Ar. To the resulting mixture was added Palladium(II) acetate (5.80 mg, 0.026 mmol, Stem) and then heated under microwave conditions at 120° C. for 10 min. The reaction mixture was quenched with H$_2$O and then extracted with EtOAc (2×). The combined organic layers were washed with brine, dried over Na$_2$SO$_4$ and concentrated in vacuo to a yellow oil. The oil was purified by flash chromatography (SiO$_2$, 0 to 20% EtOAc in Hexanes) to yield 71 mg of the desired compound as a white solid. MS (ESI) 155 (M+H).

Step B

Example 159

Example 159 was prepared according to procedures described in Example 155 and 156 substituting 2-chloro-5-cyclopropylpyrimidine for 2-chloro-5-propylpyrimidine in Example 155 step E. $^1$H NMR (400 MHz, CDCl$_3$) δ ppm 8.13 (s, 2 H), 7.77 (d, J=8.31 Hz, 2 H), 7.57 (d, J=8.31 Hz, 2 H), 7.23 (d, J=7.34 Hz, 1 H), 6.04-6.09 (m, 1 H), 5.98-6.03 (m, 1 H), 4.51-4.62 (m, 1 H), 4.12-4.24 (m, 2 H), 3.56-3.68 (m, 2 H), 2.77 (s, 3 H), 1.98-2.13 (m, 2 H), 1.77-1.89 (m, 2 H), 1.66-1.77 (m, 1 H), 0.86-0.95 (m, 2 H), 0.53-0.65 (m, 2 H). MS (ESI) 451 (M+H).

Example 160

Preparation of 4-(1-(5-cyclopropylpyrimidin-2-yl)piperidin-4-yloxy)-5-methyl-1-(4-(methylsulfonyl)phenyl)pyridin-2(1H)-one

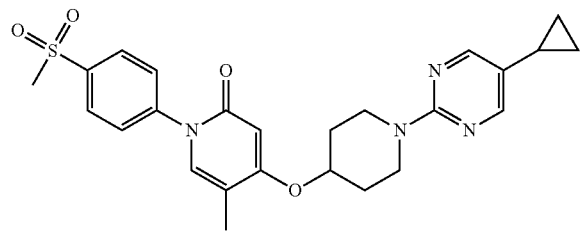 [SMILES: Cc1cn(-c2ccc(S(C)(=O)=O)cc2)c(=O)cc1OC1CCN(c2ncc(C3CC3)cn2)CC1]

Step A. Preparation of 5-methyl-1-(4-(methylsulfonyl)phenyl)-4-(piperidin-4-yloxy)pyridin-2(1H)-one To a suspension of 10% Pd/C (100 mg, 0.940 mmol) in 5 mL MeOH under nitrogen was added Example 158 (218 mg, 0.439 mmol), flushed with vacuum then hydrogen three times, then placed under a balloon of hydrogen for 150 minutes. The reaction passed through a 15 mm id×30 mm CELITE® 545 filter aid plug eluting with 15 mL of additional MeOH. Concentrated the filtrate to 135 mg of a pale yellow-grey foam. MS (ESI) 363.2 (M+1).

Step B

Preparation of Example 160

To the compound from Step A above (30 mg, 0.083 mmol), 2-chloro-5-cyclopropylpyrimidine (25.6 mg, 0.166 mmol), and potassium carbonate (11.44 mg, 0.083 mmol) were added in 0.3 mL DMF and then heated in a 100° C. oil bath for 15.5 hours. To the reaction mixture was added 2 mL EtOAc and then washed with 2 mL each of saturated aqueous NH$_4$Cl, NaHCO$_3$, NaCl, and water. The EtOAc layer was passed through a 4 mm id×25 mm silica column eluting with ~7 mL EtOAc. Concentrated eluate to 38 mg pale yellow oil which was crystallized from EtOAc to yield Example 160 (17 mg, 0.034 mmol, 42%) as an off-white solid. $^1$H NMR (500 MHz, CDCl$_3$) δ ppm 0.51-0.66 (m, 2 H) 0.86-0.97 (m, 2 H) 1.65-1.81 (m, 2 H) 1.83-1.95 (m, 3 H) 1.96-2.14 (m, 6 H) 3.09 (s, 3 H) 3.71-3.88 (m, 2 H) 3.99-4.11 (m, 2 H) 4.55-4.70 (m, 1 H) 6.00 (s, 1 H) 7.07 (s, 1 H) 7.63 (d, J=8.80 Hz, 2 H) 8.06 (d, J=8.80 Hz, 2 H) 8.15 (s, 2 H). MS (ESI) 481.3 (M+1).

Example 161

Preparation of tert-butyl 4-(5-methyl-1-(4-(methylsulfonyl)phenyl)-2-oxo-1,2-dihydropyridin-4-yloxy)piperidine-1-carboxylate

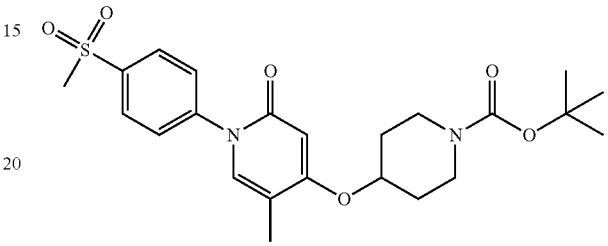

The compound obtained in Example 160, Step A (30 mg, 0.083 mmol) was dissolved in dichloromethane (0.5 mL) and N-ethyl-N-isopropylpropan-2-amine (0.022 mL, 0.124 mmol) and DMAP (1.011 mg, 8.28 nmol) was added followed by di-tert-butyl dicarbonate (19.87 mg, 0.091 mmol). The mixture was stirred at rt for 16 hours. To the reaction was added 2 mL CH$_2$Cl$_2$ then the mixture was washed with 2 mL each of saturated aqueous NH$_4$Cl, NaHCO$_3$, NaCl, and 2 mL of water. The organic layer was passed through a 4 mm id×25 mm silica column eluting with ~5 mL CH$_2$Cl$_2$ then 5 mL 5% CH$_3$OH/CHCl$_3$. Concentration of the 5 mL 5% CH$_3$OH/CHCl$_3$ provided Example 161 (34 mg, 0.074 mmol, 89%) as a pale yellow solid. $^1$H NMR (500 MHz, CDCl$_3$) δ ppm 1.46 (s, 9 H) 1.77-1.89 (m, 2 H) 1.92-2.09 (m, 5 H) 3.09 (s, 3 H) 3.33-3.52 (m, 2 H) 3.57-3.71 (m, 2 H) 4.48-4.63 (m, 1 H) 5.98 (br. s., 1 H) 7.09 (s, 1 H) 7.61 (d, J=8.25 Hz, 2 H) 8.05 (d, J=8.80 Hz, 2 H). MS (ESI) 463.3 (M+1).

Example 162

Preparation of 4-(1-(5-cyclopropylpyrimidin-2-yl)piperidin-4-yloxy)-6-methyl-1-(4-(methylsulfonyl)phenyl)pyridin-2(1H)-one

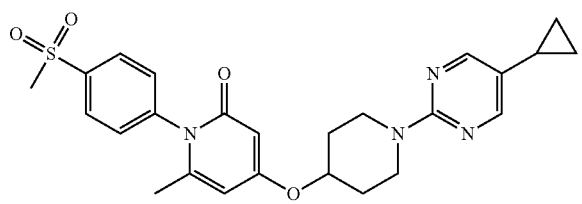 [SMILES: Cc1cc(OC2CCN(c3ncc(C4CC4)cn3)CC2)cc(=O)n1-c1ccc(S(C)(=O)=O)cc1]

Step A. Preparation of tert-butyl 4-(6-methyl-1-(4-(methylsulfonyl)phenyl)-2-oxo-1,2-dihydropyridin-4-yloxy)piperidine-1-carboxylate The intermediate was prepared according to procedures described in Example 1 substituting 4-hydroxy-6-methylpyridin-2(1H)-one for 4-(benzyloxy)pyridin-2(1H)-one in Step A. MS (ESI) 463 (M+H).

Step B. Preparation of 6-methyl-1-(4-(methylsulfonyl)phenyl)-4-(piperidin-4-yloxy)pyridin-2(1H)-one hydrochloride The compound was prepared according to procedures described in Example 2 substituting tert-butyl 4-(6-methyl-1-(4-(methylsulfonyl)phenyl)-2-oxo-1,2-dihydropyridin-4-yloxy)piperidine-1-carboxylate for tert-butyl 4-(1-(4-(methylsulfononyl)phenyl)-2-oxo-1,2-dihydropyridin-4-yloxy)piperidine-1-carboxylate in Step A. MS (ESI) 363 (M+H).

Step C

Example 162

A mixture of 6-methyl-1-(4-(methylsulfonyl)phenyl)-4-(piperidin-4-yloxy)pyridin-2(1H)-one hydrochloride (44 mg, 0.110 mmol), 2-chloro-5-cyclopropylpyrimidine (20 mg, 0.129 mmol) and cesium carbonate (180 mg, 0.552 mmol) in DMF (0.5 mL) was placed in a closed vial and stirred at 120° C. for 10 h. The reaction mixture was diluted with EtOAc (20 mL) and washed with water 3 times. The organic layer was then dried (Na$_2$SO$_4$) and evaporated under reduced pressure to give a yellow solid. The residue was purified by flash chromatography (SiO$_2$, O-100% EtOAc/Hexanes) to give Example 162 (16 mg, 30.2% yield) as a white solid. $^1$H NMR (500 MHz, CDCl$_3$) δ ppm 8.03-8.17 (m, 4 H), 7.44 (d, J=8.80 Hz, 2 H), 5.91 (s, 2 H), 4.48-4.58 (m, 1 H), 4.10-4.22 (m, 2 H), 3.62 (ddd, J=13.20, 8.80, 3.85 Hz, 2 H), 3.12 (s, 3 H), 1.96-2.13 (m, 2 H), 1.90 (s, 3 H), 1.75-1.86 (m, 2 H), 1.67-1.76 (m, 1 H), 1.62 (s, 4 H), 0.81-0.96 (m, 2 H), 0.47-0.64 (m, 2 H). MS (ESI) 481 (M+H).

Example 163

Preparation of 5-methyl-1-(4-(methylsulfonyl)phenyl)-4-(1-(5-propylpyrimidin-2-yl)piperidin-4-yloxy)pyridin-2(1H)-one, hydrochloride salt

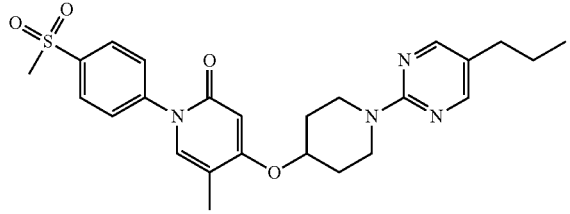 [SMILES: CCCc1cnc(N2CCC(Oc3cc(=O)n(-c4ccc(S(C)(=O)=O)cc4)cc3C)CC2)nc1]

The compound obtained in Example 160, Step A (25 mg, 0.069 mmol) and 2-chloro-5-propylpyrimidine (12.96 mg, 0.083 mmol) were dissolved in DMF (0.3 mL), potassium carbonate (38.1 mg, 0.276 mmol) was added and the mixture placed in a 100° C. oil bath for 115 minutes. To the reaction was added 2 mL EtOAc and then washed successively with 2 mL each of saturated aqueous NH$_4$Cl, NaHCO$_3$, NaCl, and water. The reaction was dried with MgSO$_4$, filtered and concentrated to 31 mg of tan solids. To the 31 mg of solids were added 0.6 mL EtOH and then 30 uL of 6 N aqueous HCl (0.18 mmol=2.6 equiv) causing complete solution. The solvent was removed in vacuo to provide 38 mg of a pale tan foam. This material readily dissolved in 0.6 mL EtOH. To this solution, hexane was added in 30 uL increments until 180 uL was added at which point cloudiness was observed and then a precipitate formed. The mixture was heated to reflux but only partial solubilization occurred. After stirring at rt overnight, the mixture was filtered and washed with EtOH (0.3 mL) then 2×1 mL hexane to provide Example 163 (22 mg, 0.042 mmol, 61%) as a white powder. $^1$H NMR (500 MHz, methanol-d$_3$) δ ppm 1.01 (t, J=7.42 Hz, 3 H) 1.18 (t, J=7.15 Hz, 1 H) 1.57-1.77 (m, 2 H) 2.02-2.18 (m, 5 H) 2.18-2.36 (m, 2 H) 2.49-2.71 (m, 2 H) 3.19 (s, 3 H) 4.07 (t, J=5.50 Hz, 4 H) 4.97-5.10 (m, 1 H) 6.29 (s, 1H) 7.64 (s, 1 H) 7.72 (d, J=8.25 Hz, 2 H) 8.14 (d, J=8.80 Hz, 2 H) 8.53 (s, 2 H). MS (ESI) 483.5 (M+1).

Example 164

Preparation of isopropyl 4-(5-methyl-1-(4-(methylsulfonyl)phenyl)-2-oxo-1,2-dihydropyridin-4-yloxy)piperidine-1-carboxylate

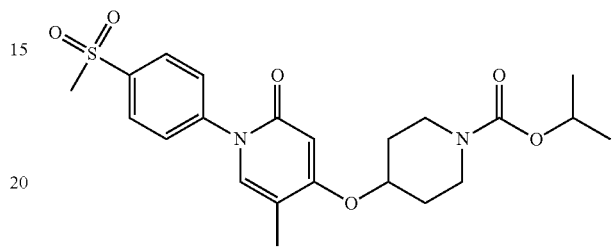

The compound obtained in Example 160, Step A (25 mg, 0.069 mmol) was dissolved in dichloromethane (0.5 mL) to which was then added triethylamine (0.029 mL, 0.207 mmol) and isopropyl carbonochloridate (10.1 mg, 0.083 mmol). After 45 minutes the solvent was removed in vacuo and the residue purified by passing through a UCT (United Chemical Technologies) 2.5 g C-18 cartridge (#CEC181(2500)$_6$) and eluting as follows:

| Fraction | Volume | Solvent |
| --- | --- | --- |
| 1 | 25 mL | water |
| 2 | 25 mL | 30% MeOH/water |
| 3-5 | 8 mL | 100% MeOH |

Fraction 3 was concentrated in vacuo to give Example 164 (24 mg, 0.052 mmol, 76%) as a tan foam. $^1$H NMR (500 MHz, methanol-d$_3$) δ ppm 1.27 (d, J=6.05 Hz, 6 H) 2.02 (dd, J=8.52, 4.12 Hz, 2 H) 2.05 (s, 3 H) 3.18 (s, 3 H) 3.47-3.55 (m, 2 H) 3.67-3.76 (m, 2 H) 4.77 (ddd, J=7.01, 3.44, 3.30 Hz, 1 H) 4.88-4.92 (m, 1 H) 6.06 (s, 1 H) 7.45 (s, 1 H) 7.67 (d, J=8.80 Hz, 2 H) 8.10 (d, J=8.25 Hz, 2 H). MS (ESI) 449.5.

Example 165

Preparation of 6-methyl-1-(4-(methylsulfonyl)phenyl)-4-(1-(5-propylpyrimidin-2-yl)piperidin-4-yloxy)pyridin-2(1H)-one

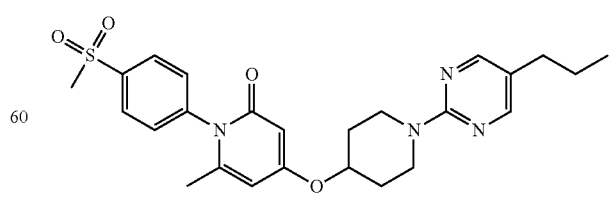

Example 165 was prepared according to the procedure described in Example 162, Step C, substituting 2-chloro-5-propylpyrimidine for 2-chloro-5-cyclopropylpyrimidine. $^1$H NMR (500 MHz, CDCl₃) δ ppm 8.16 (s, 2 H), 7.87 (dd, J=14.57, 7.97 Hz, 2 H), 7.43-7.57 (m, 1 H), 5.92 (d, J=9.90 Hz, 2 H), 4.48-4.59 (m, 1 H), 4.18 (ddd, J=10.03, 7.01, 3.30 Hz, 2 H), 3.56-3.70 (m, 2 H), 3.14 (s, 3 H), 2.40 (t, J=7.42 Hz, 2 H), 1.99-2.13 (m, 2 H), 1.94 (s, 3 H), 1.83 (ddd, J=12.65, 8.25, 3.85 Hz, 2 H), 1.46-1.66 (m, 4 H), 0.94 (t, 3 H). MS (ESI) 501 (M+H).

Example 166

Preparation of (±)-4-(1-(5-cyclopropylpyrimidin-2-yl)piperidin-4-yloxy)-1-(2-fluoro-4-(methylsulfinyl)phenyl)pyridin-2(1H)-one

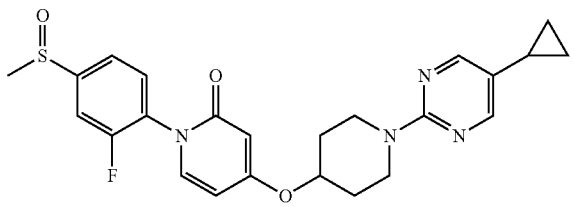 [SMILES: CS(=O)c1ccc(-n2ccc(OC3CCN(c4ncc(C5CC5)cn4)CC3)cc2=O)c(F)c1]

Example 166 was prepared according to procedures described in Example 155 and 156 substituting in Example 155 (4-bromo-3-fluorophenyl)(methyl)sulfane (Combi-Blocks) for (4-bromophenyl)(methyl)sulfane in Step C and substituting 2-chloro-5-cyclopropylpyrimidine (prepared according to the procedure described in Step A of Example 159) for 2-chloro-5-propylpyrimidine in Step E, except that the product of step C was purified by preparative HPLC (C₁₈ column, 10-100% MeOH in water containing 0.1% trifluoroacetic acid). ¹H NMR (400 MHz, CDCl₃) δ ppm 8.11 (s, 2 H), 7.44-7.63 (m, 3 H), 7.11 (d, J=7.82 Hz, 1 H), 6.00-6.07 (m, 1 H), 5.94-6.01 (m, 1 H), 4.45-4.63 (m, 1 H), 4.09-4.25 (m, 2 H), 3.55-3.67 (m, 2 H), 2.77 (s, 3 H), 1.97-2.14 (m, 2 H), 1.76-1.90 (m, 2 H), 1.64-1.75 (m, 1 H), 0.79-0.95 (m, 2 H), 0.51-0.64 (m, 2 H). MS (ESI) 469 (M+H).

Example 167

Preparation of (±)-1-(2-fluoro-4-(methylsulfinyl)phenyl)-4-(1-(5-propylpyrimidin-2-yl)piperidin-4-yloxy)pyridin-2(1H)-one

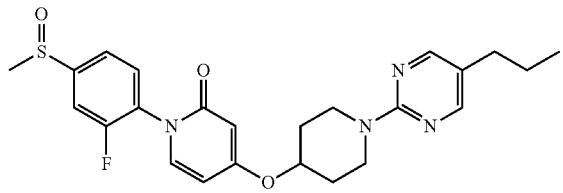 [SMILES: CCCc1cnc(N2CCC(Oc3ccn(-c4ccc(S(C)=O)cc4F)c(=O)c3)CC2)nc1]

Example 167 was prepared according to procedures described in Example 155 and 156 substituting in Example 155 (4-bromo-3-fluorophenyl)(methyl)sulfane (Combi-Blocks) for (4-bromophenyl)(methyl)sulfane in Step C, except that the product of step C was purified by preparative HPLC (C₁₈ column, 10-100% MeOH in water containing 0.1% trifluoroacetic acid). ¹H NMR (400 MHz, CDCl₃) δ ppm 8.18 (s, 2 H), 7.48-7.66 (m, 3 H), 7.14 (d, J=7.34 Hz, 1 H), 6.06-6.09 (m, 1 H), 6.01-6.06 (m, 1 H), 4.54-4.66 (m, 1 H), 4.14-4.27 (m, 2 H), 3.59-3.72 (m, 2 H), 2.80 (s, 3 H), 2.42 (t, J=7.58 Hz, 2 H), 2.02-2.16 (m, 2 H), 1.80-1.95 (m, 2 H), 1.50-1.69 (m, 2 H), 0.95 (t, J=7.34 Hz, 3 H). MS (ESI) 471 (M+H).

Example 168

Preparation of tert-butyl 4-(1-(2-chloro-4-(methylsulfonyl)phenyl)-2-oxo-1,2-dihydropyridin-4-yloxy)piperidine-1-carboxylate

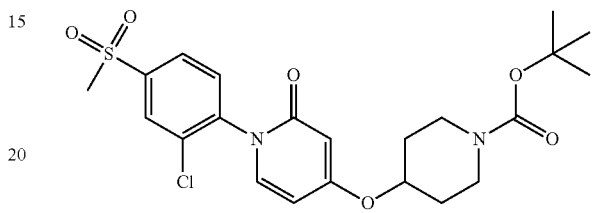

Example 168 was prepared according to the procedures described in Example 1 substituting 2-chloro-1-fluoro-4-(methylsulfonyl)benzene for 1-bromo-4-(methylsulfonyl)benzene in Step A and except that sodium hydride was used instead of copper(I) iodide, 8-hydroxyquinoline and potassium carbonate and the mixture was heated at 100° C. for 2 h instead of heating in Microwave at 145° C. ¹H NMR (500 MHz, CDCl₃) δ ppm 8.16 (s, 1 H), 7.98 (dd, J=8.25, 2.20 Hz, 1 H), 7.61 (d, J=8.25 Hz, 1 H), 7.05 (d, J=7.70 Hz, 1 H), 6.08 (dd, J=7.70, 2.75 Hz, 1 H), 5.99 (d, J=2.75 Hz, 1 H), 4.41-4.60 (m, 1 H), 3.75 (d, J=4.95 Hz, 2 H), 3.27-3.41 (m, 2 H), 3.14 (s, 3 H), 1.95-2.05 (m, 2 H), 1.80 (dd, J=7.70, 4.40 Hz, 2 H), 1.42-1.55 (m, 9 H). MS (ESI) 483 (M+H).

Example 169

Preparation of 1-(2-chloro-4-(methylsulfonyl)phenyl)-4-(1-(5-propylpyrimidin-2-yl)piperidin-4-yloxy)pyridin-2(1H)-one

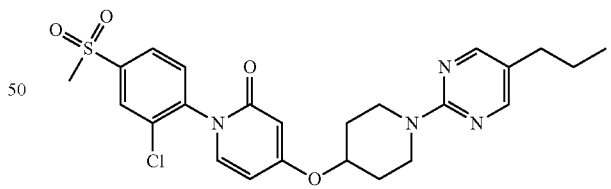

Example 169 was prepared according to the procedures described in Example 168 and Example 162 substituting 1-(2-chloro-4-(methylsulfonyl)phenyl)-4-(piperidin-4-yloxy)pyridin-2(1H)-one hydrochloride for 6-methyl-1-(4-(methylsulfonyl)phenyl)-4-(piperidin-4-yloxy)pyridin-2 (1H)-one hydrochloride and 2-chloro-5-propylpyrimidine for 2-chloro-5-cyclopropylpyrimidine in Step C. ¹H NMR (500 MHz, CDCl₃) δ ppm 8.19 (s, 2 H), 8.16 (s, 1 H), 7.99 (dd, J=8.25, 2.20 Hz, 1 H), 7.62 (d, J=8.25 Hz, 1 H), 7.06 (d, J=7.70 Hz, 1 H), 6.10 (dd, J=7.70, 2.75 Hz, 1 H), 6.05 (d, J=2.75 Hz, 1 H), 4.55-4.64 (m, 1 H), 4.23 (dd, J=11.55, 6.05 Hz, 2 H), 3.59-3.69 (m, 2 H), 3.14 (s, 3 H), 2.43 (t, J=7.42 Hz, 2 H), 2.11 (td, J=6.32, 3.30 Hz, 2 H), 1.88 (ddd, J=8.39, 4.40, 4.26 Hz, 2 H), 1.55-1.61 (m, 2 H), 0.96 (t, 3 H). MS (ESI) 503 (M+H).

Example 170

Preparation of 4-(1-(5-cyclopentenylpyrimidin-2-yl) piperidin-4-yloxy)-1-(4-(methylsulfonyl)phenyl) pyridin-2(1H)-one

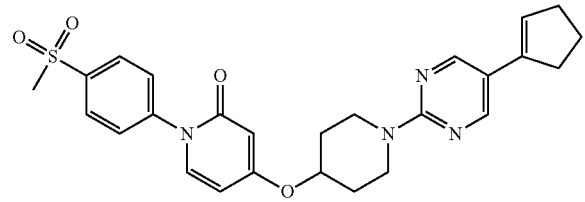 [SMILES: CS(=O)(=O)c1ccc(-n2ccc(OC3CCN(c4ncc(C5=CCCC5)cn4)CC3)cc2=O)cc1]

Example 170 was prepared according to procedures described in Example 109 substituting cyclopentenylboronic acid (Combi-Blocks) for phenylboronic acid except that the reaction was heated under microwave condition at 120° C. for 15 min and that the crude product was purified by flash chromatography (SiO$_2$, 0 to 100% EtOAc in CH$_2$Cl$_2$). $^1$H NMR (400 MHz, CDCl$_3$) δ ppm 8.40 (s, 2 H), 8.04-8.11 (m, 2 H), 7.57-7.67 (m, 2 H), 7.18-7.24 (m, 1 H), 6.07-6.11 (m, 1 H), 6.03-6.07 (m, 1 H), 6.01 (d, J=1.47 Hz, 1 H), 4.50-4.65 (m, 1 H), 4.16-4.26 (m, 2 H) 3.64-3.77 (m, 2 H) 3.09 (s, 3 H) 2.59-2.72 (m, 2 H) 2.43-2.57 (m, 2 H) 2.04-2.17 (m, 2 H) 1.94-2.04 (m, 2 H) 1.78-1.92 (m, 2 H). MS (ESI) 493 (M+H).

Example 171

Preparation of 4-(1-(5-cyclopentylpyrimidin-2-yl) piperidin-4-yloxy)-1-(4-(methylsulfonyl)phenyl) pyridin-2(1H)-one

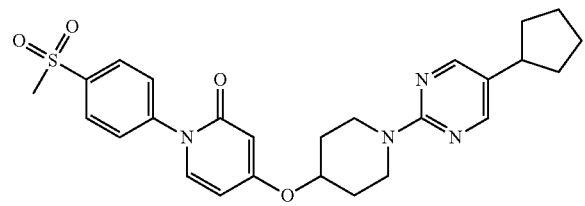 [SMILES: CS(=O)(=O)c1ccc(-n2ccc(OC3CCN(c4ncc(C5CCCC5)cn4)CC3)cc2=O)cc1]

Example 171 was prepared according to procedures described in Example 120 Step C, substituting 4-(1-(5-cyclopentenylpyrimidin-2-yl)piperidin-4-yloxy)-1-(4-(methylsulfonyl)phenyl)pyridin-2(1H)-one for 1-(4-(methylsulfonyl)phenyl)-4-(1-(5-(prop-1-en-2-yl)pyrimidin-2-yl)piperidin-4-yloxy)pyridin-2(1H)-one except that the reaction was stirred for 2 h and that the crude product was purified by flash chromatography (SiO$_2$, 0 to 100% EtOAc in CH$_2$Cl$_2$). $^1$H NMR (400 MHz, CDCl$_3$) δ ppm 8.15 (s, 2 H), 8.00 (d, J=8.80 Hz, 2 H), 7.56 (d, J=8.80 Hz, 2 H), 7.16 (d, J=7.34 Hz, 1 H), 6.00 (dd, J=7.34, 2.45 Hz, 1 H), 5.95 (d, J=2.45 Hz, 1 H), 4.45-4.57 (m, 1 H), 4.06-4.19 (m, 2 H), 3.50-3.61 (m, 2 H), 3.03 (s, 3 H), 2.69-2.81 (m, 1 H), 1.92-2.08 (m, 4 H), 1.68-1.85 (m, 4 H), 1.56-1.69 (m, 2 H), 1.36-1.46 (m, 2 H). MS (ESI) 495 (M+H).

Example 172

Preparation of 1-(2-chloro-4-(methylsulfonyl)phenyl)-4-(1-(5-cyclopropylpyrimidin-2-yl)piperidin-4-yloxy)pyridin-2(1H)-one

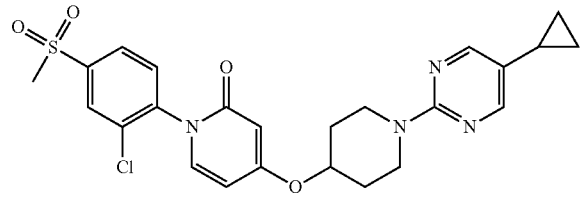 [SMILES: CS(=O)(=O)c1ccc(-n2ccc(OC3CCN(c4ncc(C5CC5)cn4)CC3)cc2=O)c(Cl)c1]

Example 172 was prepared according to the procedures described in Example 169 substituting 2-chloro-5-cyclopropylpyrimidine for 2-chloro-5-propylpyrimidine. $^1$H NMR (500 MHz, CDCl$_3$) δ ppm 8.14-8.15 (m, 3 H), 7.91-8.03 (m, 1 H), 7.60 (d, J=8.25 Hz, 1 H), 7.03 (d, J=7.70 Hz, 1 H), 6.07 (dd, J=7.42, 2.47 Hz, 1 H), 6.01 (d, J=2.75 Hz, 1 H), 4.58 (ddd, J=7.29, 3.85, 3.71 Hz, 1 H), 4.12-4.24 (m, 1 H), 3.67 (m, 2 H), 3.10-3.18 (m, 1 H), 3.09 (s, 3 H), 1.97-2.15 (m, 2 H), 1.86 (d, J=3.85 Hz, 2 H), 1.65-1.77 (m, 1 H), 0.85-1.00 (m, 2 H), 0.48-0.66 (m, 2 H). MS (ESI) 501 (M+H).

Example 173

Preparation of 1-(3-methyl-4-(methylsulfonyl)phenyl)-4-(1-(5-propylpyrimidin-2-yl)piperidin-4-yloxy) pyridin-2(1H)-one

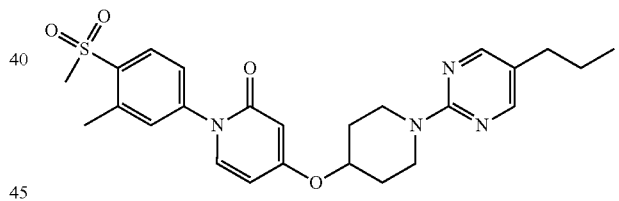

Step A. Preparation of 1-(5-propylpyrimidin-2-yl)piperidin-4-ol

To a stirring solution of piperidin-4-ol (2.33 g, 23.0 mmol, Aldrich) and potassium carbonate (6.36 g, 46.0 mmol, EMD) in DMF (15 mL) at room temperature was added 2-chloro-5-propylpyrimidine (4.33 g, 27.6 mmol, Wako). The reaction mixture was heated at 100° C. for 3 h then diluted with H$_2$O. The resulting mixture was extracted with EtOAc (2×). The organic layers were combined, dried over Na$_2$SO$_4$ and concentrated in vacuo to a brown oil. The oil was purified by flash chromatography (SiO$_2$, 0 to 100% EtOAc in CH$_2$Cl$_2$) to yield 5.01 g of desired product as a white solid. MS (ESI) 222 (M+H).

Step B. Preparation of 1-(5-propylpyrimidin-2-yl)piperidin-4-yl methanesulfonate To a stirring solution of 1-(5-propylpyrimidin-2-yl)piperidin-4-ol (9.2 g, 41.6 mmol), Et$_3$N (12.85 mL, 91 mmol, Aldrich) in CH$_2$Cl$_2$ (80 mL) at 0° C. was added a solution of Methanesulfonyl chloride (3.54 mL, 45.7 mmol, Acros) in CH$_2$Cl$_2$ (20 mL) dropwise. The reaction mixture was stirred at room temperature for 1 h and washed with 1N HCl in H$_2$O, saturated NaHCO$_3$ in H$_2$O and brine. The organic layer was dried over Na$_2$SO$_4$ and concentrated in vacuo to yield 11.7 g of the desired product as an off-white solid. MS (ESI) 300 (M+H).

Step C. Preparation of 4-(1-(5-propylpyrimidin-2-yl) piperidin-4-yloxy)pyridin-2(1H)-one A stirring suspension of 4-hydroxypyridin-2(1H)-one (5.23 g, 47.1 mmol, Aldrich), 1-(5-propylpyrimidin-2-yl)piperidin-4-yl methanesulfonate (11.7 g, 39.2 mmol), potassium carbonate (12.5 g, 90.0 mmol, EMD) and DMSO (48 mL) was heated at 100° C. for 3 hours and then cooled to room temperature. The resulting mixture was diluted with H$_2$O and extracted with EtOAc (2×). The organic layers were combined and concentrated in vacuo to a brown solid. The solid was purified by flash chromatography (SiO$_2$, 100% EtOAc and then SiO$_2$, 10% MeOH in CH$_2$Cl$_2$) to yield 5.00 g of desired product as an off-white solid. MS (ESI) 315 (M+H).

Step D. Preparation of 4-bromo-2-methyl-1-(methylsulfonyl)benzene

A mixture of 4-bromo-1-iodo-2-methylbenzene (240 μL, 1.68 mmol, Aldrich), Copper(I) iodide (353 mg, 1.85 mmol, Alfa Aesar), Methanesulfinic acid, sodium salt (688 mg, 6.74 mmol, Alfa Aesar) and DMSO (7.2 mL) was purged with Argon and then heated under microwave condition at 125° C. for 20 min. The resulting mixture was stirred at 100° C. for 3 h and then cooled to room temperature. The reaction mixture was diluted with H$_2$O and extracted with EtOAc (2×). The organic layers were combined and washed with brine, dried over Na$_2$SO$_4$ and concentrated in vacuo to a white solid. The solid was purified by flash chromatography (SiO$_2$, 0-50% EtOAc in hexanes) to yield 270 mg of desired product as a white solid. MS (ESI) 249 (M+H).

Step E

Example 173

A mixture of 4-bromo-2-methyl-1-(methylsulfonyl)benzene (79 mg, 0.32 mmol), 4-(1-(5-propylpyrimidin-2-yl)piperidin-4-yloxy)pyridin-2(1H)-one (100 mg, 0.318 mmol), quinolin-8-ol (18.5 mg, 0.127 mmol, Alfa Aesar), potassium carbonate (57.1 mg, 0.414 mmol), Copper(I) iodide (24.2 mg, 0.127 mmol, Alfa Aesar) in DMSO (4 mL) was stirred under Ar at 140° C. overnight. The resulting mixture was diluted with H$_2$O and extracted with EtOAc (2×). The combined organic layers were washed with brine, dried over Na$_2$SO$_4$ and concentrated in vacuo to a green oil. The oil was purified by flash chromatography (SiO$_2$, 0 to 100% EtOAc in CH$_2$Cl$_2$) to yield 107.7 mg of desired product as a yellow solid. $^1$H NMR (400 MHz, CDCl$_3$) δ ppm 8.10-8.22 (m, 3 H), 7.34-7.43 (m, 2 H), 7.18 (d, J=7.82 Hz, 1 H), 6.03 (dd, J=7.58, 2.20 Hz, 1 H), 5.99 (d, J=2.45 Hz, 1 H), 4.47-4.63 (m, 1 H), 4.13-4.22 (m, 2 H), 3.56-3.69 (m, 2 H), 3.09 (s, 3 H), 2.73 (s, 3 H), 2.39 (t, J=7.58 Hz, 2H,) 2.00-2.12 (m, 2 H), 1.75-1.92 (m, 2 H), 1.47-1.62 (m, 2 H), 0.92 (t, J=7.34 Hz, 3 H). MS (ESI) 483 (M+H).

Example 174

Preparation of 1-(3-chloro-4-(methylsulfonyl)phenyl)-4-(1-(5-propylpyrimidin-2-yl)piperidin-4-yloxy) pyridin-2(1H)-one

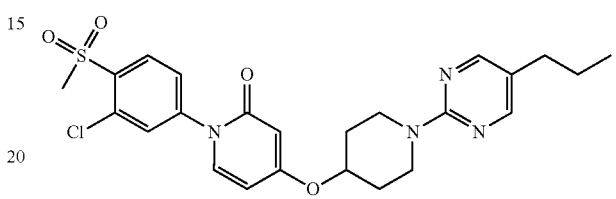

Example 174 was prepared according to procedures described in Example 173 substituting 4-bromo-2-chloro-1-iodobenzene (Alfa-Aesar) for 4-bromo-1-iodo-2-methylbenzene in Step D. $^1$H NMR (400 MHz, CDCl$_3$) δ ppm 8.28 (d, J=8.31 Hz, 1 H) 8.18 (s, 2 H) 7.69 (d, J=1.47 Hz, 1 H) 7.52 (dd, J=8.07, 1.71 Hz, 1 H) 7.21 (d, J=7.82 Hz, 1 H) 6.08 (dd, J=7.58, 2.20 Hz, 1 H) 6.01 (d, J=2.45 Hz, 1 H) 4.52-4.63 (m, 1 H) 4.13-4.27 (m, 2 H) 3.58-3.71 (m, 2 H) 3.30 (s, 3 H) 2.42 (t, J=7.34 Hz, 2 H) 2.04-2.16 (m, 2 H) 1.78-1.94 (m, 2 H) 1.51-1.66 (m, 2 H) 0.95 (t, J=7.34 Hz, 3 H). MS (ESI) 503 (M+H).

Example 175

Preparation of 1-(3-fluoro-4-(methylsulfonyl)phenyl)-4-(1-(5-propylpyrimidin-2-yl)piperidin-4-yloxy) pyridin-2(1H)-one

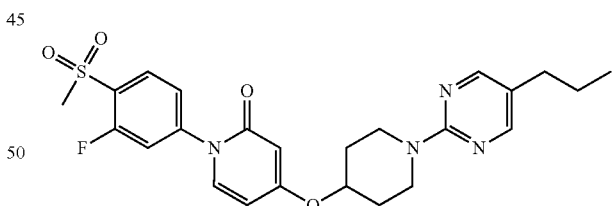

Example 175 was prepared according to procedures described in Example 173 substituting 4-bromo-2-fluoro-1-iodobenzene (Aldrich) for 4-bromo-1-iodo-2-methylbenzene in Step D. $^1$H NMR (400 MHz, CDCl$_3$) δ ppm 8.15 (s, 2 H), 8.06 (t, J=8.07 Hz, 1 H), 7.42 (dd, J=10.27, 1.96 Hz, 1 H), 7.34 (dd, J=8.56, 1.71 Hz, 1 H), 7.19 (d, J=7.34 Hz, 1 H), 6.06 (dd, J=7.82, 2.45 Hz, 1 H), 5.98 (d, J=2.45 Hz, 1 H), 4.50-4.61 (m, 1 H), 4.12-4.25 (m, 2 H), 3.53-3.70 (m, 2 H), 3.23 (s, 3 H), 2.39 (t, J=7.58 Hz, 2 H), 1.99-2.15 (m, 2 H), 1.75-1.90 (m, 2 H), 1.45-1.62 (m, 2 H), 0.92 (t, J=7.34 Hz, 3 H). MS (ESI) 487 (M+H).

Example 176

Preparation of tert-butyl 4-(1-(4-cyano-2-fluorophenyl)-2-oxo-1,2-dihydropyridin-4-yloxy)piperidine-1-carboxylate

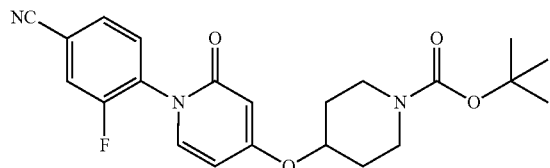

To a mixture of tert-butyl 4-(2-oxo-1,2-dihydropyridin-4-yloxy)piperidine-1-carboxylate (730 mg, 2.480 mmol, Step A of Example 132) and DMF (12 mL) at room temperature was added sodium hydride (114 mg, 2.85 mmol). After stirring at room temperature for 1 hr, 3,4-difluorobenzonitrile (345 mg, 2.480 mmol, Aldrich) was added and the reaction mixture was heated at 100° C. for 1.5 hrs and cooled to room temperature. The resulting mixture was diluted with EtOAc and water and the aqueous layer was extracted further with EtOAc (3x). The combined organic extracts were washed with water and brine, dried (MgSO$_4$) and evaporated under reduced pressure. The residue was purified by flash chromatography on silica gel (0-100% EtOAc in hexanes) to give the title compound (602.4 mg, 58.7%) as an off-white solid. $^1$H NMR (500 MHz, CDCl$_3$) δ 7.47-7.64 (m, 3 H), 7.10 (d, J=7.70 Hz, 1 H), 6.04 (dd, J=7.70, 2.20 Hz, 1 H), 5.96 (d, J=2.20 Hz, 1 H), 4.41-4.55 (m, 1 H), 3.65-3.80 (m, 2 H), 3.27-3.39 (m, 2 H), 1.91-2.04 (m, 2 H), 1.71-1.84 (m, 2 H), 1.48 (s, 9 H). MS (ESI) 358 (M+H—C$_4$H$_8$).

Example 177

Preparation of 3-fluoro-4-(2-oxo-4-(1-(5-propylpyrimidin-2-yl)piperidin-4-yloxy)pyridin-1(2H)-yl)benzonitrile, TFA salt

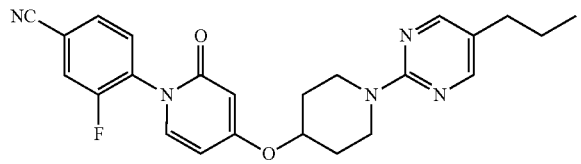 [SMILES: CCCc1cnc(N2CCC(Oc3ccn(-c4ccc(C#N)cc4F)c(=O)c3)CC2)nc1]

Example 177 was prepared according to procedures described in Example 132 substituting tert-butyl 4-(1-(4-cyano-2-fluorophenyl)-2-oxo-1,2-dihydropyridin-4-yloxy)piperidine-1-carboxylate (Example 176) for tert-butyl 4-(2-oxo-1-(pyridin-3-yl)-1,2-dihydropyridin-4-yloxy)piperidine-1-carboxylate at Step C. $^1$H NMR (500 MHz, CDCl$_3$) δ 8.17 (s, 2 H), 7.49-7.64 (m, 3 H), 7.10 (d, J=7.70 Hz, 1 H), 6.06 (dd, J=7.70, 2.75 Hz, 1 H), 6.01 (d, J=2.20 Hz, 1 H), 4.53-4.62 (m, 1 H), 4.15-4.25 (m, 2 H), 3.56-3.70 (m, 2 H), 2.41 (t, J=7.70 Hz, 2 H), 2.02-2.14 (m, 2 H), 1.76-1.92 (m, 2 H), 1.51-1.65 (m, 2 H), 0.94 (t, J=7.15 Hz, 3 H). MS (ESI) 434 (M+H).

Example 178

Preparation of 1-(2-methyl-4-(methylsulfonyl)phenyl)-4-(1-(5-propylpyrimidin-2-yl)piperidin-4-yloxy)pyridin-2(1H)-one

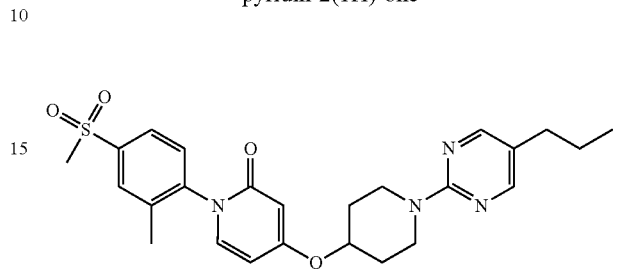

Example 178 was prepared according to the procedures described in Example 162 substituting 4-(1-(5-propylpyrimidin-2-yl)piperidin-4-yloxy)pyridin-2(1H)-one for isopropyl 4-(methylsulfonyloxy)piperidine-1-carboxylate and 1-fluoro-2-methyl-4-(methylsulfonyl)benzene for 4-bromobenzonitrile in Step C except that the reaction was heated at 160° C. for 20 min. with copper(I) iodide, potassium carbonate and quinolin-8-ol in a Microwave as described in Step A of Example 1 instead of reflux at 120° C. in the presence of cesium carbonate for 10 h. $^1$H NMR (500 MHz, CDCl$_3$) δ ppm 8.21 (br. s., 2 H), 7.92 (s, 1 H), 7.88 (d, J=7.70 Hz, 1 H), 7.40 (d, J=7.70 Hz, 1 H), 7.06 (d, J=6.05 Hz, 1 H), 5.93-6.11 (m, 2 H), 4.58 (br. s., 1 H), 4.21 (br. s., 2 H), 3.56-3.80 (m, 2 H), 3.08 (s, 3 H), 2.41 (t, J=7.42 Hz, 2 H), 2.28 (s, 3 H), 2.09 (d, J=9.90 Hz, 2 H), 1.87 (br. s., 2 H), 1.48-1.65 (m, 2 H), 0.93 (t, J=7.42 Hz, 3 H). MS (ESI) 483 (M+H).

Example 179

Preparation of 3-fluoro-4-(2-oxo-4-(1-(5-propylpyrimidin-2-yl)piperidin-4-yloxy)pyridin-1(2H)-yl)benzamide, TFA salt

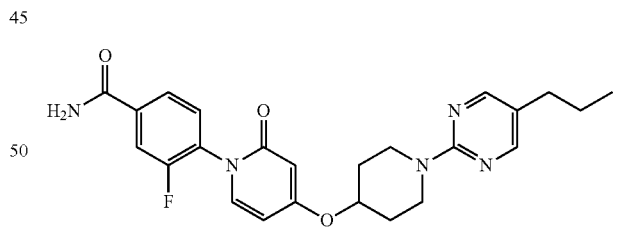

A mixture of 3-fluoro-4-(2-oxo-4-(1-(5-propylpyrimidin-2-yl)piperidin-4-yloxy)pyridin-1(2H)-yl)benzonitrile (55.9 mg, 0.129 mmol, Example 177), acetamide (30.5 mg, 0.516 mmol, Aldrich) and zinc chloride (70.3 mg, 0.516 mmol, Alfa Aesar) in water (1.5 mL) and THF (1.5 mL) was heated under microwave conditions (155° C., 45 min). Additional acetamide (7.6 mg, 1 eq.) and zinc chloride (17.5 mg, 1.0 eq.) was added and the resulting mixture was heated again under microwave conditions (155° C., 15 min). The reaction mixture was diluted with water and CH$_2$Cl$_2$ and aqueous layer was extracted further with CH$_2$Cl$_2$ (2x). The combined extracts were washed with brine, dried (Na$_2$SO$_4$) and evaporated under reduced pressure. The residue was purified by preparative HPLC ($C_{18}$ column; 0-60% acetonitrile in water containing 0.05% trifluoroacetic acid) to give Example 179 (36.1 mg, 62%) as a light yellow solid. $^1$H NMR (400 MHz, CDCl$_3$) δ 8.33 (s, 2 H), 7.70 (t, J=9.01 Hz, 2 H), 7.43 (t, J=7.69 Hz, 1 H), 7.18 (d, J=7.47 Hz, 1 H), 6.68 (brs, 1 H), 6.06-6.17 (m, 2 H), 5.89 (brs, 1 H), 4.59-4.72 (m, 1 H), 4.05-4.18 (m, 2 H), 3.79-3.93 (m, 2 H), 2.48 (t, J=7.69 Hz, 2 H), 2.06-2.17 (m, 2 H), 1.90-2.03 (m, 2 H), 1.55-1.67 (m, 2 H), 0.96 (t, J=7.25 Hz, 3 H). MS (ESI) 452 (M+H).

Example 180

Preparation of 1-(2-fluoro-4-(methylsulfonyl)phenyl)-5-phenyl-4-(1-(5-propylpyrimidin-2-yl)piperidin-4-yloxy)pyridin-2(1H)-one

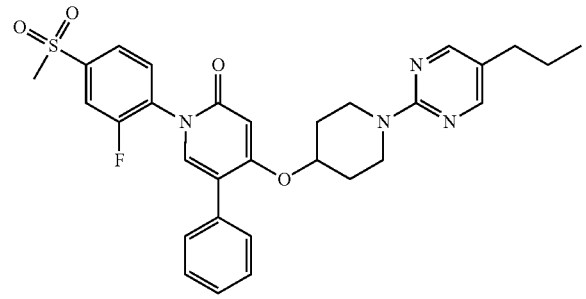 [SMILES: CCCc1cnc(N2CCC(Oc3cc(=O)n(-c4ccc(S(C)(=O)=O)cc4F)cc3-c3ccccc3)CC2)nc1]

Step A. Preparation of 6-chloro-4-hydroxy-5-phenylpyridin-2(1H)-one

To malonyl dichloride (17.43 mL, 179 mmol) under nitrogen in a 200 mL recovery flask was added 2-phenylacetonitrile (9.80 mL, 85 mmol) and the mixture was stirred under nitrogen at room temperature for 23 hours. To the resulting thick brown mixture was added ether (200 mL). This resulted in the formation of a brown, powder-like precipitate which was filtered at rt, washed with ether (4×50 mL), and then dried under vacuum to give crude product as a tan-amber powder (7.28 g). MS (ESI) 222 (M+H).

Step B. Preparation of 4-hydroxy-5-phenylpyridin-2(1H)-one

A suspension of palladium on carbon (480 mg, 50 wt % wet, 0.451 mmol) and 6-chloro-4-hydroxy-5-phenylpyridin-2(1H)-one (1000 mg, 4.51 mmol) in EtOH (40 mL) was placed under a hydrogen balloon and stirred at 60° C. After stirring under hydrogen for 30 h, the mixture was filtered while hot through a pad of CELITE® 545 filter aid and rinsed with hot ethanol. The filtrate was concentrated to give 490 mg crude product as a yellow solid. MS (ESI) 188 (M+H).

Step C. Preparation of 5-phenyl-4-(1-(5-propylpyrimidin-2-yl)piperidin-4-yloxy)pyridin-2(1H)-one The compound in Step C was prepared according to the procedures described in Example 1 substituting 4-hydroxy-5-phenylpyridin-2(1H)-one for 4-hydroxy-1-(4-(methylsulfonyl)pyridin-2(1H)-one and 1-(5-propylpyrimidin-2-yl)piperidin-4-yl methanesulfonate for tert-butyl 4-(methylsulfonyloxy)piperidine-1-carboxylate in Step D. MS (ESI) 391 (M+H).

Step D. Example 180

Example 180 was prepared according to the procedures described in Example 8 substituting 5-phenyl-4-(1-(5-propylpyrimidin-2-yl)piperidin-4-yloxy)pyridin-2(1H)-one for isopropyl 4-(methylsulfonyloxy)piperidine-1-carboxylate and 1,2-difluoro-4-(methylsulfonyl)benzene for 4-bromobenzonitrile in Step C except that the Microwave reaction was run at 180° C. for 25 min. $^1$H NMR (500 MHz, CDCl$_3$) δ ppm 8.16 (br. s., 2 H), 7.82-7.93 (m, 2 H), 7.64-7.74 (m, 1 H), 7.30-7.46 (m, 5 H), 7.19 (s, 1 H), 6.12 (s, 1 H), 4.71 (br. s., 1 H), 3.85 (br. s., 4 H), 3.04-3.18 (m, 3 H), 2.42 (t, J=7.47 Hz, 2 H), 1.82-2.11 (m, 4 H), 1.49-1.65 (m, 2 H), 0.93 (t, J=7.25 Hz, 3 H). MS (ESI) 563 (M+H).

Example 181

Preparation of 1-(2-fluoro-4-(methylsulfonyl)phenyl)-4-(1-(5-(3,3,3-trifluoropropyl)pyrimidin-2-yl)piperidin-4-yloxy)pyridin-2(1H)-one, hydrochloride salt

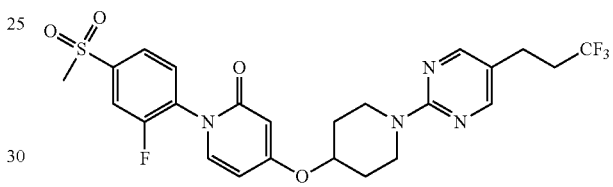

Step A. Preparation of 2-chloro-5-(3,3,3-trifluoropropyl)pyrimidine

To magnesium (1.373 g, 56.5 mmol) in a 500 mL tear-shaped flask applied vacuum then nitrogen, added 50 mL THF, added 3-bromo-1,1,1-trifluoropropane (6.02 mL, 56.5 mmol), and then 1 crystal of iodine. Within 1 minute the mixture became warm and by 5 minutes was refluxing. The mixture was cooled for 2 minutes with an ice bath to control the exothermic reaction then allowed to warm back up to rt. By 65 minutes, nearly all of the Mg had dissolved. Added zinc(II) chloride (3.85 g, 28.3 mmol) which caused a small amount of heat to be generated. Nearly all was dissolved within 10 minutes to provide ~1.1 M of $Zn(CH_2CH_2CF_3)_2$ in THF. To 5-bromo-2-chloropyrimidine (7.72 g, 39.9 mmol) and bis(tri-t-butylphosphine)palladium(0) (404 mg, 0.791 mmol) applied vacuum then placed under an atmosphere of nitrogen, added 80 mL THF, and then added over ~2 minutes 60 mL of the ~1.1 M of $Zn(CH_2CH_2CF_3)_2$ in THF. The reaction was quenched after 23 hour)s with 300 mL saturated NH$_4$Cl+300 mL EtOAc, the organic layer was then washed with 300 mL saturated NaHCO$_3$ then 300 mL water, dried with MgSO$_4$, filtered, then concentrated to 7.6 g brown oily solids. This material was purified by flash chromatography (0-10% EtOAc/hexanes) to yield product (3.86 g, 18.4 mmol, 46% yield) as a pale yellow solid. MS (ESI) 211.1 (M+1).

Step B. Preparation of 1-(5-(3,3,3-trifluoropropyl)pyrimidin-2-yl)piperidin-4-yl methanesulfonate In a manner similar to that described in Example 142, Steps A and B, 2-chloro-5-(3,3,3-trifluoropropyl)pyrimidine (Example 181, Step A) was converted into 1-(5-(3,3,3-trifluoropropyl)pyrimidin-2-yl)piperidin-4-yl methanesulfonate.

Step C. Preparation of Example 181

To 1-(2-fluoro-4-(methylsulfonyl)phenyl)-4-hydroxypyridin-2(1H)-one (85 mg, 0.3 mmol), obtained as described in Example 142, Step D, was added 1-(5-(3,3,3-trifluoropropyl)pyrimidin-2-yl)piperidin-4-yl methanesulfonate (106 mg, 0.300 mmol), potassium carbonate (54.0 mg, 0.900 mmol), and then 1 mL DMF, the mixture placed in a 90° C. oil bath for 345 minutes. To this was added 5 mL EtOAc and the mixture washed with 2×2 mL water, dried with MgSO$_4$, filtered and concentrated to 99 mg (0.183 mmol) of yellow solids to which were added 2 mL EtOH and then 125 uL of 6 N aqueous HCl (0.75 mmol, 4.1 equiv.). All dissolved with stirring within one minute. Stirred for an additional 5 minutes the solvent was removed in vacuo to yield 110 mg of a pale yellow solid to which were added 3 mL EtOH and the mixture heated to reflux at which point the solids appeared to become white to tan and crystalline. Cooled to rt, filtered and washed with 2×0.5 mL EtOH, then dried in vacuo to yield Example 181 (33 mg, 0.057 mmol, 19%) as an off-white, crystalline powder. $^1$H NMR (500 MHz, methanol-d$_3$) δ ppm 2.01 (m, 2 H) 2.13-2.31 (m, 2 H) 2.43-2.70 (m, 2 H) 2.79-3.01 (m, 2 H) 3.22 (s, 3 H) 3.86-4.03 (m, 2 H) 4.05-4.30 (m, 2 H) 6.13 (d, J=2.75 Hz, 1 H) 6.31 (dd, J=7.70, 2.20 Hz, 1 H) 7.57 (d, J=7.15 Hz, 1 H) 7.67-7.82 (m, 1 H) 7.87-8.07 (m, 2 H) 8.58 (s, 2 H). MS (ESI) 541.1.

Example 182

Preparation of 1-(4-(methylsulfonyl)-3-(trifluoromethyl)phenyl)-4-(1-(5-propylpyrimidin-2-yl)piperidin-4-yloxy)pyridin-2(1H)-one

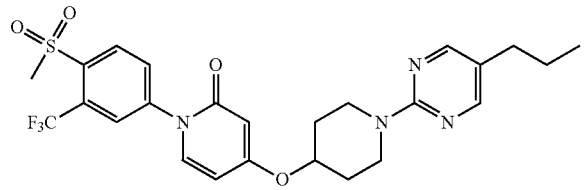 [SMILES: CCCc1cnc(N2CCC(Oc3ccn(-c4ccc(S(C)(=O)=O)c(C(F)(F)F)c4)c(=O)c3)CC2)nc1]

Example 182 was prepared according to procedures described in Example 173 substituting 4-bromo-1-iodo-2-(trifluoromethyl)benzene (Oakwood) for 4-bromo-1-iodo-2-methylbenzene in Step D. $^1$H NMR (500 MHz, CDCl$_3$) δ ppm 8.43 (d, J=8.80 Hz, 1 H), 8.16 (s, 2 H), 7.95 (d, J=2.20 Hz, 1 H), 7.85 (dd, J=8.25, 2.20 Hz, 1H), 7.23 (d, J=7.70 Hz, 1 H), 6.11 (dd, J=7.70, 2.20 Hz, 1 H), 6.01 (d, J=2.75 Hz, 1 H), 4.51-4.63 (m, 1 H), 4.14-4.24 (m, 2 H), 3.60-3.69 (m, 2 H), 3.21 (s, 3 H), 2.40 (t, J=7.70 Hz, 2 H), 2.04-2.12 (m, 2 H), 1.79-1.90 (m, 2 H), 1.52-1.64 (m, 2 H), 0.94 (t, J=7.15 Hz, 3 H). MS (ESI) 537 (M+H).

Example 183

Preparation of 5-cyclopropyl-1-(2-fluoro-4-(methylsulfonyl)phenyl)-4-(1-(5-propylpyrimidin-2-yl)piperidin-4-yloxy)pyridin-2(1H)-one, TFA salt

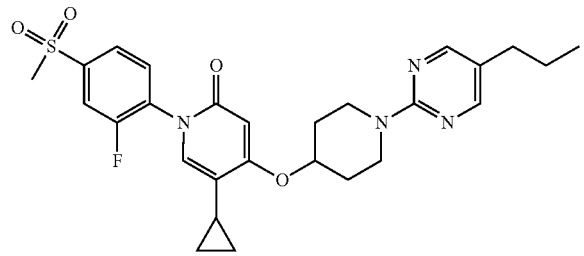 [SMILES: CCCc1cnc(N2CCC(Oc3cc(=O)n(-c4ccc(S(C)(=O)=O)cc4F)cc3C3CC3)CC2)nc1]

Example 183 was prepared according to the procedures described in Example 180 substituting 2-cyclopropylacetonitrile for 2-phenylacetonitrile in Step A. $^1$H NMR (500 MHz, CDCl$_3$) δ ppm 8.34-8.50 (m, 2 H), 7.77-7.95 (m, 2 H), 7.60 (t, J=7.69 Hz, 1 H), 6.95 (s, 1 H), 6.45 (s, 1 H), 4.84 (br. s., 1 H), 4.24-4.39 (m, 2 H), 3.89-4.06 (m, 2 H), 3.12 (s, 3 H), 2.55 (t, J=7.47 Hz, 2 H), 2.17 (d, 4 H), 1.71-1.80 (m, 1 H), 1.55-1.70 (m, 2 H), 0.91-1.05 (m, 3 H), 0.81-0.92 (m, 2 H), 0.40-0.54 (m, 2 H). MS (ESI) 527 (M+H).

Example 185

Preparation of 1-(4-(methylsulfonyl)phenyl)-4-(1-phenylpiperidin-4-yloxy)pyridin-2(1H)-one, TFA salt

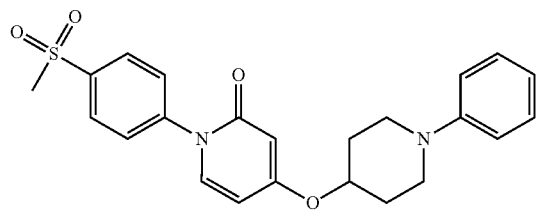 [SMILES: CS(=O)(=O)c1ccc(-n2ccc(OC3CCN(c4ccccc4)CC3)cc2=O)cc1]

To 1-(4-(methylsulfonyl)phenyl)-4-(piperidin-4-yloxy)pyridin-2(1H)-one, HCl salt (35 mg, 0.100 mmol), phenylboronic acid (24.50 mg, 0.201 mmol), copper (II) acetate (27.4 mg, 0.151 mmol), and 75 mg of 4 A molecular sieves (oven dried) was added 1.5 mL of CH$_2$Cl$_2$, and then pyridine (0.016 mL, 0.201 mmol. The tan suspension was stirred open to air for 2-3 minutes then capped with continued stirring. The mixture developed a pale green-blue tint within 3-4 minutes. After 89 hours, added 4 mL CH$_2$Cl$_2$ then washed with 3×3 mL saturated aqueous NH$_4$Cl, dried organic layer with MgSO$_4$, filtered, then concentrated to provide 14 mg pale grey-green solids which was purified by preparative HPLC (C$_{18}$ column; MeOH in water containing 0.1% TFA) to yield Example 185 (1.27 mg, 0.001 mmol, 1%) as a pale yellow oil. MS (ESI) 425.1 (M+1). $^1$H NMR (500 MHz, methanol-d$_3$) δ ppm 2.05-2.18 (m, 2 H) 2.23-2.38 (m, 2 H) 3.17 (s, 3 H) 3.44 (s, 1 H) 3.57-3.74 (m, 1 H) 6.11 (d, J=2.75 Hz, 1 H) 6.31 (dd, J=7.70, 2.75 Hz, 1 H) 7.16 (br. s., 1 H) 7.31 (d, J=7.70 Hz, 1 H) 7.41 (t, J=7.70 Hz, 1 H) 7.61 (d, J=7.70 Hz, 1 H) 7.64-7.73 (m, 2 H) 8.11 (d, 2 H). MS (ESI) 425.1 (M+1).

Example 186

Preparation of 1-(2-methylpyridin-3-yl)-4-(1-(5-propylpyrimidin-2-yl)piperidin-4-yloxy)pyridin-2(1H)-one

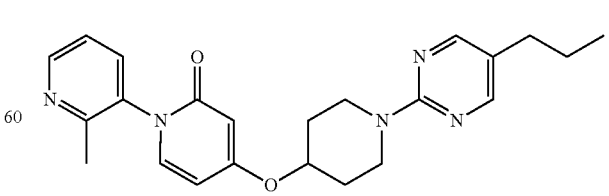

Example 186 was prepared according to procedures described in Example 173 substituting 3-bromo-2-methylpyridine (3B Pharmachem) for 4-bromo-2-methyl-1-(methylsulfonyl)benzene in Step E except that crude solid was purified by flash chromatography (SiO$_2$, 0 to 10% MeOH in CH$_2$Cl$_2$) and by preparative HPLC (C$_{18}$ column, 10-100% MeOH in water containing 0.1% trifluoroacetic acid). $^1$H NMR (500 MHz, CDCl$_3$) δ ppm 8.52 (d, J=3.85 Hz, 1 H), 8.10 (s, 2 H), 7.47 (dd, J=8.25, 1.10 Hz, 1 H), 7.20-7.23 (m, 1 H), 6.98 (d, J=7.70 Hz, 1 H), 5.97-5.99 (m, 1 H), 5.96 (s, 1 H), 4.48-4.53 (m, 1 H), 4.12-4.18 (m, 2 H), 3.53-3.58 (m, 2 H), 2.37 (s, 3 H), 2.34 (t, J=7.70 Hz, 2 H), 2.00-2.05 (m, 2 H), 1.75-1.82 (m, 2 H), 1.47-1.55 (m, 2 H), 0.87 (t, J=7.42 Hz, 3 H). MS (ESI) 406 (M+H).

Example 187

Preparation of 1-(6-(methylsulfonyl)pyridin-3-yl)-4-(1-(5-propylpyrimidin-2-yl)piperidin-4-yloxy)pyridin-2(1H)-one

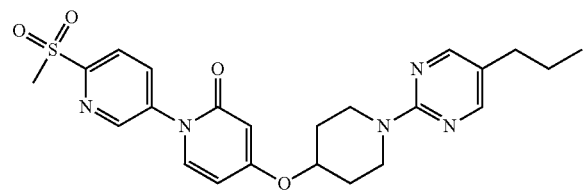

Example 187 was prepared according to procedures described in Example 173 substituting 5-bromo-2-(methylsulfonyl)pyridine (Synthonix) for 4-bromo-2-methyl-1-(methylsulfonyl)benzene in Step E except that reaction was heated under microwave condition at 160° C. for 30 min. $^1$H NMR (400 MHz, CDCl$_3$) δ ppm 8.79 (d, J=2.20 Hz, 1 H) 8.23 (d, J=8.24 Hz, 1 H) 8.17 (s, 2 H) 8.07 (dd, J=8.25, 2.20 Hz, 1 H) 7.23 (d, J=7.70 Hz, 1 H) 6.12 (dd, J=7.70, 2.20 Hz, 1 H) 6.02 (d, J=2.20 Hz, 1 H) 4.55-4.62 (m, 1 H) 4.16-4.24 (m, 2 H) 3.60-3.68 (m, 2 H) 3.27 (s, 3 H) 2.41 (t, 2 H) 2.05-2.13 (m, 2 H) 1.80-1.90 (m, 2 H) 1.53-1.63 (m, 2 H) 0.94 (t, J=7.42 Hz, 3 H). MS (ESI) 470 (M+H).

Example 188

Preparation of isopropyl 4-(1-(4-cyano-2-fluorophenyl)-2-oxo-1,2-dihydropyridin-4-yloxy)piperidine-1-carboxylate

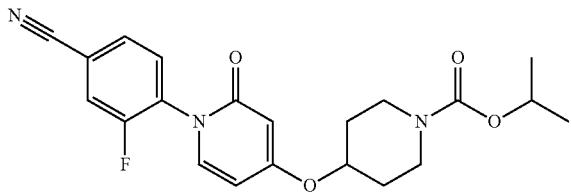 [SMILES: CC(C)OC(=O)N1CCC(Oc2ccn(-c3ccc(C#N)cc3F)c(=O)c2)CC1]

Example 188 was prepared according to procedures described in Example 132 substituting tert-butyl 4-(1-(4-cyano-2-fluorophenyl)-2-oxo-1,2-dihydropyridin-4-yloxy)piperidine-1-carboxylate (Example 176) for tert-butyl 4-(2-oxo-1-(pyridin-3-yl)-1,2-dihydropyridin-4-yloxy)piperidine-1-carboxylate in Step C and substituting isopropyl carbonochloridate (1 Molar in Toluene, Aldrich) for 2-chloro-5-propylpyrimidine and substituting triethyl amine for cesium carbonate in Step D except that reaction was stirred at room temperature for 20 min and then washed with HCl solution (1 Molar in H$_2$O). The crude solid was purified by flash chromatography (SiO$_2$, 0 to 100% EtOAc in CH$_2$Cl$_2$). $^1$H NMR (500 MHz, CDCl$_3$) δ ppm 7.49-7.58 (m, 3 H), 7.08 (d, J=7.70 Hz, 1 H), 6.02 (dd, J=7.70, 2.20 Hz, 1 H), 5.93 (d, J=2.20 Hz, 1 H), 4.87-4.95 (m, 1 H), 4.45-4.49 (m, 1 H), 3.69-3.77 (m, 2 H), 3.32-3.39 (m, 2 H), 1.92-2.00 (m, 2 H), 1.72-1.81 (m, 2 H), 1.24 (d, J=6.60 Hz, 6 H). MS (ESI) 400 (M+H).

Example 189

Preparation of isopropyl 4-(1-(6-(methylsulfonyl)pyridin-3-yl)-2-oxo-1,2-dihydropyridin-4-yloxy)piperidine-1-carboxylate

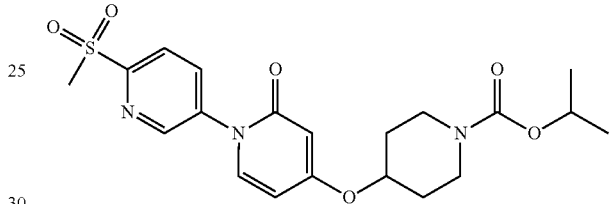

Step A. Preparation of isopropyl 4-hydroxypiperidine-1-carboxylate

To a stirring solution of piperidin-4-ol (5.22 g, 51.6 mmol, Aldrich), Et$_3$N (13.2 mL, 95 mmol, Aldrich) in CH$_2$Cl$_2$ (50 mL) at 0° C. was added a solution of Isopropyl chloroformate (1 Molar in Toluene, 43.0 mL, 43.0 mmol, Aldrich) dropwise. The reaction mixture was stirred at room temperature for 1 h and washed with 1N HCl in H$_2$O. The H$_2$O layer was extracted with DCM (2×). The organic layers were combined and concentrated in vacuo to yield 5.71 g of the desired product as a light brown oil. MS (ESI) 188 (M+H).

Step B

Example 189

Example 189 was prepared according to procedures described in Example 173 substituting isopropyl 4-hydroxypiperidine-1-carboxylate for 1-(5-propylpyrimidin-2-yl)piperidin-4-ol in Step B and substituting 5-bromo-2-(methylsulfonyl)pyridine for 4-bromo-2-methyl-1-(methylsulfonyl)benzene in Step E except that reaction was heated under microwave condition at 160° C. for 30 min. $^1$H NMR (500 MHz, CDCl$_3$) δ ppm 8.78 (d, J=2.20 Hz, 1 H), 8.22 (d, J=8.25 Hz, 1 H), 8.06 (dd, J=8.25, 2.75 Hz, 1 H), 7.23 (d, J=7.70 Hz, 1 H), 6.11 (dd, J=7.70, 2.20 Hz, 1 H), 5.98 (d, J=2.75 Hz, 1 H), 4.90-4.98 (m, 1 H), 4.49-4.54 (m, 1 H), 3.72-3.79 (m, 2 H), 3.36-3.42 (m, 2 H), 3.27 (s, 3 H), 1.96-2.03 (m, 2 H), 1.76-1.84 (m, 2 H), 1.26 (d, J=6.05 Hz, 6 H). MS (ESI) 436 (M+H).

Example 190

Preparation of 4-(4-(1-(5-cyclopropylpyrimidin-2-yl)piperidin-4-yloxy)-2-oxopyridin-1(2H)-yl)-3-fluorobenzonitrile

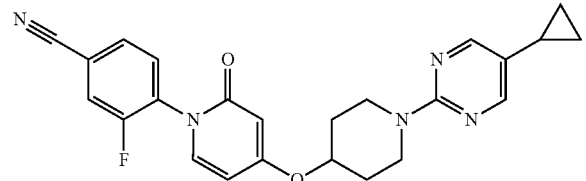

Example 190 was prepared according to procedures described in Example 132 substituting tert-butyl 4-(1-(4-cyano-2-fluorophenyl)-2-oxo-1,2-dihydropyridin-4-yloxy)piperidine-1-carboxylate (Example 176) for tert-butyl 4-(2-oxo-1-(pyridin-3-yl)-1,2-dihydropyridin-4-yloxy)piperidine-1-carboxylate in Step C and substituting 2-chloro-5-cyclopropylpyrimidine (prepared according to the procedure described in Step A of Example 159) for 2-chloro-5-propylpyrimidine and substituting potassium carbonate for cesium carbonate in Step D except that reaction was stirred at 100° C. for 7 h. The crude solid was purified by flash chromatography (SiO$_2$, 0 to 100% EtOAc in CH$_2$Cl$_2$). $^1$H NMR (500 MHz, CDCl$_3$) δ ppm 8.14 (s, 2 H), 7.51-7.62 (m, 3 H), 7.11 (d, J=7.70 Hz, 1 H), 6.06 (dd, J=7.70, 2.75 Hz, 1 H), 6.01 (d, J=2.75 Hz, 1H), 4.52-4.62 (m, 1 H), 4.15-4.26 (m, 2 H), 3.58-3.68 (m, 2 H), 1.96-2.14 (m, 2 H), 1.79-1.96 (m, 2 H), 1.69-1.77 (m, 1 H), 0.88-0.96 (m, 2 H), 0.57-0.64 (m, 2 H). MS (ESI) 432 (M+H).

Example 191

Preparation of isopropyl 4-(2-oxo-1-(pyrimidin-5-yl)-1,2-dihydropyridin-4-yloxy)piperidine-1-carboxylate

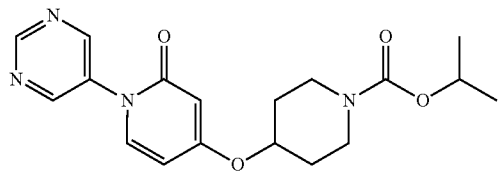 [SMILES: CC(C)OC(=O)N1CCC(Oc2ccn(-c3cncnc3)c(=O)c2)CC1]

Example 191 was prepared according to procedures described in Example 189 substituting 5-bromopyrimidine (Aldrich) for 5-bromo-2-(methylsulfonyl)pyridine in Step B. $^1$H NMR (400 MHz, CDCl$_3$) δ ppm 9.28 (br. s., 1 H), 8.91 (br. s., 2 H), 7.23 (d, J=7.53 Hz, 1 H), 6.11 (dd, J=7.65, 2.64 Hz, 1 H), 5.99 (d, J=2.76 Hz, 1 H), 4.91-5.01 (m, 1 H), 4.50-4.56 (m, 1 H), 3.72-3.82 (m, 2 H), 3.34-3.46 (m, 2 H), 1.96-2.05 (m, 2 H), 1.75-1.86 (m, 2 H), 1.28 (d, J=6.27 Hz, 6 H). MS (ESI) 359 (M+H).

Example 192

Preparation of 4-(1-(5-propylpyrimidin-2-yl)piperidin-4-yloxy)-1-(pyrimidin-5-yl)pyridin-2(1H)-one

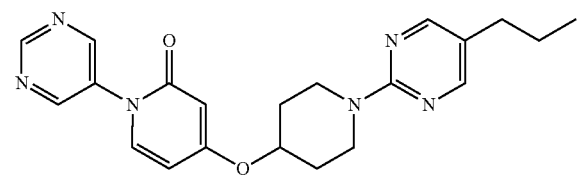 [SMILES: CCCc1cnc(N2CCC(Oc3ccn(-c4cncnc4)c(=O)c3)CC2)nc1]

Example 192 was prepared according to procedures described in Example 187 substituting 5-bromopyrimidine (Aldrich) for 5-bromo-2-(methylsulfonyl)pyridine. $^1$H NMR (400 MHz, CDCl$_3$) δ ppm 9.27 (br. s., 1 H), 8.91 (br. s., 2 H), 8.19 (s, 2 H), 7.23 (d, J=7.78 Hz, 1 H), 6.12 (dd, J=7.65, 2.64 Hz, 1 H), 6.04 (d, J=2.76 Hz, 1 H), 4.57-4.64 (m, 1 H), 4.18-4.25 (m, 2 H), 3.62-3.71 (m, 2 H), 2.43 (t, J=7.53 Hz, 2 H), 2.06-2.15 (m, 2 H), 1.82-1.92 (m, 2 H), 1.57-1.65 (m, 2 H), 0.96 (t, J=7.28 Hz, 3 H). MS (ESI) 393 (M+H).

Example 193

Preparation of 4-(1-(5-sec-butylpyrimidin-2-yl)piperidin-4-yloxy)-1-(4-(methylsulfonyl)phenyl)pyridin-2(1H)-one, hydrochloride salt

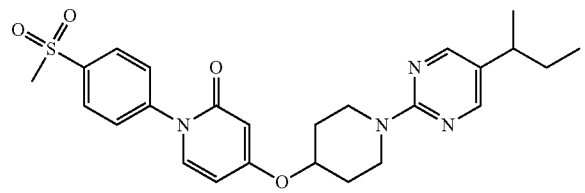 [SMILES: CCC(C)c1cnc(N2CCC(Oc3ccn(-c4ccc(S(C)(=O)=O)cc4)c(=O)c3)CC2)nc1]

To Example 57 (51 mg, 0.101 mmol) and bis(tri-t-butylphosphine)palladium (4 mg, 0.020 mmol) was added 0.5 mL THF under nitrogen giving a pale tan suspension. Added at rt 0.605 mL of sec-butylzinc(II) bromide (0.605 mL, 0.303 mmol, 0.5 M in THF) and stirred for 19.5 hours at which point the reaction was quenched with 2 mL EtOAc then washed with 1 mL each of saturated aqueous NH$_4$Cl, NaHCO$_3$, then NaCl. Dried with MgSO$_4$, filtered and then concentrated to 43 mg brown solids. Added ~1 mL of 90% MeOH/10% water/0.1% TFA which did not dissolve the solids. Purified this material on a 500 uM silica TLC plate developed with 5% MeOH/CHCl$_3$ to provide 28 mg (0.058 mmol) of an off-white powder. This material was suspended in 0.5 mL EtOH and to which was then added 40 uL of 6N aqueous HCl (0.240 mmol, 4.1 equiv) causing complete dissolution. Within 2 minutes, crystals began to form. Filtered after 30 minutes plus 2×0.3 mL EtOH wash to give Example 193 (18 mg, 0.034 mmol, 33%) as pale tan crystals. $^1$H NMR (400 MHz, CDCl$_3$) δ ppm 1.04 (t, J=7.25 Hz, 3 H) 1.43 (d, J=7.03 Hz, 3 H) 1.67-1.87 (m, 2 H) 2.15-2.36 (m, 4 H) 2.77-2.89 (m, 1 H) 3.28 (br. s., 3H) 4.10-4.27 (m, 3 H) 4.94 (br. s., 1 H) 6.19 (s, 1 H)

6.28-6.39 (m, 1 H) 7.45-7.54 (m, 3 H) 7.47-7.53 (m, 2 H) 7.77 (d, J=8.35 Hz, 2 H) 8.23 (d, J=8.35 Hz, 2 H) 8.57 (br. s., 2 H). MS (ESI) 483.1 (M+1).

Example 194

Preparation of 5-chloro-1-(4-(methylsulfonyl)phenyl)-4-(1-(5-propylpyrimidin-2-yl)piperidin-4-yloxy)pyridin-2(1H)-one, TFA salt

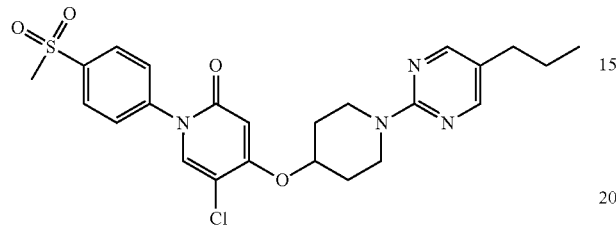

Step A. Preparation of 1-(5-propylpyrimidin-2-yl)piperidin-4-ol

A suspension of piperidin-4-ol (12 g, 119 mmol), 2-chloro-5-propylpyrimidine (20.44 g, 131 mmol) and potassium carbonate (49.2 g, 356 mmol) in DMF (100 mL) was heated at 110° C. for 12 h and cooled to rt. The mixture was diluted with EtOAc (250 ml) and washed with H$_2$O (3×). After drying over Na$_2$SO$_4$, the organic layer was evaporated to give a yellow oil. The crude oil was purified on a flash chromatography (SiO$_2$, 0 to 10% MeOH/CH$_2$Cl$_2$) to give a yellow solid. MS (ESI) 222 (M+H).

Step B. Preparation of 1-(5-propylpyrimidin-2-yl)piperidin-4-yl methanesulfonate The compound was prepared according to the procedures described in Example 1 substituting 1-(5-propylpyrimidin-2-yl)piperidin-4-ol for tert-butyl 4-hydroxypiperidine-1-carboxylate in Step C. MS (ESI) 300 (M+H).

Step C. Preparation of 5-chloro-4-(1-(5-propylpyrimidin-2-yl)piperidin-4-yloxy)pyridin-2(1H)-one A mixture of 1-(5-propylpyrimidin-2-yl)piperidin-4-yl methanesulfonate (800 mg, 2.67 mmol), 5-chloro-4-hydroxypyridin-2(1H)-one (389 mg, 2.67 mmol, AK Scientific) and cesium carbonate (2612 mg, 8.02 mmol) in DMF (20 mL) was heated at 120° C. for 6 h. The reaction was cooled to rt, diluted with EtOAc (30 mL), and washed with H$_2$O (3×). The organic layer was dried over Na$_2$SO$_4$ and concentrated under reduced pressure to give a yellow solid. The residue was purified by flash chromatography (SiO$_2$, O-10% MeOH/CH$_2$Cl$_2$) to give the desired product as a yellow solid. MS (ESI) 379 (M+H).

Step 4

Example 194

Example 194 was prepared according to the procedures described in Example 8 substituting 5-chloro-4-(1-(5-propylpyrimidin-2-yl)piperidin-4-yloxy)pyridin-2(1H)-one for isopropyl 4-(methylsulfonyloxy)piperidine-1-carboxylate and substituting 1-bromo-4-(methylsulfonyl)benzene for 4-bromobenzonitrile in Step C in addition to running the Microwave reaction at 190° C. for 25 min. $^1$H NMR (500 MHz, CDCl$_3$) δ ppm 8.43 (s, 2 H), 8.12 (d, J=8.25 Hz, 2 H), 7.62 (d, J=8.25 Hz, 2 H), 7.55 (s, 1 H), 6.64 (s, 1 H), 4.89 (br. s., 1 H), 4.24-4.37 (m, 2 H), 3.90-4.07 (m, 2 H), 3.12 (s, 3 H), 2.56 (t, J=7.70 Hz, 2 H), 2.19 (br. s., 4 H), 1.57-1.75 (m, 2 H), 0.84-1.10 (m, 3 H). MS (ESI) 503 (M+H).

Example 195

Preparation of 4-(2-(4-(1-(4-(methylsulfonyl)phenyl)-2-oxo-1,2-dihydropyridin-4-yloxy)piperidin-1-yl)pyrimidin-5-yl)benzonitrile, hydrochloride salt

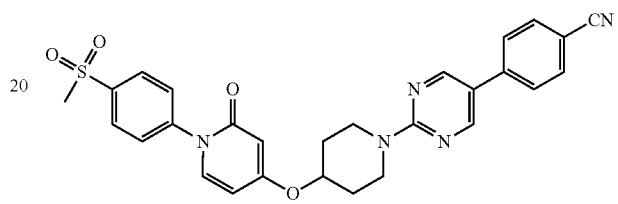

To a suspension of 4-(1-(5-bromopyrimidin-2-yl)piperidin-4-yloxy)-1-(4-(methylsulfonyl)phenyl)pyridin-2(1H)-one (51 mg, 0.101 mmol) and bis(tri-t-butylphosphine)palladium (4.08 mg, 0.020 mmol) in 0.5 mL of THF under nitrogen at rt was added 0.605 mL of 0.5 M (4-cyanophenyl)zinc(II) bromide (74.9 mg, 0.303 mmol) in THF. The reaction was quenched after 25 minutes with 2 mL of saturated aqueous NaHCO$_3$+4 mL EtOAc, then removed EtOAc and washed with an additional 2 mL of saturated aqueous NaHCO$_3$, then 2 mL of brine. The poorly soluble product had precipitated out during this process and remained in a thin emulsion-like layer at the interface of the aqueous and organic phases. Upon carefully isolating this layer it was filtered and the solids washed with EtOAc (mL) to produce 17 mg of a pale yellow solid. This material was suspended in 3 mL EtOH to which were added 100 uL 6 N aqueous HCl (0.6 mmol, 9.5 equiv) and the mixture heated to reflux causing nearly complete solution and then allowed cool to rt. Small crystals formed slowly. Filtered plus 0.5 mL EtOH then 2×0.5 mL hexane washes to yield Example 195 (11 mg) as bright yellow crystals. $^1$H NMR (500 MHz, DMSO-d$_6$) δ ppm 1.54-1.76 (m, 2 H) 2.07 (d, J=8.80 Hz, 2 H) 3.35-3.55 (m, 5 H) 3.62 (t, J=10.17 Hz, 2 H) 4.31 (d, J=13.75 Hz, 2 H) 4.82 (d, J=3.85 Hz, 1 H) 6.08-6.15 (m, 2 H) 7.66 (d, J=7.70 Hz, 1 H) 7.70 (d, J=8.80 Hz, 2 H) 7.83-7.96 (m, 4 H) 8.04 (d, J=8.25 Hz, 2 H) 8.84 (s, 2 H). MS (ESI) 528.1 (M+1).

Example 196

Preparation of 1-(4-(methylsulfonyl)phenyl)-4-(1-(4-propylphenyl)piperidin-4-yloxy)pyridin-2(1H)-one, TFA salt

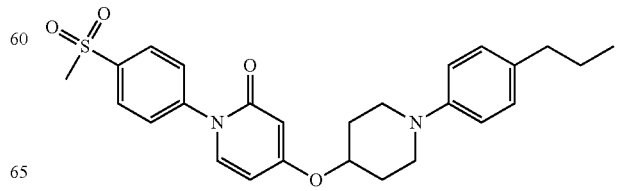

To a mixture of 1-(4-(methylsulfonyl)phenyl)-4-(piperidin-4-yloxy)pyridin-2(1H)-one hydrochloride (50 mg, 0.130 mmol, prepared according to the procedures described in Example 1), 4-propylphenylboronic acid (42.6 mg, 0.260 mmol) and diacetoxycopper (35.4 mg, 0.195 mmol) in CH₂Cl₂ (3 mL) was added pyridine (0.021 mL, 0.260 mmol). After exposure to open air for 5-10 min., the reaction mixture was capped and stirred with 4 A° molecular sieves at rt for 48 h. To the reaction mixture was diluted with CH₂Cl₂ and washed with saturated aq. NH₄Cl (3×). The organic layer was dried (Na₂SO₄) and evaporated under reduced pressure. The residue was purified by preparative HPLC (C₁₈ column; 20-90% MeOH in water containing 0.1% trifluoroacetic acid) to give Example 196 (6 mg, 9.90%) as a white solid. ¹H NMR (500 MHz, CDCl₃) δ ppm 8.10 (d, J=7.70 Hz, 2 H), 7.53-7.72 (m, 4H), 7.33 (d, J=7.70 Hz, 3 H), 6.34-6.53 (m, 1 H), 6.18-6.34 (m, 1 H), 4.72-4.87 (m, 1 H), 3.73 (d, J=7.15 Hz, 2 H), 3.62 (br. s., 2 H), 3.11 (s, 3 H), 2.84 (d, J=4.40 Hz, 2 H), 2.63 (t, J=7.42 Hz, 2 H), 2.38-2.53 (m, 2 H), 1.55-1.73 (m, 2 H), 0.95 (t, J=7.15 Hz, 3 H). MS (ESI) 466 (M+H).

Example 197

Preparation of isopropyl 4-(1-(4-cyano-3-fluorophenyl)-2-oxo-1,2-dihydropyridin-4-yloxy)piperidine-1-carboxylate

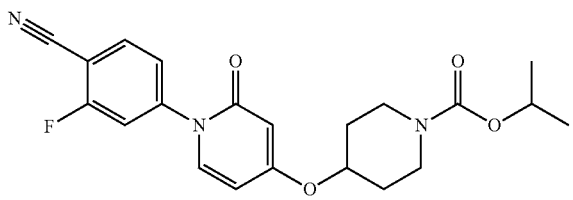 [SMILES: CC(C)OC(=O)N1CCC(Oc2ccn(-c3ccc(C#N)c(F)c3)c(=O)c2)CC1]

Example 197 was prepared according to procedures described in Example 189 substituting 4-bromo-2-fluorobenzonitrile (Lancaster) for 5-bromo-2-(methylsulfonyl)pyridine in Step B. ¹H NMR (400 MHz, CDCl₃) δ 7.76 (dd, J=8.03, 7.03 Hz, 1 H), 7.32-7.43 (m, 2 H), 7.22 (d, J=7.78 Hz, 1 H), 6.07 (dd, J=7.78, 2.51 Hz, 1 H), 5.96 (d, J=2.51 Hz, 1 H), 4.91-5.00 (m, 1 H), 4.48-4.55 (m, 1 H), 3.72-3.82 (m, 2 H), 3.36-3.44 (m, 2 H), 1.96-2.05 (m, 2 H), 1.75-1.85 (m, 2 H), 1.28 (d, J=6.27 Hz, 6 H). MS (ESI) 400 (M+H).

Example 198

Preparation of 4-(1-(5-propylpyrimidin-2-yl)piperidin-4-yloxy)-1-(pyrazin-2-yl)pyridin-2(1H)-one

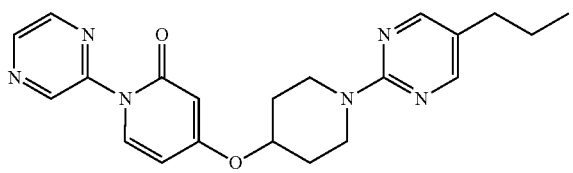 [SMILES: CCCc1cnc(N2CCC(Oc3ccn(-c4cnccn4)c(=O)c3)CC2)nc1]

Example 198 was prepared according to procedures described in Example 187 substituting 2-iodopyrazine (Aldrich) for 5-bromo-2-(methylsulfonyl)pyridine except that the reaction was heated under microwave conditions at 140° C. for 20 min. ¹H NMR (400 MHz, CDCl₃) δ ppm 9.40 (s, 1 H), 8.58 (d, J=2.51 Hz, 1 H), 8.50-8.55 (m, 1 H), 8.19 (s, 2 H), 7.85 (d, J=7.78 Hz, 1 H), 6.12 (dd, J=7.91, 2.64 Hz, 1 H), 6.02 (d, J=2.26 Hz, 1 H), 4.58-4.65 (m, 1 H), 4.17-4.25 (m, 2 H), 3.63-3.71 (m, 2 H), 2.40-2.46 (m, 2 H), 2.07-2.14 (m, 2 H), 1.82-1.92 (m, 2 H), 1.55-1.64 (m, 2 H), 0.96 (t, J=7.40 Hz, 3 H). MS (ESI) 393 (M+H).

Example 199

Preparation of 2-fluoro-4-(2-oxo-4-(1-(5-propylpyrimidin-2-yl)piperidin-4-yloxy)pyridin-1(2H)-yl)benzonitrile

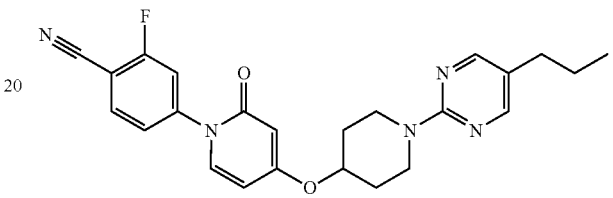

Example 199 was prepared according to procedures described in Example 187 substituting 2-fluoro-4-iodobenzonitrile (Matrix Scientific) for 5-bromo-2-(methylsulfonyl)pyridine except that the reaction was heated under microwave conditions at 125° C. for 1 h. ¹H NMR (400 MHz, CDCl₃) δ ppm 8.18 (s, 2 H), 7.76 (dd, J=8.28, 7.03 Hz, 1 H), 7.31-7.44 (m, 2 H), 7.21 (d, J=7.78 Hz, 1 H), 6.08 (dd, J=7.78, 2.51 Hz, 1 H), 6.00 (d, J=2.51 Hz, 1 H), 4.51-4.63 (m, 1 H), 4.14-4.27 (m, 2 H), 3.58-3.70 (m, 2 H), 2.42 (t, J=7.53 Hz, 2 H), 1.97-2.16 (m, 2 H), 1.79-1.97 (m, 2 H), 1.53-1.65 (m, 2 H), 0.95 (t, J=7.40 Hz, 3 H). MS (ESI) 434 (M+H).

Example 200

Preparation of isopropyl 4-(2-oxo-1-(pyrazin-2-yl)-1,2-dihydropyridin-4-yloxy)piperidine-1-carboxylate

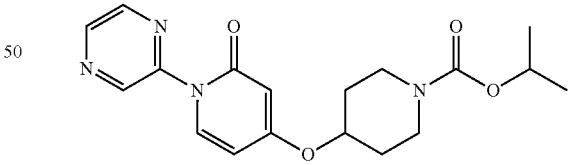

Example 200 was prepared according to procedures described in Example 189 substituting 2-iodopyrazine (Aldrich) for 5-bromo-2-(methylsulfonyl)pyridine in Step B. ¹H NMR (400 MHz, CDCl₃) δ ppm 9.37 (d, J=1.51 Hz, 1 H), 8.57 (d, J=2.51 Hz, 1 H), 8.50-8.54 (m, 1 H), 7.85 (d, J=8.03 Hz, 1 H), 6.11 (dd, J=7.91, 2.64 Hz, 1 H), 5.95 (d, J=2.51 Hz, 1 H), 4.91-5.00 (m, 1 H), 4.50-4.57 (m, 1 H), 3.71-3.81 (m, 2 H), 3.37-3.47 (m, 2 H), 1.96-2.06 (m, 2 H), 1.77-1.87 (m, 2 H), 1.28 (d, J=6.27 Hz, 6 H). MS (ESI) 359 (M+H).

Example 201

Preparation of 5-chloro-4-(1-(5-cyclopropylpyrimidin-2-yl)piperidin-4-yloxy)-1-(4-(methylsulfonyl)phenyl)pyridin-2(1H)-one, TFA salt

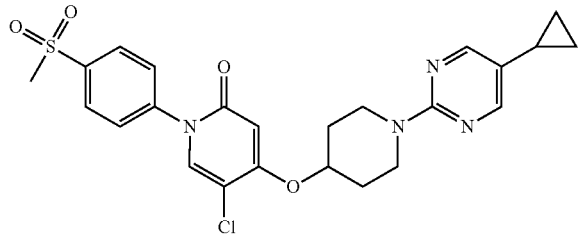 [SMILES: CS(=O)(=O)c1ccc(-n2cc(Cl)c(OC3CCN(c4ncc(C5CC5)cn4)CC3)cc2=O)cc1]

Example 201 was prepared according to the procedures described in Example 194 substituting 2-chloro-5-cyclopropylpyrimidine for 2-chloro-5-propylpyrimidine in Step A. $^1$H NMR (500 MHz, CDCl$_3$) δ ppm 8.37 (s, 2 H), 8.11 (d, J=8.25 Hz, 2 H), 7.62 (d, J=8.80 Hz, 2 H), 7.53 (s, 1 H), 6.55 (br. s., 1 H), 4.78-4.93 (m, 1 H), 4.26 (br. s., 2 H), 3.96 (br. s., 2 H), 3.12 (s, 3 H), 2.16 (br. s., 4 H), 1.83 (br. s., 1 H), 1.71-1.92 (m, 1 H), 1.10 (d, J=8.25 Hz, 2 H), 0.74 (d, J=5.50 Hz, 2 H). MS (ESI) 501 (M+H).

Example 203

Preparation of 1-(4-aminophenyl)-4-(1-(5-propylpyrimidin-2-yl)piperidin-4-yloxy)pyridin-2(1H)-one

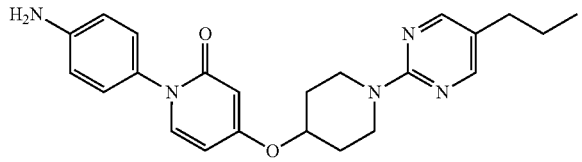 [SMILES: CCCc1cnc(N2CCC(Oc3ccn(-c4ccc(N)cc4)c(=O)c3)CC2)nc1]

Example 203 was prepared according to procedures described in Example 173 substituting tert-butyl 4-iodophenylcarbamate (Oakwood) for 4-bromo-2-methyl-1-(methylsulfonyl)benzene in Step E except that reaction was heated at 100° C. overnight and then heated at 140° C. for 3 h. The crude solid was purified by flash chromatography (SiO$_2$, 0 to 10% MeOH in CH$_2$Cl$_2$). $^1$H NMR (400 MHz, CDCl$_3$) δ ppm 8.18 (s, 2 H), 7.22 (d, J=7.53 Hz, 1 H), 7.11-7.16 (m, 2 H), 6.72-6.78 (m, 2H), 6.02 (d, J=2.76 Hz, 1 H), 5.96 (dd, J=7.53, 2.76 Hz, 1 H), 4.52-4.59 (m, 1 H), 4.17-4.25 (m, 2 H), 3.81 (s, 2 H), 3.58-3.67 (m, 2 H), 2.39-2.45 (m, 2 H), 2.05-2.13 (m, 2 H), 1.79-1.89 (m, 2 H), 1.54-1.64 (m, 2 H), 0.96 (t, J=7.40 Hz, 3 H). MS (ESI) 406 (M+H).

Example 205

Preparation of 1-(4-(2-oxopyrrolidin-1-yl)phenyl)-4-(1-(5-propylpyrimidin-2-yl)piperidin-4-yloxy)pyridin-2(1H)-one, hydrochloride salt

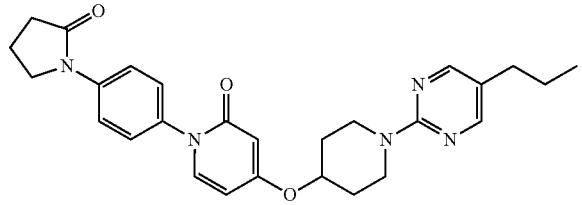 [SMILES: CCCc1cnc(N2CCC(Oc3ccn(-c4ccc(N5CCCC5=O)cc4)c(=O)c3)CC2)nc1]

Example 205 was prepared according to procedures described in Example 187 substituting 1-(4-bromophenyl)pyrrolidin-2-one (Oakwood) for 5-bromo-2-(methylsulfonyl)pyridine except that the crude solid was purified by flash chromatography (SiO$_2$, 0 to 100% EtOAc in hexanes) and then converted to the hydrochloride salt by addition of 1 equivalent of HCl (1N HCl in Et$_2$O) to the compound stirring in CH$_2$Cl$_2$ for 5 min followed by concentration in vacuo to the desired product. $^1$H NMR (400 MHz, CDCl$_3$) δ ppm 8.43 (br. s., 2 H), 7.77 (d, J=8.53 Hz, 2 H), 7.39 (d, J=8.53 Hz, 2 H), 7.29-7.33 (m, 1 H), 6.12 (br. s., 1 H), 6.06 (d, J=7.53 Hz, 1 H), 4.68-4.77 (m, 1 H), 4.27-4.38 (m, 2 H), 4.07-4.19 (m, 2 H), 3.92 (t, J=7.03 Hz, 2 H), 2.66 (t, J=8.16 Hz, 2 H), 2.55 (t, J=7.53 Hz, 2 H), 2.16-2.26 (m, 2 H), 2.10-2.16 (m, 4 H), 1.61-1.71 (m, 2 H), 1.00 (t, J=7.28 Hz, 3 H). MS (ESI) 474 (M+H).

Example 206

Preparation of 1-(2-methyl-6-(methylsulfonyl)pyridin-3-yl)-4-(1-(5-propylpyrimidin-2-yl)piperidin-4-yloxy)pyridin-2(1H)-one, TFA salt

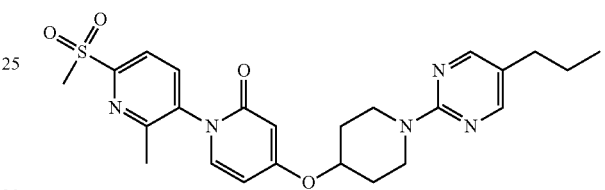

Example 206 was prepared according to procedures described in Example 173 substituting 3,6-dibromo-2-methylpyridine (Synchem) for 4-bromo-1-iodo-2-methylbenzene in Step D and the final product was purified by preparative HPLC (C$_{18}$ column, 10-100% MeOH in water containing 0.1% trifluoroacetic acid). $^1$H NMR (400 MHz, CDCl$_3$) δ ppm 8.44 (s, 2 H), 8.11 (d, J=8.03 Hz, 1 H), 7.81 (d, J=8.28 Hz, 1 H), 7.13 (d, J=7.78 Hz, 1 H), 6.31 (d, J=2.26 Hz, 1 H), 6.24 (dd, J=7.65, 2.38 Hz, 1 H), 4.71-4.79 (m, 1 H), 4.03-4.10 (m, 4 H), 3.31 (s, 3 H), 2.52-2.57 (m, 5 H), 2.13-2.21 (m, 2 H), 2.04-2.12 (m, 2 H), 1.61-1.71 (m, 2 H), 1.00 (t, J=7.28 Hz, 3 H). MS (ESI) 484 (M+H).

Example 207

Preparation of isopropyl 4-(1-(2-methyl-6-(methylsulfonyl)pyridin-3-yl)-2-oxo-1,2-dihydropyridin-4-yloxy)piperidine-1-carboxylate, TFA salt

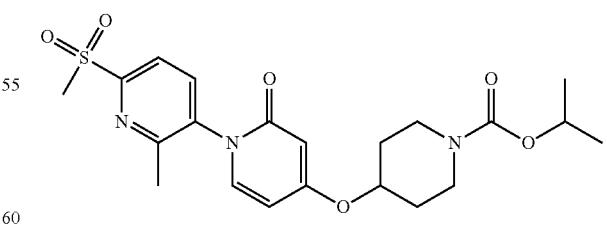

Example 207 was prepared according to procedures described in Example 189 substituting 3-bromo-2-methyl-6-(methylsulfonyl)pyridine (prepared according to the procedure described in Step D of Example 173 substituting 3,6-dibromo-2-methylpyridine for 4-bromo-1-iodo-2-methylbenzene) for 5-bromo-2-(methylsulfonyl)pyridine in Step B except that reaction was heated at 140° C. overnight and that the crude product was purified by preparative HPLC (C$_{18}$ column, 10-100% MeOH in water containing 0.1% trifluoroacetic acid). $^1$H NMR (400 MHz, CDCl$_3$) δ ppm 8.07 (d, J=8.03 Hz, 1 H), 7.78 (d, J=8.03 Hz, 1 H), 7.10 (d, J=7.78 Hz, 1 H), 6.33 (d, J=2.26 Hz, 1 H), 6.23 (dd, J=7.65, 2.38 Hz, 1 H), 4.87-5.01 (m, 1 H), 4.51-4.61 (m, 1 H), 3.72-3.83 (m, 2 H), 3.36-3.44 (m, 2 H), 3.28 (s, 3 H), 2.49 (s, 3 H), 1.97-2.07 (m, 2 H), 1.75-1.86 (m, 2 H), 1.26 (d, J=6.27 Hz, 6 H). MS (ESI) 450 (M+H).

Example 208

Preparation of N-(4-(2-oxo-4-(1-(5-propylpyrimidin-2-yl)piperidin-4-yloxy)pyridin-1(2H)-yl)phenyl) isobutyramide

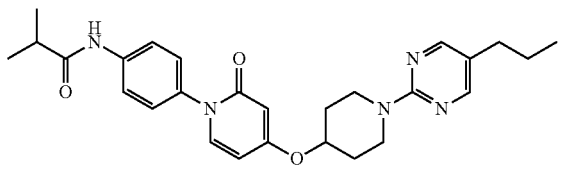 [SMILES: CCCc1cnc(N2CCC(Oc3ccn(-c4ccc(NC(=O)C(C)C)cc4)c(=O)c3)CC2)nc1]

To a stirring solution of 1-(4-aminophenyl)-4-(1-(5-propylpyrimidin-2-yl)piperidin-4-yloxy)pyridin-2(1H)-one (50 mg, 0.12 mmol) and Et$_3$N (0.052 mL, 0.37 mmol, Aldrich) in CH$_2$Cl$_2$ (1 mL) at room temperature was added isobutyl chloride (0.014 mL, 0.136 mmol, Aldrich). The reaction mixture was stirred at room temperature for 1 h and then quenched with H$_2$O. The solvent was evaporated and the crude solid was purified by flash chromatography (SiO$_2$, 0 to 10% MeOH in CH$_2$Cl$_2$) to yield 34.2 mg of the desired product as a white solid. $^1$H NMR (400 MHz, CDCl$_3$) δ ppm 8.16 (s, 2 H), 7.55-7.61 (m, 3 H), 7.26-7.28 (m, 2 H), 7.20 (d, J=7.78 Hz, 1H), 5.98-6.05 (m, 1 H), 5.92-5.98 (m, 1 H), 4.52-4.59 (m, 1 H), 4.14-4.22 (m, 2 H), 3.57-3.66 (m, 2 H), 2.47-2.57 (m, 1 H), 2.37-2.42 (m, 2 H), 2.03-2.11 (m, 2 H), 1.78-1.87 (m, 2 H), 1.48-1.69 (m, 2 H), 1.24 (d, J=6.78 Hz, 6 H), 0.93 (t, J=7.28 Hz, 3 H). MS (ESI) 476 (M+H).

Example 209

Preparation of isopropyl 4-(1-(4-isobutyramidophenyl)-2-oxo-1,2-dihydropyridin-4-yloxy)piperidine-1-carboxylate

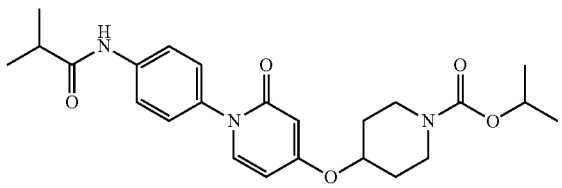 [SMILES: CC(C)OC(=O)N1CCC(Oc2ccn(-c3ccc(NC(=O)C(C)C)cc3)c(=O)c2)CC1]

Step A. Preparation of isopropyl 4-(1-(4-aminophenyl)-2-oxo-1,2-dihydropyridin-4-yloxy)piperidine-1-carboxylate Isopropyl 4-(1-(4-aminophenyl)-2-oxo-1,2-dihydropyridin-4-yloxy)piperidine-1-carboxylate was prepared according to procedures described in Example 189 substituting tert-butyl 4-iodophenylcarbamate (Oakwood) for 5-bromo-2-(methylsulfonyl)pyridine in Step B except that reaction was heated at 100° C. overnight and then heated at 140° C. for 6 h. The crude solid was purified by flash chromatography (SiO$_2$, 0 to 10% MeOH in CH$_2$Cl$_2$). MS (ESI) 372 (M+H).

Step B

Example 209

Example 209 was prepared according to procedures described in Example 208 substituting isopropyl 4-(1-(4-aminophenyl)-2-oxo-1,2-dihydropyridin-4-yloxy)piperidine-1-carboxylate for 1-(4-aminophenyl)-4-(1-(5-propylpyrimidin-2-yl)piperidin-4-yloxy)pyridin-2(1H)-one. $^1$H NMR (400 MHz, CDCl$_3$) δ ppm 7.62 (br. s., 1 H), 7.59 (d, J=8.78 Hz, 2 H), 7.25-7.30 (m, 2 H), 7.22 (d, J=7.53 Hz, 1 H), 6.00 (d, J=2.51 Hz, 1 H), 5.93-5.99 (m, 1 H), 4.87-5.00 (m, 1 H), 4.44-4.56 (m, 1H), 3.70-3.82 (m, 2 H), 3.33-3.43 (m, 2 H), 2.45-2.61 (m, 1 H), 1.94-2.07 (m, 2 H), 1.72-1.87 (m, 2 H), 1.22-1.29 (m, 12 H). MS (ESI) 442 (M+H).

Example 210

Preparation of N-(4-(2-oxo-4-(1-(5-propylpyrimidin-2-yl)piperidin-4-yloxy)pyridin-1(2H)-yl)phenyl) pivalamide, hydrochloride salt

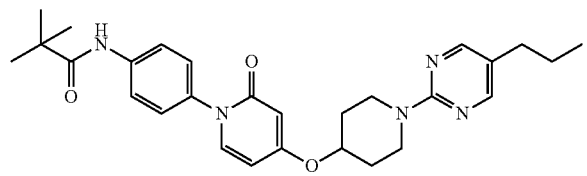

Example 210 was prepared according to procedures described in Example 208 substituting pivaloyl chloride (Aldrich) for isobutyl chloride and was then converted to the hydrochloride salt by addition of 1 equivalent of HCl (1N HCl in Et$_2$O) to the compound stirring in CH$_2$Cl$_2$ for 5 min followed by concentration in vacuo to the desired product. $^1$H NMR (400 MHz, CDCl$_3$) δ ppm 8.17 (s, 2 H), 7.61-7.67 (m, 2 H), 7.49 (s, 1 H), 7.29-7.35 (m, 2 H), 7.22 (d, J=7.53 Hz, 1 H), 5.95-6.04 (m, 2 H), 4.52-4.62 (m, 1 H), 4.15-4.26 (m, 2 H), 3.58-3.68 (m, 2 H), 2.41 (t, J=7.53 Hz, 2 H), 2.04-2.14 (m, 2 H), 1.79-1.90 (m, 2 H), 1.52-1.64 (m, 2 H), 1.33 (s, 9 H), 0.95 (t, J=7.28 Hz, 3 H). MS (ESI) 490 (M+H).

Example 211

Preparation of isopropyl 4-(2-oxo-1-(4-pivalamidophenyl)-1,2-dihydropyridin-4-yloxy)piperidine-1-carboxylate

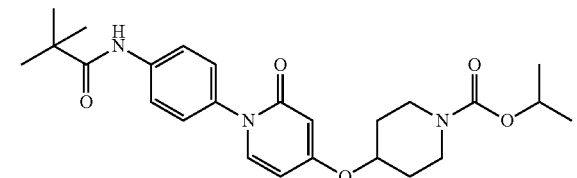

Example 211 was prepared according to procedures described in Example 208 substituting isopropyl 4-(1-(4-aminophenyl)-2-oxo-1,2-dihydropyridin-4-yloxy)piperidine-1-carboxylate (prepared according to the procedure described in Step A of Example 209) for 1-(4-aminophenyl)-4-(1-(5-propylpyrimidin-2-yl)piperidin-4-yloxy)pyridin-2(1H)-one and substituting pivaloyl chloride (Aldrich) for isobutyl chloride. $^1$H NMR (400 MHz, CDCl$_3$) δ ppm 7.61-7.67 (m, 2 H), 7.51 (s, 1 H), 7.28-7.34 (m, 2 H), 7.22 (d, J=7.53 Hz, 1 H), 5.97-6.02 (m, 1 H), 5.92-5.97 (m, 1 H), 4.87-4.99 (m, 1 H), 4.45-4.53 (m, 1 H), 3.71-3.81 (m, 2 H), 3.33-3.43 (m, 2 H), 1.89-2.04 (m, 2 H), 1.73-1.89 (m, 2 H), 1.33 (s, 9 H), 1.26 (d, J=6.27 Hz, 6 H). MS (ESI) 456 (M+H).

Example 212

Preparation of 2,2,2-trifluoro-N-(4-(2-oxo-4-(1-(5-propylpyrimidin-2-yl)piperidin-4-yloxy)pyridin-1(2H)-yl)phenyl)acetamide, TFA salt

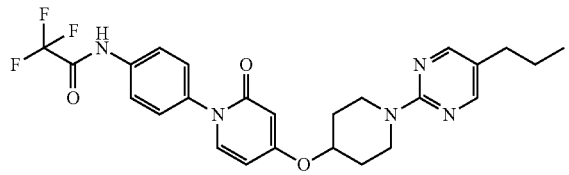 [SMILES: CCCc1cnc(N2CCC(Oc3ccn(-c4ccc(NC(=O)C(F)(F)F)cc4)c(=O)c3)CC2)nc1]

Example 212 was prepared according to procedures described in Example 208 substituting 2,2,2-trifluoroacetic anhydride (Aldrich) for isobutyl chloride except that the crude product was purified by preparative HPLC (C$_{18}$ column, 10-100% MeOH in water containing 0.1% trifluoroacetic acid). $^1$H NMR (500 MHz, DMSO-d6) δ ppm 11.43 (br. s., 1 H), 8.24 (s, 2 H), 7.76 (d, J=8.80 Hz, 2 H), 7.56 (d, J=7.70 Hz, 1 H), 7.42 (d, J=8.80 Hz, 2 H), 5.98-6.10 (m, 2 H), 4.69-4.83 (m, 1 H), 4.16-4.28 (m, 2 H), 3.41-3.56 (m, 2 H), 2.32-2.41 (m, 2 H), 1.95-2.10 (m, 2 H), 1.43-1.66 (m, 4 H), 0.88 (t, J=7.15 Hz, 3 H). MS (ESI) 502 (M+H).

Example 214

Preparation of cis-1-(4-(methylsulfonyl)phenyl)-4-((1r,4r)-4-(pyrimidin-2-yl)cyclohexyloxy)pyridin-2(1H)-one, TFA salt

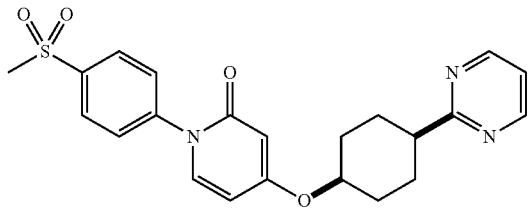

Step A. Preparation of 4-(benzyloxy)cyclohexanecarbonitrile

To a solution of 4-(benzyloxy)cyclohexanone (2.94 g, 14.39 mmol, prepared according to procures described in Goodman et al., U.S. Patent Application Publication No. 2006/0292073 A1) in 1,2-dimethoxyethane (14.39 mL, Aldrich) was added tosylmethyl isocyanide (5.62 g, 28.8 mmol, Aldrich) in one portion. The resulting mixture was cooled to 0° C. and potassium t-butoxide solution (3.82 mL, 3.82 mmol, 1.0 M in 2-methyl-2-propanol, Aldrich) was added dropwise. The reaction mixture was stirred at 0° C. for 10 min and at room temperature for 5 hrs and then quenched with 1N HCl (45 mL). The aqueous layer was extracted further with EtOAc (3×). The combined organic extracts were washed with brine, dried (MgSO$_4$) and evaporated under reduced pressure. The residue was purified by flash chromatography on silica gel (0-40% EtOAc/hexanes) to give a cis and trans mixture of 4-(benzyloxy)cyclohexanecarbonitrile (2.14 g, 69%) as a light orange oil. MS (ESI) 216 (M+H).

Step B. Preparation of 4-(benzyloxy)cyclohexanecarboximidamide

To a solution of 4-(benzyloxy)cyclohexanecarbonitrile (1.12 g, 5.20 mmol) in EtOH (8.0 mL) at 0° C. was bobbled HCl gas (Aldrich) for 35 min and the resulting mixture was continuously stirred at 0° C. for 1 hr and then evaporated under reduced pressure. The residue was dissolved in EtOH (6.0 mL) followed by addition of NH$_3$/MeOH (7.0 M, Aldrich) at 0° C. After stirring at room temperature for 30 min, the mixture was evaporated and the residue was partitioned between 4N NaOH and chloroform. The aqueous layer was extracted further with chloroform (3×). The combined organic layers were washed with water/brine (1:1), dried (MgSO$_4$) and evaporated under reduced pressure to yield a cis and trans mixture of 4-(benzyloxy)cyclohexanecarboximidamide (1.193 g, 99%) as a light yellow gum. This crude product was used in the next step without further purification. MS (ESI) 233 (M+H).

Step C. Preparation of 2-(4-(benzyloxy)cyclohexyl)pyrimidine

A mixture of 4-(benzyloxy)cyclohexanecarboximidamide (330 mg, 1.420 mmol) and (E)-3-(dimethylamino)acrylaldehyde (0.568 mL, 5.68 mmol, Aldrich) in pyridine (6.0 mL) was heated at 100° C. for 3 hrs and evaporated under reduced pressure. The residue was then partitioned between ether and water. The aqueous layer was extracted further with ether (3×) and the combined extracts were washed with water and brine, dried (Na$_2$SO$_4$) and concentrated in vacuo. The crude product was purified by flash chromatography on silica gel (0-100% EtOAc/hexanes) to give a cis and trans mixture of 2-(4-(benzyloxy)cyclohexyl)pyrimidine (239.3 mg, 62.8%) as a colorless oil. MS (ESI) 269 (M+H).

Step D. Preparation of 4-(pyrimidin-2-yl)cyclohexanol

To a solution of 2-(4-(benzyloxy)cyclohexyl)pyrimidine (289.9 mg, 1.080 mmol) in CH$_2$Cl$_2$ (25 mL) and water (1.0 mL) at room temperature was added 2,3-dichloro-5,6-dicyano-1,4-benzoquinone (392 mg, 1.728 mmol, Aldrich). The reaction mixture was heated at 40° C. for 10 hrs, cooled to room temperature and diluted with CH$_2$Cl$_2$ and NaHCO$_3$ aqueous solution. The aqueous layer was extracted further with CH$_2$Cl$_2$ (3×) and the combined extracts were washed with brine, dried (Na$_2$SO$_4$) and evaporated under reduced pressure. The residue was purified by flash chromatography on silica gel (0-15% MeOH/CH$_2$Cl$_2$) to give a cis and trans mixture of 4-(pyrimidin-2-yl)cyclohexanol (157.5 mg, 82%) as an orange oil. MS (ESI) 179 (M+H).

Step E

Example 214

A mixture of 4-hydroxy-1-(4-(methylsulfonyl)phenyl)pyridin-2(1H)-one (53.1 mg, 0.200 mmol, Example 1), 4-(pyrimidin-2-yl)cyclohexyl methanesulfonate (51.3 mg, 0.2 mmol, prepared according to procedures described at Step C of Example 1 substituting 4-(pyrimidin-2-yl)cyclohexanol for tert-butyl-4-hydroxy-1-piperidinecarboxylate) and potassium carbonate (55.3 mg, 0.400 mmol) in DMF (1.0 mL) was heated at 140° C. for 3 hrs and 100° C. overnight and cooled to room temperature. The mixture was diluted with EtOAc and water and the aqueous layer was extracted further with EtOAc (4×). The combined organic layers were washed with brine/water (1:1, 2×), dried ($Na_2SO_4$) and evaporated under reduced pressure. The residue was purified first by preparative HPLC ($C_{18}$ column; 0-90% methanol in water containing 0.05% trifluoroacetic acid) followed by further purification by preparative HPLC ($C_{18}$ column; 0-90% acetonitrile in water containing 0.05% trifluoroacetic acid) to provide cis isomer of Example 214 (16.1 mg, yellow solid, 18%) upon lyophilization. $^1$H NMR (500 MHz, $CDCl_3$) δ 8.91 (d, J=5.50 Hz, 2 H), 8.09 (d, J=8.25 Hz, 2 H), 7.62 (d, J=8.25 Hz, 2 H), 7.32 (d, J=7.70 Hz, 1 H), 6.31-6.36 (m, 2 H), 4.74 (app brs, 1 H), 3.13-3.22 (m, 1 H), 3.11 (s, 3 H), 2.23-2.30 (m, 2 H), 2.08-2.22 (m, 2 H), 1.90-1.98 (m, 2 H), 1.81-1.90 (m, 2 H). MS (ESI) 426 (M+H).

Example 215

Preparation of trans-1-(4-(methylsulfonyl)phenyl)-4-((1r,4r)-4-(pyrimidin-2-yl)cyclohexyloxy)pyridin-2(1H)-one, TFA salt

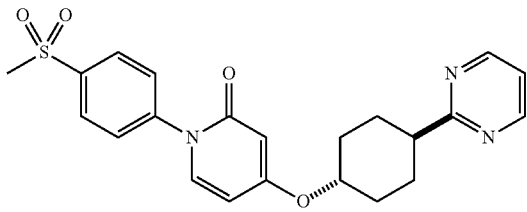

Example 215 was prepared as described above in Example 214 and was separated from the cis-isomer by preparative HPLC at Step E to yield the title compound. $^1$H NMR (500 MHz, $CDCl_3$). δ 8.79 (d, J=4.95 Hz, 2 H), 8.08 (d, J=8.80 Hz, 2 H), 7.62 (d, J=8.25 Hz, 2 H), 7.23-7.31 (m, 2 H), 6.19 (d, J=2.75 Hz, 1 H), 6.15 (dd, J=7.70, 2.20 Hz, 1 H), 4.32-4.44 (m, 1 H), 3.10 (s, 3 H), 2.99-3.09 (m, 1H), 2.31-2.40 (m, 2 H), 2.16-2.23 (m, 2 H), 1.80-1.93 (m, 2 H), 1.62-1.75 (m, 2 H). MS (ESI) 426 (M+H).

Example 217

Preparation of 1,1,1-trifluoro-N-(4-(2-oxo-4-(1-(5-propylpyrimidin-2-yl)piperidin-4-yloxy)pyridin-1(2H)-yl)phenyl)methanesulfonamide, TFA salt

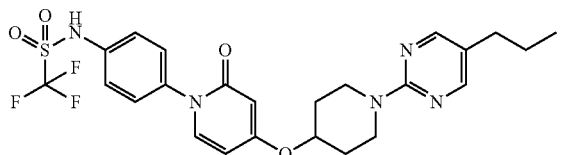

Example 217 was prepared according to procedures described in Example 212 substituting trifluoromethanesulfonic anhydride (Aldrich) for 2,2,2-trifluoroacetic anhydride. $^1$H NMR (400 MHz, $CDCl_3$) δ ppm 8.42 (s, 2 H), 7.30 (d, J=7.53 Hz, 1 H), 7.16-7.27 (m, 4 H), 6.28 (d, J=2.26 Hz, 1 H), 6.19 (dd, J=7.78, 2.51 Hz, 1 H), 4.71-4.79 (m, 1 H), 4.03-4.14 (m, 2 H), 3.92-4.03 (m, 2 H), 2.54 (t, J=7.53 Hz, 2 H), 2.09-2.21 (m, 2 H), 1.97-2.09 (m, 2 H), 1.60-1.71 (m, 2 H), 1.00 (t, J=7.28 Hz, 3 H). MS (ESI) 538 (M+H).

Example 218

Preparation of N,N-dimethyl-4-(2-oxo-4-(1-(5-propylpyrimidin-2-yl)piperidin-4-yloxy)pyridin-1(2H)-yl)benzenesulfonamide, hydrochloride salt

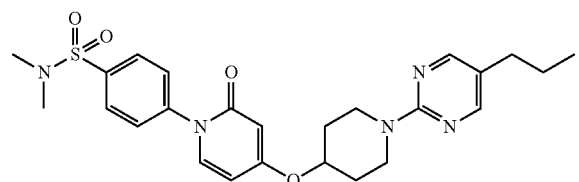

Example 218 was prepared according to procedures described in Example 187 substituting 4-bromo-N,N-dimethylbenzenesulfonamide (Alfa-Aesar) for 5-bromo-2-(methylsulfonyl)pyridine and was then converted to the hydrochloride salt by addition of 1 equivalent of HCl (1N HCl in $Et_2O$) to the compound stirring in $CH_2Cl_2$ for 5 min followed by concentration in vacuo to the desired product. $^1$H NMR (400 MHz, $CDCl_3$) δ ppm 8.39 (br. s., 2 H), 7.92 (d, J=8.53 Hz, 2 H), 7.61 (d, J=8.53 Hz, 2 H), 7.29-7.33 (m, 1 H), 6.09 (d, J=8.78 Hz, 1 H), 5.96-6.05 (m, 1 H), 4.65-4.79 (m, 1 H), 4.07-4.31 (m, 4 H), 2.80 (s, 6 H), 2.54 (t, J=7.53 Hz, 2 H), 2.06-2.22 (m, 4 H), 1.60-1.70 (m, 2 H), 0.99 (t, J=7.28 Hz, 3 H). MS (ESI) 498 (M+H).

Example 221

Preparation of 1-(4-(methylsulfonyl)phenyl)-6-oxo-4-(1-(5-propylpyrimidin-2-yl)piperidin-4-yloxy)-1,6-dihydropyridine-3-carbonitrile, TFA salt

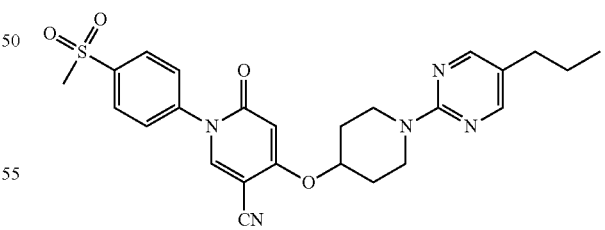

Step A. Preparation of 4-hydroxy-1-(4-(methylsulfonyl)phenyl)-6-oxo-1,6-dihydropyridine-3-carbonitrile A mixture of 4-hydroxy-6-oxo-1,6-dihydropyridine-3-carbonitrile (200 mg, 1.469 mmol, Medinoah), 1-bromo-4-(methylsulfonyl)benzene (345 mg, 1.469 mmol), 4,7-dimethoxy-1,10-phenanthroline (70.6 mg, 0.294 mmol), copper(I) iodide (56.0 mg, 0.294 mmol) and potassium carbonate (609 mg, 4.41 mmol) in DMSO (3 mL) was heated at 190° C. To the reaction mixture was added H$_2$O (10 mL) and the pH adjusted to ~2 using with 1N HCl. The resulting aqueous mixture was extracted with EtOAc (40 mL, 2×). The combined extracts were dried over Na$_2$SO$_4$ and concentrated to give a brown oil. The crude oil was purified by flash chromatography (SiO$_2$, 0-5% MeOH/CH$_2$Cl$_2$) to give a yellow solid (35 mg, 0.084 mmol, 5.74%). MS (ESI) 291 (M+H).

Step B

Example 221

A stirred mixture of 1-(5-propylpyrimidin-2-yl)piperidin-4-yl methanesulfonate (46.4 mg, 0.155 mmol), 4-hydroxy-1-(4-(methylsulfonyl)phenyl)-6-oxo-1,6-dihydropyridine-3-carbonitrile (30 mg, 0.103 mmol) and cesium carbonate (67.3 mg, 0.207 mmol) in DMF (1.5 mL) was heated at 120° C. for 16 h and then cooled to room temperature. The resulting mixture was diluted with EtOAc and H$_2$O and the aqueous layer was extracted with EtOAc (3×). The combined extracts were washed with H$_2$O, dried (Na$_2$SO$_4$) and evaporated. The residue was purified by preparative HPLC (C$_{18}$ column; 20-90% MeOH in water containing 0.1% trifluoroacetic acid) to give Example 221 (5 mg, 10.13%) as an off-white solid. $^1$H NMR (methylene-chloride) δ ppm 8.29-8.37 (m, 2 H), 8.09 (d, J=8.80 Hz, 2 H), 7.85 (s, 1 H), 7.59 (d, J=8.80 Hz, 2 H), 6.01 (s, 1 H), 4.76 (d, J=3.30 Hz, 1 H), 4.03-4.14 (m, 2 H), 3.88-4.03 (m, 2 H), 3.09 (s, 3 H), 2.48 (t, J=7.42 Hz, 2 H), 1.94-2.19 (m, 4 H), 1.52-1.69 (m, 2 H), 0.95 (t, J=7.42 Hz, 3 H). MS (ESI) 494 (M+H).

Example 223

Preparation of N-tert-butyl-4-(2-oxo-4-(1-(5-propylpyrimidin-2-yl)piperidin-4-yloxy)pyridin-1(2H)-yl)benzenesulfonamide

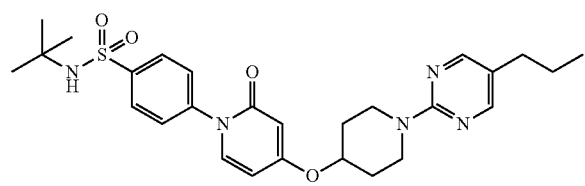 [SMILES: CCCc1cnc(N2CCC(Oc3ccn(-c4ccc(S(=O)(=O)NC(C)(C)C)cc4)c(=O)c3)CC2)nc1]

Example 223 was prepared according to procedures described in Example 187 substituting 4-bromo-N-tert-butyl-benzenesulfonamide (Combi-Blocks) for 5-bromo-2-(methylsulfonyl)pyridine. $^1$H NMR (400 MHz, CDCl$_3$) δ ppm 8.18 (s, 2 H), 8.00 (d, J=8.53 Hz, 2 H), 7.53 (d, J=8.53 Hz, 2 H), 7.23 (d, J=7.53 Hz, 1 H), 6.05 (dd, J=7.65, 2.38 Hz, 1 H), 6.01 (d, J=2.26 Hz, 1 H), 4.54-4.63 (m, 1 H), 4.50 (s, 1 H), 4.15-4.25 (m, 2 H), 3.59-3.69 (m, 2 H), 2.42 (t, J=7.53 Hz, 2 H), 2.03-2.15 (m, 2H), 1.79-1.91 (m, 2 H), 1.53-1.66 (m, 2 H), 1.30 (s, 9 H), 0.95 (t, J=7.28 Hz, 3 H). MS (ESI) 526 (M+H).

Example 224

Preparation of 5-chloro-1-(3-fluoro-4-(methylsulfonyl)phenyl)-4-(1-(5-propylpyrimidin-2-yl)piperidin-4-yloxy)pyridin-2(1H)-one, TFA salt

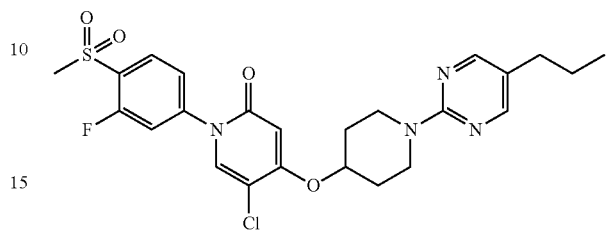

Step A. Preparation of 5-chloro-1-(3-fluoro-4-(methylsulfonyl)phenyl)-4-hydroxypyridin-2(1H)-one 5-Chloro-1-(3-fluoro-4-(methylsulfonyl)phenyl)-4-hydroxypyridin-2(1H)-one was prepared according to procedures described in Example 263 Step B substituting 4-bromo-2-fluoro-1-(methylsulfonyl)benzene (prepared according to the procedure described in Step D of Example 173 substituting 4-bromo-2-fluoro-1-iodobenzene for 4-bromo-1-iodo-2-methylbenzene) for 2-fluoro-4-iodobenzonitrile except that the reaction was heated at 190° C. for 1 h. MS (ESI) 318 (M+H).

Step B

Example 224

Example 224 was prepared according to procedures described in Example 173 Step C substituting 5-chloro-1-(3-fluoro-4-(methylsulfonyl)phenyl)-4-hydroxypyridin-2(1H)-one for 4-hydroxypyridin-2(1H)-one except that the reaction was heated at 140° C. for 6 h. The crude product was purified by preparative HPLC (C$_{18}$ column, 10-100% MeOH in water containing 0.1% trifluoroacetic acid). $^1$H NMR (400 MHz, CDCl$_3$) δ ppm 8.45 (s, 2 H), 8.14 (t, J=7.91 Hz, 1 H), 7.48 (s, 1 H), 7.35-7.47 (m, 2 H), 6.27 (s, 1 H), 4.78-4.87 (m, 1 H), 4.20-4.29 (m, 2 H), 3.90-4.02 (m, 2 H), 3.28 (s, 3 H), 2.55 (t, J=7.53 Hz, 2 H), 2.08-2.22 (m, 4 H), 1.60-1.72 (m, 2 H), 1.00 (t, J=7.28 Hz, 3 H). MS (ESI) 521 (M+H).

Example 225

Preparation of 4-(1-(5-cyclopropylpyrimidin-2-yl)piperidin-4-yloxy)-1-(4-(methylsulfonyl)phenyl)-6-oxo-1,6-dihydropyridine-3-carbonitrile, TFA salt

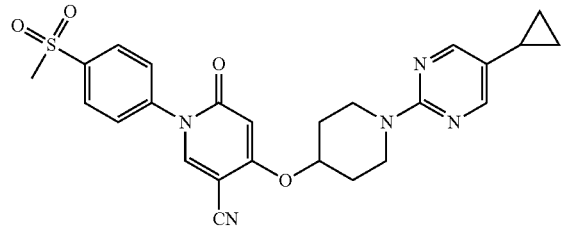

Example 225 was prepared according to the procedures described in Example 221 substituting 1-(5-cyclopropylpyrimidin-2-yl)piperidin-4-yl methanesulfonate for 1-(5-propylpyrimidin-2-yl)piperidin-4-yl methanesulfonate in Step B. $^1$H NMR (500 MHz, CDCl$_3$) δ ppm 8.37 (s, 2 H), 8.13 (d, J=8.25 Hz, 2 H), 7.86 (s, 1 H), 7.60 (d, J=8.80 Hz, 2 H), 6.17 (s, 1 H), 4.84 (br. s., 1 H), 4.35 (d, J=14.85 Hz, 2 H), 3.93-4.01 (m, 2 H), 3.12 (s, 3 H), 2.08-2.23 (m, 4 H), 1.83-1.85 (m, 1 H), 1.10-1.25 (m, 2 H), 0.74 (m, 2 H). MS (ESI) 491 (M+H).

Example 226

Preparation of tert-butyl 4-(5-chloro-1-(4-(methylsulfonyl)phenyl)-2-oxo-1,2-dihydropyridin-4-yloxy)piperidine-1-carboxylate

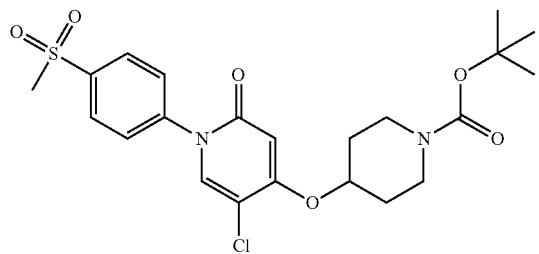 [SMILES: CC(C)(C)OC(=O)N1CCC(Oc2cc(=O)n(-c3ccc(S(C)(=O)=O)cc3)cc2Cl)CC1]

Example 226 was prepared according to the procedures described in Example 221 substituting tert-butyl 4-(methylsulfonyloxy)piperidine-1-carboxylate for 1-(5-cyclopropylpyrimidin-2-yl)piperidin-4-yl methanesulfonate, 2-(5-chloro-4-hydroxy-2-oxopyridin-1(2H)-yl)-5-(methylsulfonyl)benzene-1-ylium for 4-hydroxy-1-(4-(methylsulfonyl)phenyl)-6-oxo-1,6-dihydropyridine-3-carbonitrile in Step B. $^1$H NMR (500 MHz, CDCl$_3$) δ ppm 8.07 (d, J=8.25 Hz, 2 H), 7.61 (d, J=8.80 Hz, 2 H), 7.42 (s, 1 H), 6.03 (s, 1 H), 4.52-4.68 (m, 1 H), 3.57-3.73 (m, 2 H), 3.40-3.56 (m, 2 H), 3.08 (s, 3 H), 1.76-2.02 (m, 4 H), 1.46 (s, 9 H). MS (ESI) 482 (M+H).

Example 227

Preparation of 4-(5-chloro-2-oxo-4-(1-(5-propylpyrimidin-2-yl)piperidin-4-yloxy)pyridin-1(2H)-yl)-2-fluorobenzonitrile

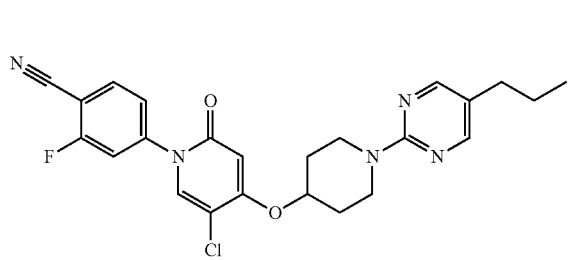 [SMILES: CCCc1cnc(N2CCC(Oc3cc(=O)n(-c4ccc(C#N)c(F)c4)cc3Cl)CC2)nc1]

Example 227 was prepared according to procedures described in Example 173 Step C substituting 4-(5-chloro-4-hydroxy-2-oxopyridin-1(2H)-yl)-2-fluorobenzonitrile (prepared according to the procedure described in Step B of example 263) for 4-hydroxypyridin-2(1H)-one except that the reaction was heated at 140° C. for 5 h and the crude solid was purified by flash chromatography (SiO$_2$, O to 100% EtOAc in CH$_2$Cl$_2$). $^1$H NMR (400 MHz, CDCl$_3$) δ ppm 8.18 (s, 2 H), 7.77 (dd, J=8.28, 6.78 Hz, 1 H), 7.37-7.43 (m, 2 H), 7.34 (dd, J=8.41, 1.63 Hz, 1 H), 6.05 (s, 1 H), 4.63-4.71 (m, 1 H), 3.96-4.14 (m, 2 H), 3.77-3.96 (m, 2 H), 2.42 (t, J=7.53 Hz, 2 H), 2.01-2.14 (m, 2 H), 1.88-2.01 (m, 2 H), 1.53-1.62 (m, 2 H), 0.95 (t, J=7.28 Hz, 3 H). MS (ESI) 468 (M+H).

Example 228

Preparation of 4-(2-oxo-4-(1-(5-propylpyrimidin-2-yl)piperidin-4-yloxy)pyridin-1(2H)-yl)benzenesulfonamide

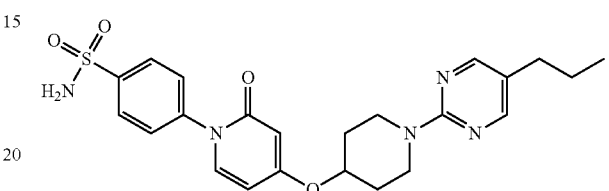

To a stirring solution of N-tert-butyl-4-(2-oxo-4-(1-(5-propylpyrimidin-2-yl)piperidin-4-yloxy)pyridin-1(2H)-yl)benzenesulfonamide (23 mg, 0.044 mmol) in CH$_2$Cl$_2$ (1 mL) was added trifluoroacetic acid (0.4 mL, 5 mmol, Aldrich). The reaction was stirred at room temperature for 2 days and then concentrated in vacuo to a yellow oil. The oil was purified by flash chromatography (SiO$_2$, 0 to 5% MeOH in CH$_2$Cl$_2$) to yield 11 mg of the desired product as an off-white solid. $^1$H NMR (400 MHz, CDCl$_3$) δ ppm 8.18 (s, 2 H), 8.03 (d, J=8.53 Hz, 2 H), 7.54 (d, J=8.28 Hz, 2 H), 7.23 (d, J=7.78 Hz, 1 H), 6.07 (dd, J=7.65, 2.63 Hz, 1 H), 6.03 (d, J=2.51 Hz, 1 H), 4.56-4.65 (m, 1 H), 4.16-4.25 (m, 2 H), 3.60-3.71 (m, 2 H), 2.42 (t, J=7.53 Hz, 2 H), 2.04-2.14 (m, 2 H), 1.80-1.90 (m, 2 H), 1.53-1.64 (m, 2 H), 0.95 (t, J=7.28 Hz, 3 H). MS (ESI) 470 (M+H).

Example 229

Preparation of 4-(5-chloro-4-(1-(5-cyclopropylpyrimidin-2-yl)piperidin-4-yloxy)-2-oxopyridin-1(2H)-yl)-2-fluorobenzonitrile

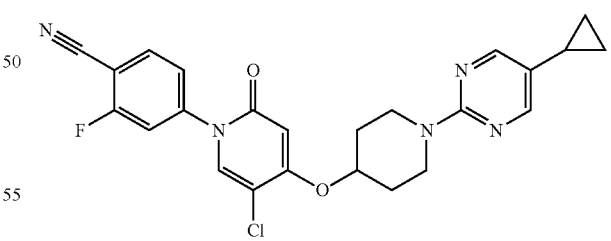

Step A. Preparation of 1-(5-cyclopropylpyrimidin-2-yl)piperidin-4-yl methanesulfonate 1-(5-Cyclopropylpyrimidin-2-yl)piperidin-4-yl methanesulfonate was prepared according to procedures described in Example 173 Step A and B substituting 2-chloro-5-cyclopropylpyrimidine for 2-chloro-5-propylpyrimidine in Step A.

Step B

Example 229

Example 229 was prepared according to procedures described in Example 173 Step C substituting 4-(5-chloro-4-hydroxy-2-oxopyridin-1(2H)-yl)-2-fluorobenzonitrile (prepared according to the procedure described in Step B of Example 263) for 4-hydroxypyridin-2(1H)-one except that the reaction was heated at 140° C. for 2 h and at 100° C. overnight. The crude solid was purified by flash chromatography (SiO₂, 0 to 100% EtOAc in CH₂Cl₂). ¹H NMR (400 MHz, CDCl₃) δ ppm 8.15 (s, 2 H), 7.77 (dd, J=8.28, 6.78 Hz, 1 H), 7.38-7.43 (m, 2 H), 7.34 (dd, J=8.41, 1.88 Hz, 1 H), 6.05 (s, 1 H), 4.63-4.71 (m, 1 H), 4.01-4.11 (m, 2 H) 3.79-3.88 (m, 2 H), 2.00-2.11 (m, 2 H), 1.88-2.00 (m, 2 H), 1.69-1.79 (m, 1 H), 0.89-0.96 (m, 2 H), 0.56-0.66 (m, 2 H). MS (ESI) 466 (M+H).

Example 230

Preparation of 4-(4-(1-(5-cyclopropylpyrimidin-2-yl)piperidin-4-yloxy)-2-oxopyridin-1(2H)-yl)-2-fluorobenzonitrile

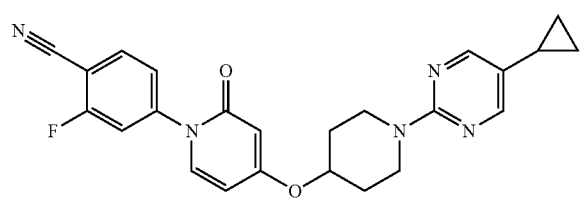 [SMILES: N#Cc1ccc(-n2ccc(OC3CCN(c4ncc(C5CC5)cn4)CC3)cc2=O)cc1F]

Step A. Preparation of tert-butyl 4-(2-oxo-1,2-dihydropyridin-4-yloxy)piperidine-1-carboxylate Tert-butyl 4-(2-oxo-1,2-dihydropyridin-4-yloxy)piperidine-1-carboxylate was prepared according to procedures described in Example 8 Step B substituting tert-butyl 4-(methylsulfonyloxy)piperidine-1-carboxylate (prepared according to the procedure described in Step C of Example 1) for isopropyl 4-(methylsulfonyloxy)piperidine-1-carboxylate. MS (ESI) 295 (M+H).

Step B. Preparation of 4-(piperidin-4-yloxy)pyridin-2(1H)-one 4-(Piperidin-4-yloxy)pyridin-2(1H)-one was prepared according to procedures described in Example 106 Step A substituting tert-butyl 4-(2-oxo-1,2-dihydropyridin-4-yloxy)piperidine-1-carboxylate for tert-butyl 4-(1-(4-(methylsulfonyl)phenyl)-2-oxo-1,2-dihydropyridin-4-yloxy)piperidine-1-carboxylate. MS (ESI) 195 (M+H).

Step C. Preparation of 4-(1-(5-cyclopropylpyrimidin-2-yl)piperidin-4-yloxy)pyridin-2(1H)-one 4-(1-(5-Cyclopropylpyrimidin-2-yl)piperidin-4-yloxy)pyridin-2(1H)-one was prepared according to procedures described in Example 106 Step B substituting 2-chloro-5-cyclopropylpyrimidine for 2-chloro-5-propylpyrimidine except that the crude solid was purified by flash chromatography (SiO₂, 100% EtOAc in CH₂Cl₂ and then 0 to 10% MeOH in CH₂Cl₂). MS (ESI) 313 (M+H).

Step D

Example 230

Example 230 was prepared according to procedures described in Example 173 Step E substituting 2-fluoro-4-iodobenzonitrile (Matrix scientific) for 4-bromo-2-methyl-1-(methylsulfonyl)benzene except that the reaction was heated under microwave condition at 125° C. for 30 min. ¹H NMR (400 MHz, CDCl₃) δ ppm 8.14 (s, 2 H), 7.75 (dd, J=8.28, 7.03 Hz, 1 H), 7.31-7.43 (m, 2 H), 7.21 (d, J=7.78 Hz, 1H), 6.07 (dd, J=7.65, 2.64 Hz, 1 H), 5.99 (d, J=2.51 Hz, 1 H), 4.52-4.62 (m, 1 H), 4.13-4.25 (m, 2 H), 3.56-3.71 (m, 2 H), 1.96-2.12 (m, 2 H), 1.78-1.91 (m, 2 H), 1.65-1.78 (m, 1 H), 0.76-0.96 (m, 2 H), 0.57-0.76 (m, 2 H). MS (ESI) 432 (M+H).

Example 231

Preparation of 4-(1-(5-cyclopropylpyrimidin-2-yl)piperidin-4-yloxy)-1-(3-fluoro-4-(methylsulfonyl)phenyl)pyridin-2(1H)-one

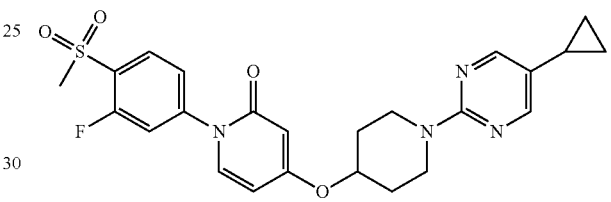

Example 231 was prepared according to procedures described in Example 230 substituting 4-bromo-2-fluoro-1-(methylsulfonyl)benzene (prepared according to the procedure described in Step D of Example 173 substituting 4-bromo-2-fluoro-1-iodobenzene for 4-bromo-1-iodo-2-methylbenzene) for 2-fluoro-4-iodobenzonitrile in Step D except that the reaction was heated under microwave condition at 160° C. for 30 min. ¹H NMR (400 MHz, CDCl₃) δ ppm 8.07 (s, 2 H), 8.02 (t, J=7.91 Hz, 1 H), 7.37 (dd, J=10.29, 1.76 Hz, 1 H), 7.30 (dd, J=8.41, 1.88 Hz, 1 H), 7.15 (d, J=7.78 Hz, 1 H), 6.01 (dd, J=7.65, 2.64 Hz, 1 H), 5.93 (d, J=2.51 Hz, 1 H), 4.43-4.56 (m, 1 H), 4.05-4.17 (m, 2 H), 3.50-3.62 (m, 2 H), 3.19 (s, 3 H), 1.89-2.07 (m, 2 H), 1.70-1.89 (m, 2 H), 1.60-1.70 (m, 1 H), 0.68-0.92 (m, 2 H), 0.46-0.68 (m, 2 H). MS (ESI) 485 (M+H).

Example 233

Preparation of 5-bromo-4-(1-(5-cyclopropylpyrimidin-2-yl)piperidin-4-yloxy)-1-(4-(methylsulfonyl)phenyl)pyridin-2(1H)-one, TFA salt

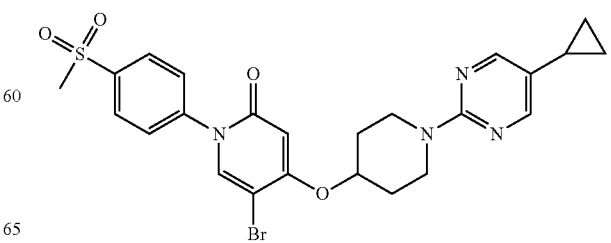

Step A. Preparation of 3,5-dibromo-4-hydroxypyridin-2(1H)-one

To 4-hydroxypyridin-2(1H)-one (5.55 g, 50 mmol) was added 48% aqueous hydrobromic acid (50 mL, 921 mmol) to produce a pale tan solution. Bromine (5.67 mL, 110 mmol) was added to produce an amber solution. After 3 days a yellow precipitate had formed. To the reaction was added 300 mL of water causing a thick white slurry to form which was stirred for 1 hour. The reaction was filtered and washed with 4×50 mL of water. to yield product (13.506 g, 1.81 mmol, quantitative yield) as a white powder. MS (ESI) 190 (M+1).

Step B. Preparation of 5-bromo-4-hydroxypyridin-2(1H)-one

To 3,5-dibromo-4-hydroxypyridin-2(1H)-one (5.4 g, 20.08 mmol) in a 200 mL recovery flask was added hydrogen bromide, (50 mL, 442 mmol, 48% aqueous) to produce an off-white suspension. To the reaction was added aniline (1.830 mL, 20.08 mmol) to produce a pale tan suspension and the mixture was stirred at 60° C. for 4 h. A white precipitate was formed. After cooling to room temperature, the solid was filtered and washed with 25 mL of water to yield pure product (2.071 g, 10.9 mmol, 54%) as a tan powder. The aqueous mixture was adjusted to pH ~12 (pH paper) using 21 mL of 50% aqueous NaOH, causing more off-white gelatinous precipitate to form. The precipitate was collected and washed with water to yield additional pure product (1.1 g, 29%). MS (ESI) 190 (M+H).

Step C. Preparation of 5-bromo-4-hydroxy-1-(4-(methylsulfonyl)phenyl)pyridin-2(1H)-one The intermediate was prepared according to the procedures described in Example 221 substituting 5-bromo-4-hydroxy-pyridin-2(1H)-one for 4-hydroxy-6-oxo-1,6-dihydropyridine-3-carbonitrile in Step A. MS (ESI) 345 (M+H).

Step D

Example 233

Example 233 was prepared according to the procedures described in Example 221 substituting 5-bromo-4-hydroxy-1-(4-(methylsulfonyl)phenyl)pyridin-2(1H)-one for 4-hydroxy-1-(4-(methylsulfonyl)phenyl)-6-oxo-1,6-dihydropyridine-3-carbonitrile in Step B. $^1$H NMR (500 MHz, CDCl$_3$) δ ppm 8.36 (s, 2 H), 8.11 (d, J=8.80 Hz, 2 H), 7.48-7.70 (m, 3 H), 6.55 (s, 1 H), 4.88 (s, 1 H), 4.28 (d, J=13.75 Hz, 2 H), 3.92 (t, J=10.17 Hz, 2 H), 3.11 (s, 3 H), 2.06-2.25 (m, 4 H), 1.77-1.92 (m, 1 H), 1.02-1.15 (m, 2 H), 0.66-0.78 (m, 2 H). MS (ESI) 494 (M+H).

Example 235

Preparation of (E)-1-(2-fluoro-4-(methylsulfonyl)phenyl)-4-(1-(5-(prop-1-enyl)pyrimidin-2-yl)piperidin-4-yloxy)pyridin-2(1H)-one

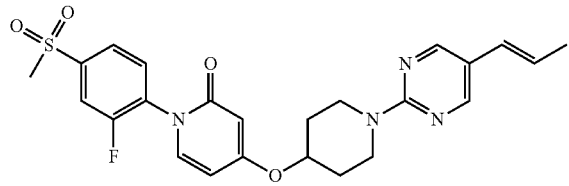 [SMILES: C/C=C/c1cnc(N2CCC(Oc3ccn(-c4ccc(S(C)(=O)=O)cc4F)c(=O)c3)CC2)nc1]

Step A. Preparation of (E)-2-chloro-5-(prop-1-enyl)pyrimidine

To 5-bromo-2-chloropyrimidine (2.027 g, 10.48 mmol), (E)-prop-1-enylboronic acid (1.350 g, 15.72 mmol), PdCl$_2$(dppf)-CH$_2$Cl$_2$ (0.428 g, 0.524 mmol), and potassium carbonate (4.35 g, 31.4 mmol) in toluene (20 mL) and water (0.5 mL) was bubbled nitrogen subsurface for 1 minute and then placed in a 90° C. oil bath for 5 hours. 200 mL EtOAc was added and the reaction was then washed with 3×200 mL of water, dried with MgSO$_4$, filtered and concentrated to 1.53 g brown solids. This was purified by flash chromatography (5% EtOAc in hexanes) to yield product (681 mg) as an off-white solid. MS (ESI) 155.7 (M+1).

Step B. Preparation of (E)-1-(5-(prop-1-enyl)pyrimidin-2-yl)piperidin-4-ol

Using (E)-2-chloro-5-(prop-1-enyl)pyrimidine (Ex. 235, Step A), the (E)-1-(5-(prop-1-enyl)pyrimidin-2-yl)piperidin-4-ol was prepared as described in Example 142, Step A. MS (ESI) 220.2 (M+1).

Step C

Preparation of Example 235

To 1-(2-fluoro-4-(methylsulfonyl)phenyl)-4-hydroxypyridin-2(1H)-one (28 mg, 0.099 mmol) from Example 142, Step D, (E)-1-(5-(prop-1-enyl)pyrimidin-2-yl)piperidin-4-ol (26.0 mg, 0.119 mmol) and triphenylphosphine (33.7 mg, 0.128 mmol) was added THF (0.5 mL). To this white suspension was added diethyl azodicarboxylate (0.020 mL, 0.128 mmol) to produce a yellow solution. A pale tan precipitate formed in 135 minutes. After 230 minutes, 2 mL ether was added. The reaction was filtered and then washed with 3×1 mL of ether to give Example 235 (24 mg. 0.049 mmol, 49%) as an off-white solid. $^1$H NMR (500 MHz, CDCl$_3$) δ ppm 1.81-1.86 (m, 1 H) 1.88 (d, J=6.60 Hz, 4 H) 2.08 (ddd, J=13.06, 3.71, 3.57 Hz, 2H) 3.12 (s, 3 H) 3.64-3.73 (m, 2 H) 4.16-4.24 (m, 2 H) 4.56-4.62 (m, 1 H) 6.02 (d, J=2.20 Hz, 1 H) 6.06-6.14 (m, 2 H) 6.20 (d, 1 H) 7.13 (d, J=7.15 Hz, 1 H) 7.64 (t, J=7.70 Hz, 1H) 7.80-7.93 (m, 2 H) 8.32 (s, 2 H). MS (ESI) 485.2 (M+1).

Example 236

Preparation of (Z)-1-(2-fluoro-4-(methylsulfonyl)phenyl)-4-(1-(5-(prop-1-enyl)pyrimidin-2-yl)piperidin-4-yloxy)pyridin-2(1H)-one

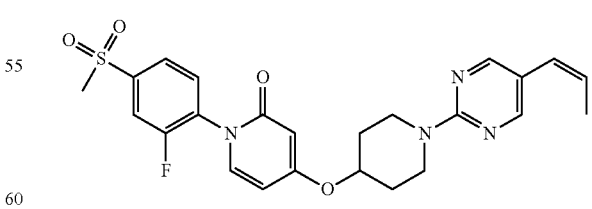

Example 236 was prepared using the sequence described for Example 235 and substituting (Z)-prop-1-enylboronic acid for (E)-prop-1-enylboronic acid in Step A. $^1$H NMR (500 MHz, CDCl$_3$) δ ppm 1.77-1.97 (m, 3 H) 2.04-2.17 (m, 1 H) 3.12 (s, 3 H) 3.49 (q, J=6.78 Hz, 1 H) 3.63-3.80 (m, 1 H) 4.11-4.30 (m, 1 H) 4.60 (ddd, J=7.29, 3.85, 3.71 Hz, 1 H) 5.79

(dq, J=11.55, 7.15 Hz, 1 H) 6.03 (d, J=2.20 Hz, 1 H) 6.09 (dd, J=7.70, 2.75 Hz, 1 H) 6.18 (d, J=11.55 Hz, 1 H) 7.14 (d, J=7.70 Hz, 1 H) 7.64 (t, J=7.70 Hz, 1 H) 7.79-7.95 (m, 1 H) 8.33 (s, 1 H). MS (ESI) 485.2 (M+1).

Example 238

Preparation of 1-(4-amino-3-fluorophenyl)-4-(1-(5-propylpyrimidin-2-yl)piperidin-4-yloxy)pyridin-2(1H)-one

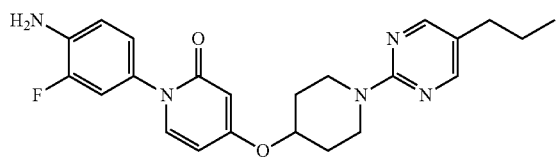 [SMILES: CCCc1cnc(N2CCC(Oc3ccn(-c4ccc(N)c(F)c4)c(=O)c3)CC2)nc1]

Example 238 was prepared according to procedures described in Example 173 substituting 2-fluoro-4-iodoaniline (Aldrich) for 4-bromo-2-methyl-1-(methylsulfonyl)benzene in Step E except that reaction was heated under microwave condition at 100° C. for 30 min and then at 130° C. at 30 min. $^1$H NMR (400 MHz, CDCl$_3$) δ ppm 8.18 (s, 2 H), 7.20 (d, J=7.53 Hz, 1 H), 7.07 (dd, J=11.29, 2.26 Hz, 1 H), 6.92-6.99 (m, 1 H), 6.80-6.88 (m, 1 H), 6.01 (d, J=2.51 Hz, 1 H), 5.97 (dd, J=7.53, 2.51 Hz, 1 H), 4.51-4.62 (m, 1 H), 4.15-4.28 (m, 2 H), 3.88 (br. s., 2 H), 3.57-3.69 (m, 2 H), 2.42 (t, J=7.53 Hz, 2 H), 1.97-2.18 (m, 2 H), 1.77-1.97 (m, 2 H), 1.53-1.66 (m, 2 H), 0.96 (t, J=7.28 Hz, 3 H). MS (ESI) 424 (M+H).

Example 239

Preparation of N-(2-fluoro-4-(2-oxo-4-(1-(5-propylpyrimidin-2-yl)piperidin-4-yloxy)pyridin-1(2H)-yl)phenyl)pivalamide

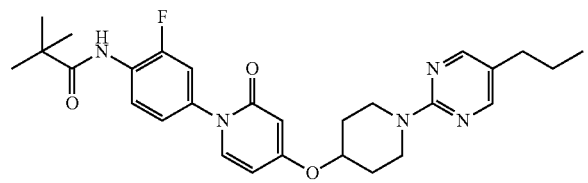 [SMILES: CCCc1cnc(N2CCC(Oc3ccn(-c4ccc(NC(=O)C(C)(C)C)c(F)c4)c(=O)c3)CC2)nc1]

Example 239 was prepared according to procedures described in Example 208 substituting 1-(4-amino-3-fluorophenyl)-4-(1-(5-propylpyrimidin-2-yl)piperidin-4-yloxy)pyridin-2(1H)-one for 1-(4-aminophenyl)-4-(1-(5-propylpyrimidin-2-yl)piperidin-4-yloxy)pyridin-2(1H)-one and substituting pivaloyl chloride (Aldrich) for Isobutyryl chloride except that the crude solid purified by flash chromatography (SiO$_2$, 0 to 100% EtOAc in CH$_2$Cl$_2$). $^1$H NMR (400 MHz, CDCl$_3$) δ ppm 8.51 (t, J=8.66 Hz, 1 H), 8.19 (s, 2 H), 7.68 (d, J=3.51 Hz, 1 H), 7.25-7.30 (m, 1 H), 7.17-7.25 (m, 1 H), 7.12 (d, J=8.78 Hz, 1 H), 5.96-6.06 (m, 1 H), 4.51-4.63 (m, 1 H), 4.15-4.26 (m, 2 H), 3.59-3.69 (m, 2 H), 2.43 (t, J=7.53 Hz, 2 H), 1.97-2.15 (m, 2 H), 1.79-1.97 (m, 2 H), 1.54-1.65 (m, 2 H), 1.36 (s, 9 H), 0.96 (t, J=7.28 Hz, 3 H). MS (ESI) 508 (M+H).

Example 240

Preparation of N-(2-fluoro-4-(2-oxo-4-(1-(5-propylpyrimidin-2-yl)piperidin-4-yloxy)pyridin-1(2H)-yl)phenyl)isobutyramide

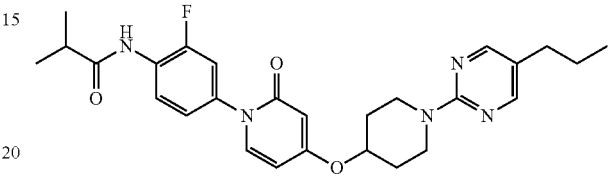

Example 240 was prepared according to procedures described in Example 208 substituting 1-(4-amino-3-fluorophenyl)-4-(1-(5-propylpyrimidin-2-yl)piperidin-4-yloxy)pyridin-2(1H)-one for 1-(4-aminophenyl)-4-(1-(5-propylpyrimidin-2-yl)piperidin-4-yloxy)pyridin-2(1H)-one except that the crude solid purified by flash chromatography (SiO$_2$, 0 to 100% EtOAc in CH$_2$Cl$_2$). $^1$H NMR (400 MHz, CDCl$_3$) δ ppm 8.54 (t, J=8.66 Hz, 1 H), 8.43 (s, 2 H), 7.46 (d, J=3.26 Hz, 1 H), 7.32 (d, J=7.53 Hz, 1 H), 7.25 (dd, J=11.42, 2.38 Hz, 1 H), 7.12 (d, J=8.78 Hz, 1 H), 6.39 (d, J=2.51 Hz, 1 H), 6.18 (dd, J=7.65, 2.64 Hz, 1 H), 4.67-4.77 (m, 1 H), 4.05-4.18 (m, 2 H), 3.93-4.05 (m, 2 H), 2.57-2.70 (m, 1 H), 2.53 (t, J=7.53 Hz, 2 H), 2.10-2.21 (m, 2 H), 1.97-2.10 (m, 2 H), 1.59-1.71 (m, 2 H), 1.31 (d, J=7.03 Hz, 6 H), 1.00 (t, J=7.28 Hz, 3 H). MS (ESI) 494 (M+H).

Example 241

Preparation of 2,2,2-trifluoro-N-(2-fluoro-4-(2-oxo-4-(1-(5-propylpyrimidin-2-yl)piperidin-4-yloxy)pyridin-1(2H)-yl)phenyl)acetamide

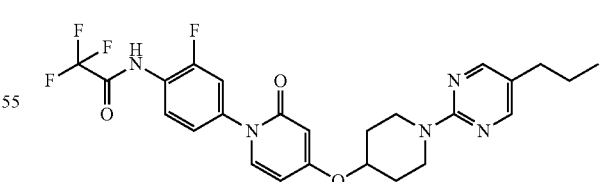

Example 241 was prepared according to procedures described in Example 239 substituting 2,2,2-trifluoroacetic anhydride (Aldrich) for pivaloyl chloride. $^1$H NMR (400 MHz, CDCl$_3$) δ ppm 8.29-8.42 (m, 2 H), 8.19 (s, 2 H), 7.36 (dd, J=11.17, 2.38 Hz, 1 H), 7.16-7.25 (m, 2 H), 6.05 (dd, J=7.65, 2.64 Hz, 1 H), 6.02 (d, J=2.51 Hz, 1 H), 4.53-4.65 (m, 1 H), 4.15-4.26 (m, 2 H), 3.60-3.71 (m, 2 H), 2.43 (t, J=7.53

Hz, 2 H), 2.00-2.15 (m, 2 H), 1.75-1.98 (m, 2 H), 1.52-1.66 (m, 2 H), 0.96 (t, J=7.40 Hz, 3 H). MS (ESI) 520 (M+H).

Example 242

Preparation of N-methyl-N-(4-(2-oxo-4-(1-(5-propylpyrimidin-2-yl)piperidin-4-yloxy)pyridin-1(2H)-yl)phenyl)pivalamide

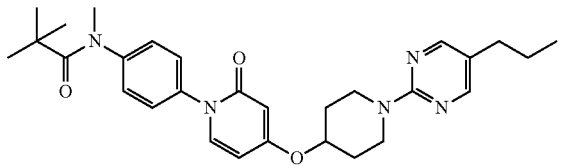 [SMILES: CCCc1cnc(N2CCC(Oc3ccn(-c4ccc(N(C)C(=O)C(C)(C)C)cc4)c(=O)c3)CC2)nc1]

To a stirring suspension of sodium hydride (9.1 mg, 0.23 mmol), N-(4-(2-oxo-4-(1-(5-propylpyrimidin-2-yl)piperidin-4-yloxy)pyridin-1(2H)-yl)phenyl)pivalamide (15 mg, 0.030 mmol) in DMF (2 mL) was added Methyl iodide (10 μL, 0.16 mmol). The reaction was stirred at room temperature for 1.5 h. The reaction was quenched with H$_2$O and extracted with EtOAc. The organic layer was concentrated in vacuo to a white solid. The solid was purified by flash chromatography (SiO$_2$, 0 to 100% EtOAc in CH$_2$Cl$_2$) to yield 10 mg of the desired product as a white solid. $^1$H NMR (400 MHz, CDCl$_3$) δ ppm 8.19 (s, 2 H), 7.39-7.48 (m, 2 H), 7.32-7.39 (m, 2 H), 7.26 (d, J=2.01 Hz, 1 H), 5.98-6.09 (m, 2 H), 4.55-4.64 (m, 1 H), 4.16-4.28 (m, 2 H), 3.59-3.71 (m, 2 H), 3.27 (s, 3 H), 2.43 (t, J=7.40 Hz, 2 H), 1.98-2.22 (m, 2 H), 1.74-1.98 (m, 2 H), 1.53-1.66 (m, 2 H), 1.12 (s, 9 H), 0.96 (t, J=7.28 Hz, 3 H). MS (ESI) 504 (M+H).

Example 243

Preparation of 4-(1-(5-cyclobutylpyrimidin-2-yl)piperidin-4-yloxy)-1-(2-fluoro-4-(methylsulfonyl)phenyl)pyridin-2(1H)-one

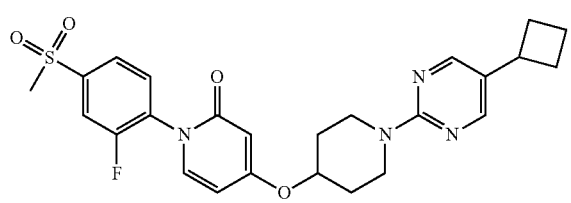 [SMILES: CS(=O)(=O)c1ccc(-n2ccc(OC3CCN(c4ncc(C5CCC5)cn4)CC3)cc2=O)c(F)c1]

Step A. Preparation of 2-chloro-5-cyclobutylpyrimidine

To a 100 mL recovery flask containing 5-bromo-2-chloropyrimidine (816 mg, 4.22 mmol) was applied vacuum then placed under a nitrogen atmosphere. To the flask was added dichloromethane (3 mL), PdCl$_2$(dppf)-CH$_2$Cl$_2$ (172 mg, 0.211 mmol) and then cyclobutylzinc(II) bromide (8.44 mL, 4.22 mmol, 1.3 M in THF) over 1-2 minutes. The reaction was quenched at 2 hours with 20 mL of saturated aqueous NH$_4$Cl and 50 mL EtOAc. The organic layer was washed with 20 mL each of saturated aqueous NaHCO$_3$ and then NaCl, dried with MgSO$_4$, filtered and concentrated to 0.88 g of yellow oil containing some solids. This was purified by flash chromatography (5-10% EtOAc in hexanes) to yield product (253 mg, 1.50 mmol, 36%) as a faintly pale yellow liquid with some small amount of crystalline material. MS (ESI) 169.1 (M+1).

Step B. Preparation of 1-(5-cyclobutylpyrimidin-2-yl)piperidin-4-ol

This material was prepared as described in described in Example 142, Step A, substituting 2-chloro-5-cyclobutylpyrimidine for 2-chloro-5-propylpyrimidine. MS (ESI) 234.2 (M+1).

Step C. Preparation of Example 243

To 1-(2-fluoro-4-(methylsulfonyl)phenyl)-4-hydroxypyridin-2(1H)-one (56.7 mg, 0.20 mmol), 1-(5-cyclobutylpyrimidin-2-yl)piperidin-4-ol (56.0 mg, 0.240 mmol), and triphenylphosphine (68.2 mg, 0.260 mmol) added THF (1 mL) to produce a white suspension then added (E)-diethyl diazene-1,2-dicarboxylate (0.041 mL, 0.260 mmol) leading to a complete dissolution of solids and produced a yellow solution within 1-2 minutes. After 55 minutes, with the reaction still a clear light yellow solution, added 5 mL of ether causing an off-white precipitate to form. Filtered after stirring 5 minutes and washed with 4×1 mL of ether to yield Example 243 (74 mg, 0.145 mmol, 73%) as an off-white powder. $^1$H NMR (400 MHz, CDCl$_3$) δ ppm 1.21 (t, J=7.03 Hz, 2 H) 1.75-1.95 (m, 3 H) 1.96-2.18 (m, 5 H) 2.25-2.40 (m, 2 H) 3.12 (s, 3 H) 3.38 (t, J=8.57 Hz, 1 H) 3.48 (q, J=7.03 Hz, 1 H) 3.58-3.70 (m, 2 H) 4.21 (ddd, J=13.51, 6.92, 3.73 Hz, 2 H) 4.45-4.69 (m, 1 H) 4.58 (ddd, J=7.58, 3.95, 3.84 Hz, 1 H) 6.02 (d, J=2.64 Hz, 1 H) 6.08 (dd, J=7.91, 2.64 Hz, 1 H) 7.13 (d, J=7.47 Hz, 1 H) 7.51-7.70 (m, 1 H) 7.80-7.93 (m, 2 H) 8.23 (s, 2 H). MS (ESI) 499.2 (M+1).

Example 244

Preparation of 4-(2-oxo-4-(1-(5-propylpyrimidin-2-yl)piperidin-4-yloxy)pyridin-1(2H)-yl)phthalonitrile

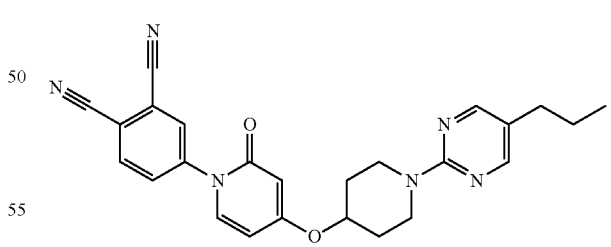

Example 244 was prepared according to procedures described in Example 173 substituting 4-iodophthalonitrile (Aldrich) for 4-bromo-2-methyl-1-(methylsulfonyl)benzene in Step E except that reaction was heated under microwave condition at 140° C. for 30 min. $^1$H NMR (400 MHz, CDCl$_3$) δ ppm 8.19 (s, 2 H), 7.92-8.00 (m, 2 H), 7.84 (dd, J=8.53, 2.01 Hz, 1 H), 7.22 (d, J=7.53 Hz, 1 H), 6.13 (dd, J=7.78, 2.51 Hz, 1 H), 6.01 (d, J=2.51 Hz, 1 H), 4.55-4.65 (m, 1 H), 4.16-4.27 (m, 2 H), 3.60-3.71 (m, 2 H), 2.43 (t, J=7.53 Hz, 2 H), 1.98-2.15 (m, 2 H), 1.81-1.98 (m, 2 H), 1.54-1.66 (m, 2 H), 0.96 (t, J=7.28 Hz, 3 H). MS (ESI) 441 (M+H).

Example 245

Preparation of 4-(4-(1-(5-ethylpyrimidin-2-yl)piperidin-4-yloxy)-2-oxopyridin-1(2H)-yl)-2-fluorobenzonitrile

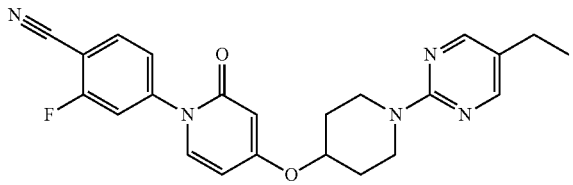 [SMILES: CCc1cnc(N2CCC(Oc3ccn(-c4ccc(C#N)c(F)c4)c(=O)c3)CC2)nc1]

Example 245 was prepared according to procedures described in Example 230 substituting 2-chloro-5-ethylpyrimidine (Aldrich) for 2-chloro-5-cyclopropylpyrimidine in Step C. In step D the reaction was heated under microwave condition at 140° C. for 30 min. ¹H NMR (400 MHz, CDCl₃) δ ppm 8.20 (s, 2 H) 7.76 (dd, J=8.16, 6.90 Hz, 1 H) 7.32-7.42 (m, 2 H) 7.21 (d, J=7.78 Hz, 1 H) 6.07 (dd, J=7.65, 2.64 Hz, 1 H) 6.00 (d, J=2.76 Hz, 1 H) 4.53-4.62 (m, 1 H) 4.14-4.26 (m, 2 H) 3.58-3.70 (m, 2 H) 2.49 (q, J=7.70 Hz, 2 H) 1.97-2.14 (m, 2 H) 1.76-1.97 (m, 2 H) 1.21 (t, J=7.53 Hz, 3 H). MS (ESI) 420 (M+H).

Example 246

Preparation of 4-(1-(5-ethylpyrimidin-2-yl)piperidin-4-yloxy)-1-(3-fluoro-4-(methylsulfonyl)phenyl)pyridin-2(1H)-one

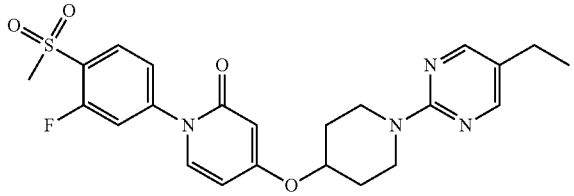 [SMILES: CCc1cnc(N2CCC(Oc3ccn(-c4ccc(S(C)(=O)=O)c(F)c4)c(=O)c3)CC2)nc1]

Example 246 was prepared according to procedures described in Example 230 substituting 2-chloro-5-ethylpyrimidine (Aldrich) for 2-chloro-5-cyclopropylpyrimidine in Step C and substituting 4-bromo-2-fluoro-1-(methylsulfonyl)benzene (prepared according to the procedure described in Step D of Example 173 substituting 4-bromo-2-fluoro-1-iodobenzene for 4-bromo-1-iodo-2-methylbenzene) for 2-fluoro-4-iodobenzonitrile in Step D except that the reaction was heated under microwave condition at 160° C. for 30 min. ¹H NMR (400 MHz, CDCl₃) δ ppm 8.21 (s, 2 H), 8.05-8.17 (m, 1 H), 7.46 (dd, J=10.29, 1.76 Hz, 1 H), 7.38 (dd, J=8.28, 2.01 Hz, 1 H), 7.23 (d, J=7.78 Hz, 1 H), 6.10 (dd, J=7.78, 2.51 Hz, 1 H), 6.02 (d, J=2.51 Hz, 1 H), 4.54-4.64 (m, 1 H), 4.16-4.27 (m, 2 H), 3.60-3.71 (m, 2 H), 3.27 (s, 3 H), 2.50 (q, J=7.53 Hz, 2 H), 1.98-2.16 (m, 2 H), 1.80-1.98 (m, 2 H), 1.22 (t, J=7.65 Hz, 3 H). MS (ESI) 473 (M+H).

Example 247

Preparation of 4-(4-(1-(5-ethylpyrimidin-2-yl)piperidin-4-yloxy)-2-oxopyridin-1(2H)-yl)-3-fluorobenzonitrile

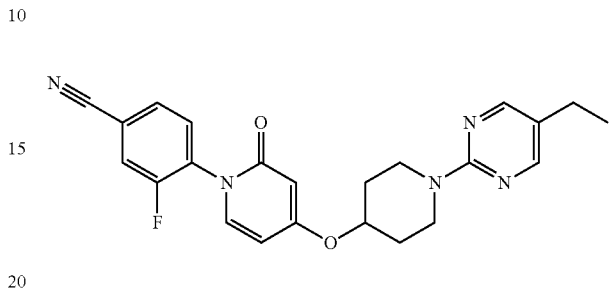

Example 247 was prepared according to procedures described in Example 190 substituting 2-chloro-5-ethylpyrimidine (Adlrich) for 2-chloro-5-cyclopropylpyrimidine except that reaction was stirred at 120° C. for 6 h. ¹H NMR (400 MHz, CDCl₃) δ ppm 8.21 (s, 2 H), 7.52-7.63 (m, 3 H), 7.12 (dd, J=7.78, 1.00 Hz, 1 H), 6.08 (dd, J=7.78, 2.51 Hz, 1 H), 6.02 (d, J=2.51 Hz, 1 H), 4.54-4.64 (m, 1 H), 4.17-4.26 (m, 2 H), 3.60-3.71 (m, 2 H), 2.50 (q, J=7.61 Hz, 2 H), 2.04-2.16 (m, 2 H), 1.79-1.93 (m, 2 H), 1.22 (t, J=7.65 Hz, 3 H). MS (ESI) 420 (M+H).

Example 248

Preparation of 4-(1-(5-ethylpyrimidin-2-yl)piperidin-4-yloxy)-1-(2-fluoro-4-(methylsulfonyl)phenyl)pyridin-2(1H)-one

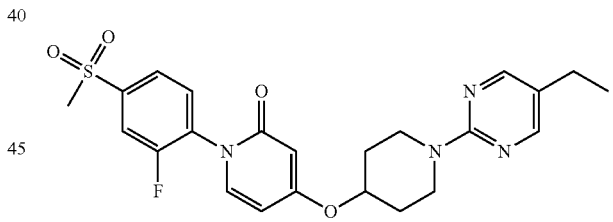

A suspension of 4-(1-(5-ethylpyrimidin-2-yl)piperidin-4-yloxy)pyridin-2(1H)-one (127 mg, 0.424 mmol, prepared according to procedures described in Example 230 Step C substituting 2-chloro-5-ethylpyrimidine (Aldrich) for 2-chloro-5-cyclopropylpyrimidine), sodium hydride (60 wt % mineral oil, 21 mg, 0.51 mmol) and DMF (5 mL) was purged with Argon and then stirred at room temperature for 1 h. To the reaction was added 1,2-difluoro-4-(methylsulfonyl)benzene (90 mg, 0.47 mmol, Matrix Scientific) and then heated at 110° C. for 1 h. The resulting mixture was quenched with H₂O and extracted with EtOAc. The organic layer was concentrated in vacuo to a yellow solid. The solid was purified by flash chromatography (SiO₂, 0 to 100% EtOAc in CH₂Cl₂) to yield 91 mg of the desired product as an off-white solid. ¹H NMR (400 MHz, CDCl₃) δ ppm 8.20 (s, 2 H), 7.83-7.91 (m, 2 H), 7.64 (dd, J=8.53, 6.78 Hz, 1 H), 7.13 (dd, J=7.53, 1.00 Hz, 1 H), 6.08 (dd, J=7.65, 2.64 Hz, 1 H), 6.03 (d, J=2.51 Hz, 1 H), 4.54-4.63 (m, 1 H), 4.16-4.27 (m, 2 H), 3.60-3.70 (m, 2

H), 3.12 (s, 3 H), 2.49 (q, J=7.53 Hz, 2 H), 1.97-2.15 (m, 2 H), 1.78-1.97 (m, 2 H), 1.21 (t, J=7.53 Hz, 3 H). MS (ESI) 473 (M+H).

Example 249

Preparation of 1-(4-(2-hydroxybutylsulfonyl)phenyl)-4-(1-(pyrimidin-2-yl)piperidin-4-yloxy)pyridin-2(1H)-one, TFA salt

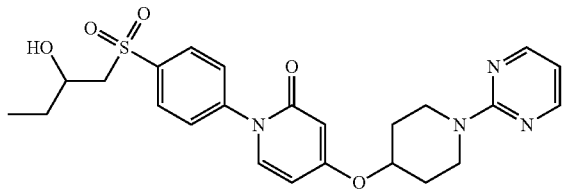 [SMILES: CCC(O)CS(=O)(=O)c1ccc(-n2ccc(OC3CCN(c4ncccn4)CC3)cc2=O)cc1]

A suspension of (methylsulfonyl)phenyl)pyridin-2(1H)-one (104 mg, 0.206 mmol) in THF (12 mL) was cooled to −78° C. and t-butyllithium (0.242 mL, 0.411 mmol, 1.7 M in pentane) was added. The pale yellow fine suspension became much thicker. After 30 minutes, propionaldehyde (0.030 mL, 0.411 mmol) was added and then cooling bath was removed. The reaction was quenched within 10 minutes with 20 mL of saturated aqueous NH$_4$Cl then extracted with 30 mL of CH$_2$Cl$_2$. The organic layer was dried with MgSO$_4$, filtered and concentrated to give 102 mg of tan-yellow solids. This material was purified by preparative HPLC (C18, 10-90% MeOH in water containing 0.1% TFA) to give Example 249 (15 mg, 0.028 mmol, 14%) as a pale yellow oil. $^1$H NMR (400 MHz, CDCl$_3$) δ ppm 0.82-0.94 (m, 3 H) 1.41-1.58 (m, 2 H) 1.76-1.96 (m, 2 H) 1.93-2.15 (m, 2 H) 3.13-3.40 (m, 6 H) 3.64-3.80 (m, 2 H) 3.95-4.18 (m, 2 H) 4.48-4.71 (m, 1 H) 6.00 (d, J=2.20 Hz, 1 H) 6.05-6.17 (m, 1 H) 6.54 (t, J=4.83 Hz, 1 H) 7.25 (d, J=7.91 Hz, 2 H) 7.55 (d, J=8.35 Hz, 2 H) 8.03 (d, J=8.79 Hz, 2 H) 8.33 (d, J=4.83 Hz, 1 H). MS (ESI) 485.2 (M+1).

Example 250

Preparation of (Z)-5-chloro-1-(4-(methylsulfonyl)phenyl)-4-(1-(5-(prop-1-enyl)pyrimidin-2-yl)piperidin-4-yloxy)pyridin-2(1H)-one, TFA salt

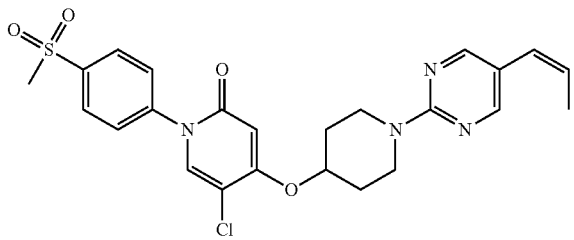 [SMILES: C/C=C\c1cnc(N2CCC(Oc3cc(=O)n(-c4ccc(S(C)(=O)=O)cc4)cc3Cl)CC2)nc1]

To a mixture of 5-chloro-4-hydroxy-1-(4-(methylsulfonyl)phenyl)pyridin-2(1H)-one (35 mg, 0.117 mmol), (Z)-1-(5-(prop-1-enyl)pyrimidin-2-yl)piperidin-4-ol (30.7 mg, 0.140 mmol, prepared as described in Example 236) and triphenylphosphine (39.8 mg, 0.152 mmol) in THF (2 mL) was added (E)-diethyl diazene-1,2-dicarboxylate (0.024 mL, 0.125 mmol) slowly. The mixture was stirred at rt for 16 h. To the reaction mixture was added diethyl ether (10 mL). A precipitate was collected and washed with diethyl ether (2×) to give Example 250 (5 mg, 8.55%) as a white solid. $^1$H NMR (500 MHz, CDCl$_3$) δ ppm 8.31-8.44 (m, 2 H), 8.09 (d, J=8.25 Hz, 2 H), 7.63 (d, J=8.25 Hz, 2 H), 7.43 (s, 1 H), 6.18 (d, J=11.55 Hz, 1 H), 6.02-6.10 (m, 1 H), 5.81-5.93 (m, 1 H), 4.74 (br. s., 1 H), 3.98-4.11 (m, 4 H), 3.49 (s, 3 H), 3.09 (s, 3 H), 2.07 (br. s., 4 H). MS (ESI) 501 (M+H).

Example 251

Preparation of 1-(3,4-difluorophenyl)-4-(1-(5-propylpyrimidin-2-yl)piperidin-4-yloxy)pyridin-2(1H)-one

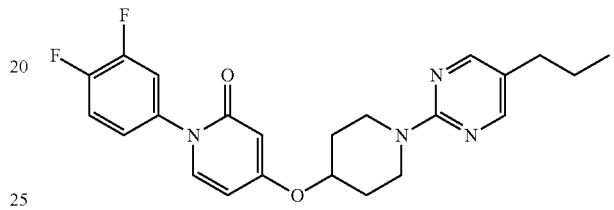

Example 251 was prepared according to procedures described in Example 244 substituting 1,2-difluoro-4-iodobenzene (Matrix Scientific) for 4-iodophthalonitrile. $^1$H NMR (400 MHz, CDCl$_3$) δ ppm 8.19 (s, 2 H), 7.29-7.33 (m, 1 H), 7.24-7.28 (m, 1 H), 7.20 (d, J=7.28 Hz, 1 H), 7.13 (d, J=8.03 Hz, 1 H), 5.88-6.18 (m, 2 H), 4.49-4.68 (m, 1 H), 4.09-4.32 (m, 2 H), 3.48-3.77 (m, 2 H), 2.43 (t, J=7.40 Hz, 2 H), 2.00-2.23 (m, 2 H), 1.75-1.95 (m, 2 H), 1.47-1.70 (m, 2 H), 0.96 (t, J=7.28 Hz, 3 H). MS (ESI) 427 (M+H).

Example 252

Preparation of 3,4-difluoro-2-(2-oxo-4-(1-(5-propylpyrimidin-2-yl)piperidin-4-yloxy)pyridin-1(2H)-yl)benzonitrile

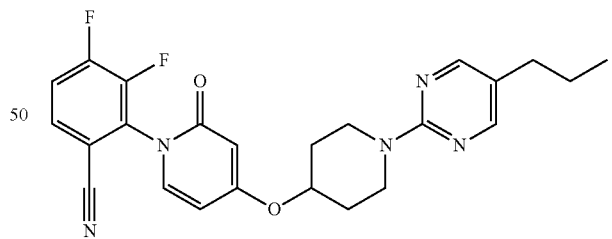

Example 252 was prepared according to procedures described in Example 248 substituting 4-(1-(5-propylpyrimidin-2-yl)piperidin-4-yloxy)pyridin-2(1H)-one (prepared according to procedures described in Example 173 Step C) for 4-(1-(5-ethylpyrimidin-2-yl)piperidin-4-yloxy)pyridin-2 (1H)-one and substituting 2,3,4-trifluorobenzonitrile (Oakwood) for 1,2-difluoro-4-(methylsulfonyl)benzene. $^1$H NMR (400 MHz, CDCl$_3$) δ ppm 8.10 (s, 2 H), 7.43-7.60 (m, 1 H), 7.27-7.43 (m, 1 H), 7.02 (d, J=7.78 Hz, 1 H), 6.05 (dd, J=7.65, 2.64 Hz, 1 H), 5.96 (d, J=2.51 Hz, 1 H), 4.43-4.60 (m, 1 H), 4.08-4.24 (m, 2 H), 3.49-3.66 (m, 2 H), 2.34 (t, J=7.53 Hz, 2

H), 1.99-2.08 (m, 2 H), 1.71-1.88 (m, 2 H), 1.43-1.59 (m, 2 H), 0.87 (t, J=7.28 Hz, 3 H). MS (ESI) 452 (M+H).

Example 253

Preparation of 2,3-difluoro-4-(2-oxo-4-(1-(5-propylpyrimidin-2-yl)piperidin-4-yloxy)pyridin-1(2H)-yl)benzonitrile

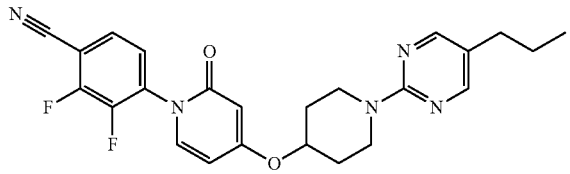 [SMILES: CCCc1cnc(N2CCC(Oc3ccn(-c4ccc(C#N)c(F)c4F)c(=O)c3)CC2)nc1]

Example 253 was prepared according to procedures described in Example 248 substituting 4-(1-(5-propylpyrimidin-2-yl)piperidin-4-yloxy)pyridin-2(1H)-one (prepared according to procedures described in Example 173 Step C) for 4-(1-(5-ethylpyrimidin-2-yl)piperidin-4-yloxy)pyridin-2(1H)-one and substituting 2,3,4-trifluorobenzonitrile (Oakwood) for 1,2-difluoro-4-(methylsulfonyl)benzene. $^1$H NMR (400 MHz, CDCl$_3$) δ ppm 8.10 (s, 2 H), 7.35-7.53 (m, 1 H), 7.21-7.35 (m, 1H), 7.03 (d, J=7.03 Hz, 1 H), 6.01 (dd, J=7.65, 2.64 Hz, 1 H), 5.93 (d, J=2.51 Hz, 1 H), 4.43-4.54 (m, 1 H), 4.05-4.19 (m, 2 H), 3.50-3.66 (m, 2 H), 2.34 (t, J=7.53 Hz, 2 H), 1.93-2.11 (m, 2 H), 1.72-1.83 (m, 2 H), 1.42-1.56 (m, 2 H), 0.87 (t, J=7.28 Hz, 3 H). MS (ESI) 452 (M+H).

Example 254

Preparation of 4-(2-oxo-4-(1-(5-propylpyrimidin-2-yl)piperidin-4-yloxy)pyridin-1(2H)-yl)-2-(trifluoromethyl)benzonitrile

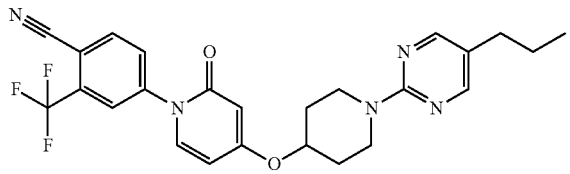 [SMILES: CCCc1cnc(N2CCC(Oc3ccn(-c4ccc(C#N)c(C(F)(F)F)c4)c(=O)c3)CC2)nc1]

Example 254 was prepared according to procedures described in Example 244 substituting 4-iodo-2-(trifluoromethyl)benzonitrile (Aldrich) for 4-iodophthalonitrile. $^1$H NMR (400 MHz, CDCl$_3$) δ ppm 8.19 (s, 2 H), 7.98 (d, J=8.28 Hz, 1 H), 7.88 (d, J=2.01 Hz, 1 H), 7.80 (dd, J=8.28, 2.01 Hz, 1 H), 7.24 (d, J=7.78 Hz, 1 H), 6.12 (dd, J=7.65, 2.64 Hz, 1 H), 6.02 (d, J=2.51 Hz, 1 H), 4.55-4.65 (m, 1 H), 4.14-4.28 (m, 2 H), 3.60-3.73 (m, 2 H), 2.43 (t, J=7.53 Hz, 2 H), 2.05-2.15 (m, 2 H), 1.80-1.93 (m, 2 H), 1.53-1.66 (m, 2 H), 0.96 (t, J=7.28 Hz, 3 H). MS (ESI) 484 (M+H).

Example 255

Preparation of 4-(2-oxo-4-(1-(5-propylpyrimidin-2-yl)piperidin-4-yloxy)pyridin-1(2H)-yl)benzonitrile

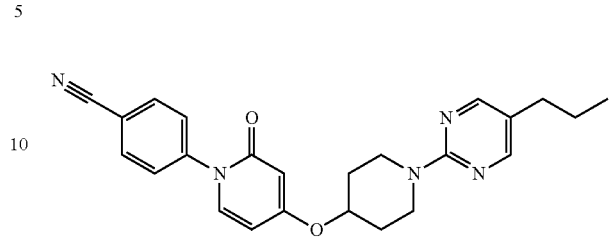

Example 255 was prepared according to procedures described in Example 244 substituting 4-iodobenzonitrile (Transworld) for 4-iodophthalonitrile. $^1$H NMR (400 MHz, CDCl$_3$) δ ppm 8.19 (s, 2 H), 7.77-7.83 (m, 2 H), 7.53-7.59 (m, 2 H), 7.23 (d, J=7.53 Hz, 1 H), 6.07 (dd, J=7.65, 2.64 Hz, 1 H), 6.02 (d, J=2.51 Hz, 1 H), 4.54-4.64 (m, 1 H), 4.16-4.28 (m, 2 H), 3.59-3.70 (m, 2 H), 2.43 (t, J=7.53 Hz, 2H), 1.98-2.17 (m, 2 H), 1.78-1.98 (m, 2 H), 1.51-1.66 (m, 2 H), 0.96 (t, J=7.40 Hz, 3 H). MS (ESI) 416 (M+H).

Example 256

Preparation of 2,5-difluoro-4-(2-oxo-4-(1-(5-propylpyrimidin-2-yl)piperidin-4-yloxy)pyridin-1(2H)-yl)benzonitrile

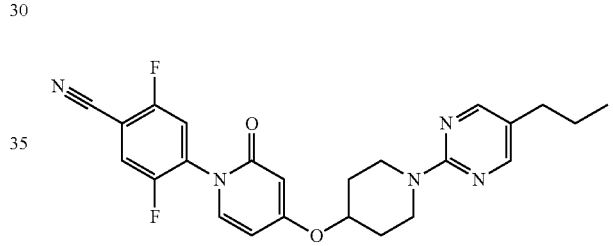

Example 256 was prepared according to procedures described in Example 252 substituting 2,4,5-Trifluorobenzonitrile (Aldrich) for 2,3,4-trifluorobenzonitrile. $^1$H NMR (500 MHz, CDCl$_3$) δ ppm 8.13 (s, 2 H), 7.49 (dd, J=8.25, 5.50 Hz, 1 H), 7.33 (dd, J=8.25, 5.50 Hz, 1 H), 7.06 (d, J=7.70 Hz, 1 H), 6.03 (dd, J=7.70, 2.20 Hz, 1 H), 5.96 (d, J=2.75 Hz, 1 H), 4.48-4.59 (m, 1 H), 4.10-4.20 (m, 2 H), 3.52-3.69 (m, 2 H), 2.37 (t, J=7.70 Hz, 2 H), 2.00-2.09 (m, 2 H), 1.75-1.85 (m, 2 H), 1.45-1.59 (m, 2 H), 0.90 (t, J=7.42 Hz, 3 H). MS (ESI) 452 (M+H).

Example 257

Preparation of cis-1-(4-(methylsulfonyl)phenyl)-4-(4-(5-propylpyrimidin-2-yl)cyclohexyloxy)pyridin-2(1H)-one, TFA salt

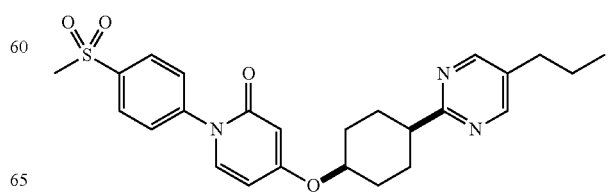

Step A. Preparation of 2-((dimethylamino)methylene)pentanal

To a solution of phosphorus oxychloride (2.330 mL, 25.00 mmol, Aldrich) in 1,2-dichloroethane (5.0 mL) at 0° C. was added DMF (7.74 mL, 100 mmol, EMD) in 1,2-dichloroethane (10.0 mL) during the course of 10 min. The mixture was stirred at 0° C. for 20 min and then warmed up to room temperature. After stirring at room temperature for 3 hrs, valeraldehyde (2.66 mL, 25.0 mmol, Aldrich) in 1,2-dichloroethane (5.0 mL) was added dropwise (5 min) and the resulting mixture was stirred at room temperature for 50 min and at 85° C. for 50 min. The cooled reaction mixture was poured into a mixture of ice and $K_2CO_3$ (7.5 g) followed by addition of saturated $K_2CO_3$ aqueous solution until the pH of the mixture was around 10. To the above mixture, dimethyl amine (8.0 mL, 40 wt. % solution in water, Aldrich) was added and the reaction mixture was heated at 80° C. for 1 hr, cooled and evaporated under reduced pressure to remove 1,2-dichloroethane. The resulting mixture was then heated at 95° C. for 1 hr, cooled to room temperature and extracted with EtOAc (3×). The combined extracts were washed with brine, dried ($Na_2SO_4$) and concentrated in vacuo. The residue was distilled under reduced pressure (1 torr at 145-155° C. of oil bath) to yield the title compound (200 mg, 5.7%) as an orange oil. $^1$H NMR (500 MHz, $CDCl_3$) δ 8.85 (s, 1 H), 6.48 (s, 1 H), 3.13 (s, 6 H), 2.30-2.45 (m, 2 H), 1.32-1.53 (m, 2 H), 0.93 (t, J=7.42 Hz, 3 H).

Step B

Example 257

Example 257 was prepared according to procedures described in Example 214 substituting 2-((dimethylamino) methylene)pentanal for (E)-3-(dimethylamino)acrylaldehyde at Step C. $^1$H NMR (400 MHz, $CDCl_3$) δ 8.59 (s, 2 H), 8.08 (d, J=8.61 Hz, 2 H), 7.64 (d, J=8.42 Hz, 2 H), 7.24 (d, J=7.69 Hz, 1 H), 6.16 (dd, J=7.69, 2.38 Hz, 1 H), 6.05 (d, J=2.38 Hz, 1 H), 4.67 (app brs, 1 H), 3.11 (s, 3 H), 3.00-3.10 (m, 1 H), 2.60 (t, J=7.60 Hz, 2 H), 2.07-2.29 (m, 4 H), 1.90-1.98 (m, 2 H), 1.82 (t, J=13.37 Hz, 2 H), 1.63-1.75 (m, 2 H), 1.01 (t, J=7.33 Hz, 3 H). MS (ESI) 468 (M+H).

Example 258

Preparation of trans-1-(4-(methylsulfonyl)phenyl)-4-(4-(5-propylpyrimidin-2-yl)cyclohexyloxy)pyridin-2(1H)-one, TFA salt

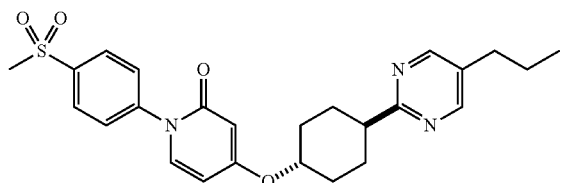

Example 258 was prepared as described above in Example 257 and was separated form the cis-isomer by preparative HPLC to yield the title compound. $^1$H NMR (400 MHz, $CDCl_3$) δ 8.57 (s, 2 H), 8.09 (d, J=8.61 Hz, 2 H), 7.64 (d, J=8.61 Hz, 2 H), 7.24 (d, J=7.51 Hz, 1 H), 6.03-6.13 (m, 2 H), 4.30-4.44 (m, 1 H), 3.11 (s, 3 H), 2.88-3.06 (m, 1 H), 2.60 (t, J=7.69 Hz, 2 H), 2.30-2.41 (m, 2 H), 2.24-2.36 (m, 2 H), 2.14-2.26 (m, 2 H), 1.78-1.92 (m, 2 H), 1.64-1.75 (m, 2 H), 1.01 (t, J=7.33 Hz, 3 H). MS (ESI) 468 (M+H).

Example 259

Preparation of 3-chloro-4-(2-oxo-4-(1-(5-propylpyrimidin-2-yl)piperidin-4-yloxy)pyridin-1(2H)-yl)benzonitrile

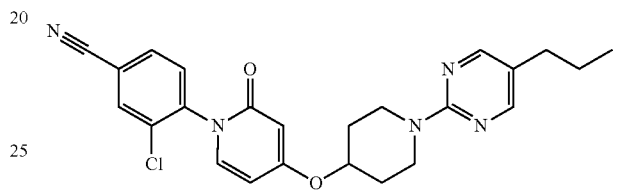

Example 259 was prepared according to procedures described in Example 252 substituting 3-chloro-4-fluorobenzonitrile (Aldrich) for 2,3,4-trifluorobenzonitrile except that the reaction was heated at 80° C. for 3 h. $^1$H NMR (500 MHz, $CDCl_3$) δ ppm 8.19 (s, 2 H), 7.88 (d, J=1.76 Hz, 1 H), 7.72 (dd, J=8.16, 1.63 Hz, 1 H), 7.53 (d, J=8.03 Hz, 1 H), 7.04 (d, J=7.53 Hz, 1 H), 6.08 (dd, J=7.78, 2.51 Hz, 1 H), 6.03 (d, J=2.26 Hz, 1 H), 4.54-4.66 (m, 1 H), 4.13-4.32 (m, 2 H), 3.57-3.72 (m, 2 H), 2.43 (t, J=7.53 Hz, 2 H), 2.05-2.19 (m, 2 H), 1.79-2.00 (m, 2 H), 1.53-1.67 (m, 2 H), 0.96 (t, J=7.40 Hz, 3 H). MS (ESI) 450 (M+H).

Example 260

Preparation of 6-(2-oxo-4-(1-(5-propylpyrimidin-2-yl)piperidin-4-yloxy)pyridin-1(2H)-yl)nicotinonitrile

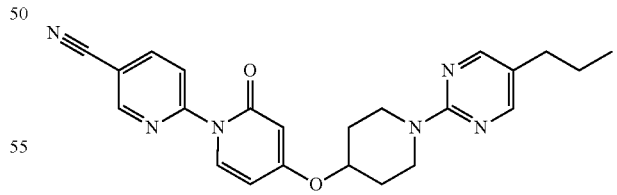

Example 260 was prepared according to procedures described in Example 244 substituting 6-bromonicotinonitrile (Matrix Scientific) for 4-iodophthalonitrile. $^1$H NMR (400 MHz, $CDCl_3$) δ ppm 8.82 (d, J=1.76 Hz, 1 H), 8.35 (d, J=8.78 Hz, 1H), 8.19 (s, 2 H), 8.08 (dd, J=8.66, 2.13 Hz, 1 H), 8.02 (d, J=8.03 Hz, 1 H), 6.12 (dd, J=8.03, 2.51 Hz, 1 H), 5.98 (d, J=2.51 Hz, 1 H), 4.55-4.68 (m, 1 H), 4.14-4.28 (m, 2 H), 3.60-3.73 (m, 2 H), 2.43 (t, J=7.53 Hz, 2 H), 1.99-2.18 (m, 2 H), 1.77-1.99 (m, 2 H), 1.51-1.66 (m, 2 H), 0.96 (t, J=7.28 Hz, 3 H). MS (ESI) 417 (M+H).

Example 261

Preparation of 1-(4-(methylsulfonyl)phenyl)-4-(1-(5-propylpyrimidin-2-yl)azepan-4-yloxy)pyridin-2(1H)-one, TFA salt

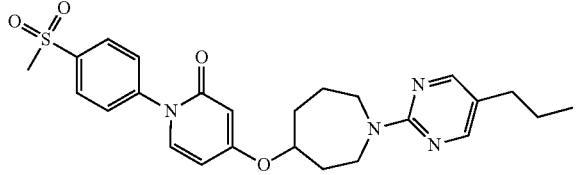 [SMILES: CCCc1cnc(N2CCCC(Oc3ccn(-c4ccc(S(C)(=O)=O)cc4)c(=O)c3)CC2)nc1]

Example 261 was prepared according to procedures described in Example 132 substituting tert-butyl 4-(1-(4-(methylsulfonyl)phenyl)-2-oxo-1,2-dihydropyridin-4-yloxy)azepane-1-carboxylate (Example 6) for tert-butyl 4-(2-oxo-1-(pyridin-3-yl)-1,2-dihydropyridin-4-yloxy)piperidine-1-carboxylate at Step C. $^1$H NMR (400 MHz, CDCl$_3$) δ 8.44 (s, 2 H), 8.08 (d, J=8.25 Hz, 2 H), 7.61 (d, J=8.25 Hz, 2 H), 7.24 (d, J=7.15 Hz, 1 H), 6.01-6.08 (m, 2 H), 4.55-4.61 (m, 1 H), 3.90-4.04 (m, 3 H), 3.77-3.88 (m, 1 H), 3.10 (s, 3 H), 2.46-2.56 (m, 2 H), 2.04-2.27 (m, 4 H), 1.84-2.01 (m, 2 H), 1.56-1.69 (m, 2 H), 0.98 (t, J=7.15 Hz, 3 H). MS (ESI) 483 (M+H).

Example 262

Preparation of 4-(1-(5-cyclopropylpyrimidin-2-yl)azepan-4-yloxy)-1-(4-(methylsulfonyl)phenyl)pyridin-2(1H)-one, TFA salt

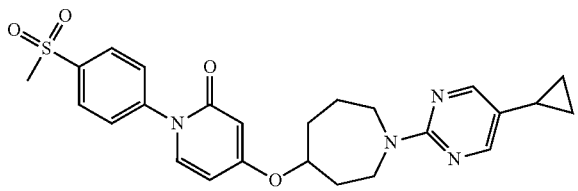 [SMILES: CS(=O)(=O)c1ccc(-n2ccc(OC3CCCN(c4ncc(C5CC5)cn4)CC3)cc2=O)cc1]

Example 262 was prepared according to procedures described in Example 132 substituting tert-butyl 4-(1-(4-(methylsulfonyl)phenyl)-2-oxo-1,2-dihydropyridin-4-yloxy)azepane-1-carboxylate for tert-butyl 4-(2-oxo-1-(pyridin-3-yl)-1,2-dihydropyridin-4-yloxy)piperidine-1-carboxylate at Step C and 2-chloro-5-cyclopropylpyrimidine for 2-chloro-5-propylpyrimidine at Step D. $^1$H NMR (400 MHz, CDCl$_3$) δ 8.40 (s, 2 H), 8.08 (d, J=8.25 Hz, 2 H), 7.61 (d, J=8.80 Hz, 2 H), 7.25-7.28 (m, 1 H), 6.13 (d, J=2.20 Hz, 1 H), 6.06 (dd, J=7.42, 2.47 Hz, 1 H), 4.55-4.63 (m, 1 H), 3.87-4.03 (m, 3 H), 3.78-3.88 (m, 1 H), 3.10 (s, 3 H), 2.03-2.28 (m, 4 H), 1.86-2.00 (m, 2 H), 1.77-1.89 (m, 1 H), 1.02-1.07 (m, 2 H), 0.65-0.77 (m, 2 H). MS (ESI) 481 (M+H).

Example 263

Preparation of 4-(5-chloro-2-oxo-4-(1-(5-(3,3,3-trifluoropropyl)pyrimidin-2-yl)piperidin-4-yloxy)pyridin-1(2H)-yl)-2-fluorobenzonitrile, TFA salt

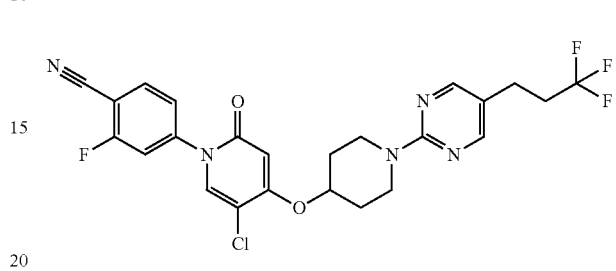

Step A. Preparation of 4-(5-chloro-4-hydroxy-2-oxopyridin-1(2H)-yl)-2-fluorobenzonitrile A mixture of 2-fluoro-4-iodobenzonitrile (4000 mg, 16.19 mmol), 5-chloro-4-hydroxypyridin-2(1H)-one (2357 mg, 16.19 mmol), 4,7-dimethoxy-1,10-phenanthroline (778 mg, 3.24 mmol), copper(I) iodide (617 mg, 3.24 mmol) and potassium carbonate (4476 mg, 32.4 mmol) in DMSO (40 mL) was stirred at 140° C. under N$_2$ for 3 h. After cooled to rt, the reaction mixture was diluted with H$_2$O (50 mL) and added 1N HCl to adjust the pH to ~2 (pH paper). The resulting mixture was extracted with EtOAc (400 mL, 2×). The combined extracts were dried (Na$_2$SO$_4$) and evaporated under reduced pressure to give black oil. The residue was purified by flash chromatography (SiO$_2$, 0 to 7% MeOH/CH$_2$Cl$_2$) to give brown oil (3.2 g, 43.3%). MS (ESI) 265 (M+H).

Step B. Preparation of tert-butyl 4-(5-chloro-1-(4-cyano-3-fluorophenyl)-2-oxo-1,2-dihydropyridin-4-yloxy)piperidine-1-carboxylate The intermediate was prepared according to the procedures described in Example 221 substituting 4-(5-chloro-4-hydroxy-2-oxopyridin-1(2H)-yl)-2-fluorobenzonitrile for 4-hydroxy-6-oxo-1,6-dihydropyridine-3-carbonitrile and tert-butyl 4-(methylsulfonyloxy)piperidine-1-carboxylate for 1-(5-propylpyrimidin-2-yl)piperidin-4-yl methanesulfonate in Step B. MS (ESI) 392 (M+H).

Step C. Preparation of 4-(5-chloro-2-oxo-4-(piperidin-4-yloxy)pyridin-1(2H)-yl)-2-fluorobenzonitrile A suspension of tert-butyl 4-(5-chloro-1-(4-cyano-3-fluorophenyl)-2-oxo-1,2-dihydropyridin-4-yloxy)piperidine-1-carboxylate (2.2 g, 4.18 mmol) in MeOH (15 mL) was added hydrogen chloride (4M in 1,4-dioxane) (0.609 g, 16.70 mmol) and stirred at rt. After 6 h stirring, solvent MeOH was evaporated and the resulting crude was diluted with EtOAc (50 mL). After saturated aqueous NaHCO$_3$ was added to adjust PH>7, the resulting mixture was vigorously stirred for 2 h. The organic layers was collected and the aqueous layer was back-extracted with EtOAc 2×. The combined extracts were dried (Na$_2$SO$_4$) and evaporated under reduced pressure to give a brown solid as a crude product (1 g, 2.88 mmol). MS (ESI) 348 (M+H).

Step D

Example 263

A mixture of 4-(5-chloro-2-oxo-4-(piperidin-4-yloxy)pyridin-1(2H)-yl)-2-fluorobenzonitrile (50 mg, 0.144 mmol), 2-chloro-5-(3,3,3-trifluoropropyl)pyrimidine (60.6 mg, 0.288 mmol, prepared as described in Example 181) and potassium carbonate (59.6 mg, 0.431 mmol) in DMF (0.4 mL) was stirred at 90° C. in a closed vial for 24 h. After cooled to rt, the reaction mixture was diluted with EtOAc (60 mL) and H$_2$O (40 mL). The aqueous phase was acidified by 1N HCl to PH=2. The organic extract was collected, dried over Na$_2$SO$_4$ and evaporated to give brown oil. The crude oil was purified by preparative HPLC (C$_{18}$ column; 20-90% MeOH in water containing 0.05% trifluoroacetic acid) to give Example 263 as a brown solid (5 mg, 6.33%). $^1$H NMR (500 MHz, CDCl$_3$) δ ppm 8.50 (s, 2 H), 7.80 (t, J=7.42 Hz, 1 H), 7.48 (s, 1 H), 7.36 (dd, J=18.42, 8.52 Hz, 2 H), 6.41 (s, 1 H), 4.84 (br. s., 1 H), 4.29 (d, J=12.65 Hz, 2 H), 3.89-4.05 (m, 2 H), 2.79-2.92 (m, 2 H), 2.34-2.52 (m, 2 H), 2.16 (br. s., 4 H). MS (ESI) 522 (M+H).

Example 264

Preparation of 4-(5-chloro-4-(1-(5-fluoropyrimidin-2-yl)piperidin-4-yloxy)-2-oxopyridin-1(2H)-yl)-2-fluorobenzonitrile, TFA salt

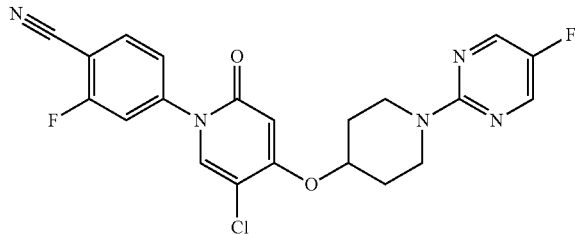 [SMILES: N#Cc1ccc(-n2cc(Cl)c(OC3CCN(c4ncc(F)cn4)CC3)cc2=O)cc1F]

Example 264 was prepared according to the procedures described in Example 263 substituting 2-chloro-5-fluoropyrimidine for 2-chloro-5-(3,3,3-trifluoropropyl)pyrimidine for 2-chloro-5-(3,3,3-trifluoropropyl)pyrimidine in Step 4. $^1$H NMR (500 MHz, CDCl$_3$) δ ppm 8.24 (s, 2 H), 7.75-7.80 (m, 1 H), 7.42 (s, 1 H), 7.38 (d, J=9.35 Hz, 1 H), 7.34 (d, J=8.25 Hz, 1 H), 6.18 (s, 1 H), 4.67-4.73 (m, 1 H), 4.01 (td, J=8.80, 3.85 Hz, 2 H), 3.85-3.93 (m, 2 H), 2.06 (dt, J=8.80, 4.40 Hz, 2 H), 1.96 (td, 2 H). MS (ESI) 444 (M+H).

Example 265

Preparation of 4-(5-chloro-4-(1-(5-cyclopropylpyrimidin-2-yl)piperidin-4-yloxy)-2-oxopyridin-1(2H)-yl)-3-fluorobenzonitrile

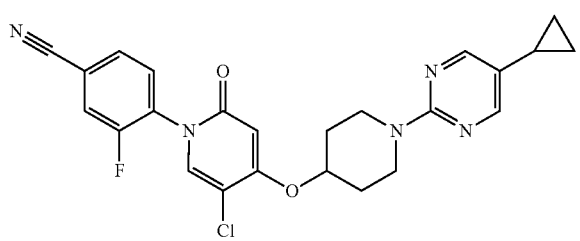 [SMILES: N#Cc1ccc(-n2cc(Cl)c(OC3CCN(c4ncc(C5CC5)cn4)CC3)cc2=O)c(F)c1]

Step A. Preparation of 5-chloro-4-(1-(5-cyclopropylpyrimidin-2-yl)piperidin-4-yloxy)pyridin-2(1H)-one To a stirring mixture of 5-chloro-4-hydroxypyridin-2(1H)-one (212 mg, 1.46 mmol), 1-(5-cyclopropylpyrimidin-2-yl)piperidin-4-ol (320 mg, 1.459 mmol, prepared according to procedures described in Example 173 Step A substituting 2-chloro-5-cyclopropylpyrimidine for 2-chloro-5-propylpyrimidine) and triphenylphosphine (574 mg, 2.19 mmol) in DMF (10 mL) at 0° C. was added diisopropyl azodicarboxylate (0.43 mL, 2.2 mmol). The reaction was stirred under Ar at room temperature for 2 days and then H$_2$O was added. The resulting mixture was concentrated in vacuo to a yellow oil. The oil was purified by flash chromatography (SiO$_2$, 0 to 100% EtOAc in CH$_2$Cl$_2$ and then SiO$_2$, 0 to 10% MeOH in CH$_2$Cl$_2$) to yield 153 mg of desired product as a white solid. MS (ESI) 347 (M+H).

Step B

Example 265

Example 265 was prepared according to procedures described in Example 252 substituting 5-chloro-4-(1-(5-cyclopropylpyrimidin-2-yl)piperidin-4-yloxy)pyridin-2(1H)-one for 4-(1-(5-propylpyrimidin-2-yl)piperidin-4-yloxy)pyridin-2(1H)-one and substituting 3,4-difluorobenzonitrile (Aldrich) for 2,3,4-trifluorobenzonitrile except that the reaction was heated at 110° C. for 3 days and then at 140° C. for 5 h. $^1$H NMR (500 MHz, CDCl$_3$) δ ppm 8.07 (s, 2 H), 7.42-7.60 (m, 3 H), 7.23 (s, 1 H), 5.99 (s, 1 H), 4.50-4.69 (m, 1 H), 3.93-4.04 (m, 2 H), 3.67-3.82 (m, 2 H), 1.93-2.07 (m, 2 H), 1.78-1.92 (m, 2 H), 1.61-1.72 (m, 1 H), 0.78-0.91 (m, 2 H), 0.47-0.61 (m, 2 H). MS (ESI) 466 (M+H).

Example 267

Preparation of tert-butyl 4-(5-chloro-1-(4-cyano-3-fluorophenyl)-2-oxo-1,2-dihydropyridin-4-yloxy)piperidine-1-carboxylate

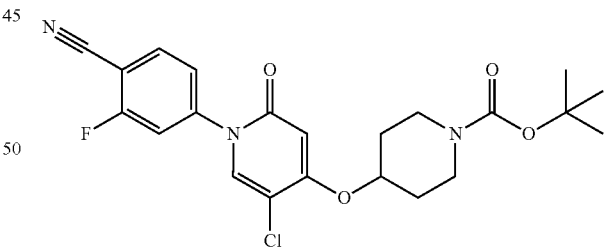

Example 267 was prepared according to procedures described in Example 173 Step C substituting 4-(5-chloro-4-hydroxy-2-oxopyridin-1(2H)-yl)-2-fluorobenzonitrile (prepared according to the procedure described in Step B of Example 263) for 4-hydroxypyridin-2(1H)-one and substituting tert-butyl 4-(methylsulfonyloxy)piperidine-1-carboxylate (prepared according to the procedure described in Step C of Example 1) for 1-(5-propylpyrimidin-2-yl)piperidin-4-yl methanesulfonate except that the crude product was purified by flash chromatography (SiO$_2$, 0 to 100% EtOAc in CH$_2$Cl$_2$). $^1$H NMR (400 MHz, CDCl$_3$) δ ppm 7.77 (t, J=7.53 Hz, 1 H), 7.37-7.46 (m, 2 H), 7.30-7.36 (m, 1 H), 6.00 (s, 1 H), 4.54-4.68 (m, 1 H), 3.58-3.71 (m, 2 H), 3.40-3.56 (m, 2 H), 1.93-2.07 (m, 2 H), 1.78-1.93 (m, 2 H), 1.49 (s, 9 H). MS (ESI) 392 (M-56+H).

Example 268

Preparation of isopropyl 4-(5-chloro-1-(4-cyano-3-fluorophenyl)-2-oxo-1,2-dihydropyridin-4-yloxy)piperidine-1-carboxylate

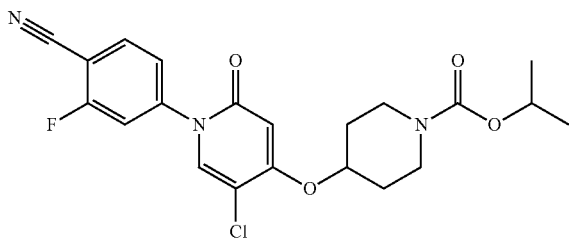 [SMILES: CC(C)OC(=O)N1CCC(Oc2cc(=O)n(-c3ccc(C#N)c(F)c3)cc2Cl)CC1]

Example 268 was prepared according to procedures described in Example 2 substituting tert-butyl 4-(5-chloro-1-(4-cyano-3-fluorophenyl)-2-oxo-1,2-dihydropyridin-4-yloxy)piperidine-1-carboxylate for tert-butyl 4-(1-(4-(methylsulfonyl)phenyl)-2-oxo-1,2-dihydropyridin-4-yloxy)piperidine-1-carboxylate in Step A and substituting isopropyl chloroformate for 1,1,1-trifluoropropan-2-yl chloroformate in Step C except that the crude product was purified by flash chromatography (SiO$_2$, 0 to 100% EtOAc in CH$_2$Cl$_2$). $^1$H NMR (400 MHz, CDCl$_3$) δ ppm 7.67-7.87 (m, 1 H), 7.30-7.49 (m, 3 H), 6.00 (s, 1 H), 4.86-5.11 (m, 1 H), 4.53-4.70 (m, 1 H), 3.44-3.76 (m, 4 H), 1.79-2.15 (m, 4 H), 1.26 (s, 6 H). MS (ESI) 434 (M+H).

Example 269

Preparation of 4-(1-(5-ethoxypyrazin-2-yl)piperidin-4-yloxy)-1-(4-(methylsulfonyl)phenyl)pyridin-2(1H)-one, TFA salt

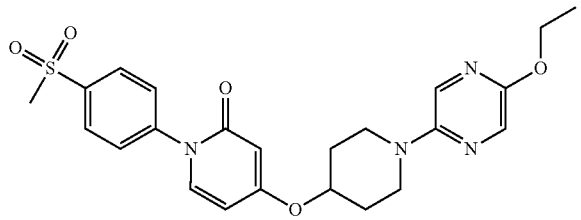 [SMILES: CCOc1cnc(N2CCC(Oc3ccn(-c4ccc(S(C)(=O)=O)cc4)c(=O)c3)CC2)cn1]

A mixture of 1-(4-(methylsulfonyl)phenyl)-4-(piperidin-4-yloxy)pyridin-2(1H)-one, HCl (39.5 mg, 0.113 mmol), 2-bromo-5-ethoxypyrazine (23 mg, 0.113 mmol), and potassium carbonate (20.39 mg, 0.340 mmol) in DMSO (0.2 mL) was heated in a 180° C. oil bath for 1.5 hours. The reaction mixture was added to 2 mL EtOAc and washed with 3×2 mL of water, dried EtOAc over MgSO$_4$, filtered and concentrated to 6 mg of an amber oil. This material was purified by preparative HPLC (C18, 50-90% MeOH in water containing 0.1% TFA) to give Example 269 (2.3 mg, 0.003 mmol, 3%) as a brown oil. MS (ESI) 471.2 (M+1).

Example 270

Preparation of tert-butyl 4-(1-(4-cyano-3-fluorophenyl)-2-oxo-1,2-dihydropyridin-4-yloxy)piperidine-1-carboxylate

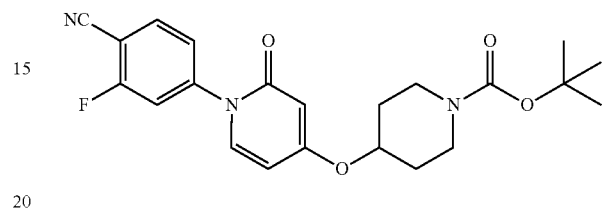

Step A. Preparation of tert-butyl 4-(2-oxo-1,2-dihydropyridin-4-yloxy)piperidine-1-carboxylate To 4-hydroxypyridin-2(1H)-one (11.11 g, 100 mmol) and tert-butyl 4-(methylsulfonyloxy)piperidine-1-carboxylate (27.9 g, 100 mmol) in a 100 mL round bottom flask was applied vacuum 5 minutes, vented to nitrogen, added DMSO (100 mL), and then added potassium carbonate (13.20 g, 220 mmol). Placed in a 90° C. oil bath under nitrogen for 4.5 hours. The reaction mixture was added to 1000 mL water and 1000 mL EtOAc, then washed EtOAc with additional water (4×500 mL), dried with MgSO$_4$, filtered and concentrated to 27.3 g oily white solids. This material was slurried 200 mL refluxing EtOAc, allowed to cool to rt, filtered, and washed with 2×50 mL EtOAc then 2×50 mL of hexane to give product (4.86 g, 16.5 mmol, 17%) as a white crystalline powder. MS (ESI) 239.1 (M+1-56, indicating loss of t-butyl group the Boc group in the MS).

Step B. Preparation of tert-butyl 4-(2-oxo-1,2-dihydropyridin-4-yloxy)piperidine-1-carboxylate To tert-butyl 4-(2-oxo-1,2-dihydropyridin-4-yloxy)piperidine-1-carboxylate (294 mg, 1 mmol), copper(I) iodide (229 mg, 1.200 mmol), quinolin-8-ol (174 mg, 1.200 mmol), and potassium carbonate (180 mg, 3.00 mmol) added DMSO (5 mL), bubbled nitrogen subsurface for 20 seconds, capped under nitrogen and let stir at rt for 20 minutes then added 2-fluoro-4-iodobenzonitrile (296 mg, 1.200 mmol), bubbled nitrogen subsurface 20 seconds, capped under nitrogen and placed in a 90° C. oil bath for 60 minutes. The reaction mixture was added to 50 mL EtOAc+25 mL water and then filtered to remove solids and break the emulsion. The lower aqueous layer was removed and washed the green EtOAc layer with an additional 4×25 mL of water, dried with MgSO$_4$, filtered and concentrated to 419 mg of a light green oil. This material was purified by flash chromatography (0-1% MeOH in CH$_2$Cl$_2$) to provide Example 270 (28 mg, 0.067 mmol, 7%) as a pale yellow solid. $^1$H NMR (500 MHz, CDCl$_3$) δ ppm 1.48 (s, 9 H) 1.72-1.84 (m, 2 H) 1.92-2.03 (m, 2H) 3.28-3.38 (m, 2 H) 3.72 (br. s., 2 H) 4.49 (br. s., 1 H) 5.95 (br. s., 1 H) 6.06 (d, J=7.70 Hz, 1 H) 7.21 (d, J=7.70 Hz, 1 H) 7.33 (d, J=8.25 Hz, 1 H) 7.38 (d, J=9.35 Hz, 1 H) 7.75 (t, J=7.70 Hz, 1 H). MS (ESI) 414.2 (M+1).

Example 271

Preparation of 3-fluoro-4-(2-oxo-4-(1-(5-(3,3,3-trifluoropropyl)pyrimidin-2-yl)piperidin-4-yloxy)pyridin-1(2H)-yl)benzonitrile, TFA salt

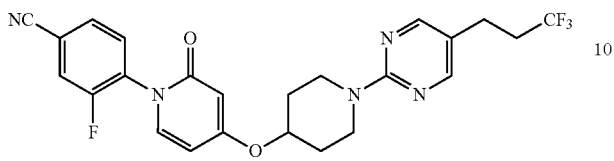

Step A. Preparation of 4-(4-(benzyloxy)-2-oxopyridin-1(2H)-yl)-3-fluorobenzonitrile To 4-(benzyloxy)pyridin-2(1H)-one (0.358 g, 1.779 mmol) under nitrogen was added DMF (5 mL) to produce a tan suspension. To the reaction was added NaH (60% in oil) (0.074 g, 1.860 mmol) and stirred for 1.5 hours and then 3,4-difluorobenzonitrile (0.225 g, 1.618 mmol) was added. The reaction was placed in a 90° C. oil bath for 2 hours. To the tan suspension was added 50 mL of EtOAc and the mixture washed with 4×25 mL of water, dried over MgSO$_4$, filtered and concentrated to give 0.42 g pale yellow solids. This material was purified by flash chromatography (1-5% MeOH in CH$_2$Cl$_2$) to yield product (263 mg, 0.805 mmol, 50%) as a tan solid. MS (ESI) 321.2 (M+1).

Step B. Preparation of 3-fluoro-4-(4-hydroxy-2-oxopyridin-1(2H)-yl)benzonitrile To 4-(4-(benzyloxy)-2-oxopyridin-1(2H)-yl)-3-fluorobenzonitrile (250 mg, 0.780 mmol) and 10% palladium on carbon (50 mg, 0.470 mmol) was applied vacuum then placed under an atmosphere of nitrogen. Methanol (5 mL) was added and vacuum applied briefly. The reaction was placed under an atmosphere of hydrogen for 6 hours. The reaction mixture was passed through a 10×10 mm CELITE® 545 filter aid plug eluting with an additional 10 mL each of MeOH and CH$_2$Cl$_2$. The filtrate was concentrated to 170 mg of a pale tan foam. Added 5 mL MeOH and heated to reflux, filtered hot and rinsed with 3×2 mL warm MeOH. The filtrate was concentrated to crude product (166 mg, 0.577 mmol, 74%) as a pale yellow solid which was used as obtained in the subsequent step. MS (ESI) 231.1 (M+1).

Step C

Preparation of Example 271

3-Fluoro-4-(4-hydroxy-2-oxopyridin-1(2H)-yl)benzonitrile (46.0 mg, 0.2 mmol), 1-(5-(3,3,3-trifluoropropyl)pyrimidin-2-yl)piperidin-4-yl methanesulfonate (70.7 mg, 0.200 mmol), and potassium carbonate (36.0 mg, 0.600 mmol) in DMF (1 mL) was placed in a 90° C. oil bath for 15 hours. The reaction mixture was added to 5 mL each of EtOAc and water. The layers were separated and the organic layer was washed with 2 mL of additional water. Back-extracted the first aqueous with 5 mL of EtOAc, combined EtOAc solutions, then washed with a third water volume (2 mL). Dried EtOAc with MgSO$_4$, filtered and concentrated to 43 mg. This material was purified by preparative HPLC (C18, 50-90% MeOH in water containing 0.1% TFA) to give Example 271 (23 mg, 0.003 mmol, 3%) as a pale yellow foam. $^1$H NMR (500 MHz, CDCl$_3$) δ ppm 2.07 (d, J=4.40 Hz, 2 H) 2.11-2.28 (m, 2 H) 2.31-2.54 (m, 2 H) 2.86 (t, J=7.70 Hz, 2 H) 3.79-4.18 (m, 4 H) 4.75 (br. s., 1 H) 6.25 (d, J=7.70 Hz, 1 H) 6.45 (br. s., 1 H) 7.23 (d, J=7.70 Hz, 1 H) 7.48-7.70 (m, 3 H) 8.49 (s, 2 H). MS (ESI) 488.2 (M+1).

Example 272

Preparation of 4-(1-(5-methoxypyrazin-2-yl)piperidin-4-yloxy)-1-(4-(methylsulfonyl)phenyl)pyridin-2(1H)-one, TFA salt

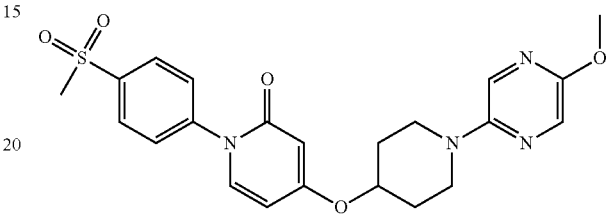

Example 272 was prepared using the procedure described for Example 269 and substituting 2-bromo-5-methoxypyrazine for 2-bromo-5-ethoxypyrazine. MS (ESI) 457.3 (M+1).

Example 273

Preparation of 4-(1-(5-chloropyrazin-2-yl)piperidin-4-yloxy)-1-(4-(methylsulfonyl)phenyl)pyridin-2(1H)-one, TFA salt

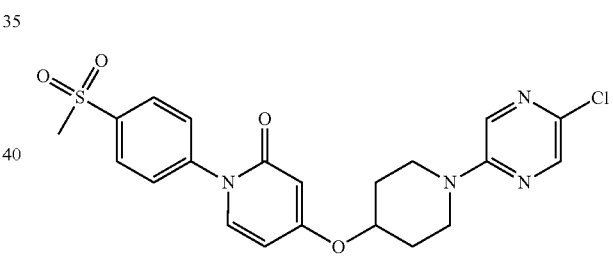

Example 273 was isolated from the reaction mixture used to produce Example 272 and resulted from the impurity 2-chloro-5-methoxypyrazine contained within the reagent 2-bromo-5-methoxypyrazine. MS (ESI) 461.1 (M+1).

Example 274

Preparation of 4-(4-(1-(5-cyclobutylpyrimidin-2-yl)piperidin-4-yloxy)-2-oxopyridin-1(2H)-yl)-3-fluorobenzonitrile

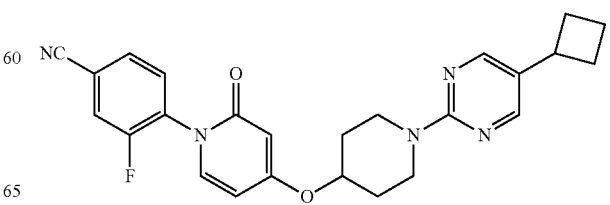

To a mixture of 3-fluoro-4-(4-hydroxy-2-oxopyridin-1(2H)-yl)benzonitrile (46.0 mg, 0.2 mmol), 1-(5-cyclobutylpyrimidin-2-yl)piperidin-4-yl methanesulfonate (62.3 mg, 0.200 mmol), and potassium carbonate (36.0 mg, 0.600 mmol) was added DMF (1 mL), capped and placed in a 90° C. oil bath for 110 minutes. The reaction mixture was added to 5 mL EtOAc plus 5 mL water, backwashed water layer with 2×2 mL EtOAc then washed combined EtOAc solutions with 2×2 mL water. Dried EtOAc with $MgSO_4$, filtered, and concentrated to 71 mg of a pale yellow solid. This material was purified by preparative HPLC (C18, 50-90% MeOH in water containing 0.1% TFA) to give Example 274 (42 mg, 0.074 mmol, 37%) as an off-white foam. $^1H$ NMR (500 MHz, $CDCl_3$) δ ppm 1.86-2.01 (m, 1 H) 2.01-2.23 (m, 6 H) 2.32-2.50 (m, 2 H) 3.39-3.57 (m, 1 H) 4.07 (br. s., 3 H) 4.73 (br. s., 1 H) 6.21 (d, J=7.70 Hz, 1 H) 6.34 (br. s., 1 H) 7.21 (d, J=7.70 Hz, 1 H) 7.48-7.69 (m, 3 H) 8.45 (s, 2 H). MS (ESI) 446.3 (M+1).

Assays for GPR119 G Protein-Coupled Receptor Activity

The in vitro modulation of recombinant human GPR119 was determined as follows.

HIT-T15 cAMP Assay

A HIT-T15 hamster insulinoma cell line was purchased from ATCC and grown in the medium recommended by ATCC (i.e., Growth Medium: F12K Medium (Invitrogen 21127-022; 10% D-horse Serum; and 2.5% FBS).

To conduct the cAMP assay, cells expressing a GPR119 receptor are plated on 96 well plates (e.g., BD Falcon: REF 353948, black side, clear bottom, TC surface) at a density of about $4.5 \times 10^4$ cells per well in growth medium and incubated overnight. Following incubation, the growth medium is removed from the wells followed by a single rinse with the assay buffer from the Hit Hunter cAMP kit (100 μl/well). Following the rinse, 20 μl of assay buffer is added to each well followed by addition of 10 μl of a 3× concentration of compound working solution. The solution is then mixed well. The final concentration range of compound is from about $10^{-5}$M to about $10^{-11}$M. The reaction is incubated at 37° C., in a 5% $CO_2$ for 1 hour. Following incubation, the cAMP concentration is determined using the Hit Hunter cAMP kit according to the manufacturer's protocol.

Human Tet-inducible cAMP Assay

Cell lines expressing GPR119 are generated using the Flp-In-T-REx 293 tetracycline inducible gene expression system are cultured in culture medium comprising the following components: DMEM#11965, 10% FBS, 2 mM L-glutamine, 200 ug/ml Hygromycin B, and 15 ug/ml blasticidin.

For cAMP assays, cells are plated on 96 well plates (e.g., BD Falcon: REF 353948, black side, clear bottom, TC surface) at a density of about $4.5 \times 10^4$ cells per well in growth medium containing LOug/ml tetracycline (1.0 mg/ml stock). The cells are then incubated for 48 hours at 37° C.

Following the incubation, the growth medium is removed from the wells and the wells rinsed (once) with the assay buffer included in the Hit Hunter cAMP kit (100 μl/well). Following the wash, 20 μl of assay buffer is added to each well, followed by addition of 10 μl of a 3× concentration compound working solution. The solution is then mixed. The final concentration range of compound is from about $10^{-5}$M to about $10^{-11}$M. The reagents are then incubated at 37° C. at 5% $CO_2$ for 1 hour.

The manufacturer's protocol may be followed for cAMP determination. The Hit Hunter cAMP kit protocol is outlined for the HIT-T15 cAMP assays described above.

Compounds of the present invention were tested in the Human Tet-inducible cAMP assay described immediately above and the results shown in Table 1 below were obtained.

TABLE 1

| Example | hGPR119 $EC_{50}$ (nM) |
|---------|------------------------|
| 12      | 3489                   |
| 27      | 3502                   |
| 51      | 314                    |
| 74      | 275                    |
| 78      | 303                    |
| 82      | 4027                   |
| 83      | 4340                   |
| 84      | 3274                   |
| 86      | 3519                   |
| 91      | 304                    |
| 108     | 261                    |
| 125     | 293                    |
| 133     | 250                    |
| 143     | 274                    |
| 153     | 273                    |
| 162     | 5000                   |
| 165     | 5000                   |
| 175     | 8                      |
| 177     | 8                      |
| 178     | 265                    |
| 179     | 276                    |
| 184     | 5000                   |
| 189     | 7143                   |
| 191     | 5088                   |
| 192     | 241                    |
| 194     | 5                      |
| 199     | 7                      |
| 202     | 2                      |
| 206     | 293                    |
| 207     | 7075                   |
| 209     | 3388                   |
| 224     | 6                      |
| 227     | 1                      |
| 229     | 4                      |
| 239     | 9                      |
| 243     | 9                      |
| 261     | 257                    |
| 263     | 4                      |
| 265     | 4                      |
| 267     | 4                      |

Luciferase Assay

HEK 293 cells may be plated on poly-D-lysine treated 96-well BD black side/clear bottom plates at a density of about $3 \times 10^4$ cells/well in growth medium. The growth medium may comprise the following: D-MEM (Cat #12430) with high glucose and 10% fetal bovine serum.

Cells may be transfected with vectors comprising native or non-native GPR119 sequences using commercially available vectors (e.g., Stratagene) and transfection reagents. The standard manufacturer's protocols may be followed to transfect the cells. Following transfection, the transfection medium may be removed and assay medium added to the wells of the assay plates.

Once the assay plates are prepared, compound dilution plates may be made. To do so, make a first compound dilution plate using 10 mM of the compound of interest diluted to about 1 mM in DMSO. Then make 12 point half-log dilutions of the compounds (in DMSO) using an automated liquid handler. Next, make a second dilution plate by diluting the wells in the first plate ten fold (10×) using assay medium. Once the plates are complete, the highest dose is about 10 μM and the lowest dose is about 0.03 nM.

Once the dilution plates are complete, one can add about 10 μl of the 10× compound dilution to the assay plate containing the assay medium transiently transfected cells. Tap the plate to mix the reagents and incubate the plate overnight at 37° C., 95% $O_2$, and 5% $CO_2$ in an incubator.

Following incubation, a luciferase assay system may be used (e.g., Stead-Glo Luciferase Assay System from Promega) according to the manufacturer's instructions. Following completion of the reaction, immediately measure the readout of the assay using a top count luminometer.

Mouse Oral Glucose Tolerance Test 24 male C57BL/6J mice (8-10 weeks old, average weight 28 g) were randomized into 4 groups (1 mouse/cage) of 6 mice per group based on fed plasma glucose and body weight. Prior to initiating the study, mice were fasted overnight and the next morning they were weighed and placed in the experimental lab. After 30 min in the environment, the mice were bled via tail tip at −30 min and immediately given their first oral administration of vehicle (0.5% Methocel, 0.1% Tween 80 in water) or compound solutions (5 ml/kg). At time 0 the mice were bled and given 50% glucose (2 g/kg) to initiate the oral glucose tolerance test (oGTT). The mice were bled 30, 60 and 120 min after the glucose load. Blood samples were drawn into potassium EDTA, placed on ice during the study and subsequently centrifuged for 10 min at 3000 rpm at 4° C. Plasma samples were diluted 11-fold for glucose analysis in the Cobas Mira System (Roche Diagnostics). Area under the curve was calculated from the plasma glucose time course data using the trapezoid rule with fasting plasma glucose as the baseline (GraphPad Prism Software). The statistical significance of the changes in the glucose AUCs resulting from the different treatments was determined by one-way ANOVA followed by Dunnett's test using the vehicle group as the control (JMP software, release 5.1.2).

TABLE 2

| Example | Glucose Lowering (%) |
|---------|----------------------|
| 3       | −29                  |

Utilities and Combinations

A. Utilities

The compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of Formula I and IA, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR119 receptor agonists or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar); SGLT2 inhibitors (e.g., 3-(Benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis)); 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, and denagliptin); glucagon-like peptide-1 (GLP-1) receptor agonists (e.g., Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™); aldose reductase inhibitors (e.g., those disclosed in WO 99/26659); RXR agonists (e.g., reglitizar (JTT-501), 5-[[6-[(2-fluorophenyl)methoxy]-2-naphthalenyl]methyl]-2,4-Thiazolidinedione (MCC-555), 5-[[3-(5,6,7,8-tetrahydro-3,5,5,8,8-pentamethyl-2-naphthalenyl)-4-(trifluoromethoxy)phenyl]methylene]-2,4-Thiazolidinedione (MX-6054), DRF2593, farglitazar, (±)-5-

[(2,4-dioxothiazolidin-5-yl)methyl]-2-methoxy-N-[[(4-trifluoromethyl)phenyl]methyl]benzamide (KRP-297), 6-[1-(5,6,7,8-tetrahydro-3,5,5,8,8-pentamethyl-2-naphthalenyl)cyclopropyl]-3-Pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., Methyl ester [4-[(2R)-2-[[(2R)-2-(3-chlorophenyl)-2-hydroxyethyl]amino]propyl]phenoxy]-Acetic acid (BRL 35135), 2-[4-[(2S)-2-[[(2S)-2-(3-chlorophenyl)-2-hydroxyethyl]amino]propyl]phenoxy]-Acetic acid (BRL 37344), 4-[(3R)-3-[bis[(2R)-2-hydroxy-2-phenylethyl]amino]butyl]-Benzamide (Ro 16-8714), 2-[4-[2-[[(2S)-2-hydroxy-3-phenoxypropyl]amino]ethoxy]phenoxy]-N-(2-methoxyethyl)-Acetamide (ICI D7114), 5-[(2R)-2-[[(2R)-2-(3-chlorophenyl)-2-hydroxyethyl]amino]propyl]-3-Benzodioxole-2,2-dicarboxylic acid, disodium salt (CL 316,243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386,398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-Cyclohexadiene-1,4-dione (L-783281), TER17411, TER17529); gluconeogenesis inhibitors (e.g., GP3034); somatostatin analogs and antagonists; antilipolytic agents (e.g., nicotinic acid, acipimox, N-cyclohexyl-2'-O-methyl-Adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (KaroBio)); Glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-Pyridinecarboxylic acid (GKA-50 AstraZeneca)); GPR119 agonists (e.g., 1,1-dimethylethyl ester 4-[[3-(4-pyridinyl)-1,2,4-oxadiazol-5-yl]methoxy]-1-Piperidinecarboxylic acid (PSN-632408 OSI Prosidion)); GDIR agonists (e.g., APD668 (Arena)); GPR40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy)phenyl)-1H-benzo[d]imidazole).

Examples of suitable lipid lowering agents and anti-atherosclerotic agents for use in combination with the compounds of the present invention include one or more MTP/ApoB secretion inhibitors (e.g., dirlopatide, N-(2,2,2-Trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fabric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na$^+$/bile acid cotransporter inhibitors (e.g., compounds as disclosed in Drugs of the Future, 24:425-430 (1999); upregulators of LDL receptor activity (e.g., (3R)-3-[(13R)-β-hydroxy-10-oxotetradecyl]-5,7-dimethoxy-1(3H)-Isobenzofuranone (Taisho Pharmaceutical Co. Ltd) and (3α,4α,5α)-4-(2-propenyl)-Cholestan-3-ol (Eli Lilly); bile acid sequestrants (e.g., WELCHOL®, COLESTID®, LOCHOLEST® and QUESTRAN®; and fabric acid derivatives, such as ATROMID®, LOPID® and TRICOT®); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", Brit. J. Pharmacology, 120:1199-1206 (1997), and Cornicelli et al., "15-Lipoxygenase and its Inhibition: A Novel Therapeutic Target for Vascular Disease", Current Pharmaceutical Design, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl)sulfonyl]-4,5-dihydro-N'-methyl-4-phenyl-1H-Pyrazole-1-carboximidamide (SLV 319), CP-945598 (Pfizer), Surinabant (SR-147778, Sanofi-Aventis), N-[(1S,2S)-3-(4-Chlorophenyl)-2-(3-cyanophenyl)-1-methylpropyl]-2-methyl-2-{[5-(trifluoromethyl)pyridin-2-yl]oxy}propanamide (Merck) and those discussed in Hertzog, D. L., Expert Opin. Ther. Patents, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-Benzenesulfonamide (L750355, Merck), or CP331648 (Pfizer,) or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buprorion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b][1,4]diazepino[6,7,1hi]indole]: with lorcaserin hydrochloride being preferred); 5-HT6 receptor antagonists (Suven, Biovitrum, Epix), anti-epileptics topiramate (Johnson & Johnson) and zonisamide, a ciliary neurotrophic factor agonist (e.g., axokine (Regeneron); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer)); acetyl-CoA carboxylase (ACC) inhibitors (e.g., N-(4-(4-(4-isopropoxyphenoxy)phenyl)but-3-yn-2-yl)acetamide (A-80040, Abbott), (R)-anthracen-9-yl(3-(morpholine-4-carbonyl)-1,4'-bipiperidin-1'-yl)methanone (CP-640186, Pfizer)), SCD-1 inhibitors as described by Jiang et al., *Diabetes* (2004) 53, (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH$_2$ (Unigene)), NPY-Y4 agonists (7™ Pharma WO 2005/089786(A2,A3)-1), NPY-5 antagonists (e.g., NPYSRA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-Glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to Reyataz® and Kaletra®.

Examples of suitable memory enhancing agents, anti-dementia agents, or cognition promoting agents for use in combination with the compounds of the present invention include, but are not limited to aricept, razadyne, donepezil, rivastigmine, galantamine, memantine, tacrine, metrifonate, muscarine, xanomelline, deprenyl and physostigmine Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, remicade, orencia, and enbrel.

The aforementioned patents and patent applications are incorporated herein by reference.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

The compounds of Formula I and IA can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of Formula I and/or IA, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of Formula I and/or IA (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of Formula I and/or IA into a vial, aseptically freeze-drying and sealing. For use, the contents of the vial are mixed with 2 mL of physiological saline, to produce an injectable preparation.

What is claimed is:
1. A compound of the formula

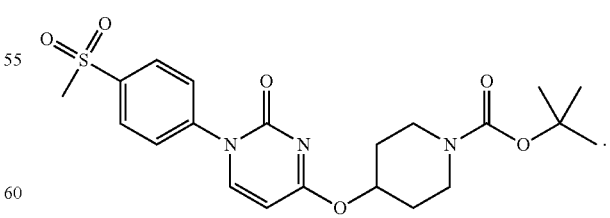

2. A pharmaceutical composition comprised of a therapeutically effective amount of a compound of claim 1 and, optionally, a pharmaceutically acceptable carrier.

3. The pharmaceutical composition of claim 2 further comprising one or more other therapeutically active agents.

4. A pharmaceutical composition comprising a therapeutically effective amount of a compound of claim 1 and a therapeutically effective amount of a dipeptidyl peptidase-IV inhibitor.

5. The pharmaceutical composition of claim 4 wherein the dipeptidyl peptidase-IV inhibitor is saxagliptin.

* * * * *